US 7,141,564 B2

Nov. 28, 2006

(54) NITROGEN-CONTAINING BICYCLIC HETEROCYCLES FOR USE AS ANTIBACTERIALS

(75) Inventors: Gerald Brooks, Harlow (GB); David Thomas Davies, Harlow (GB); Graham Elgin Jones, Harlow (GB); Roger Edward Markwell, Harlow (GB); Neil David Pearson, Harlow (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 10/478,154

(22) PCT Filed: May 24, 2002

(86) PCT No.: PCT/EP02/05708

§ 371 (c)(1),
(2), (4) Date: Apr. 6, 2004

(87) PCT Pub. No.: WO03/087098

PCT Pub. Date: Oct. 23, 2003

(65) Prior Publication Data

US 2004/0171620 A1 Sep. 2, 2004

(30) Foreign Application Priority Data

May 25, 2001 (GB) ............................. 0112834

(51) Int. Cl.
| A61K 31/542 | (2006.01) |
| A61K 31/4375 | (2006.01) |
| C07D 513/04 | (2006.01) |
| C07D 471/04 | (2006.01) |
| A61P 31/04 | (2006.01) |

(52) U.S. Cl. ............... 514/224.2; 514/230.5; 514/259.2; 514/260.1; 514/502; 514/301; 514/300; 514/248; 544/52; 544/51; 544/48; 544/105; 544/255; 544/282; 544/293; 546/115; 546/114; 546/113; 546/122; 546/159

(58) Field of Classification Search ................ 546/115, 546/114, 113, 122; 544/52, 51, 48, 105, 255, 544/282; 514/224.2, 230.5, 259.2, 260.1, 514/302, 301, 300, 248, 502; 542/113, 114, 542/115, 122, 159
See application file for complete search history.

(56) References Cited

U.S. PATENT DOCUMENTS

| 4,472,404 | A | * | 9/1984 | Paxton et al. ............... 514/311 |
| 5,849,757 | A | * | 12/1998 | Takemura et al. .......... 514/312 |
| 6,187,797 | B1 | | 2/2001 | Prvitt et al. |
| 6,602,882 | B1 | | 8/2003 | Davies et al. |
| 2003/0229119 | A1 | * | 12/2003 | Kym et al. ................ 514/313 |
| 2004/0077655 | A1 | | 4/2004 | Dartois et al. |
| 2004/0077656 | A1 | | 4/2004 | Markwell et al. |
| 2004/0138219 | A1 | | 7/2004 | Davies et al. |
| 2004/0198755 | A1 | | 10/2004 | Dartois et al. |
| 2004/0198756 | A1 | | 10/2004 | Davies et al. |
| 2005/0085494 | A1 | | 4/2005 | Daines et al. |
| 2005/0159411 | A1 | | 7/2005 | Daines et al. |

FOREIGN PATENT DOCUMENTS

| DE | 19955476 | 5/2001 |
| EP | 0 238 868 | 9/1987 |
| EP | 0 374 095 | 6/1990 |
| EP | 0 304 493 | 9/1992 |
| EP | 0 541 486 | 5/1993 |
| EP | 0 716 855 | 6/1996 |
| EP | 0 823 429 | 7/2000 |
| JP | 07179407 | 7/1995 |
| WO | WO9406284 | 3/1994 |
| WO | WO9509853 | 4/1995 |
| WO | WO9535287 | 12/1995 |
| WO | WO9615128 | 5/1996 |
| WO | WO9703069 | 1/1997 |
| WO | WO9718193 | 5/1997 |
| WO | WO9728167 | 8/1997 |
| WO | WO9738984 | 10/1997 |
| WO | WO9802434 | 1/1998 |
| WO | WO9802438 | 1/1998 |
| WO | WO9818461 | 5/1998 |
| WO | WO9827053 | 6/1998 |
| WO | WO9828269 | 7/1998 |
| WO | WO9937635 | 7/1999 |
| WO | WO9948492 | 9/1999 |
| WO | WO9967203 | 12/1999 |
| WO | WO0021948 | 4/2000 |
| WO | WO 00/21948 | 4/2000 |
| WO | WO 00/34265 | 6/2000 |
| WO | WO0035909 | 6/2000 |
| WO | WO0043383 | 7/2000 |
| WO | WO0045635 | 8/2000 |
| WO | WO0068199 | 11/2000 |
| WO | WO0068200 | 11/2000 |
| WO | WO0068201 | 11/2000 |
| WO | WO0078716 | 12/2000 |
| WO | WO0078748 | 12/2000 |
| WO | WO0107432 | 2/2001 |
| WO | WO0107433 | 2/2001 |
| WO | WO0119788 | 3/2001 |
| WO | WO01025227 | 4/2001 |
| WO | WO0170673 | 9/2001 |
| WO | WO0170737 | 9/2001 |

(Continued)

OTHER PUBLICATIONS

U.S. Appl. No. 10/518,653; "Compounds"; filed Jun. 25, 2003 in the names of J. Axten, R. Daines, D. Davies, T. Gallagher, G. Jones, W. Miller, N. Pearson, I. Pendrak; Preliminary Amendment mailed Dec. 16, 2004 therein.

*Primary Examiner*—Amelia A. Owens
(74) *Attorney, Agent, or Firm*—Loretta J. Sauermelch; Mary E. McCarthy; Charles M. Kinzig

(57) ABSTRACT

Cyclohexane and cyclohexene derivatives and pharmaceutically acceptable derivatives thereof useful in methods of treatment of bacterial infections in mammals, particularly man.

14 Claims, No Drawings

FOREIGN PATENT DOCUMENTS

| | | |
|---|---|---|
| WO | WO0172708 | 10/2001 |
| WO | WO0172712 | 10/2001 |
| WO | WO0174774 | 10/2001 |
| WO | WO0208224 | 1/2002 |
| WO | WO0224684 | 3/2002 |
| WO | WO0240474 | 5/2002 |
| WO | WO0250040 | 6/2002 |
| WO | WO0250061 | 6/2002 |
| WO | WO0256882 | 7/2002 |
| WO | WO02072572 | 9/2002 |
| WO | WO0296907 | 12/2002 |
| WO | WO03010138 | 2/2003 |
| WO | WO03064421 | 8/2003 |
| WO | WO03064431 | 8/2003 |
| WO | WO03/087098 | 10/2003 |
| WO | WO 2004002992 * | 1/2004 |
| WO | WO04024712 | 3/2004 |
| WO | WO04024713 | 3/2004 |
| WO | WO04035569 | 4/2004 |
| WO | WO04089947 | 10/2004 |

* cited by examiner

NITROGEN-CONTAINING BICYCLIC HETEROCYCLES FOR USE AS ANTIBACTERIALS

This invention relates to novel compounds, compositions containing them and their use as antibacterials.

WO099/37635, WO00/21948, WO00/21952, WO00/43383, WO00/78748, WO01/07433, WO01/07432, WO02/08224, WO02/24684 and WO01/25227 disclose quinoline and naphthyridine derivatives having antibacterial activity.

This invention provides a compound of formula (I) or a pharmaceutically acceptable derivative thereof:

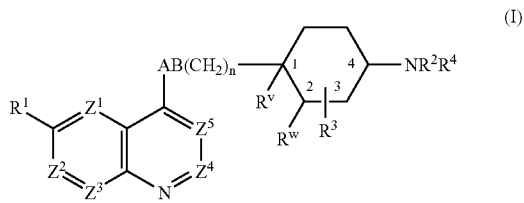

wherein:

one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^v$ and $R^w$ are hydrogen or $R^v$ and $R^w$ together are a bond;

$R^1$ and $R^{1a}$ are independently selected from hydrogen; hydroxy; $(C_{1-6})$ alkoxy optionally substituted by $(C_{1-6})$ alkoxy, amino, piperidyl, guanidino or amidino any of which is optionally N-substituted by one or two $(C_{1-6})$ alkyl, acyl or $(C_{1-6})$alkylsulphonyl groups, CONH2, hydroxy, $(C_{1-6})$alkylthio, heterocyclylthio, heterocyclyloxy, arylthio, aryloxy, acylthio, acyloxy or $(C_{1-6})$alkylsulphonyloxy, $(C_{1-6})$alkoxy-substituted $(C_{1-6})$ alkyl; halogen; $(C_{1-6})$alkyl; $(C_{1-6})$alkylthio; triflurom-ethyl; nitro; azido; acyl; acyloxy; acylthio; $(C_{1-6})$ alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when $Z^1$ is $CR^{1a}$, $R^1$ and $R^{1a}$ may together represent $(C_{1-2})$ akylenedioxy, provided that when $Z^1$, $Z^2$, $Z^3$, $Z^4$ and $Z^5$ are $CR^{1a}$ or CH, then $R^1$ is not hydrogen;

$R^2$ is hydrogen or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$ alkylcarbonyl; $(C_{2-4})$alkenyloxycarbonyl; $(C_{2-4})$ alkenylcarbonyl; aminocarbonyl wherein the amino group is optionally substituted by hydroxy, $(C_{1-4})$alkyl, hydroxy $(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$ alkenylsulphonyl, $(C_{1-4})$alkoxycarbonyl, $(C_{1-4})$ alkylcarbonyl, $(C_{2-4})$alkenyloxycarbonyl or $(C_{2-4})$ alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-yl-aminocarbonyl; 1,2,4-triazol-5-yl optionally substituted by $R^{10}$; 5-oxo-1,2,4-oxadiazol-3-yl; halogen; $(C_{1-4})$ alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$ alkenylcarbonyl; oxo; $(C_{1-4})$alkylsulphonyl; $(C_{2-4})$ alkenylsulphonyl; or $(C_{1-4})$aminosulphonyl wherein the amino group is optionally substituted by $(C_{1-4})$alkyl or $(C_{2-4})$alkenyl;

$R^3$ is hydrogen; or when $R^v$ and $R^w$ are a bond, $R^3$ is in the 2-, 3- or 4-position and when $R^v$ and $R^w$ are not a bond, $R^3$ is in the 1-, 2-, 3- or 4-position and $R^3$ is:

carboxy; $(C_{1-6})$alkoxycarbonyl; aminocarbonyl wherein the amino group is optionally substituted by hydroxy, $(C_{1-6})$ alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$ alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl, hydroxy$(C_{1-6})$ alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$ alkoxycarbonyl; $(C_{1-6})$alkylcarbonyl; $(C_{2-6})$ alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$ alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$ alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$ alkenylcarbonyl, $(C_{1-6})$alkyl, $(C_{2-6})$alkenyl, $(C_{1-6})$ alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$ alkyl, $(C_{2-6})$alkenyl, $(C_{1-6})$alkoxycarbonyl, $(C_{1-6})$ alkylcarbonyl, $(C_{2-6})$alkenyloxycarbonyl or $(C_{2-6})$ alkenylcarbonyl and optionally further substituted by $(C_{1-6})$alkyl, hydroxy$(C_{1-6})$alkyl, aminocarbonyl$(C_{1-6})$ alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$acyl or $(C_{2-6})$alkenyl; or hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$ alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; or amino optionally mono- or disubstituted by $(C_{1-6})$ alkoxycarbonyl; $(C_{1-6})$alkylcarbonyl; $(C_{2-6})$ alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$ alkenylsulphonyl or aminocarbonyl wherein the amino group is optionally substituted by $(C_{1-6})$alkyl or $(C_{2-6})$ alkenyl;

provided that when $R^3$ is in the 4-position it is not optionally substituted hydroxyl or amino;

in addition when $R^3$ is disubstituted with a hydroxy or amino containing substituent and a carboxy containing substituent these may optionally together form a cyclic ester or amide linkage, respectively;

$R^{10}$ is selected from $(C_{1-4})$alkyl and $(C_{2-4})$alkenyl either of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

$R^4$ is a group $-CH_2-R^5{}_1$, in which $R^5{}_1$ is selected from:
$(C_{4-8})$alkyl; hydroxy$(C_{4-8})$alkyl; $(C_{1-4})$alkoxy$(C_{4-8})$alkyl; $(C_{1-4})$alkanoyloxy$(C_{4-8})$alkyl; $(C_{3-8})$cycloalkyl$(C_{4-8})$alkyl; hydroxy-, $(C_{1-6})$alkoxy- or $(C_{1-6})$alkanoyloxy-$(C_{3-8})$cycloalkyl$(C_{4-8})$alkyl; cyano$(C_{4-8})$alkyl; $(C_{4-8})$alkenyl; (C; 8)alkynyl; tetrahydrofuryl; mono- or di-$(C_{1-6})$alkylamino$(C_{4-8})$alkyl; acylamino$(C_{4-8})$alkyl; $(C_{1-6})$alkyl- or acyl-aminocarbonyl$(C_{4-8})$alkyl; mono- or di-$(C_{1-6})$alkylamino(hydroxy) $(C_{4-8})$alkyl; or $R^4$ is a group $-U-R^5{}_2$ where $R^5{}_2$ is an optionally substituted bicyclic carbocyclic or heterocyclic ring system (A):

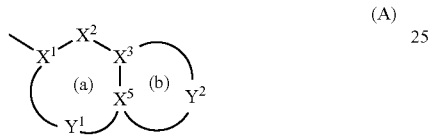

(A)

containing up to four heteroatoms in each ring in which
at least one of rings (a) and (b) is aromatic;

$X^1$ is C or N when part of an aromatic ring or $CR^{14}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 to 6 atom linker group, each atom of $Y^2$ being independently selected from N, $NR^{13}$, O, $S(O)_x$, CO and $CR^{14}$ when part of an aromatic or non-aromatic-ring or may additionally be $CR^{14}R^{15}$ when part of a non aromatic ring; each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl; aryl$(C_{1-4})$alkyl; aryl$(C_{1-4})$alkoxy;

each $R^{13}$ is independently H; trifluoromethyl; $(C_{1-4})$alkyl optionally substituted by hydroxy, carboxy, $(C_{1-6})$alkoxycarbonyl, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2;

U is CO, $SO_2$ or $CH_2$; or $R^4$ is a group $-X^{1a}-X^{2a}-X^{3a}-X^{4a}$ in which:

$X^{1a}$ is $CH_2$, CO or $SO_2$;

$X^{2a}$ is $CR^{14a}R^{15a}$;

$X^{3a}$ is $NR^{13a}$, O, S, $SO_2$ or $CR^{14a}R^{15a}$; wherein:
each of $R^{14a}$ and $R^{15a}$ is independently selected from the groups listed above for $R^{14}$ and $R^{15}$, provided that $R^{14a}$ and $R^{15a}$ on the same carbon atom are not both selected from optionally substituted hydroxy and optionally substituted amino; or $R^{14a}$ and $R^{15a}$ together represent oxo;

$R^{13a}$ is hydrogen; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl; or two $R^{14a}$ groups or an $R^{13a}$ and an $R^{14a}$ group on adjacent atoms together represent a bond and the remaining $R^{13a}$, $R^{14a}$ and $R^{15a}$ groups are as above defined; or two $R^{14a}$ groups and two $R^{15a}$ groups on adjacent atoms together represent bonds such that $X^{2a}$ and $X^{3a}$ is triple bonded;

$X^{4a}$ is phenyl or C or N linked monocyclic aromatic 5- or 6-membered heterocycle containing up to four heteroatoms selected from O, S and N and: optionally C-substituted by up to three groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl, aryl$(C_{1-4})$alkyl or aryl$(C_{1-4})$alkoxy; and optionally N substituted by trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl$(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

n is 0 or 1 and AB is $NR^{11}$ CO, $CONR^{11}$, $CO-CR^8R^9$, $CR^6R^7-CO$, $O-CR^8R^9$, $CR^6R^7-O$, $NHR^{11}-CR^8R^9$, $CR^6R^7-NHR^{11}$, $NR^{11}SO_2$, $CR^6R^7-SO_2$ or $CR^6R^7-CR^8R^9$, provided that when $R^v$ and $R^w$ are a bond and n=0, B is not $NR^{11}$, O or $SO_2$, or n is 0 and AB is NH—CO—NH or NH—CO—O and $R^v/R^w$ are not a bond;

or n is 0 and AB is $CR^6R^7SO_2NR^2$, $CR^6R^7CONR^2$ or $CR^6R^7CH_2NR^2$ and $R^v/R^w$ are not a bond;

provided that $R^6$ and $R^7$, and $R^8$ and $R^9$ are not both optionally substituted hydroxy or amino; and wherein:

each of $R^6$, $R^7$, $R^8$ and $R^9$ is independently selected from: H; $(C_{1-6})$alkoxy, $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

and each $R^{11}$ is independently H; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage or where —$R^3$ contains a carboxy group and A or B is NH they may be condensed to form a cyclic amide.

The invention also provides the use of a compound of formula (I) or a pharmaceutically acceptable derivative thereof in the manufacture of a medicament for use in the treatment of bacterial infections in mammals.

The invention also provides a pharmaceutical composition, in particular for use in the treatment of bacterial infections in mammals, comprising a compound of formula (I), or a pharmaceutically acceptable derivative thereof, and a pharmaceutically acceptable carrier.

The invention further provides a method of treatment of bacterial infections in mammals, particularly in man, which method comprises the administration to a mammal in need of such treatment of an effective amount of a a compound of formula (I), or a pharmaceutically acceptable derivative thereof.

In one aspect $R^1$ and $R^{1a}$ do not together represent $(C_{1-2})$alkylenedioxy, and R13 does not represent carboxy or $(C_{1-6})$alkoxycarbonyl.

Preferably $Z^5$ is CH or N, $Z^3$ is CH or CF and $Z^1$, $Z^2$ and $Z^4$ are each CH, or $Z^1$ is N, $Z^3$ is CH or CF and $Z^2$, $Z^4$ and $Z^5$ are each CH.

When $R^1$ or $R^{1a}$ is substituted alkoxy it is preferably $(C_{2-6})$alkoxy substitituted by optionally N-substituted amino, guanidino or amidino, or $(C_{1-6})$alkoxy substituted by piperidyl. Suitable examples of $R^1$ alkoxy include methoxy, trifluoromethoxy, n-propyloxy, i-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy. Preferably $R^1$ is methoxy, amino$(C_{3-5})$alkyloxy, guanidino$(C_{3-5})$alkyloxy, piperidyl$(C_{3-5})$alkyloxy, nitro or fluoro.

Preferably $R^1$ and $R^{1a}$ are independently methoxy, amino $(C_{3-5})$alkyloxy, guanidino$(C_{3-5})$alkyloxy, piperidyl$(C_{3-5})$ alkyloxy, nitro or fluoro; more preferably methoxy, fluoro, amino$(C_{3-5})$allyloxy or guanidino$(C_{3-5})$alkyloxy. Preferably $R^{1a}$ is H or F. Most preferably $R^1$ is methoxy or fluoro and $R^{1a}$ is H or when $Z^3$ is $CR^{1a}$ it may be C—F.

When $Z^5$ is $CR^{1a}$, $R^{1a}$ is preferably hydrogen, cyano, hydroxymethyl or carboxy, most preferably hydrogen.

$R^2$ is preferably hydrogen; $(C_{1-4})$alkyl substituted with carboxy, optionally substituted hydroxy, optionally substituted aminocarbonyl, optionally substituted amino or $(C_{1-4})$ alkoxycarbonyl; or $(C_{2-4})$alkenyl substituted with $(C_{1-4})$ alkoxycarbonyl or carboxy. More preferred groups for $R^2$ are hydrogen, carboxymethyl, hydroxyethyl, aminocarbonylmethyl, ethoxycarbonylmethyl, ethoxycarbonylallyl and carboxyallyl, most preferably hydrogen.

Preferred examples of $R^3$ include hydrogen; hydroxy; $(C_{1-4})$ alkyl; ethenyl; optionally substituted 1-hydroxy- $(C_{1-4})$ alkyl; optionally substituted aminocarbonyl; carboxy $(C_{1-4})$alkyl; optionally substituted aminocarbonyl$(C_{1-4})$ allyl; cyano$(C_{1-4})$alkyl; optionally substituted 2-oxo-oxazolidinyl and optionally substituted 2-oxo-oxazolidinyl $(C_{1-4}$alkyl). More preferred $R^3$ groups are hydrogen; hydroxy; $CONH_2$; 1-hydroxyalkyl e.g. $CH_2OH$, $CH(OH)$ $CH_2CN$; $CH_2CO_2H$; $CH_2CONH_2$; —$CONHCH_2CONH_2$; 1,2-dihydroxyalkyl e.g. $CH(OH)CH_2OH$; $CH_2CN$; 2-oxo-oxazolidin-5-yl; 2-oxo-oxazolidin-5-yl$(C_{1-4}$ alkyl); optionally substituted hydroxy. Most preferably $R^3$ is hydrogen or hydroxy, and if hydroxy, most preferably substituted in the 1-or 3-position. $R^3$ in the 3-position preferably has R stereochemistry.

When $R^3$ and $R^6$, $R^7$, $R^8$ or $R^9$ together form a cyclic ester or amide linkage, it is preferred that the resulting ring is 5–7 membered. It is further preferred that the group A or B which does not form the ester or amide linkage is $CH_2$.

When A is CH(OH) the R-stereochemistry is preferred.

Preferably A is NH, $NCH_3$, $CH_2$, CHOH, $CH(NH_2)$, C(Me)(OH) or CH(Me).

Preferably B is $CH_2$ or CO.

Preferably n=0.

Preferably, when $R^v$ and $R^w$ are not a bond and n=1 or $AB(CH_2)_n$ is NHCONH or NHCOO, $AB(CH_2)_n$ and $NR^2R^4$ are cis.

Preferably, when $R^v$ and $R^w$ are not a bond and n=0 and AB is not NHCONH or NHCOO, $AB(CH_2)_n$ and $NR^2R^4$ are trans.

Most preferably:
n is 0 and either A is CHOH, $CH_2$ and B is $CH_2$ or A is NH and B is CO.

Preferably $R^{11}$ is hydrogen or $(C_{1-4})$alkyl e.g. methyl, more preferably hydrogen.

When $R^4$ is $CH_2R^5_1$, preferably $R^5_1$ is $(C_{6-8})$alkyl.

When $R^4$ is a group —$X^{1a}$—$X^{2a}$—$X^{3a}$—$X^{4a}$:

$X^{1a}$ is preferably $CH_2$.

$X^{2a}$ is preferably $CH_2$ or together with $X^{3a}$ forms a CH=CH or C≡C group.

$X^{3a}$ is preferably $CH_2$, O, S or NH, or together with $X^{2a}$ forms a CH=CH or C≡C group.

Preferred linker groups —$X^{1a}$—$X^{2a}$—$X^{3a}$ include —$(CH_2)_2$—O—, —$CH_2$—CH=CH—, —$(CH_2)_3$—, —$(CH_2)_2$—NH— or —$CH_2CONH$—.

Monocyclic aromatic heterocyclic groups for $X^{4a}$ include pyridyl, pyrazinyl, pyrimidinyl, triazolyl, tetrazolyl, thienyl, isoimidazolyl, thiazolyl, furanyl and imidazolyl, 2H-pyridazone, 1H-pyrid-2-one. Preferred aromatic heterocyclic groups include pyrid-2-yl, pyrid-3-yl, thiazole-2-yl, pyrimidin-2-yl, pyrimidin-5-yl and fur-2-yl.

Preferred substituents on heterocyclic $X^{4a}$ include halo especially fluoro, trifluoromethyl and nitro.

Preferred substituents on phenyl $X^{4a}$ include halo, especially fluoro, nitro, cyano, trifluoromethyl, methyl, methoxycarbonyl and methylcarbonylamino.

Preferably $X^{4a}$ is 2-pyridyl, 3-fluorophenyl, 3,5-difluorophenyl or thiazol-2-yl.

Preferably $R^4$ is —U—$R^5_2$.

The group —U— is preferably —$CH_2$—.

Preferably $R^5_2$ is an aromatic heterocyclic ring (A) having 8–11 ring atoms including 2–4 heteroatoms of which at least one is N or $NR^{13}$ in which preferably $Y^2$ contains 2–3 heteroatoms, one of which is S and 1–2 are N, with one N bonded to $X^3$.

Alternatively and preferably the heterocyclic ring (A) has ring (a) aromatic selected from optionally substituted benzo and pyrido and ring (b) non-aromatic and $Y^2$ has 3–5 atoms including a heteroatom bonded to $X^5$ selected from O, S or $NR^{13}$, where $R^{13}$ is other than hydrogen, and NHCO bonded via N to $X^3$, or O bonded to $X^3$. Examples of rings (A) include optionally substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2-yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrinmidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl (a) is non aromatic (2S)-2,3-dihydro-1H-indol-2-yl, (2S)-2,3-dihydro-benzo[1,4]dioxine-2-yl, 3-(R, S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, (b) is non aromatic 1,1,3-trioxo-1,2,3,4-tetrahydro-1 $1^6$-benzo[1,4] thiazin-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzooxazol-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, benzo[1,3]dioxol-5-yl, 2-oxo-2,3-dihydro-1H-pyrido[2,3-b][1,4]thiazin-7-yl, 2-oxo-2,3-dihydro-1H-pyrido[3,4-b][1,4]thiazin-7-yl, 3-oxo-3,4-dihydro-2H-pyrido[3,2-b][1,4]thiazin-6-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 6,7-dihydro-[1,4]dioxino[2,3-d]pyrimidin-2-yl, 3-oxo-3,4-dihydro-2H-pyrido[3,2-b][1,4]oxazin-6-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7-dihydro-5H-8-thia-1,2,5-triaza-naphthalen-3-yl, 3,4-dihydro-2H-benzo[1,4]oxazin-6-yl, 3,4-dihydro-2H-benzo[1,4]oxazin-6-yl, 3-substituted-3H-benzooxazol-2-one-6-yl, 3-substituted-3H-benzooxazole-2-thione-6-yl, 3-substituted-3H-benzothiazol-2-one-6-yl, 2,3-dihydro-1H-pyrido[2,3-b][1,4]thiazin-7-yl, 3,4-dihydro-2H-benzo[1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl.

$R^{13}$ is preferably H if in ring (a) or in addition $(C_{1-4})$alkyl such as methyl or isopropyl when in ring (b). More preferably, in ring (b) $R^{13}$ is H when $NR^{13}$ is bonded to $X^3$ and $(C_{1-4})$alkyl when $NR^{13}$ is bonded to $X^5$.

$R^{14}$ and $R^{15}$ are preferably independently selected from hydrogen, halo, hydroxy, $(C_{1-4})$ alkyl, $(C_{1-4})$alkoxy, trifluoromethoxy, nitro, cyano, aryl$(C_{1-4})$alkoxy and $(C_{1-4})$alkylsulphonyl.

More preferably $R^{15}$ is hydrogen.

More preferably each $R^{14}$ is selected from hydrogen, chloro, fluoro, hydroxy, methyl, methoxy, trifluoromethoxy, benzyloxy, nitro, cyano and methylsulphonyl. Most preferably $R^{14}$ is selected from hydrogen, hydroxy, fluorine or nitro. Preferably 0–3 groups $R^{14}$ are substituents other than hydrogen.

Most preferably $R^{14}$ and $R^{15}$ are each H.

Most preferred groups $R^5_2$ include:

[1,2,3]thiadiazolo[5,4-b]pyridin-6-yl
1H-Pyrrolo[2,3-b]pyridin-2-yl
2,3-Dihydro-[1,4]dioxino[2,3-b]pyridin-6-yl
2,3-Dihydro-[1,4]dioxino[2,3-b]pyridin-7-yl
2,3-Dihydro-[1,4]dioxino[2,3-c]pyridin-7-yl
2,3-dihydro-benzo[1,4]-dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-Methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4]thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4] oxazin-6-yl
8-Hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
especially
benzo[1,2,5]thiadiazol-5-yl
3-oxo-3,4-dihydro-2H-benzo[1,4]thiazin-6-yl (4H-benzo[1,4]thiazin-3-one-6-yl)
2,3-dihydro-benzo[1,4]dioxin-6-yl benzo[1,2,3]thiadiazol-5-yl
3-oxo-3,4-dihydro-2H-benzo[1,4]oxazin-6-yl
7-fluoro-3-oxo-3,4-dihydro-2H-benzo[1,4]oxazin-6-yl
2-oxo-2,3-dihydro-1H-pyrido[2,3-b][1,4]thiazin-7-yl
2,3-Dihydro-[1,4]dioxino[2,3-c]pyridin-7-yl 3-oxo-3,4-dihydro-2H-pyrido[3,2-b][1,4]oxazin-6-yl
[1,2,3]thiadiazolo[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
most especially
3-oxo-3,4-dihydro-2H-pyrido[3,2-b][1,4]oxazin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo. Haloalkyl moieties include 1–3 halogen atoms.

Unless otherwise defined, the term 'heterocyclic' as used herein includes aromatic and non-aromatic, single and fused, rings suitably containing up to four hetero-atoms in each ring selected from oxygen, nitrogen and sulphur, which rings may be unsubstituted or C-substituted by, for example, up to three groups selected from $(C_{1-4})$alkylthio; halo; carboxy $(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl$(C_{1-4})$alkyl or aryl $(C_{1-4})$alkoxy and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl.

When used herein the term 'aryl', includes phenyl and naphthyl, each optionally substituted with up to five, preferably up to three, groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy, hydroxy$(C_{1-4})$alkyl; mercapto$(C_{1-4})$alkyl; $(C_{1-4})$alkoxy; nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$allyl or $(C_{2-4})$alkenyl; phenyl, phenyl$(C_{1-4})$alkyl or phenyl$(C_{1-4})$alkoxy.

The term 'acyl' includes $(C_{1-6})$alkoxycarbonyl, formyl or $(C_{1-6})$ alkylcarbonyl groups.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85% pure, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

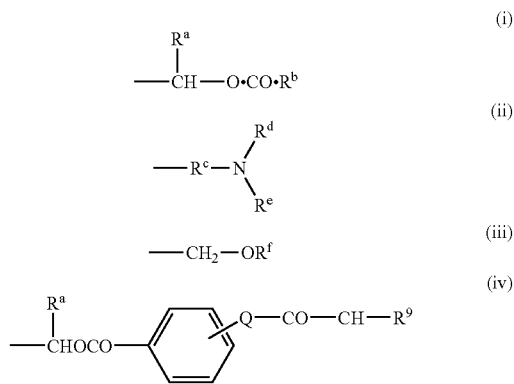

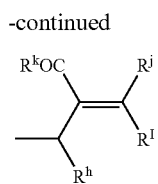
(v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ allyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ allyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$ alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino$(C_{1-4})$alkyl groups such as dimethylaminomethyl, dimethylaminoethyl, diethylaminomethyl or diethylaminoethyl; 2-($(C_{1-6})$alkoxycarbonyl)-2-$(C_{2-6})$alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

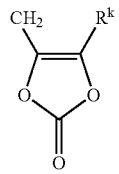

wherein $R^k$ is hydrogen, $C_{1-6}$ alkyl or phenyl.

R is preferably hydrogen.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms. For examples the invention includes compound in which an A-B group CH(OH)—CH$_2$ is in either isomeric configuration the R-isomer is preferred. The different isomeric forms maybe separated or resolved one from the other by conventional methods, or any given isomer may be obtained by conventional synthetic methods or by stereospecific or asymmetric syntheses.

In a further aspect of the invention there is provided a process for preparing compounds of formula (I), or a pharmaceutically acceptable derivative thereof, which process comprises reacting a compound of formula (IV) with a compound of formula (V):

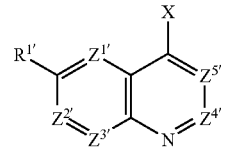
(IV)

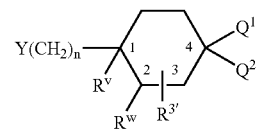
(V)

wherein n is as defined in formula (I), $Z^{1'}$, $Z^{2'}$, $Z^{3'}$, $Z^{4'}$, $Z^{5'}$, $R^{1'}$ and $R^{3'}$ are $Z^1$, $Z^2$, $Z^3$, $Z^4$, $Z^5$, $R^1$ and $R^3$ as defined in formula (I) or groups convertible thereto; $R^v$ and $R^w$ are as defined in formula (I);

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

and X and Y may be the following combinations:
(i) one of X and Y is $CO_2R^y$ and the other is $CH_2CO_2R^x$;
(ii) X is $CHR^6R^7$ and Y is $C(=O)R^9$;
(iii) X is $CR^7=PR^z_3$ and Y is $C(=O)R^9$;
(iv) X is $C(=O)R^7$ and Y is $CR^9=PR_{z3}$;
(v) one of Y and X is COW and the other is $NHR^{11'}$, NCO or $NR11'COW$;
(vi) X is $NHR^{11'}$ and Y is $C(=O)R^8$ or X is $C(=O)R^6$ and Y is $NHR^{11'}$;
(vii) X is $NHR^{11'}$ and Y is $CR^8R^9W$;
(viii) X is W or OH and Y is $CH_2OH$;
(ix) X is $NHR^{11'}$ and Y is $SO_2W$;
(x) one of X and Y is $(CH_2)_p$–W and the other is $(CH_2)_q$ $NHR^{11'}$, $(CH_2)_q OH$, $(CH_2)_q SH$ or $(CH_2)_q SCOR^x$ where p+q=1;
(xi) one of X and Y is OH and the other is —CH=N$_2$;
(xii) X is NCO and Y is OH or NH$_2$;
(xiii) X is $CR^6R^7SO_2W$, A'COW, $CR^6=CH_2$ or oxirane and Y is $NHR^{2'}$;
(xiv) X is W and Y is $CONHR^{11}$ or $OCONH_2$
(xv) X is W and Y is —C≡CH followed by hydrogenation of the intermediate —C≡C-group;

in which W is a leaving group, e.g. halo, methanesulphonyloxy, trifluoromethanesulphonyloxy or imidazolyl; $R^x$ and $R^y$ are $(C_{1-6})$alkyl; $R^z$ is aryl or $(C_{1-6})$alkyl; A' and $NR^{11'}$ are A and $NR^{11}$ as defined in formula (I), or groups convertible thereto; and oxirane is:

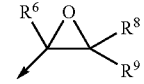

wherein $R^6$, $R^8$ and $R^9$ are as defined in formula (I);
and thereafter optionally or as necessary converting $Q^1$ and $Q^2$ to $NR^{2'}R^{4'}$; converting A', $Z^{1'}$, $Z^{2'}$, $Z^{3'}$, $Z^{4'}$, $Z^{5'}$, $R^{1'}$, $R^{2'}$, $R^{3'}$, $R^{4'}$ and $NR^{11'}$ to A, $Z^1$, $Z^2$, $Z^3$, $Z^4$, $Z^5$, $R^1$, $R^2$, $R^3$, $R^4$ and $NR^{11}$; converting A-B to other A-B, interconverting $R^v$, $R^w$, $R^1$, $R^2$, $R^3$ and/or $R^4$, and/or forming a pharmaceutically acceptable derivative thereof.

Process variant (i) initially produces compounds of formula (I) wherein A-B is CO—CH$_2$ or CH$_2$—CO.

Process variant (ii) initially produces compounds of formula (I) wherein A-B is $CR^6R^7$—$CR^9OH$.

Process variant (iii) and (iv) initially produce compounds of formula (I) wherein A-B is $CR^7$=$CR^9$.

Process variant (v) initially produces compounds of formula (I) where A-B is CO—$NR^{11}$ or $NR^{11}$—CO.

Process variant (vi) initially produces compounds of formula (I) wherein A-B is $NR^{11}$—$CHR^8$ or $CHR^6$—$NHR^{11}$.

Process variant (vii) initially produces compounds of formula (I) wherein A-B is $NR^{11'}$—$CR^8R^9$.

Process variant (viii) initially produces compounds of formula (I) wherein A-B is O—$CH_2$.

Process variant (ix) initially produces compounds where AB is $NR^{11}SO_2$.

Process variant (x) initially produces compounds of formula (I) wherein one of A and B is $CH_2$ and the other is $NHR^{11}$, O or S.

Process variant (xi) initially-produces compounds of formula(I) wherein A-B is $OCH_2$ or $CH_2O$.

Process variant (xii) initially produces compounds where AB is NH—CO—NH or NH—CO—O.

Process variant (xiii) initially produces compounds where n is 0 and AB is $CR^6R^7SO_2NR^2$, A'—$CONR^2$ or $CR^6R^7CH_2NR^2$.

Process variant (xiv) produces compounds where AB is $NR^{11}CO$ or NH—CO—O.

Process variant (xv) produces compounds where AB is —$CH_2CH_2$— or —CH=CH—.

In process variants (v) and (xiii) (second variant) the reaction is a standard amide or urea formation reaction involving e.g.:
1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups* (Ed. Patai, S.) *Suppl. B: The Chemistry of Acid Derivatives, Pt. 1* (John Wiley and Sons, 1979), pp 442–8; Beckwith, A. L. J. in *The Chemistry of Functional Groups* (Ed. Patai, S.) *Suppl. B: The Chemistry of Amides* (Ed. Zabricky, J) (John Wiley and Sons, 1970), p 73 ff. The acid and amine are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU); or
2. The specific methods of:
a. in situ conversion of an acid into the amine component by a modified Curtius reaction procedure (Shioiri, T., Murata, M., Hamada, Y., *Chem. Pharm. Bull.* 1987, 35, 2698)
b. in situ conversion of the acid component into the acid chloride under neutral conditions (Villeneuve, G. B.; Chan, T. H., *Tetrahedron. Lett.* 1997, 38, 6489).

A' may be, for example, protected hydroxymethylene.

The process variant (xiii) (third variant) is a standard addition reaction using methods well known to those skilled in the art. The process is preferably carried out in a polar organic solvent e.g. acetonitrile in the presence of an organic base e.g. triethylamine.

In process variant (xiii) (fourth variant) the coupling may be effected in acetonitrile at room temperature in the presence of one equivalent of lithium perchlorate as catalyst (general method of J. E. Chateauneuf et al, *J. Org. Chem.*, 56, 5939–5942, 1991) or more preferably with ytterbium triflate in dichloromethane. In some cases an elevated temperature such as 40–70° C. may be beneficial. Alternatively, the compound of formula (V) may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (xii) is a standard urea or carbamate formation reaction from the reaction of an isocyanate with an amine or alcohol and is conducted by methods well known to those skilled in the art (for example see March, J; *Advanced Organic Chemistry, Edition* 3 (John Wiley and Sons, 1985), p802–3). The process is preferably carried out in a polar solvent such as N,N-dimethylformamide.

In process variant (i) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0–100° C. Analogous routes are described in DE330945, EP31753, EP53964 and H. Sargent, J. Am. Chem. Soc. 68, 2688–2692 (1946). Similar Claisen methodology is described in Soszko et. al., Pr.Kom.Mat. Przyr.Poznan.Tow.Przyj.Nauk., (1962), 10, 15.

In process variant (ii) the reaction is carried out in the presence of a base, preferably organometallic or metal hydride e.g. NaH, lithium diisopropylamide or NaOEt, preferably in an aprotic solvent, preferably THF, ether or benzene at –78 to 25° C. (analogous process in Gutswiller et at. (1978) J. Am. Chem. Soc. 100, 576).

In process variants (iii) and (iv) if a base is used it is preferably NaH, KH, an alkyl lithium e.g. BuLi, a metal alkoxide e.g. NaOEt, sodamide or lithium dialkylamide e.g. diisopropylamide. An analogous method is described in U.S. Pat. No. 3,989,691 and M. Gates et. al. (1970) J. Amer.Chem.Soc., 92, 205, as well as Taylor et al. (1972) JACS 94, 6218.

In process variant (vi) the reaction is a standard reductive alkylation using, e.g., sodium borohydride or sodium triacetoxyborohydride (Gribble, G. W. in *Encyclopedia of Reagents for Organic Synthesis* (Ed. Paquette, L. A.) (John Wiley and Sons, 1995), p 4649).

The process variant (vii) is a standard alkylation reaction well known to those skilled in the art, for example where an alcohol or amine is treated with an alkyl halide in the presence of a base (for example see March, J; *Advanced Organic Chemistry*, Edition 3 (John Wiley and Sons, 1985), p364–366 and p342–343). The process is preferably carried out in a polar solvent such as N,N-dimethylformamide In process variant (xiii) (first variant) the reaction is a standard sulphonamide formation reaction well known to those skilled in the art. This may be e.g. the reaction of a sulphonyl halide with an amine.

In process variant (viii) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et.al. J Chem Soc. (1995), 623). Alternatively the X=O and Y=$CH_2OH$ groups can be reacted directly by activation with 1,3-dicyclohexylcarbodiimide (DCC) (Chem. Berichte 1962, 95, 2997 or Angewante Chemie 1963 75, 377).

In process variant (ix) the reaction is conducted in the presence of an organic base such as triethylamine or pyridine such as described by Fuhrman et.al., J. Amer. Chem. Soc.; 67, 1245, 1945. The X=NR$^{11'}$SO$_2$W or Y=SO$_2$W intermediates can be formed from the requisite amine e.g. by reaction with SO$_2$Cl$_2$ analogously to the procedure described by the same authors Fuhrman et. al., J. Amer. Chem. Soc.; 67, 1245, 1945.

In process variant (x) where one of X and Y contains NHR$^{11}$ the leaving group W is halogen and the reaction is a standard amine formation reaction such as direct alkylation described in (Malpass, J. R., in *Comprehensive Organic Chemistry*, Vol. 2 (Ed. Sutherland, I. O.), p 4 ff.) or aromatic nucleophilic displacement reactions (see references cited in *Comprehensive Organic Chemistry*, Vol. 6, p 946–947 (reaction index); Smith, D. M. in *Comprehensive Organic Chemistry*, Vol. 4 (Ed. Sammes, P. G.) p 20 ff.). This is analogous to the methods described in GB 1177849.

In process variant (x) where one of X and Y contains OH or SH, this is preferably converted to an OM or SM group where M is an alkali metal by treatment of an alcohol, thiol or thioacetate with a base. The base is preferably inorganic such as NaH, lithium diisopropylamide or sodium, or, for SH, metal alkoxide such as sodium methoxide. The X/Y group containing the thioacetate SCOR$^x$ is prepared by treatment of an alcohol or alkyl halide with thioacetic acid or a salt thereof under Mitsunobu conditions. The leaving group V is a halogen. The reaction may be carried out as described in Chapman et.al., J. Chem Soc., (1956), 1563, Gilligan et. al., J. Med. Chem., (1992), 35, 4344, Aloup et. al., J. Med. Chem. (1987), 30, 24, Gilman et al., J.A.C.S. (1949), 71, 3667 and Clinton et al., J.A.C.S. (1948), 70,491, Barluenga et al., J. Org. Chem. (1987) 52, 5190. Alternatively where X is OH and Y is CH$_2$V, V is a hydroxy group activated under Mitsunobu conditions Fletcher et.al. J Chem Soc. (1995), 623).

In process variant (xi) the reaction is as described in den Hertzog et. al., recl.Trav. Chim. Pays-Bas, (1950), 69, 700.

In process variant (xiv) the leaving group W is preferably chloro, bromo or trifluoromethylsulphonyl and the reaction is the palladium catalysed process known as the "Buchwald" reaction (J. Yin and S. L. Buchwald, Org.Lett., 2000, 2, 1101).

In process variant (xv) coupling of the acetylene compound (V) with the compound (IV) is accomplished using standard Pd-mediated chemistry, for example using Pd(Ph$_3$P)$_2$Cl$_2$ as the catalyst along with the addition of CuI in a mixture of triethylamine and dimethylformamide. Hydrogenation of the intermediate —C≡C— group is carried out conventionally over a suitable catalyst eg Pd/C, either partially to —CH=CH— or fully to —CH$_2$—CH$_2$—.

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, U.S. Pat. No. 384556 and J. Gutzwiller et al, *J. Amer. Chem. Soc.*, 1978, 100, 576.

The carbonyl group A or B may be reduced to CH$_2$ by treatment with a reducing agent such as hydrazine in ethylene glycol, at e.g. 130–160° C., in the presence of potassium hydroxide.

Reaction of a carbonyl group A or B with an organometallic reagent yields a group where R$^6$ or R$^8$ is OH and R$^7$ or R$^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group CHR$^7$CR$^9$OH or CR$^7$(OH)CHR$^9$ may be dehydrated to give the group CR$^7$=CR$^9$ by treatment with an acid anhydride such as acetic anhydride.

Methods for conversion of CR$^7$=CR$^9$ by reduction to CHR$^7$CHR$^9$ are well known to those skilled in the art, for example using hydrogenation over palladium on carbon as catalyst. Methods for conversion of CR$^7$=CR$^9$ to give the A-B group CR$^7$(OH)CHR$^9$ or CHR$^7$CR$^9$OH are well known to those skilled in the art for example by epoxidation and subsequent reduction by metal hydrides, hydration, hydroboration or oxymercuration. Where R$^v$ and R$^w$ together represent a bond it will be appreciated that such conversions may be inappropriate.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group Q$^1$ convertible to NR$^2$ R$^4$ is NR$^{2'}$R$^{4'}$ or halogen. Halogen may be displaced by an amine HNR$^{2'}$R$^{4'}$ by a conventional alkylation.

When Q$^1$ Q$^2$ together form a protected oxo group this may be an acetal such as ethylenedioxy which can subsequently be removed by acid treatment to give a compound of formula (VI):

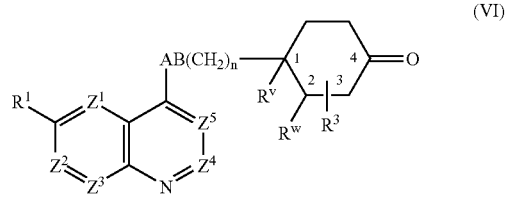

(VI)

wherein the variables are as described for formula (I)

Intermediates of formula (VI) are novel and as such form part of the invention.

The ketone of formula (VI) is reacted with an amine HNR$^{2'}$R$^{4'}$ by conventional reductive alkylation as described above for process variant (x).

Other novel intermediates of the invention are compounds of formula (VII):

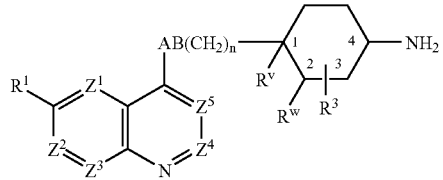

wherein the variables are as described for formula (I).

Examples of groups Z$^{1'}$, Z$^{2'}$, Z$^{3'}$, Z$^{4'}$, Z$^{5'}$, are CR$^{1a'}$ where R$^{1a'}$ is a group convertible to R$^{1a}$. Z$^{1'}$, Z$^{2'}$, Z$^{3'}$, Z$^{4'}$ and Z$^{5'}$ are preferably Z$^1$, Z$^2$, Z$^3$, Z$^4$ and Z$^5$.

R$^{1a'}$, R$^{1'}$ and R$^{2'}$ are preferably R$^{1a}$, R$^1$ and R$^2$. R$^{1'}$ is preferably methoxy. R$^{2'}$ is preferably hydrogen. R$^{3'}$ is R$^3$ or more preferably hydrogen, vinyl, alkoxycarbonyl or carboxy. R$^{4'}$ is R$^4$ or more preferably H or an N-protecting group such as t-butoxycarbonyl, benzyloxycarbonyl or 9-fluorenylmethyloxycarbonyl.

Conversions of R$^{1a'}$, R$^{1'}$, R$^{2'}$, R$^{3'}$ and R$^{4'}$ and interconversions of R$^{1a}$, R$^1$, R$^2$, R$^3$ and R$^4$ are conventional. In compounds which contain an optionally substituted hydroxy group, suitable conventional hydroxy protecting groups which may be removed without disrupting the remainder of the molecule include acyl and alkylsilyl groups. N protecting groups are removed by conventional methods.

For example $R^{1'}$ methoxy is convertible to $R^{1'}$ hydroxy by treatment with lithium and diphenylphosphine (general method described in Ireland et. al. (1973) J.Amer.Chem.Soc., 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1]nonane, epoxidation and reduction or oxymercuration.

$R^3$ 1,2-dihydroxy can be prepared from $R^{3'}$ alkenyl using osmium tetroxide or other reagents well known to those skilled in the art (see Advanced Organic Chemistry (Ed. March, J) (John Wiley and Sons, 1985), p 732–737 and refs. cited therein) or epoxidation followed by hydrolysis (see Advanced Organic Chemistry (Ed. March, J.) (John Wiley and Sons, 1985), p 332, 333 and refs. cited therein).

$R^3$ vinyl can be chain extended by standard homologation e.g by conversion to hydroxyethyl followed by oxidation to the aldehyde which is then subjected to a Wittig reaction.

Opening an epoxide $R^{3'}$ group with cyanide anion yields a $CH(OH)$—$CH_2CN$ group.

Opening an epoxide-containing $R^{3'}$ group with azide anion yields an azide derivative which can be reduced to the amine. Conversion of the amine to a carbamate is followed by ring closure with base to give the 2-oxo-oxazolidinyl containing $R^3$ group.

Substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group, hydrolysis or oxidation as appropriate or reaction with an activated acid, isocyanate or alkoxyisocyanate. Primary and secondary hydroxy groups can be oxidised to an aldehyde or ketone respectively and alkyated with a suitable agent such as an organometallic reagent to give a secondary or tertiary alcohol as appropriate. A carboxylate group may be converted to an hydroxymethyl group by reduction of an ester of this acid with a suitable reducing agent such as lithium aluminium hydride.

Substituted 2-oxo-oxazolidinyl containing $R^3$ groups may be prepared from the corresponding aldehyde by conventional reaction with a glycine anion equivalent, followed by cyclisation of the resulting amino alcohol (M Grauert et al, Ann Chem (1985) 1817, Rozenberg et al, Angew Chem Int Ed Engl (1994) 33(1) 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromic acid and sulphuric acid in water/methanol E. R. H. Jones et al, J.C.S. 1946, 39). Other oxidising agents may be used for this transformation such as sodium periodate catalysed by ruthenium trichloride (G. F. Tutwiler et al, J.Med.Chem., 1987, 30(6), 1094), chromium trioxide-pyridine (G. Just et al, Synth. Commun. 1979, 9(7), 613), potassium permanganate (D. E. Reedich et al, J. Org. Chem., 1985, 50(19), 3535, and pyridinium chlorochromate (D. Askin et al, Tetrahedron Letters, 1988, 29(3), 277.

The carboxy group may alternatively be formed in a two stage process, with an initial oxidation of the alcohol to the corresponding aldehyde using for instance dimethyl sulphoxide activated with oxalyl chloride (N.Cohen et al, J. Am. Chem. Soc., 1983, 105, 3661) or dicyclohexylcarbodiimide R. M. Wengler, Angew. Chim. Int. Ed. Eng., 1985, 24(2), 77), or oxidation with tetrapropylammonium perruthenate (Ley et al, J. Chem.Soc. Chem Commun., 1987, 1625). The aldehyde may then be separately oxidised to the corresponding acid using oxidising agents such as silver (II) oxide (R.Grigg et at, J. Chem. Soc. Perkin1, 1983, 1929), potassium permanganate (A. Zurcher, Helv. Chim. Acta., 1987, 70 (7), 1937), sodium periodate catalysed by ruthenium trichloride (T. Sakata et al, Bull. Chem. Soc. Jpn., 1988, 61(6), 2025), pyridinium chlorochromate (R. S. Reddy et al, Synth. Commun., 1988, 18(51), 545) or chromium trioxide (R. M. Coates et al, J. Am. Chem. Soc., 1982, 104, 2198).

An $R^3$ $CO_2H$ group may also be prepared from oxidative cleavage of the corresponding diol, $CH(OH)CH_2OH$, using sodium periodate catalysed by ruthenium trichloride with an acetonitrile-carbontetrachloride-water solvent system (V. S. Martin et al, Tetrahedron Letters, 1988, 29(22), 2701).

$R^3$ groups containing a cyano or carboxy group may also be prepared by conversion of an alcohol to a suitable leaving group such as the corresponding tosylate by reaction with para-toluenesulphonyl chloride (M. R. Bell, J. Med. Chem., 1970, 13, 389), or the iodide using triphenylphosphine, iodine, and imidazole (G. Lange, Synth. Commun., 1990, 20, 1473). The second stage is the displacement of the leaving group with cyanide anion (L. A. Paquette et al, J. Org. Chem., 1979, 44 (25), 4603; P. A. Grieco et al, J. Org. Chem., 1988, 53 (16), 3658). Finally acidic hydrolysis of the nitrile group gives the desired acids (H. Rosemeyer et al, Heterocycles, 1985, 23 (10), 2669). The hydrolysis may also be carried out with base e.g. potassium hydroxide (H. Rapoport, J. Org. Chem., 1958, 23, 248) or enzymatically (T. Beard et al, Tetrahedron Asymmetry, 1993, 4 (6), 1085).

Other functional groups in $R^3$ may be obtained by conventional conversions of carboxy or cyano groups.

Tetrazoles are conveniently prepared by reaction of sodium azide with the cyano group (e.g. F. Thomas et al, Bioorg. Med. Chem. Lett., 1996, 6 (6), 631; K. Kubo et al, J. Med. Chem., 1993, 36, 2182) or by reaction of azidotri-n-butyl stannane with the cyano group followed by acidic hydrolysis (P. L. Ornstein, J. Org. Chem., 1994,59,7682 and J. Med. Chem, 1996,39 (11), 2219).

The 3-hydroxy-3-cyclobutene-1,2-dion-4-yl group (e.g. R. M. Soll, Bioorg. Med. Chem. Lett., 1993, 3 (4), 757 and W. A. Kinney, J. Med. Chem., 1992, 35 (25), 4720) can be prepared by the following sequence:—(1) a compound where $R^3$ is $(CH_2)_n CHO$ (n=0, 1, 2) is treated with triethylamine, carbon tetrabromide/triphenylphosphine to give initially $(CH_2)_n CH$=$CBr_2$; (2) dehydrobromination of this intermediate to give the corresponding bromoethyne derivative $(CH_2)_n C$≡$CBr$ (for this 2 stage sequence see D. Grandjean et al, Tetrahedron Letters, 1994, 35 (21), 3529); (3) palladium-catalysed coupling of the bromoethyne with 4-(1-methylethoxy)-3-(tri-n-butylstannyl)cyclobut-3-ene-1,2-dione (Liebeskind et al, J. Org. Chem., 1990, 55, 5359); (4) reduction of the ethyne moity to —CH2CH2— under standard conditions of hydrogen and palladium on charcoal catalysis(see Howard et al, Tetrahedron, 1980, 36, 171); and finally (4) acidic hydrolysis of the methylethoxyester to generate the corresponding 3-hydroxy-3-cyclobutene-1,2-dione group (R. M. Soll, Bioorg. Med. Chem. Lett., 1993, 3 (4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, J. Med Chem, 1996, 39 (11), 2232).

The alkyl and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, J.Med.Chem., 1996, 39 (11), 2232).

The hydroxamic acid groups are prepared from the corresponding acids by standard amide coupling reactions eg N. R. Patel et al, Tetrahedron, 1987, 43 (22), 5375

2,4-thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitriles is described by Y. Kohara et al, Bioorg. Med. Chem. Lett., 1995, 5(17), 1903.

1,2,4-triazol-5-yl groups may be prepared from the corresponding nitrile by reaction with an alcohol under acid conditions followed by reaction with hydrazine and then an $R^{10}$-substituted activated carboxylic acid (see J B Polya in 'Comprehensive Heterocyclic Chemistry' Edition 1 p762, Ed A R Katritzky and C W Rees, Pergamon Press, Oxford 1984 and J. J. Ares et al, J. Heterocyclic Chem., 1991, 28(5), 1197).

The cyclohexylamine or cyclohexenylamine $NH_2$ is converted to $NR^2R^4$ by conventional means such as amide or sulphonamide formation with an acyl derivative for compounds where U or $X^{1a}$ is CO or $SO_2$ or, where $R^4$ is $CH_2R^5$, or U or $X^{1a}$ is $CH_2$, by alkylation with an alkyl halide or other alkyl derivative $R^4$-W in the presence of base, acylation/reduction or reductive alkylation with an aldehyde.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compounds of formulae (IV) and (V) or in the presence of standard peptide coupling agents.

It will be appreciated that under certain circumstances interconversions may interfere, for example, hydroxy groups in A or B and the cyclohexyl- or cyclohexenylamine will require protection e.g. as a carboxy- or silyl-ester group for hydroxy and as an acyl derivative for nitrogen, during conversion of $R^{1a'}$, $R^{1'}$, $R^{2'}$, $R^{3'}$ or $R^{4'}$, or during the coupling of the compounds of formulae (IV) and (V).

Compounds of formulae (I) and (V) are known compounds, (see for example Smith et al, J. Amer. Chem. Soc., 1946, 68, 1301) or prepared analogously, see for example the references cited above.

Compounds of formula (IV) where X is $CR^6R^7SO_2W$ may be prepared by a route analogous to that of Ahmed El Hadri et al, J. Heterocyclic Chem., 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-aminoquinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. Chem. Pharm. Bull. 35, 2698–2704 (1987)].

The 4-amino derivatives are commercially available or may be prepared by conventional procedures from a corresponding 4-chloro derivative by treatment with ammonia (O. G. Backeberg et. al., J. Chem Soc., 381, 1942) or propylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. Organic Reactions, 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$ A-4-bromo-substituent may be prepared from the quinolin- or naphthyridin-4-one by reaction with phosphorus tribromide (PBr3) in DMF. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in Heterocyclic Compounds, 6, 324 (1957) Ed. R. C. Elderfield.

Activated carboxy derivatives X=A'COW of formula (IV) may be prepared from X=A'$CO_2$H derivatives in turn prepared from $CO_2$H derivatives by conventional methods such as homologation.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in Heterocyclic Compounds, 6, 324 (1957) Ed. R. C. Elderfield. These 4-carboxy derivatives may be activated by conventional means, e.g. by conversion to an acyl halide or anhydride.

4-Carboxy derivatives such as esters may be reduced to hydroxymethyl derivatives with for example lithium aluminium hydride. Reaction with mesyl chloride and triethylamine would give the mesylate derivative. A diazo compound (X is —CH=$N_2$) may be prepared from the 4-carboxaldehyde via the tosyl hydrazone. The 4-carboxaldehyde may be obtained from form the acid by standard procedures well known to those skilled in the art.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in the art. For example, hydroxy compounds can be converted to the corresponding 4-trifluoromethanesulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the equivalent intermediates can be attained by Stille coupling of the trifluoromethanesulphonates or the analaogous chloro derivatives with (1-ethoxyvinyl)tributyl tin, (T. R. Kelly, J. Org. Chem., 1996, 61, 4623.) The alkyloxyvinyl ethers are then converted into the corresponding bromomethylketones by treatment with N-bromosuccinimide in aqueous tetrahydrofuran in a similar manner to the procedures of J. F. W. Keana, J. Org. Chem., 1983, 48, 3621 and T. R. Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxy pyridine can be converted to 4-hydroxy-6-methoxy-[1,5]naphthyridine using this method.

If a chiral reducing agent such as (+) or (−)-B-chlorodiisopinocamphenylborane ['DIP-chloride'] is substituted for sodium borohydride, the prochiral chloromethylketone is converted into the chiral chlorohydrin with ee values generally 85–95% [see C. Bohm et al, Chem. Ber. 125, 1169–1190, (1992)]. Recrystallisation of the chiral epoxide gives material in the mother liquor with enhanced optical purity (typically ee 95%).

The (R)-epoxide, when reacted with an amine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, J. Het. Chem., 1987, 24, 853–857], or by epoxidation of a 4-vinyl derivative.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A. McKillop.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5] naphthyridine-3-carboxylic acid, J. T. Adams et al., J. Amer. Chem.Soc., 1946, 68, 1317). A 4-hydroxy-[1,5] naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro, 4-methanesulphonyloxy or 4-trifluoromethanesulphonyloxy derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p581–627, Ed A. R. Katritzky and C. W. Rees, Pergamon Press, Oxford, 1984).

The 4-hydroxy and 4-amino-cinnolines may be prepared following methods well known to those skilled in the art [see A. R. Osborn and K. Schofield, J. Chem. Soc. 2100 (1955)]. For example, a 2-aminoacetophenone is diazotised with sodium nitrite and acid to produce the 4-hydroxycinnoline with conversion to chloro and amino derivatives as described for 1,5-naphthyridines.

The compounds of formula (V) are either commercially available or may be prepared by conventional methods.

For compounds of formula (V), where Y is $NHR^{11'}$ suitable amines may be prepared from the corresponding 4-substituted cyclohexyl- or cyclohexenyl acid or alcohol. In a first instance, an N-protected cyclohexyl- or cyclohexenyl amine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected cyclohexyl- or cyclohexenyl amine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, Tetrahedron Lett., 1984, 25, 3515). This undergoes cleavage on treatment with tetrabutylammonium fluoride to give the 4-amine substituted N-protected compound of formula (V). Alternatively, an acid group $(CH_2)_{n-1}CO_2H$ may be converted to $(CH_2)_nNHR^{11}$ by reaction with an activating agent such as isobutyl chloroformate followed by an amine $R^{11'}NH_2$ and the resulting amide reduced with a reducing agent such as $LiAlH_4$.

In a second instance, an N-protected cyclohexyl- or cyclohexenyl amine containing an alcohol bearing substituent undergoes a Mitsunobu reaction (for example as reviewed in Mitsunobu, Synthesis, (1981), 1), for example with succinimide in the presence of diethyl azodicarboxylate and triphenylphosphine to give the phthalimidoethylcyclohexyl- or cyclohexenyl amine. Removal of the phthaloyl group, for example by treatment with methylhydrazine, gives the amine of formula (V).

Compounds of formula (V) where n=1 may be prepared from the compound where n=0 by homologation eg starting from a compound of formula (V) where $Y=CO_2H$.

Compounds of formula (V) with a —C≡CH group may be prepared from the ketone treated with trimethylsilylacetylene and n-butyl lithium in dimethylformamide at low temperature followed by removal of the trimethylsilyl group with potassium carbonate in methanol or a fluoride source such as KF or tetrabutylammonium fluoride.

Compounds of formula (V) with a —$CONHR^{11}$ group may be prepared from the corresponding nitrile by partial hydrolysis with with concentrated mineral acid at ambient temperature, such as concentrated hydrochloric acid (M. Brown et al, J. Med. Chem., 1999, 42, (9), 1537) or with concentrated sulphuric acid (F. Macias et al Tetrahedron, 2000, 56, (21), 3409).

Compounds of formula (V) with a —$OCONH_2$ group may be prepared from the corresponding alcohol by reaction with phosgene followed by ammonia.

Compounds of formula (V) substituted by $R^3$ at the 1- or 4-position may be prepared from a 1-keto derivative via a cyanohydrin reaction with sodium cyanide/hydrochloric acid in an ether/water two phase system (J. Marco et al Tetrahedron, 1999, 55, (24), 7625), or using trimethylsilylcyanide and zinc iodide catalysis in dichloromethane (A. Abad et al, J. Chem. Soc., Perkin 1, 1996, 17, 2193), followed by hydrolysis by heating in concentrated hydrochloric acid to give the α-hydroxy acid (Compound(V), Y=CO₂H, n=0, R³'=OH and Q¹ is NR²'R⁴') or partial hydrolysis to the carboxamide —CONH₂ as described above. In examples where there is trimethylsilyl protection of the alcohol, this is removed under the acidic conditions of cyanide hydrolysis. It will be appreciated that the amine protecting group eg N-carboxylic acid tert-butyl ester is concomitantly removed during the acid hydrolysis step, necessitating a standard reprotection with di-tert-butyl dicarbonate, giving key intermediates (V) such as (4-carbamoyl-4-hydroxy-cyclohexyl)-carbamic acid tert-butyl ester. It is noteworthy that during the cyanohydrin formation there is little or no stereoselectivity with regard to relative stereochemistry, and the (4-carbamoyl-4-hydroxy-cyclohexyl)-carbamic acid tert-butyl ester produced in this process is a mixture of cis and trans stereoisomers. These isomers can be separated by careful chromatography.

The same 1-keto-derivative could undergo a Wittig reaction with Ph₃PCH=CO₂Me to give the α,β-unsaturated carboxylic ester MeO₂C—CH=C<Ring, which could be epoxidised (eg meta-chloroperbenzoic acid) to give the α,β-epoxy-ester. Alternatively this could be formed directly from the keto-derivative via a glycidic ester condensation with an α-halogeno-ester. Base hydrolysis would afford the α,β-epoxy-carboxylic acid, which on reduction (eg lithium triethylborohydride—see J. Miklefield et al J. Amer. Chem. Soc. 117, 1153–1154 (1995) or hydrogenation over platinum oxide (see Artainonow Zh.Obshch.Khim. 28 1355–1359 (1958)) would afford the β-hydroxy acid (Compound (V) Y=CO₂H, n=1, R³'=OH). Alternatively a Reformatsky reaction with the keto-derivative and an α-bromocarboxylic acid ester and zinc, followed by acid hydrolysis would afford the β-hydroxycarboxylic acid directly. The 1-keto-derivative could also undergo a Strecker type synthesis via a Bucherer-Bergs procedure (potassium cyanide/ammonium carbonate) [see T. Scott Yokum et al. Tetrahedron Letters, 38, 4013–4016 (1997)] to give the α-amino-carboxylic acid (Compound (V) Y=CO₂H, n=0, R³'=NH₂).

An alternative route to 1-substituted compounds (V) involves a Diels Alder reaction between butyl acrylate and acetoxy butadiene to give (1). Elimination of acetic acid and hetero Diels Alder reaction with an in-situ generated acyl nitroso compound gives the bicyclic hydroxylamine product (3). The ester is transformed to an amide in two steps, and catalytic hydrogenation is used to reduce the double bond, remove the nitrogen protection and cleave the NO bond. After reprotection of the amino group, the cyclohexane amide with the required stereochemistry is obtained.

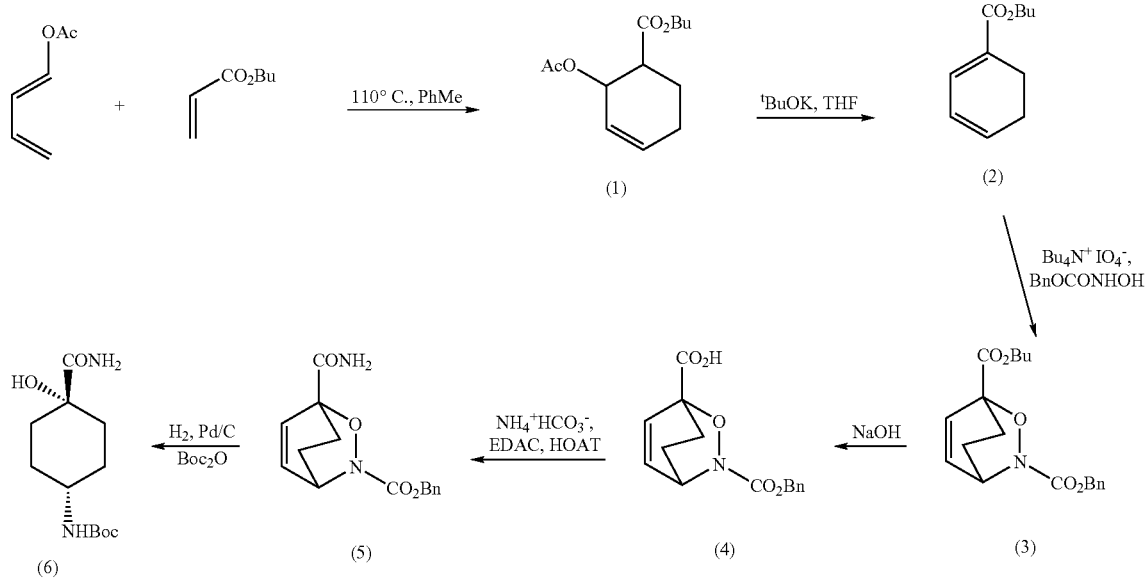

Two steps can be avoided by starting with acrylamide:

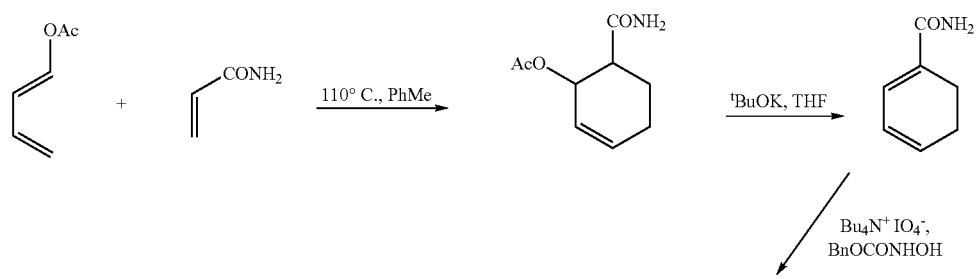

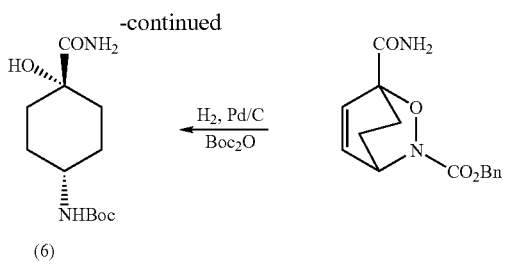

(6)

Compounds of formula (V) substituted by $R^3$ at the 2- or 3-position may be prepared from the corresponding substituted phenyl derivative 1-Y(CH$_2$)$_n$Ph(—R3)-4-NR$_2$ (eg where Y=carboxylic acid) by hydrogenation at elevated temperature and pressure using a Pt or Ru catalyst.

Compounds of formula (V) with a 3-hydroxyl group may be prepared from a 3,4 oxirane-cyclohexane carboxylic acid by reaction with an amine NHR$^2$R$^4$ or azide (followed by conversion of the azide to amino). [See for example K. Krajewski et al. Tetrahedron Asymmetry 10, 4591–4598 (1999)]. The ester group maybe epimerised by heating in strong base, hydrolysed to the carboxylic acid and cyclised to the lactone using a conventional coupling reagent (EDC). Other conventional reagents eg DCC, Im$_2$CO, HATU etc. may also be used. The lactone is readily purified by chromatography. The lactone is readily opened with aqueous ammonia in tetrahydrofuran to give the required (racemic) amide.

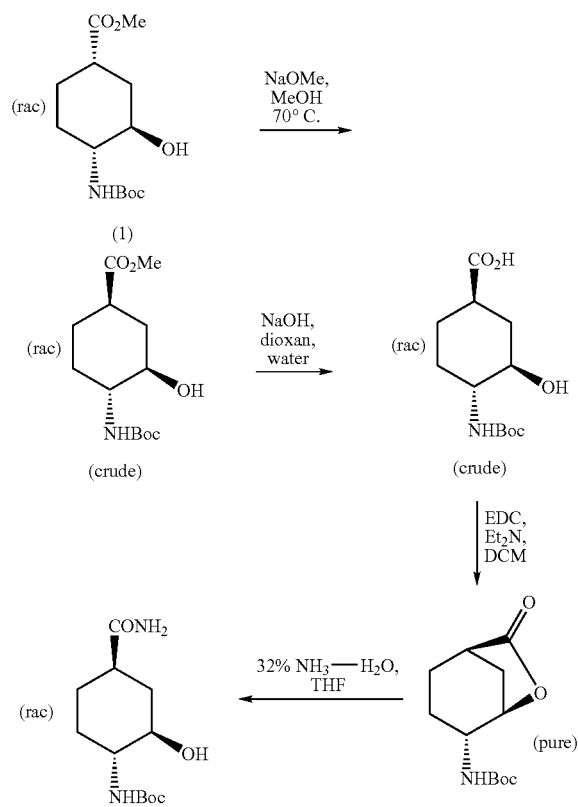

An improved procedure starting from 3-cyclohexene carboxylic acid may be used to prepare single enantiomers. 3-Cyclohexene carboxylic acid (2) is resolved via α-Me benzylamine salt (Schwartz et al, J. Am. Chem. Soc., 100, 5199, (1978)). A higher yield of lactone (3) can be achieved using a larger excess of reagents. Lactone opening with ammonia gives (4), which is treated with azide to give (5) which has the required trans relative stereochemistry between the amide and N-substituent. Finally, azide reduction and Boc protection gives (1) a compound of formula (V).

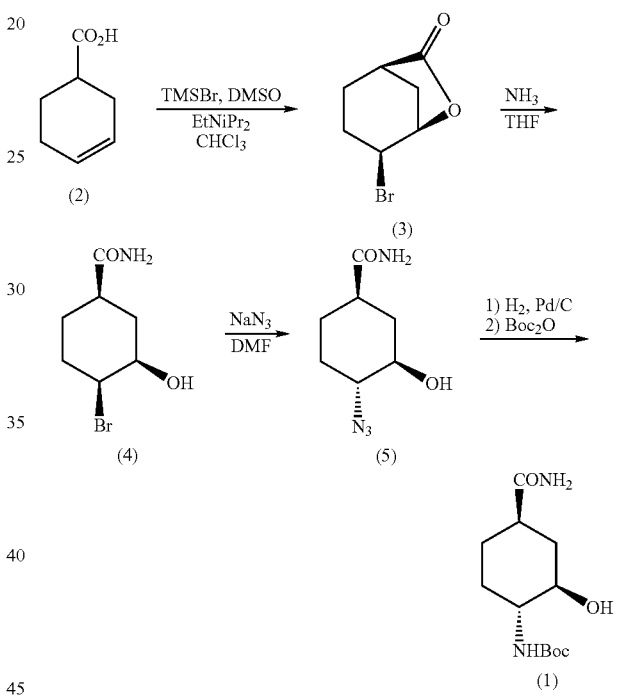

$R^4$-halides and $R^4$-W derivatives, acyl derivatives or aldehydes are commercially available or are prepared conventionally. The aldehydes may be prepared by partial reduction of the corresponding ester with lithium aluminium hydride or di-isobutylaluminium hydride or more preferably by reduction to the alcohol, with lithium aluminium hydride or sodium borohydride (see *Reductions by the Alumino- and Borohydrides in Organic Synthesis,* 2nd ed., Wiley, N.Y., 1997; JOC, 3197, 1984; Org. Synth. Coll., 102, 1990; 136, 1998; JOC, 4260, 1990; TL, 995, 1988; JOC, 1721, 1999; Liebigs Ann./Recl., 2385, 1997; JOC, 5486, 1987), followed by oxidation to the aldehyde with manganese (II) dioxide, or by a 'Swern' procedure (oxalyl chloride/DMSO), or by using potassium dichromate (PDC). The aldehydes may also be prepared from carboxylic acids in two stages by conversion to a mixed anhydride for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (II) dioxide. Acyl derivatives may be prepared by activation of the corresponding ester. $R^4$-halides such as bromides may be prepared from the alcohol $R^4OH$ by reaction with phosphorus tribromide in dichloromethane/triethylamine. Where $X^{2a}$ is CO and $X^{3a}$ is $NR^{13a}$ the $R^4$-halide may be prepared by coupling an $X^{4a}NH_2$ amine and bromoacetyl bromide. $R^4W$ derivatives such as methanesulphonyl derivatives may be prepared from the alcohol $R^4OH$ by reaction with methane sulphonyl chloride. The leaving group W may be converted to another leaving group W, e.g. a halogen group, by conventional methods. Alternatively the aldehyde $R^5{}_2CHO$ and sulphonic acid derivative $R^5{}_2SO_2W$ may be generated by treatment of the $R^5{}_2H$ heterocycle with suitable reagents. For example benzoxazinones, or more preferably their N-methylated derivatives can be formylated with hexamine in either trifluoroacetic acid or methanesulfonic acid, in a modified Duff procedure [O. I. Petrov et al. *Collect. Czech. Chem. Commun.* 62, 494–497 (1997)]. 4-Methyl-4H-benzo[1,4]oxazin-3-one may also be formylated using dichloromethyl methyl ether and aluminium chloride giving exclusively the 6-formyl derivative.

Reaction of a $R^5{}_2H$ heterocycle with chlorosulphonic acid gives the sulphonic acid derivative (by methods analogous to Techer et. al., *C. R. Hebd. Seances Acad. Sci. Ser.C;* 270, 1601, 1970).

The aldehyde $R^5{}_2CHO$ may be generated by conversion of an $R^5{}_2$ halogen or $R^5{}_2$ trifluoromethane sulphonyloxy derivative into an olefin with subsequent oxidative cleavage by standard methods. For example, reaction of a bromo derivative under palladium catalysis with trans-2-phenylboronic acid under palladium catalysis affords a styrene derivative which upon ozonolysis affords the required $R^5{}_2CHO$ (Stephenson, G. R., Adv. Asymmetric Synth. (1996), 275–298. Publisher: Chapman & Hall, London).

Where $R^5{}_2$ is an optionally substituted benzoimidazol-2-yl group, the compound of formula (V) where $R^{4'}$ is $R^4$ may be obtained by converting a $R^{4'}$ cyanomethyl group with partial hydrolysis to give the 2-ethoxycarbonimidoylethyl group which can then be condensed with an appropriately substituted 1,2-diaminobenzene to give the required benzoimidazol-2-yl group.

$R^5{}_2H$ heterocycles are commercially available or may be prepared by conventional methods. For example where a benzoxazinone is required, a nitrophenol may be alkylated with for example ethyl bromoacetate and the resulting nitro ester reduced with Fe in acetic acid (alternatively Zn/AcOH/HCl or $H_2/Pd/C$ or $H_2$/Raney Ni). The resulting amine may undergo spontaneous cyclisation to the required benzoxazinone, or cyclisation may be induced by heating in acetic acid. Alternatively a nitrophenol may be reduced to the aminophenol, which is reacted with chloroacetyl chloride [method of X. Huang and C. Chan, *Synthesis* 851 (1994)] or ethyl bromoacetate in DMSO [method of Z. Moussavi et al. *Eur. J. Med. Chem. Ther.* 24, 55–60 (1989)]. The same general routes can be applied to prepare benzothiazinones [See for example F. Eiden and F. Meinel, Arch. Pharm. 312, 302–312 (1979), H. Fenner and R Grauert *Liebigs. Ann. Chem.* 193–313 (1978)]]. A variety of routes are available to prepare aza analogues of benzothiazinones via the key corresponding aldehydes. For instance, 2-oxo-2,3-dihydro-1H-pyrido[3,4-b][1,4]thiazine-7-carbaldehyde maybe accessed from 5-fluoro-2-picoline (E. J. Blanz, F. A. French, J. R. DoAmaral and D. A. French, J. Med. Chem. 1970, 13,1124–1130) by constructing the thiazinone ring onto the pyridyl ring then functionalising the methyl substituent, as described in the Examples. The dioxin analogue of this aza substitution pattern, 2,3-dihydro-[1,4]dioxino[2,3-c]pyridine-7-carbaldehyde is accessible from Kojic acid by aminolysis from pyrone to pyridone then annelating the dioxin ring, again as described in the subsequent experimental data. Other aza substitution patterns with pyridothiazin-3-one, pyridooxazin-3-one, and pyridodioxin ring systems are also accessible, again as described in the Examples. Ortho-aminothiophenols may be conveniently prepared and reacted as their zinc complexes [see for example V. Taneja et al *Chem. Ind.* 187 (1984)]. Benzoxazolones may be prepared from the corresponding aminophenol by reaction with carbonyl diimidazole, phosgene or triphosgene. Reaction of benzoxazolones with diphosporus pentasulfide affords the corresponding 2-thione. Thiazines and oxazines can be prepared by reduction of the corresponding thiazinone or oxazinone with a reducing agent such as lithium aluminium hydride.

The amines $R^{2'}R^{4'}NH$ are available commercially or prepared conventionally. For example amines may be prepared from a bromo derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Amines where $X^{2a}$ is CO and $X^{3a}$ is $NR^{13a}$ may be prepared by reacting an N-protected glycine derivative $HO_2C$—$X^{1a}$—$NH_2$ with $X^{4a}$—$NH_2$ by conventional coupling using eg EDC.

Conversions of $R^{1a'}$, $R^{1'}$, $R^{2'}$, $R^{3'}$ and $R^{4'}$ may be carried out on the intermediates of formulae (IV) and (V) prior to their reaction to produce compounds of formula (I) in the same way as described above for conversions after their reaction.

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in vivo hydrolysable ester thereof is administered in the abovementioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

The following examples illustrate the preparation of certain compounds of formula (I) and the activity of certain compounds of formula (I) against various bacterial organisms.

EXAMPLES

Example 1

Trans-4-[(8-Hydroxy-quinolin-2-ylmethyl)-amino]-cyclohexanecarboxylic acid (6-methoxy-[1,5]naphthyridin-4-yl)-amide oxalate salt

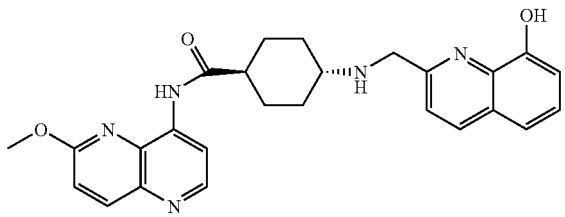

(a) 4-Hydroxy-6-methoxy-[1,5]-naphthyridine

5-Amino-2-methoxypyridine (55 g, 0.44 mol) in methanol (1000 mL) with methyl propiolate (40 mL, 0.44 mol) was stirred for 48 hours, then evaporated and the product purified by chromatography on silica gel (dichloromethane) followed by recrystallisation from dichloromethane-hexane (44.6 g, 48%).

The unsaturated ester (10.5 g, 0.05 mol) in warm Dowtherm A (50 mL) was added over 3 minutes to refluxing Dowtherm A, and after a further 20 minutes at reflux the mixture was cooled and poured into diethyl ether. The precipitate was filtered to give a solid (6.26 g, 70%).

(b) 1,1,1-Trifluoro-methanesulfonic acid 6-methoxy-[1,5]naphthyridin-4-yl ester

Pyridone (1a) (10 g, 0.057 mol) in dichloromethane (200 mL) containing 2,6-lutidine (9.94 mL, 0.086 mol) and 4-dimethylaminopyridine (0.07 g, 0.0057 mol) was cooled in ice and treated with trifluoromethanesulfonic anhydride (10.5 mL, 0.063 mol). After stirring for 2.5 hours the mixture was washed with saturated ammonium chloride solution, dried, evaporated and purified on silica gel (dichloromethane) to give a solid (13.2 g).

(c) 6-Methoxy-[1,5]naphthyridin-4-ylamine

A solution of triflate (1b) (8.0 g) and propylamine hydrochloride (15.8 g) in pyridine (120 mL) was heated at reflux for 4 hours. The solvent was evaporated and the mixture dissolved in 0.05M hydrochloric acid (600 mL) and washed with dichloromethane. The mixture was basified with 40% sodium hydroxide and extracted with dichloromethane. The extracts were dried, evaporated and chromatographed on silica gel (2–5% methanol in dichloromethane) to give an orange solid (3.6 g, 63%).

δH (CDCl$_3$, 250 MHz), 8.39 (1H, d,), 8.09 (1H, d,), 7.08 (1H, d,), 6.71 (1H, d,), 5.25 (2H, brs), 4.05 (3H, s). MS (+ve ion electrospray) m/z: 176 (MH$^+$).

(d) [4-(6-Methoxy-[1,5]naphthyridin-4-ylcarbamoyl)-cyclohexyl]-carbamic acid tert-butyl ester Amine (1c) (2.44 g, 13.94 mmol), 4-trans-tert-butoxycarbonylamino-cyclohexanecarboxylic acid (3.39 g, 13.94 mmol) and O-(7-azabenzotriazol-1-yl)-N,N,N',N'-tetramethyluronium hexafluorophosphate (5.30 g, 13.94 mmol) were combined as a slurry in N,N'-dimethylformamide (70 mL). To this mixture was added triethylamine (3.88 mL, 27.88 mmol) and the reaction vessel was heated to 60° C. for 10 hours. After this period the solvent was removed under vacuum and the residue partitioned between ethyl acetate (2×200 mL) and brine (50 mL). The organic phases were combined and dried over magnesium sulfate after which they were concentrated in vacuo. The resulting oil was purified by column chromatography on silica gel using a dichloromethane and methanol solvent gradient. This provided the desired compound as a white solid (3.33 g, 60%).

MS (APCI+) m/z 401 (MH+).

(e) 4-Amino-cyclohexanecarboxylic acid (6-methoxy-[1,5]naphthyridin-4-yl)-amide

Amide (1d) (3.33 g, 8.325 mmol) was dissolved in dichloromethane (200 mL). To this solution was added trifluoroacetic acid (50 mL) and the resulting mixture stirred at room temperature for 2 hours. The volatiles were removed under reduced pressure and the residue was treated with 4M hydrochloric acid in 1,4-dioxan (100 mL). The resulting solid was filtered and then stirred over potassium carbonate (4.59 g, 33.3 mmol) in a mixture of chloroform and 15% methanol (2×150 mL). The slurry was filtered and the filtrate concentrated under vacuum to provide the desired compound as an off white solid (1.82 g, 73%).

MS (APCI+) m/z 301 (MH+).

(f) Title Compound

Amide (1d) (796 mg, 1.99 mmol) was dissolved in dichloromethane (5 mL) and cooled to 0° C. Trifluoroacetic acid (5 mL) was added and the resulting solution stirred at room temperature for 20 hours. The reaction was concentrated under vacuum and the residue re-dissolved in anhydrous dichloromethane (5 mL) and methanol (1 mL). To this solution was added activated 3 Å molecular sieves (1 g), 8-hydroxy-quinoline-2-carbaldehyde (263 mg, 1.52 mmol) and triethylamine (0.21 mL, 1.52 mmol). The resulting solution was stirred at room temperature for 20 hours and then sodium borohydride (116 mg, 3.05 mmol) was added. The resulting slurry was stirred at room temperature for a further 10 hours. The reaction mixture was quenched by the addition of water (2 mL) and the volatiles removed in vacuo. The residue was partitioned between ethyl acetate (2×100 mL) and brine (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (33 mg, 4%).

$\delta$H (CD$_3$OD, 250 MHz) 8.46 (1H, d), 8.34 (1H, d), 8.07 (1H, d), 8.04 (1H, d), 7.35–7.19 (3H, m), 7.11 (1H, d), 6.97 (1H, dd), 4.09 (2H, s), 4.01 (3H, s), 2.61–2.49 (2H, m), 2.14–2.01 (4H, m), 1.45–1.22 (2H, m), 1.37–1.22 (2H, m). MS (APCI+) m/z 458 (MH+).

A solution of the oil (33 mg) in dichloromethane (1 mL) was added to oxalic acid (6.5 mg) in diethyl ether (10 mL) to generate the oxalate salt. The title compound was isolated by centrifugation, washing with diethyl ether and subsequent drying in vacuo.

Example 2

Trans-4-[(Benzo[1,2,5]thiadiazol-5-ylmethyl)-amino]-cyclohexanecarboxylic acid (6-methoxy-[1,5]naphthyridin-4-yl)-amide fumarate salt

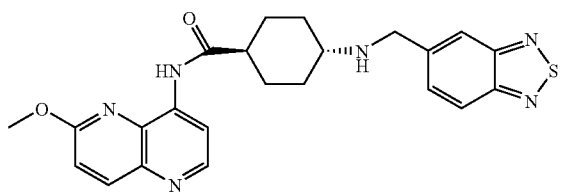

(a) Benzo[1,2,5]thiadiazol-5-yl-methanol

Benzo[1,2,5]thiadiazole-5-carboxylic acid (2.00 g, 11.11 mmol) was dissolved in tetrahydrofuran (50 mL) and cooled to 0° C. To this was added triethylamine (1.80 mL, 12.87 mmol) followed by isobutylchloroformate (1.62 mL, 12.40 mmol) in a dropwise manner. The resulting slurry was stirred for a further 30 minutes at 0° C. and then filtered into a mixture of sodium borohydride (0.83 g, 21.84 mol) in ice water (20 mL). The resulting mixture was stirred at 0° C. for 30 minutes, evaporated to one quarter of its volume and then extracted with dichloromethane (3×50 mL). The organic phases were combined and then dried over sodium sulfate. This was followed by concentration under reduced pressure to provide the desired product as a white solid which was used without further purification (1.50 g, 81%).

(b) Methanesulfonic acid benzo[1,2,5]thiadiazol-5-ylmethyl ester

Alcohol (2a) (200 mg, 1.20 mmol), was dissolved in dichloromethane (6 mL). This solution was cooled to 0° C. and triethylamine (0.22 mL, 1.57 mmol) was added. This was followed by the dropwise addition of methane sulfonylchloride (0.11 mL, 1.45 mmol). The resulting mixture was stirred at room temperature for 2 hours and then partitioned between a 10% aqueous solution of sodium hydrogen carbonate (25 mL) and dichloromethane (2×50 mL). The organic phases were combined and dried over magnesium sulfate. They were then dried under reduced pressure to afford the desired product which was used without further purification (241 mg, 70% w/w).

(c) Title Compound

Amine (1e) (160 mg, 0.533 mmol) was dissolved in N,N'-dimethylformamide (5 mL). To this solution was added potassium carbonate (74 mg, 0.533 mmol) and mesylate (2b) (130 mg, 0.533 mmol). The resulting suspension was stirred at room temperature for 10 hours. The reaction was concentrated under vacuum and the residue partitioned between ethyl acetate (2×100 mL) and brine (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (71 mg, 30%).

$\delta$H (CDCl$_3$, 250 MHz), 9.50 (1H, bs), 8.70 (1H, d), 8.54 (1H, d), 8.22 (1H, d), 7.97 (2H, m), 7.63 (1H, dd), 7.13 (1H, m), 4.10 (3H, s), 4.00 (2H, s), 2.65–2.62 (1H, m), 2.46–2.40 (1H, m), 2.21–2.17 (4H, m), 1.71–1.66 (2H, m), 1.38–1.20 (2H, m). MS (APCI+) m/z 449 (MH+).

A solution of the oil (71 mg) in dichloromethane (1 mL) was added to fumaric acid (18 mg) in dichloromethane and methanol (1:1, 10 mL) to generate the fumarate salt. The title compound was isolated by removal of volatiles in vacuo.

Example 3

Trans-4-[(1H-Pyrrolo[2,3-b]pyridin-2-ylmethyl)-amino]-cyclohexanecarboxylic acid (6-methoxy-[1,5]naphthyridin4-yl)-amide fumarate salt

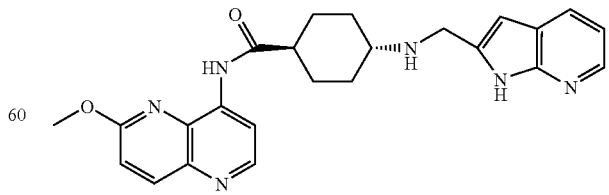

(a) 7-Azaindole-2-carboxylic acid.

A solution of 7-azaindole (2.0 g) in tetrahydrofuran (30 ml) was cooled to −70° C. and n-butyllithium (1.6M in hexanes, 11.1 ml) was added dropwise. After 0.5 h at −70° C., carbon dioxide was bubbled through for 10 min, followed by 10 min stirring. The mixture was allowed to warm to 0° C. and the mixture was evaporated under vacuum to approximately half-volume. Fresh tetrahydrofuran (15 ml) was added, the mixture was cooled to −70° C. and tert-butyl lithium (1.7M in pentane, 10.5 ml) was added dropwise. After stirring for 1 h at −70° C., carbon dioxide was bubbled through for 10 min followed by stirring for 30 min. Water (1.2 ml) was added and the mixture was allowed to warm to room temperature before pouring into saturated ammonium chloride. The aqueous solution was washed with diethyl ether, filtered and acidified to pH3.5. The white precipitate was collected and dried to give the acid (2.38 g).

MS (+ve ion electrospray) m/z 163 (MH+).

(b) Methyl 7-azaindole-2-carboxylate.

Acid (3a) (1.0 g) was partially dissolved in N,N'-dimethylformamide (20 ml) and methanol (2 ml) and treated dropwise with trimethylsilyldiazomethane (2M in hexanes, 3.1 ml). The mixture was stirred overnight then evaporated. Chromatography on silica using an ethyl acetate and hexane solvent gradient gave the ester (0.35 g).

MS (+ve ion electrospray) m/z 177 (MH+).

(c) 7-Azaindole-2-carboxaldehyde.

Ester (3b) (0.34 g) in tetrahydrofuran (5 ml) was treated dropwise with lithium aluminium hydride (1M in tetrahydrofuran, 1.9 ml) at 0° C. After 2 h the mixture was treated with 8% sodium hydroxide, dichloromethane and sodium sulfate, filtered and evaporated. The resulting crude alcohol was dissolved in tetrahydrofuran (4 ml) and stirred with manganese (II) oxide (0.74 g) for 4 h. Filtration and evaporation of solvent gave the aldehyde (100 mg).

MS (+ve ion electrospray) m/z 147 (MH+).

(d) Title Compound

Amine (1e) (245 mg, 0.822 mmol) and aldehyde (3c) (120 mg, 0.822 mmol) was dissolved in chloroform (6 mL) and methanol (2 mL). The solution was heated to 70° C. for 5 hours with 3 Å molecular sieves (1 g). After this period the mixture was cooled to 0° C. and sodium triacetoxyborohydride (522 mg, 2.466 mmol) was added. The mixture was stirred at room temperature for 10 hours and then quenched by the addition of water (2 mL). The volatiles were removed, in vacuo and the residue partitioned between ethyl acetate (2×100 mL) and brine (25 mL). The organic phases were combined and dried over magnesium sulfate then evaporated. The resulting oil was purified by silica gel chromatography using a dichloromethane and methanol solvent gradient. This provided the free base of the desired compound as a colourless oil (74 mg, 22%).

δH (CDCl$_3$, 250 MHz), 9.51 (1H, bs), 8.68 (1H, d), 8.50 (1H, d), 8.28 (1H, d), 8.22 (1H, d), 7.84 (1H, dd), 7.15 (1H, d), 7.05 (1H, dd), 6.31 (1H, s), 4.11 (2H, s), 4.09 (3H, s), 2.64–2.60 (1H, m), 2.42–2.37 (1H, m), 2.19–2.17 (4H, m), 1.73–1.63 (2H, m), 1.31–1.22 (2H, m).

MS (APCI+) m/z 431 (MH+).

The fumarate salt was prepared by the method of Example 2.

Example 4

Trans-4-[(3-Oxo-3,4-dihydro-2H-benzo[1,4]thiazin-6-ylmethyl)-amino]-cyclohexane carboxylic acid (6-methoxy-[1,5]naphthyridin-4-yl)-amide fumarate salt

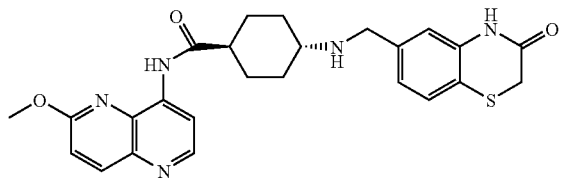

a) 3-Oxo-3,4-dihydro-2H-benzo[1,4]thiazine-6-carboxylic acid

3-Oxo-3,4-dihydro-2H-benzo[1,4]thiazine-6-carboxylic acid methyl ester (6.74 g) was suspended in tetrahydrofuran (100 mL) and 2M sodium hydroxide (30 mL) was added followed by water (20 mL). The solution was stirred for 2.5 hours, evaporated to half volume and acidified with 2M hydrochloric acid. The product was collected, washed with water and dried in vacuo, to give a white solid (6.2 g).

MS (−ve ion electrospray) m/z 208 (M−H)$^-$ (b) 6-Hydroxymethyl-4H-benzo[1,4]thiazin-3-one Acid (4a) in tetrahydrofuran (50 mL) and triethylamine (4.7 mL) was cooled to 0° C. and isobutylchloroformate (4.02 mL) was added dropwise and the solution was stirred at 0° C. for 2 hours, when it was filtered into a stirred solution of sodium borohydride (3.14 g) in ice/water (50 mL). The mixture was stirred at 0° C. for 1 hour and allowed to warm to room temperature. It was acidified with 2M hydrochloric acid, evaporated to half volume, and the resulting product was collected, washed with water and dried in vacuo, to give a white solid (4.5 g).

MS (−ve ion electrospray) m/z 194 (M−H)$^-$ (c) 3-Oxo-3,4-dihydro-2H-benzo[1,4]thiazine-6-carbaldehyde A stirred solution of alcohol (4b) (3.5 g) in chloroform (150 mL) and tetrahydrofuran (300 mL) was treated with manganese dioxide (7.8 g) for 18 hours and was filtered and evaporated to give a white solid (2.5 g).

MS (−ve ion electrospray) m/z 194 (M−H)$^-$ (d) Title Compound

Amine (1e) (260 mg, 0.866 mmol) and aldehyde (4c) (167 mg, 0.866 mmol) was dissolved in chloroform (5 mL) and methanol (3 mL). The solution was heated to 70° C. for 7 hours with 3 Å molecular sieves (1 g). After this period the mixture was cooled to 0° C. and sodium triacetoxyborohydride (550 mg, 2.598 mmol) was added. The mixture was stirred at room temperature for 10 hours and then quenched by the addition of water (2 mL). The volatiles were removed in vacuo and the residue was purified by silica gel chromatography using a dichloromethane and methanol solvent gradient. This provided the free base of the desired compound as a colourless oil (145 mg, 35%).

δH (d$_6$-DMSO, 250 MHz), 10.52 (1H, bs), 9.80 (1H, bs), 8.66 (1H, d), 8.39 (1H, d), 8.26 (1H, d), 7.31 (1H, d), 7.26 (1H, d), 6.99–6.96 (2H, m), 4.14 (3H, s), 3.73 (2H, s), 3.44 (2H, s), 2.68 (1H, m), 2.51–2.48 (1H, m), 2.04–1.90 (4H, m), 1.52–1.47 (2H, m), 1.24–1.17 (2H, m).

MS (+ve ion electrospray) m/z 478(MH+).

The fumarate salt was prepared by the method of Example 2.

Example 5

Trans-4-[(2,3-Dihydro-benzo[1,4]dioxin-6-ylmethyl)-amino]-cyclohexanecarboxylic acid (6-methoxy-[1,5]naphthyridin-4-yl)-amide fumarate salt

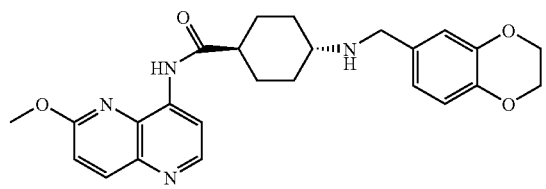

(a) (2,3-Dihydro-benzo[1,4]dioxin-6-yl)-methanol 2,3-Dihydro-benzo[1,4]dioxine-6-carbaldehyde [RN 29668-44-8] (3.04 g, 18.54 mmol) was dissolved in ethanol (100 mL) and cooled to 0° C. To the resulting solution was added sodium borohydride (1.41 g, 37.07 mmol). The resulting slurry was stirred at room temperature for 1 hour and then quenched with water (10 mL) before being concentrated to dryness under reduced pressure. The residue was partitioned between a 5% aqueous solution of sodium hydrogen carbonate (20 mL) and dichloromethane (2×50 mL). The organic phases were combined and dried over magnesium sulfate then evaporated under reduced pressure to provide and oil which was purified on silica gel using a dichloromethane and methanol solvent gradient. This provided the desired product as a colourless oil (3.00 g, 97%).

(b) Methanesulfonic acid 2,3-dihydro-benzo[1,4]dioxin-6-ylmethyl Ester

Alcohol (5a) (640 mg, 3.855 mmol), was dissolved in dichloromethane (20 mL). This solution was cooled to 0° C. and triethylamine (0.70 mL, 5.012 mmol) was added. This was followed by the dropwise addition of methane sulfonylchloride (0.36 mL, 4.627 mmol). The resulting mixture was stirred at room temperature for 2 hours and then partitioned between a 10% aqueous solution of sodium hydrogen carbonate (25 mL) and dichloromethane (2×100 mL). The organic phases were combined and dried over magnesium sulfate. They were then dried under reduced pressure to afford the desired product which was used without further purification (1.00 g, 60% w/w).

(c) Title Compound

Amine (1e) (150 mg, 0.50 mmol) was dissolved in N,N'-dimethylformamide (10 mL). To this solution was added potassium carbonate (76 mg, 0.55 mmol) and mesylate (5b) (122 mg, 0.50 mmol). The resulting suspension was stirred at 50° C. for 3 hours. The reaction was concentrated under vacuum and the residue partitioned between dichloromethane (2×100 mL) and an aqueous solution of saturated sodium hydrogen carbonate (20 mL). The organic phases were combined and dried over magnesium sulfate. The volatiles were again removed under reduced pressure and the resulting oil was subjected to purification on silica gel using a methanol and ethyl acetate gradient. This afforded the free base of the desired compound as a colourless oil (70 mg, 31%).

$\delta$H (CDCl$_3$, 250 MHZ), 9.48 (1H, bs), 8.68 (1H, d), 8.52 (1H, d), 8.21 (1H, d), 7.15 (1H, d), 6.86–6.79 (3H, m), 4.24 (4H, m), 4.14 (3H, s), 3.79 (2H, m), 2.88–2.61 (1H, m), 2.49–2.40 (1H, m), 2.20–2.15 (4H, m), 1.68–1.63 (2H, m), 1.58–1.34 (2H, m). MS (APCI+) m/z 449 (MH+).

The fumarate salt was prepared by the method of Example 2.

Example 6

Trans-4-[(Benzo[1,2,3]thiadiazol-5-ylmethyl)-amino]-cyclohexanecarboxylic acid (6-methoxy-[1,5]naphthyridin-4-yl)-amide fumarate salt

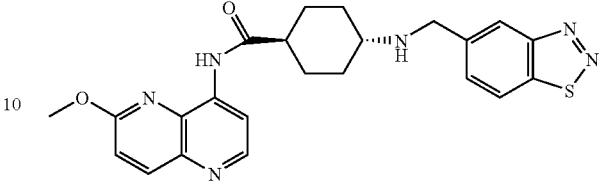

(a) Benzo[1,2,3]thiadiazol-5-yl-methanol

Benzo[1,2,3]thiadiazole-5-carboxylic acid (2.70 g, 15.0 mmol) was dissolved in tetrahydrofuran (25 mL) and cooled to 0° C. To this was added triethylamine (2.50 mL, 18.0 mmol) followed by isobutylchloroformate (2.15 mL, 16.5 mmol) in a dropwise manner. The resulting slurry was stirred for a further 30 minutes at 0° C. and then filtered into a mixture of sodium borohydride (1.14 g, 30 mmol) in ice water (20 mL). The resulting mixture was stirred at 0° C. for 15 minutes, evaporated to one quarter of its volume and then partitioned between a saturated aqueous solution of sodium hydrogen carbonate (20 mL) and ethyl acetate (3×50 mL). The organic phases were combined and then dried over sodium sulfate. This was followed by concentration under reduced pressure to provide an oil which was purified by column chromatography on silica gel using an ethyl acetate and hexane solvent system. This provided the desired product as a yellow solid (1.40 g, 56%).

(b) Methanesulfonic acid Benzo[1,2,3]thiadiazol-5-ylmethyl ester

Alcohol (6a) (150 mg, 0.904 mmol) was dissolved in dichloromethane (2 mL). This solution was cooled to 0° C. and triethylamine (0.14 mL, 0.994 mmol) was added. This was followed by the dropwise addition of methane sulfonylchloride (0.07 mL, 0.904 mmol). The resulting mixture was stirred at room temperature for 1 hour and then partitioned between water (25 mL) and dichloromethane (2×50 mL). The organic phases were combined and dried over magnesium sulfate. They were then dried under reduced pressure to afford the desired product which was used without further purification.

(c) Title Compound

Amine (1e) (50 mg, 0.166 m mol) was dissolved in N,N'-dimethylformamide (3 mL). To this solution was added potassium carbonate (46 mg, 0.332 mmol) and mesylate (6b) (218 mg, 0.893 mmol). The resulting suspension was stirred at room temperature for 10 hours. The reaction was concentrated under vacuum and the residue partitioned between ethyl acetate (2×100 mL) and brine (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (22 mg, 29%).

$\delta$H (CDCl$_3$, 250 MHz), 9.51 (1H, bs), 8.69 (1H, d), 8.61 (1H, m), 8.51 (1H, d), 8.21 (1H, d), 8.03 (1H, d), 7.72 (1H, dd), 7.16 (1H, d), 4.11 (3H, s), 4.00 (2H, s), 2.70–2.64 (1H, m), 2.47–2.41 (1H, m), 2.23–2.18 (4H, m), 1.76-1.63 (2×, m), 1.40–1.25 (211, m).

MS (APCI+) m/z 449 (MH+).

The fumarate salt was prepared by the method of Example 2.

Example 7

Trans-4-[(3-Methyl-2-oxo-2,3-dihydro-benzooxazol-6-ylmethyl)-amino]-cyclohexanecarboxylic acid (6-methoxy-[1,5]naphthyridin-4-yl)-amide oxalate salt

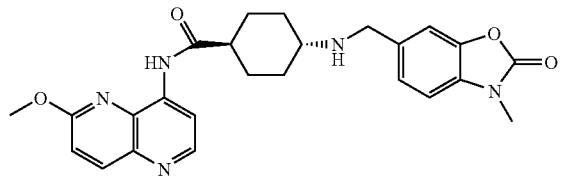

(a) 3-Methyl-2-oxo-2,3-dihydro-benzooxazole-6-carbaldehyde

3-Methyl-3H-benzooxazol-2-one (2.00 g, 13.42 mmol) and hexamethylenetetramine (3.76 g, 26.84 mmol) were dissolved in trifluoroacetic acid (20 mL) and heated at reflux for 20 hours. The volatiles were removed in vacuo and the residue was treated with ice water (60 mL). The resultant mixture was stirred for 30 minutes and then made basic with sodium carbonate. The solid was isolated by filtration and washed with water then dried under vacuum. The solid was purified by column chromatography on silica gel eluting with an ethyl acetate and hexane solvent gradient. This provided the desired product as a white solid (1.07 g, 45%).

$\delta$H (CDCl$_3$, 250 MHz), 9.95 (1H, s), 7.80–7.76 (1H, dd), 7.33 (1H, d), 7.10 (1H, d), 3.48 (3H, s).

(b) Title Compound

Amide (1d) (311 mg, 0.778 mmol) was dissolved in dichloromethane (2 mL) and cooled to 0° C. Trifluoroacetic acid (2 mL) was added and the resulting solution stirred at room temperature for 1 hour. The reaction was concentrated under vacuum and the residue re-dissolved in anhydrous dichloromethane (5 mL) and methanol (1 mL). To this solution was added activated 4 Å molecular sieves (1 g), aldehyde (7a) (138 mg, 0.778 mmol) and diisopropyl ethylamine (0.40 mL, 2.333 mmol). The resulting solution was stirred at room temperature for 5 hours and them sodium borohydride (89 mg, 2.333 mmol) was added. The resulting slurry was stirred at room temperature for a further 48 hours. The reaction mixture was quenched by the addition of water (2 mL) and the volatiles removed in vacuo. The residue was partitioned between ethyl acetate (2×100 mL) and brine (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (50 mg, 14%).

$\delta$H (CD$_3$OD, 250 MHz), 8.66 (1H, d), 8.54 (1H, d), 8.25 (1H, d), 7.40 (1H, m), 7.34–7.24 (2H, m), 7.21 (1H, d), 4.22 (3H, s), 4.03 (2H, s), 3.46 (3H, s), 2.80–2.65 (2H, m), 2.24 (4H, m), 1.58–1.53 (2H, m), 1.41–1.33 (2H, m).

MS (APCI+) m/z 462 (MH$^+$).

The oxalate salt was prepared by the method of Example 1.

Example 8

Trans-4-[(3-Oxo-3,4-dihydro-2H-benzo[1,4]oxazin-6-ylmethyl)-amino]-cyclohexanecarboxylic acid (6-methoxy-[1,5]naphthyridin-4-yl)-amide fumarate salt

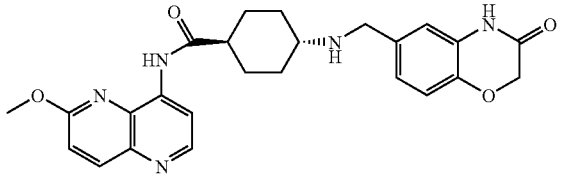

(a) (4-Formyl-2-nitro-phenoxy)-acetic acid ethyl ester

A solution of 4-hydroxy-3-nitro-benzaldehyde (6.9 g) and ethyl bromoacetate (5.0 mL) in dimethylformamide (250 mL) was treated with anhydrous potassium carbonate (10 g) and the mixture was heated at 60° C. for 18 hours and evaporated to dryness. The residue was partitioned between water and diethyl ether, and the diethyl ether layer was washed with 0.5M sodium hydroxide. It was then dried over anhydrous sodium sulfate and evaporated to give an oil that was chromatographed on silica gel (ethyl acetate/dichloromethane) to afford an oil (1.9 g).

MS (+ve ion electrospray) m/z 253 (MH+).

(b) 3-Oxo-3,4-dihydro-2H-benzo[1,4]oxazine-6-carboxaldehyde

Ester (8a) (1.9 g) in acetic acid (40 mL) was treated with iron powder (4.2 g) and the mixture was stirred at 60° C. for 0.75 hours, filtered and evaporated to dryness. It was partitioned between aqueous sodium bicarbonate and ethyl acetate. The organic fraction was chromatographed on silica gel (ethyl acetate) to give a white solid (0.88 g).

MS (−ve ion electrospray) m/z 176 (M−H)−

(c) Title Compound

Amine (1e) (200 mg, 0.66 mmol) and aldehyde (8b) (130 mg, 0.73 mmol) was dissolved in chloroform (5 mL) and methanol (3 mL). The solution was heated to reflux for 5 hours with 3 Å molecular sieves (1g). The solvents were then removed by evaporation and replaced with N,N'-dimethylformamide (2 mL) and toluene (2 mL) The mixture was stirred at reflux for a further 1 hour. These solvents were removed in vacuo and replaced with chloroform (2 mL) and methanol (2 mL). The mixture was cooled to 0° C. and sodium borohydride (230 mg, 6.05 mmol) was added. The mixture was then stirred at room temperature for 1 hour and quenched by the addition of water (2 mL). The volatiles were removed in vacuo and the residue was partitioned between chloroform (2×100 mL) and a saturated aqueous solution of sodium hydrogen carbonate (20 mL). The organic phases were combined, dried over magnesium sulfate and then concentrated under vacuum. The resulting oil was purified by silica gel chromatography using an ethyl acetate and methanol solvent gradient. This provided the desired compound as a colourless solid. Recrystallisation from ethyl acetate and methanol afforded the free base of the desired compound (60 mg, 19%).

$\delta$H (CD$_3$OD, 250 MHz), 8.62 (1H, d), 8.51 (1H, d), 8.20 (1H, d), 7.27 (1H, d), 7.03–6.93 (3H, m), 4.56 (2H, s), 4.10 (3H, s), 3.86 (2H, s), 2.75–2.60 (2H, m), 2.20–2.16 (4H, m), 1.67–1.63 (2H, m), 1.42–1.28 (2H, m).

The fumarate salt was prepared by the method of Example 2.

Example 9

Trans-4-[(7-Fluoro-3-oxo-3,4-dihydro-2H-benzo[1,4]oxazin-6-ylmethyl)-amino]-cyclohexanecarboxylic acid (6-methoxy-[1,5]naphthyridin-4-yl-amide Dioxalate Salt

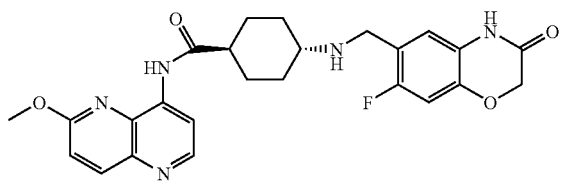

(a) 5-Amino-2-fluoro-4-hydroxy-benzonitrile

This was prepared from 2-fluoro-4-hydroxy-benzonitrile by nitration (concentrated nitric acid in acetic acid at 40° C.) followed by hydrogenation in ethanol over 10% palladium/carbon.

(b) 7-Fluoro-3-oxo-3,4-dihydro-2H-benzo[1,4]oxazine-6-carbonitrile

This was prepared by the general method of Xian Huang and Cheng-Chu Chan, *Synthesis*, 851 (1984). A mixture of nitrile (9a) (1 g), benzyltriethylammonium chloride (1.5 g) and sodium bicarbonate (2.22 g) in chloroform (20 ml) at 0° C. was treated with chloroacetyl chloride (0.632 mL) in chloroform (5 mL) and then stirred at 5° C. for 1 hour and then heated at 55° C. for 5 hours. The mixture was evaporated to dryness, treated with water, and filtered to give a solid that was recrystallised from ethanol to give a white solid (0.35 g). A further (0.24 g) was obtained after chromatography of the mother liquors on silica gel (chloroform then methanol/dichloromethane).

MS (−ve ion. electrospray) m/z 191 (M−H)⁻

(c) 7-Fluoro-3-oxo-3,4-Dihydro-2H-benzo[1,4]oxazine-6-carboxylic acid

Nitrile (9b) (0.2 g) was heated under reflux in tetrahydrofuran (20 mL) and water (20 mL) containing sodium hydroxide (0.167 g) for 72 hours. It was acidified with 2M hydrochloric acid and the product was collected and dried in vacuo to give a white solid (0.18 g).

MS (−ve ion electrospray) m/z 210 (M−H)⁻

(d) 7-Fluoro-3-hydroxymethyl-4H-benzo[1,4]oxazin-3-one

This was prepared from acid (9c) (1.7 g) via reduction of the mixed anhydride in a manner analogous to Example 4 to give a solid (0.7 g).

MS (−ve ion electrospray) m/z 196 (M−H)⁻

(e) 7-Fluoro-3-oxo-3,4-dihydro-2H-benzo[1,4]oxazine-6-carboxaldehyde

This was prepared from alcohol (9d) (0.7 g) by oxidation with manganese dioxide according to the procedure in Example 4 to give a solid (0.51 g).

MS (−ve ion electrospray) m/z 194 (M−H)⁻

(f) Title Compound

Amine (1e) (300 mg, 1.00 mmol) and aldehyde (9e) (214 mg, 1.10 mmol) were dissolved in chloroform (5 mL) and methanol (3 mL). The solution was heated to reflux for 4 hours with 3 Å molecular sieves (1 g). After this period the mixture was cooled to 0° C. and sodium borohydride (230 mg, 6.05 mmol) was added. The mixture was stirred at room temperature for 10 hours and then quenched by the addition of water (2 mL). The volatiles were removed in vacuo and the residue was partitioned between chloroform (2×100 mL) and a saturated aqueous solution of sodium hydrogen carbonate (20 mL). The organic phases were combined, dried over magnesium sulfate and then concentrated under vacuum. The resulting oil was purified by silica gel chromatography using an ethyl acetate and methanol solvent gradient. This provided the free base of the desired compound as a colourless oil (43 mg, 9%).

δH (CDCl₃, 250 MHz), 9.51 (1H, bs), 8.68 (1H, d), 8.51 (1H, d), 8.22 (1H, d), 7.16 (1H, d), 6.87 (1H, d), 6.70 (1H, d), 4.56 (2H, s), 4.10 (3H, s), 3.78 (2H, s), 2.60–2.40 (2H, m), 2.16–2.05 (4H, m), 1.76–1.66 (2H, m), 1.39–1.25 (2H, m).

MS (APCI+) m/z 480 (MH+).

The oxalate salt was prepared by the method of Example 1.

Example 10

Trans-4-[(2,3-Dihydro-benzo[1,4]dioxin-6-ylmethyl)-amino]-cyclohexanecarboxylic acid (8-fluoro-6-methoxy-quinolin-4-yl)-amide Fumarate Salt

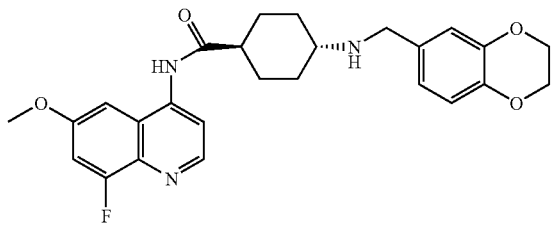

(a) 8-Fluoro-6-methoxy-quinolin-4-ol

2-Fluoro-4-methoxy-phenylamine (3.80 g, 26.7 mmol) and methyl propiolate (2.37 ml, 0.267 mol) in methanol (100 ml) was stirred for 72 hours at room temperature, then heated at 50° C. for 24 hours. It was evaporated and the product purified by chromatography on silica gel (dichloromethane) to give a solid (1.66 g), a portion of which was recrystallised from dichloromethane-hexane.

The unsaturated ester (0.96 g) in warm Dowtherm A (5 ml) was added over 3 minutes to refluxing Dowtherm A (5 ml), and after a further 20 minutes at reflux the mixture was cooled and poured into diethyl ether. The precipitate was filtered to give the title compound (0.50 g, 61%)

(b) 1,1,1-Trifluoro-methanesulfonic acid 8-fluoro-6-methoxy-quinolin-4-yl ester

Pyridone (10a) (0.48 g) and dimethylaminopyridine (0.03 g) in dichloromethane (20 ml) and 2,6-lutidine (0.48 ml) was treated dropwise with triflic anhydride (0.48 ml) and the mixture was stirred at room temperature for 4 hours. It was washed with saturated ammonium chloride, dried, evaporated, and chromatographed on silica gel (dichloromethane) to afford a yellow solid (0.69 g).

MS (+ve ion electrospray) m/z 326 (MH+).

(c) 8-Fluoro-6-methoxy-quinolin-4-ylamine

A solution of triflate (10b) (0.69 g) in pyridine (10 ml) was treated with n-propylamine hydrochloride (1.2 g) and the mixture heated at reflux for 16 hours. The reaction mixture was evaporated, dissolved in 0.05M HCl, washed with dichloromethane, basified with sodium hydroxide solution and re-extracted with dichloromethane. The combined organic phases were dried over sodium sulfate, evaporated, and chromatographed on silica gel (2–5% methanol in dichloromethane) to afford an orange solid (1.0 g).

MS (+ve ion electrospray) m/z 193 (MH⁺).

(d) [4-(8-Fluoro-6-methoxy-quinolin-4-ylcarbamoyl)-cyclohexyl]-carbamic acid tert-butyl ester Amine (10c) (1.333 g, 6.943 mmol), 4-trans-tert-butoxycarbonylamino-cyclohexanecarboxylic acid (1.68 g, 6.943 mmol) and O-(7-azabenzotriazol-1-yl)—N,N,N'N'- tetramethyluronium hexafluorophosphate (2.64 g, 6.943 mmol) were combined as a slurry in N,N'-dimethylformamide (70 mL). To this mixture was added triethylamine (1.93 mL, 13.87 mmol) and the reaction vessel was heated to 60° C. for 10 hours. After this period the solvent was removed under vacuum and the residue partitioned between ethyl acetate (2×200 mL) and brine (50 mL). The organic phases were combined and dried over magnesium sulfate after which they were concentrated in vacuo. The resulting oil was purified by column chromatography on silica gel using a dichloromethane and methanol solvent gradient. This provided the desired compound as an off white solid (1.67 g, 58%).

MS (APCI+) m/z 418 (MH+).

(e) 4-Amino-cyclohexanecarboxylic Acid (8-fluoro-6-methoxy-quinolin-4-yl)-amide

Amide (10d) (1.47 g, 3.525 mmol) was dissolved in dichloromethane (20 mL). To this solution was added trifluoroacetic acid (10 mL) and the resulting mixture stirred at room temperature for 3 hours. The volatiles were removed under reduced pressure and the residue was treated with 4M hydrochloric acid in 1,4-dioxan (50 mL). The resulting solid was filtered and then stirred over potassium carbonate (1.95 g, 14.1 mmol) in a mixture of chloroform and 15% methanol (2×100 mL). The slurry was filtered and the filtrate concentrated under vacuum to provide the desired compound as an off white solid (0.615 g, 55%).

MS (APCI+) m/z 318 (MH+).

(f) Title Compound

4-Amino-cyclohexanecarboxylic acid (8-fluoro-6-methoxy-quinolin-4-yl)-amide (10e) (186 mg, 0.587 mmol) was dissolved in N,N'-dimethylformamide (5 mL). To this solution was added potassium carbonate (130 mg, 0.939 mmol) methanesulfonic acid 2,3-dihydro-benzo[1,4]dioxin-6-ylmethyl ester (5b) (215 mg, 0.881 mmol). The resulting suspension was stirred at room temperature for 10 hours. The reaction was concentrated under vacuum and the residue partitioned between ethyl acetate (2×100 mL) and brine (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (130 mg, 48%).

δH (CDCl₃, 250 MHz), 8.81 (1H, bs), 8.67 (1H, d), 8.16 (1H, d), 7.12 (1H, m), 7.08 (1H, dd), 7.01 (1H, m), 6.88 (1H, m), 6.80 (1H, m), 4.21 (4H, m), 3.96 (3H, s), 3.77 (2H, m), 2.68 (1H, m), 2.46 (1H, m), 2.12–1.95 (4H, m), 1.58–1.53 (2H, m), 1.32–1.25 (2H, m). MS (APCI+) m/z 466 (MH+).

The fumarate salt was prepared by the method of Example 2.

Example 11

Trans-4-[(2,3-Dihydro-benzo[1,4]dioxin-6-ylmethyl)-amino]-cyclohexanecarboxylic acid (6-methoxy-quinolin-4-yl)-amide fumarate salt

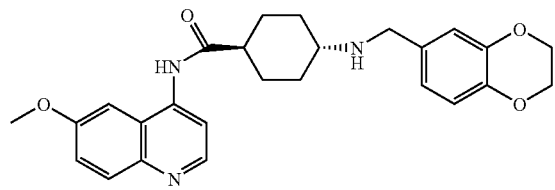

(a) 4-Amino-6-methoxyquinoline

Curtius rearrangement of 6-methoxyquinoline-4-carboxylic acid (Example 51a of WO99/37635)(4 g, 20 mmol) with diphenylphosphoryl azide (4.3 mL, 20 mmol) and triethylamine (3.5 mL) in tert-butanol (25 ml) at 85° C. gave, after chromatography (silica gel, ethyl acetate-dichloromethane) the N-tert-butoxycarbamate (2.47 g). Treatment with aqueous hydrochloric acid at reflux, followed by basification and extraction with ethyl acetate gave the 4-aminoquinoline (0.74 g).

This compound may also be prepared from 4-hydroxy-6-methoxyquinoline by chlorination with phosphorus oxychloride, to give the 4-chloroquinoline, followed by treatment with n-propylamine hydrochloride.

(b) [4-(6-Methoxy-quinolin-4-ylcarbamoyl)-cyclohexyl]-carbamic acid tert-butyl ester Amine (11a) (4.31 g, 24.77 mmol), 4-trans-tert-butoxycarbonylamino-cyclohexanecarboxylic acid (6.02 g, 24.77 mmol) and O-(7-azabenzotriazol-1-yl)-N,N,N',N'-tetramethyluronium hexafluorophosphate (9.41 g, 24.17 mmol) were combined as a slurry in N,N'-dimethylformamide (100 mL). To this mixture was added triethylamine (6.89 mL, 49.54 mmol) and the reaction vessel was heated to 60° C. for 10 hours. After this period the solvent was removed under vacuum and the residue partitioned between ethyl acetate (2×200 mL) and brine (50 mL). The organic phases were combined and dried over magnesium sulfate after which they were concentrated in vacuo. The resulting oil was purified by column chromatography on silica gel using a dichloromethane and methanol solvent gradient. This provided the desired compound as a white solid (9.50 g, 96%).

MS (APCI+) m/z 400 (+).

(c) 4-Amino-cyclohexanecarboxylic acid (6-methoxy-quinolin-4-yl)-amide

Amide (11b) (13.0 g, 32.58 mmol) was dissolved in dichloromethane (200 mL). To this solution was added trifluoroacetic acid (50 mL) and the resulting mixture stirred at room temperature for 3 hours. The volatiles were removed under reduced pressure and the residue was treated with 4M hydrochloric acid in 1,4-dioxan (100 mL). The resulting solid was isolated by filtration and stirred over potassium carbonate (12.66 g, 91.75 mmol) in a mixture of chloroform and 15% methanol (2×150 mL). The slurry was filtered and the filtrate concentrated under vacuum to provide the desired compound as an off white solid (6.00 g, 62%).

MS (APCI+) m/z 300 (MH+)

(d) Title Compound

Amine (11c) (200 mg, 0.667 mmol) was dissolved in N,N'-dimethylformamide (10 mL). To this solution was added potassium carbonate (276 mg, 2.00 mmol) methanesulfonic acid 2,3-dihydro-benzo[1,4]dioxin-6-ylmethyl ester (5b) (488 mg, 2.00 mmol). The resulting suspension was stirred at room temperature for 10 hours and then at 60° C. for 2 hours. The reaction was concentrated under vacuum and the residue partitioned between ethyl acetate (2×100 mL) and an aqueous solution of saturated sodium hydrogen carbonate (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (87 mg, 48%).

δH (CDCl₃, 250 MHz), 8.68 (1H, d), 8.32 (1H, d), 8.30 (1H, bs), 8.00 (1H, d), 7.39 (1H, dd), 7.12 (1H, d), 6.84–6.76 (3H, m), 4.25 (4H, s), 3.93 (3H, s), 3.71 (2H, s), 2.58 (1H, m), 2.44 (1H, m), 2.20–2.01 (4H, m), 1.75–1.55 (2H, m), 1.25–1.10 (2H, m). MS (APCI+) m/z 448 (MH+).

The fumarate salt was prepared by the method of Example 2.

Example 12

Trans-4-[(Benzo[1,2,5]thiadiazol-5-ylmethyl)-amino]-cyclohexanecarboxylic acid (6-methoxy-quinolin-4-yl)-amide fumarate salt

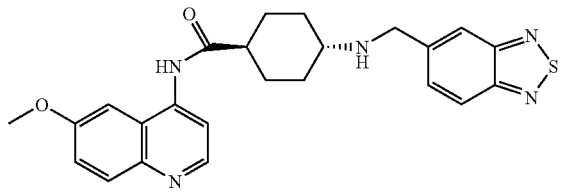

Amine (11c) (138 mg, 0.45 mmol) was dissolved in N,N'-dimethylformamide (3 mL). To this solution was added potassium carbonate (169 mg, 0.69 mmol) methanesulfonic acid benzo[1,2,5]thiadiazol-5-ylmethyl ester (2b) (169 mg, 0.69 mmol). The resulting suspension was stirred at room temperature for 10 hours. The reaction was concentrated under vacuum and the residue partitioned between ethyl acetate (2×100 mL) and brine (20 mL). The organic phases were combined and dried over magnesium sulfate. The volatiles were again removed under reduced pressure and the resulting oil was subjected to purification on silica gel using a methanol and dichloromethane gradient. This afforded the free base of the desired compound as a colourless oil (67 mg, 33%).

$\delta$H (CDCl$_3$, 250 MHz), 8.71 (1H, d), 8.16 (1H, d), 8.04 (1H, d), 7.95 (2H, m), 7.67–7.60 (2H, m), 7.22 (1H, dd), 7.00 (1H, d), 4.05 (2H, s), 3.98 (3H, s), 2.65 (1H, m), 2.44 (1H, m), 2.17 (4H, m), 1.75–1.71 (2H, m), 1.33–1.25 (2H, m). MS (+ve ion electrospray) m/z 448 (MH+).

The fumarate salt was prepared by the method of Example 2.

Example 13

Trans-4-[(2-Oxo-2,3-dihydro-1H-pyrido[2,3-b][1,4]thiazin-7-ylmethyl)-amino]-cyclohexanecarboxylic Acid (6-methoxy-[1,5]naphthyridin-4-yl)-amide oxalate salt

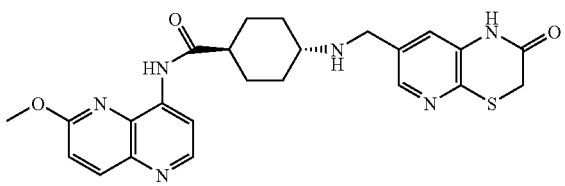

(a) 6-Methoxycarbonylmethylsulfanyl-5-nitro-nicotinic acid methyl ester

A solution of 6-chloro-5-nitro-nicotinic acid methyl ester (1.0 g) [prepared as described by A. H. Berrie et al. *J. Chem. Soc.* 2590–2594 (1951)] in dichloromethane (10 mL) containing triethylamine (0.76 mL) was treated with mercaptoacetic acid methyl ester (0.44 mL) and the solution was stirred at room temperature for 1 hour and evaporated to dryness. Sodium bicarbonate solution was added and the mixture was extracted with dichloromethane, dried (anhydrous sodium sulfate) and evaporated to afford a solid (1.0 g).

MS (+ve ion electrospray) m/z 287 (MH+).

(b) 2-Oxo-2,3-dihydro-1H-pyrido[2,3-b][1,4]thiazine-7-carboxylic acid methyl ester The ester (13a) (1.0 g) in acetic acid (50 mL) was treated with iron powder (10 g) and the mixture was stirred and heated at 60° C. for 1 hour, cooled and filtered. The filtrate was evaporated, treated with sodium bicarbonate solution and extracted with warm chloroform. It was dried (anhydrous sodium sulfate) and evaporated to give a white solid (0.85 g).

MS (+ve ion electrospray) m/z 225 (MH+).

(c) 2-Oxo-2,3-dihydro-1H-pyrido[2,3-b][1,4]thiazine-7-carboxylic acid

The ester (13b) (2.8 g) was hydrolysed with aqueous sodium hydroxide in tetrahydrofuran by the method of Example (4a) to afford a solid (2.5 g).

MS (–ve ion electrospray) m/z 209 (M–H$^-$).

(d) 7-Hydroxymethyl-1H-pyrido[2,3-b][1,4]thiazin-2-one

The carboxylic acid (13c) (2.48 g) was reacted with isobutylchloroformate and sodium borohydride by the method of Example (4b) to afford a solid (1.3 g), after recrystallisation from chloroform-methanol (9:1).

MS (+ve ion electrospray) m/z 197 (MH+).

(e) 2-Oxo-2,3-dihydro-1H-pyrido[2,3-b][1,4]thiazine-7-carboxaldehyde

The alcohol (13d) (1.22 g) was oxidised with manganese dioxide by the method of Example (4c) to afford a solid (0.7 g).

MS (–ve ion electrospray) m/z 193 (M–H$^-$).

(f) Title Compound

This was prepared from amine (1e) (200 mg) and carboxaldehyde (13e) (129 mg) by the method of Example (4d) to provide the free base of the desired compound as a colourless solid (138 mg).

$\delta$H (CDCl$_3$/CD$_3$OD 250 MHz), 8.65 (1H, d), 8.52 (1H, d), 8.22 (1H, d), 8.10 (1H, d), 7.28 (1H, d), 7.21 (1H, d), 4.15 (3H, s), 3.90 (2H, s), 3.60 (2H, s), 2.74 (1H, m), 2.52 (1H, m), 2.20 (4H, m), 1.70 (2H, m) 1.40 (2H, m). MS (+ve ion electrospray) m/z 479 MH+).

The oxalate salt was prepared by the method of Example 1

Example 14

Trans-4-[(2-Oxo-2,3-dihydro-1H-pyrido[2,3-b][1,4]thiazin-7-ylmethyl)-amino]-cyclohexanecarboxylic acid (6-methoxy-quinolin-4-yl)-amide oxalate salt

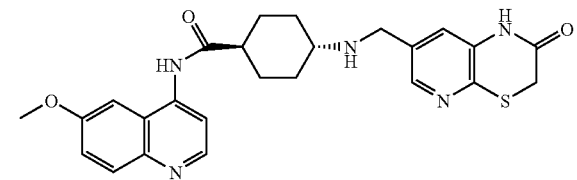

This was prepared from amine (11c) (200 mg) and carboxaldehyde (13e) (129 mg) by the method of Example (4d) to provide the free base of the desired compound as a colourless solid (43 mg).

$\delta$H (CDCl$_3$/CD$_3$OD 250 MHz), 8.55 (1H, d), 8.07 (1H, d), 8.02 (1H, d), 7.90 (1H, d), 7.43 (1H, d), 7.38 (1H, dd), 7.30 (1H, d), 3.97 (3H, s), 3.90 (2H, s), 3.55 (2H, s), 2.60 (2H, m), 2.10 (4H, m), 1.70 (2H, m) 1.30 (2H, m). MS (+ve ion electrospray) m/z 478(MH+).

The oxalate salt was prepared by the method of Example 1

Example 15

Trans-4-[(3,4-Dihydro-2H-benzo[1,4]oxazin-6-ylmethyl)-amino]-cyclohexanecarboxylic acid (6-methoxy-[1,5]naphthyridin-4-yl)-amide oxalate salt

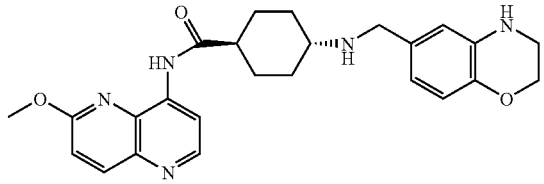

(a) (3,4-Dihydro-2H-benzo[1,4]oxazin-6-yl)-methanol

A solution of carboxaldehyde (8b) (1.45 g) in dry tetrahydrofuran (100 mL) was treated with a 1M solution of lithium aluminium hydride in diethyl ether (24 mL) and the mixture was heated under reflux for 18 hours. It was cooled and a solution of saturated sodium carbonate was added cautiously. Chloroform was added and anhydrous sodium sulfate and the mixture was stirred for 1 hour and filtered. The fitrate was evaporated to afford a white solid (0.70 g).

MS (−ve ion electrospray) m/z 164(M−H⁻).

(b) 3,4-Dihydro-2H-benzo[1,4]oxazine-6-carboxaldehyde and 4H-benzo[1,4]oxazine-6-carboxaldehyde A solution of the alcohol (15a) (0.22 g) in dichloromethane (10 mL) was stirred with manganese dioxide (0.6 g) for 6 hours. It was then filtered, evaporated and chromatographed on silica gel, eluting with chloroform, to give a mixture of two aldehydes as an oil (90 mg).

MS (+ve ion electrospray) m/z 162 and 164 (MH⁺)

(c) Title Compound

This was prepared from amine (1e) (165 mg) and the mixture of carboxaldehydes (15b) (90 mg) by the method of Example (4d). The product in tetrahydrofuran (15 mL) and methanol (15 mL) was treated with sodium cyanoborohydride (25 mg) for 18 hours. The mixture was evaporated, treated with water and extracted with chloroform-methanol (99:1), dried (sodium sulfate), evaporated and chromatographed on silica gel (chloroform then methanol-dichloromethane) to provide the title compound (free base) as a colourless solid (55 mg).

δH (CDCl₃/CD₃OD 250 MHz), 8.65 (1H, d), 8.50 (1H, d), 8.18 (1H, d), 7.22 (1H, d) 6.75 (2H, m), 6.60 (1H, dd), 4.25 (1H, m), 4.15 (3H, s), 3.92 (2H, s), 3.40 (4H, m), 3.00 (1H, m), 2.65 (1H, m), 2.25 (4H, m), 1.70 (4H, m). MS (+ve ion electrospray) m/z 448(MH+).

The oxalate salt was prepared by the method of Example 1

Example 16

Trans-4-[(Thiazolo[5,4-b]-pyridin-6-ylmethyl)-amino]-cyclohexanecarboxylic acid (6-methoxy-[1,5]naphthyridin-4-yl)-amide oxalate salt

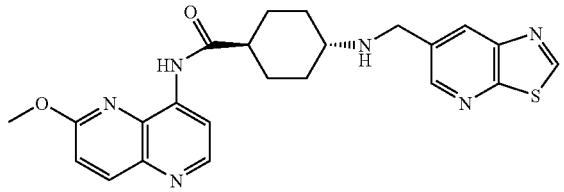

(a) 5-Amino-6-thioxo-1,6-dihydro-pyridine-3-carboxylic acid methyl ester

A mixture of sodium sulfide nonahydrate (2.17 g) and sulfur (0.29 g) was heated in boiling water (20 mL) until the solution was homogeneous and added to a solution of 6-chloro-5-nitro-nicotinic acid methyl ester (see Example 13a) (3.10 g) in methanol (50 mL) The mixture was boiled for 15 minutes and cooled. The resulting disulfide was collected and washed with water to give a yellow solid (2.46 g). The solid (5 g) in acetic acid (100 mL) and 4M HCl in dioxan (50 mL) was treated with zinc dust (12 g) and the mixture was stirred at room temperature for 30 minutes, filtered and evaporated to dryness. Sodium acetate and sodium sulfate were added and the mixture was extracted with warm chloroform and chromatographed on silica gel, eluting with chloroform then methanol-chloroform to afford a yellow solid (2.3 g).

MS (+ve ion electrospray) m/z 185(MH+)

(b) Thiazolo[5,4-b]pyridine-6-carboxylic acid methyl ester

The amine (16a) (0.7 g) was heated in formic acid (30 mL) under reflux for 30 minutes and was evaporated and chromatographed on silica gel (chloroform) to give a solid (0.65 g).

MS (+ve ion electrospray) m/z 195(MH+)

(c) Thiazolo[5,4-b]pyridin-6-yl-methanol

A solution of ester (16b) (200 mg) in dry tetrahydrofuran (15 mL) and dry diethyl ether (15 mL), cooled to −45° C., was treated with a 1M solution of lithium aluminium hydride in diethyl ether (1.55 mL) and the mixture was heated under reflux for 18 hours. It was cooled and an aqueous solution of saturated sodium carbonate was added cautiously. Dichloromethane and anhydrous sodium sulfate were added and the mixture was stirred for 15 minutes and filtered. The fitrate was evaporated to afford a white solid (95 mg).

MS (+ve ion electrospray) m/z 167(MH+)

(d) Thiazolo[5,4-b]pyridine-6-carboxaldehyde

The alcohol (16c) (65 mg) in chloroform (10 mL) was stirred with manganese dioxide (200 mg) for 5 hours, filtered and evaporated and chromatographed on silica gel, eluting with dichloromethane then chloroform, to give a solid (65 mg).

MS (+ve ion electrospray) m/z 165(MH+)

(e) Title Compound

This was prepared from amine (1e) (181 mg) and carboxaldehyde (16d) (90 mg) by the method of Example (4d) to provide the free base of the desired compound as a colourless solid (89 mg).

δH (CDCl₃ 250 MHz), 9.50 (1H, br.s) 9.15 (1H, s), 8.70 (2H, m), 8.55 (1H, d), 8.38 (1H, d), 8.25 (1H, d), 7.16 (1H, d), 4.12 (3H, s), 4.10 (2H, s), 2.70 (1H, m), 2.48 (1H, m), 2.20 (4H, m), 1.70 (2H, m) 1.40 (2H, m). MS (+ve ion electrospray) m/z 449(MH+).

The oxalate salt was prepared by the method of Example 1

Example 17

Trans-4-[(8-Hydroxy-1-oxo-1,2-dihydro-isoquinolin-3-ylmethyl)-amino]-cyclohexanecarboxylic acid (6-methoxy-[1,5]naphthyridin-4-yl)-amide dihydrochloride salt

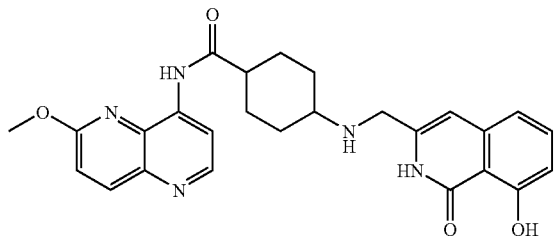

(a) Ethyl 2-methoxymethoxy-6-methylbenzoic acid

A solution of ethyl 2-hydroxy-6-methylbenzoic acid (4.56 g, 25.3 mmol) and diisopropylethylamine (13.2 mL, 76 mmol) in dry dichloromethane (30 mL) was cooled in an ice-bath. Chloromethyl methyl ether (3.83 mL, 50.6 mmol) was added slowly and the mixture was allowed to stand at 0° C., warming slowly to room temperature. After 36 hours a further portion of chloromethyl methyl ether (1.9 mL) was added and the mixture was left at room temperature overnight. The mixture was then washed with 10% citric acid, water and brine, dried and evaporated to give the title compound (6.34 g, 100%).

MS (+ve ion electrospray) m/z 225 (MH+).

(b) 8-Methoxymethoxy-1-oxo-1H-isochromene-3-carboxylic acid ethyl ester n-Butyllithium (1.6M in hexanes, 16.0 mL, 25.5 mmol) was added to a solution of diisopropylamine (3.64 mL, 25.5 mmol) and N,N,N',N'-tetramethylethylenediamine (4.01 mL, 25.5 mmol) in dry tetrahydrofuran (36 mL) at −78° C. After 10 min a solution of the ester (17a, 5.10 g, 22.8 mmol) in dry tetrahydrofuran (18 mL) was added dropwise, keeping the internal temperature <−60° C. The deep red solution was stirred at −78° C. for 40 min, then diethyl oxalate (3.10 mL, 22.8 mmol) in tetrahydrofuran (18 mL) was added over 5 min. The mixture was stirred at −78° C. for 6.5 hours, then treated with 10% citric acid. After warming to room temperature the phases were separated and the aqueous phase was extracted with ethyl acetate. The combined organic phases were washed with brine, dried and evaporated. Chromatography on silica gel (20–40% ethyl acetate/hexane) gave the title compound (2.05 g, 32%).

MS (+ve ion electrospray) m/z 235 (loss of methoxymethyl from MH+).

(c) 8-Methoxymethoxy-1,2-dihydro-1-oxo-isoquinoline-3-carboxylic acid ethyl ester The isochromene (17b, 2.04 g, 7.34 mmol) was heated under reflux with ammonium acetate (4.99 g) in ethanol (200 mL) for 24 hours. Solvent was evaporated and the residue was dissolved in ethyl acetate and water. The aqueous phase was extracted with ethyl acetate and combined organics were washed with water, dried and evaporated. Chromatography on silica gel (50–100% ethyl acetate/hexane) gave impure product and recovered isochromene. The latter was treated again with ammonium acetate (1.3 g) in refluxing ethanol (50 mL) for 48 hours, then worked up as before. The crude material was combined with the initial impure product for chromatography on silica gel (0–2% methanol/dichloromethane). Eluted material was re-chromatographed (50–100% ethyl acetate/hexane) to give the title compound (0.87 g, 42%).

MS (+ve ion electrospray) m/z 278 (MH+).

(d) 8-Hydroxy-3-hydroxymethyl-2H-isoquinolin-1-one

The ester (17c, 0.66 g, 2.38 mmol) and sodium borohydride (0.14 g, 3.6 mmol) were heated in refluxing tert-butanol (3 mL) while methanol (0.6 mL) was added over 1 hour. Heating was continued for 2 hours, then the cooled mixture was partitioned between ethyl acetate and water. The aqueous phase was re-extracted with ethyl acetate and the combined organics were washed with brine, dried and evaporated to give the title compound (0.51 g, 91%).

MS (+ve ion electrospray) m/z 236 (MH+).

(e) 8-Methoxymethoxy-1,2-dihydro-1-oxo-isoquinoline-3-carboxaldehyde

The alcohol (17d, 0.51 g, 2.17 mol) was stirred with manganese (IV) oxide (3.12 g) in 1:1 dichloromethane/tetrahydrofuran (40 mL) at room temperature for 5 hours. The mixture was filtered and evaporated to give the aldehyde (0.32 g, 63%).

MS (−ve ion electrospray) m/z 232 (M−H⁻).

(f) 4-[(8-Methoxymethoxy-1-oxo-1,2-dihydro-isoquinolin-3-ylmethyl)-amino]-cyclohexanecarboxylic acid (6-methoxy-[1,5]naphthyridin-4-yl)-amide The aldehyde (17e, 0.23 g, 0.99 mol) and amine (1e, 0.30 g, 1 mmol) were heated with 3 Å molecular sieves under reflux in dry chloroform (8 mL) and methanol (1 mL) for 7 hours. After cooling, sodium triacetoxyborohydride (1.06 g, 5 mmol) was added and the mixture was stirred at room temperature for 3 days. Water and dichloromethane were added, the aqueous phase was basified with sodium carbonate and extracted with dichloromethane. Combined organics were washed with water, dried and evaporated. Chromatography on silica gel (2–10% methanol/dichloromethane) gave the title compound (0.157 g, 30%).

MS (+ve ion electrospray) m/z 518 (MH+).

(g) Title Compound

The methoxymethyl compound (17f, 0.157 g, 0.3 mmol) was partially dissolved in 5M hydrochloric acid (10 mL) and 1,4-dioxane (10 mL) and stirred at room temperature for 3.5 hours. Evaporation to dryness gave the title compound (0.16 g, 98%).

δH (CDCl₃, 250 MHz), 12.88 (1H, br s), 11.92 (1H, s), 10.30 (1H, s), 9.69 (1H, br s), 8.91 1H, d), 8.68 (1H, d), 8.50 (1H, d), 7.59 (2H, m), 7.09 (1H, d), 6.92 (1H, s), 6,86 (1H, d), 4.24 (3H, s), 4.16 (2H, m), 3.19 (1H, m), 2.29 (1H, m), 2.26 (2H, m), 2.15 (2H, m), 1.59 (4H, m). MS (+ion electrospray) m/z: 474 (MH⁺).

Example 18

Trans-4-[(2,3-Dihydro-[1,4]dioxino[2,3-b]pyridin-6-ylmethyl)-amino]-cyclohexanecarboxylic acid (6-methoxy-[1,5]naphthyridin-4-yl)-amide oxalate salt

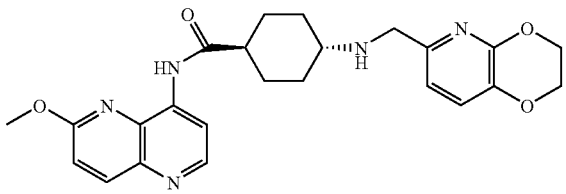

(a) 2-(2-Iodo-6-methyl-pyridin-3-yloxy)-ethanol

2-Iodo-6-methyl-pyridin-3-ol (6.49 g, 27.6 mmol) was dissolved in an aqueous solution of sodium hydroxide (1M, 30 mL). 2-bromoethanol (3.91 mL, 55.2 mmol) was added dropwise and then the solution was heated to 100° C. for 3 hours. The resulting mixture was extracted with chloroform (2×200 mL) and the combined organic phases then back extracted with aqueous sodium hydroxide solution (1M, 50 mL). The organic phase was dried over magnesium sulfate and the volatiles removed in vacuo to afford the desired product (5.26 g) which was used without further purification.

MS (APCI+) m/z 210 (MH+).

(b) 6-Methyl-2,3-dihydro-[1,4]dioxino[2,3-b]pyridine

Alcohol (18a) (6.52 g, 23.37 mmol) was dissolved in N,N'-dimethylformamide (30 mL) and cooled to 0° C. To this was added sodium hydride (60% w/w, 1.12 g, 28.04 mmol), powdered copper (0.62 g, 9.82 mmol) and copper (II)sulfate (1.87 g, 11.69 mmol). The resulting slurry was heated to 100° C. for 18 hours and then the solvent removed under reduced pressure. The residue was partitioned between ethyl acetate (2×100 mL) and water (25 mL). The organic phases were combined and dried over magnesium sulfate then the volatiles removed in vacuo. The residue was subjected to purification on silica gel using a dichloromethane and methanol gradient. This afforded the desired product as a brown crystalline solid (480 mg, 14%).

MS (APCI+) m/z 152 (MH+).

(c) 6-Methyl-2,3-dihydro-[1,4]dioxino[2,3-b]pyridine-N-oxide

Pyridyldioxin (18b) (190 mg, 1.26 mmol) was dissolved in dichloromethane (10 mL) and cooled to 0° C. To this solution was added meta-chloroperbenzoic acid (388 mg, 1.26 mmol) and stirring was continued for 5 hours at room temperature. The volatiles were removed under reduced pressure and the residue purified on silica gel using a dichloromethane and methanol gradient. This provided the desired compound as a white solid (146 mg, 69%).

MS (APCI+) m/z 168 (MH+).

(d) Acetic Acid 2,3-dihydro-[1,4]dioxino[2,3-b]pyridin-6-ylmethyl ester

N-oxide (18c)(146 mg, 0.874 mmol) was dissolved in acetic anhydride (5 mL). The solution was heated to reflux for 10 hours after which time the volatiles were removed. This afforded the desired product which was used without further purification.

(e) (2,3-Dihydro-[1,4]dioxino[2,3-b]pyridin-6-yl)-methanol

Ester (18d) (182 mg, 0.87 mmol) was dissolved in a mixture of tetrahydrofuran and water (1:1, 4 mL) and treated with sodium hydroxide (70 mg, 1.74 mmol). The resulting solution was stirred at room temperature for 12 hours after which time the solvent was removed under reduced pressure. The product obtained in this fashion was used without further purification.

(f) 2,3-Dihydro-[1,4]dioxino[2,3-b]pyridine-6-carbaldehyde

Alcohol (18e) (145 mg, 0.87 mmol) was dissolved in dichloromethane (5 mL) and treated with manganese dioxide (151 mg, 1.74 mmol). The resulting slurry was stirred at room temperature and after 5 hours a further batch of manganese dioxide (151 mg, 1.74 mmol) was added. The slurry was stirred for a further 10 hours and then filtered through Celite and the volatiles removed in vacuo. The residue was purified on silica gel to afford the desired product (95 mg, 66%).

MS (APCI+) m/z 166 (MH+).

(g) Title Compound

This was prepared from amine (1e) (260 mg, 0.864 mmol) and carboxaldehyde (18f) (95 mg, 0.576 mmol) by the method of Example (4d) to provide the free base of the desired compound as a colourless solid (220 mg, 85%).

δH (CDCl₃, 250 MHz), 9.48 (1H, s), 8.67 (1H, d), 8.50 (1H, d), 8.24 (1H, d), 7.18 (1H, d), 7.14 (1H, d), 6.91 (1H, d), 4.45 (2H, m), 4.27 (2H, m), 4.13 (3H, s), 3.99 (2H, s), 2.76 (1H, m), 2.45 (1H, m), 2.20–2.15 (4H, m), 1.74–1.51 (4H, m). MS (+ve ion electrospray) m/z 450 (MH+).

The oxalate salt was prepared by the method of Example 1.

Example 19

Trans-4-[(2,3-Dihydro-[1,4]dioxino[2,3-c]pyridin-7-ylmethyl)-amino]-cyclohexanecarboxylic acid (6-methoxy-[1,5]naphthyridin-4-yl)-amide oxalate salt

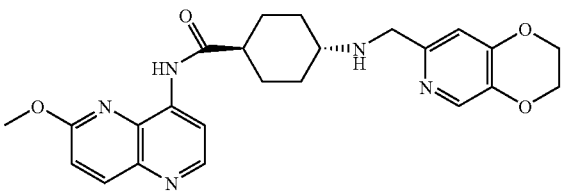

(a) 4,5-Dihydroxy-pyridine-2-carboxylic acid ethyl ester 4,5-Dihydroxy-pyridine-2-carboxylic acid (844 mg, 5.45 mmol) was dissolved in ethanol (20 mL). Gaseous hydrochloric acid was bubbled through the mixture for 5 minutes whilst it was cooled in an ice bath. The solution was then heated to reflux for 2 hours. This procedure was repeated a further two times and then the mixture heated for 24 hours. The volatiles were removed in vacuo and water added (5 mL). This was also removed under reduced pressure. The hydrochloride salt of the desired product was produced in this way and used without further purification.

MS (APCI+) m/z 184 (MH+).

(b) 2,3-Dihydro-[1,4]dioxino[2,3-c]pyridine-7-carboxylic acid ethyl ester

Ester (19a) (540 mg, 2.95 mmol) was dissolved in N,N'-dimethylformamide and potassium carbonate (1.22 g, 8.85 mmol) was added. The mixture was slurried by stirring rapidly and 1,2-dibromoethane (0.51 mL, 5.90 mmol) was added. The reaction was heated to 70° C. for 10 hours after which time the solvent was removed under reduced pressure. The residue was subjected to column chromatography on silica gel using a dichloromethane and methanol gradient. This provided the desired compound as a brown solid (284 mg, 46%).

MS (APCI+) m/z 210 (MH+).

(c) (2,3-Dihydro-[1,4]dioxino[2,3-c]pyridin-7-yl)-methanol

Pyridyldioxin (19b) (284 mg, 1.36 mmol) was dissolved in tetrahydrofaran (10 mL) and cooled to −30° C. A solution of lithium aluminium hydride (1M, 2.72 mL, 2.72 mmol) was added dropwise. The solution was allowed to warm to room temperature over 2 hours after which time the reaction was quenched by the addition of water (2 mL). The volatiles were removed in vacuo and the residue partitioned between ethyl acetate/chloroform (2×200 mL) and a saturated solution of sodium hydrogen carbonate (20 mL). The organic phases were combined and dried over magnesium sulfate. The solvent was removed under reduced pressure and the residue purified on silica gel using a methanol and dichloromethane solvent gradient. This provided the desired compound as a colourless oil (98 mg, 43%).

MS (APCI+) m/z 168 (MH+).

(d) 2,3-Dihydro-[1,4]dioxino[2,3-c]pyridine-7-carbaldehyde

Alcohol (19c) (98 mg, 0.587 mmol) was dissolved in dichloromethane (10 mL) and manganese dioxide (152 mg, 1.76 mmol) was added. The slurry was stirred at room temperature for 3 hours and then another batch of manganese dioxide (152 mg, 1.76 mmol) added. After 10 hours further stirring at room temperature the oxidant was removed by filtration through Celite and the solvent removed under reduced pressure to provide the desired product which was used without further purification.

MS (APCI+) m/z 166 (MH+).

(e) Title Compound

This was prepared from amine (1e) (176 mg, 0.587 mmol and aldehyde (19f) (65 mg, 0.392 mmol) by the method of Example (4d) to provide the free base of the desired compound as a colourless solid (120 mg, 68%).

δH (CDCl₃, 250 MHz), 9.47 (1H, s), 8.69 (1H, d), 8.53 (1H, d), 8.25 (1H, d), 8.08 (1H, s), 7.16 (1H, d), 6.87 (1H, s), 4.40–4.30 (4H, m), 4.13 (3H, s), 4.04 (2H, s), 2.77 (1H, m), 2.48 (1H, m), 2.30–2.06 (4H, m), 1.69–1.57 (4H, m). MS (+ve ion electrospray) m/z 450 (MH+).

The oxalate salt was prepared by the method of Example 1.

Example 20

Trans-4-[(2,3-Dihydro-[1,4]dioxino[2,3-b]pyridin-7-ylmethyl)-amino]-cyclohexanecarboxylic acid (6-methoxy-[1,5]naphthyridin-4-yl)-amide oxalate salt

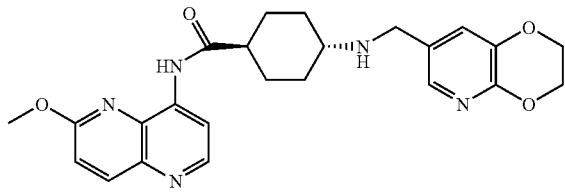

(a) 5-Bromo-pyridine-2,3-diol

This compound was made according to the procedure of Dallacker, F; Fechter, P; Mues, V Journal Z. Naturforsch, 1979, 34b, 1729–1736 from 2-furaldehyde.

MS (APCI+) m/z 190/192 (MH+).

(b) 7-Bromo-2,3-dihydro-[1,4]dioxino[2,3-b]pyridine

Diol (20a) (13.50 g, 71.43 mmol) was treated in a similar manner to Example (19b) to obtain the desired compound as a brown oily solid (1.14 g, 7%).

MS (APCI+) m/z 216/218 (MH+).

(c) 2,3-Dihydro-[1,4]dioxino[2,3-b]pyridine-7-carboxylic Acid Butyl Ester

Bromide (20b) was slurried in butanol at room temperature and degassed with a stream of carbon monoxide gas for 10 minutes. 1,8-diazabicyclo[5.4.0]undec-7-ene (0.50 mL, 3.38 mmol), palladium dichloride (30 mg, 0.169 mmol) and 1,3-bis(diphenylphosphino)propane (139 mg, 0.338 mmol) was added. The mixture was heated to 100° C. under an atmosphere of carbon monoxide for 12 hours. The volatiles were then removed under reduced pressure and the residue partitioned between ethyl acetate (2×100 mL) and water (20 mL). The organic phases were combined and dried over magnesium sulfate. The solvent was once again removed in vacuo and the residue subjected to purification on silica gel employing an ethyl acetate and hexane solvent gradient. This provided the desired product as a colourless oil (0.436 g, 54%).

MS (APCI+) m/z 238 (MH+).

(d) (2,3-Dihydro-[1,4]dioxino[2,3-b]pyridin-7-yl)-methanol

Ester (20c) was dissolved in tetrahydrofuran (10 mL). The solution was cooled to 0° C. and a solution of lithium aluminium hydride in tetrahydrofuran (1M, 3.68 mL, 3.68 mmol) was added dropwise. The reaction was stirred at 0° C. for 1 hour and then quenched by the addition of water (2 mL). The volatiles were removed in vacuo and the residue partitioned between ethyl acetate (3×100 mL) and water (20 mL). The organic phases were combined and concentrated to provide the desired compound which was used-without further purification (320 mg).

MS (APCI+) m/z 168 (MH+).

(e) 2,3-Dihydro-[1,4]dioxino[2,3-b]pyridine-7-carbaldehyde

The alcohol (20d) was transformed into an aldehyde according to the procedure used in Example (19d). This provided the desired compound as a colourless oil (282 mg, 89%).

MS (APCI+) m/z 166 (MH+).

(f) Title Compound

This was prepared from amine (1e) (252 mg, 0.836 mmol) and aldehyde (20e) (138 mg, 0.836 mmol) by the method of Example (4d) to provide the free base of the desired compound as a colourless solid (195 mg, 52%).

δH (CDCl₃, 250 MHz), 9.50 (1H, s), 8.67 (1H, d), 8.51 (1H, d), 8.25 (1H, d), 7.79 (1H, d), 7.30 (1H, d), 7.15 (1H, d), 4.50 (2H, m), 4.27 (2H, m), 4.13 (3H, s), 3.84 (2H, s), 2.73 (1H, m), 2.48 (1H, m), 2.20–2.10 (4H, m), 1.72–1.60 (2H, m), 1.55–1.40 (2H, m). MS (+ve ion electrospray) m/z 450 (MH+).

The oxalate salt was prepared by the method of Example 1.

Example 21

Trans-6-({4-[2-Hydroxy-2-(6-methoxy-quinolin-4-yl)-ethyl]-cyclohexylamino}-methyl)-4-H-benzo[1,4]thiazin-3-one oxalate salt

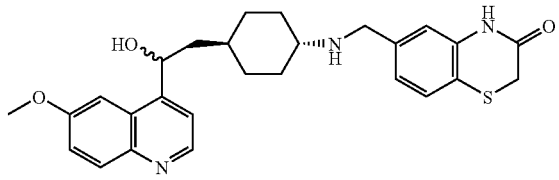

(a) 2-(4-tert-Butoxycarbonylamino-cyclohexyl)-3-(6-methoxy-quinolin-4-yl)-3-oxo-propionic acid methyl ester (4-Tert-Butoxycarbonylamino-cyclohexyl)-acetic acid methyl ester (1.00 g, 3.69 mmol) was dissolved in tetrahydrofuran (20 mL) and cooled to −78° C. To the solution lithium hexamethyldisilazide in tetrahydrofuran (1M, 11.0 mL, 11.0 mmol) was added dropwise. The reaction mixture was stirred for 20 minutes at −78° C. and then 6-methoxy-quinoline-4-carboxylic acid methyl ester (1.60 g, 7.38 mmol) was added as a solution in tetrahydrofuran (10 mL). The mixture was allowed to warm to room temperature and stirred for 12 hours. The reaction was quenched by the addition of water (2 mL), the solvent removed in vacuo and the residue partitioned between ethyl acetate (2×100 mL) and water (20 mL). The pH of the aqueous phase was adjusted to 10 to obtain the maximum degree of extracted material into the organic phases. The organic phases were combined, dried over magnesium sulfate and the volatiles removed under suction. The resulting residue was purified by column chromatography on silica gel using an ethyl acetate and hexane solvent gradient to provide the desired compound as a colourless oil (190 mg, 12%).

MS (APCI+) m/z 457 (MH+).

(b) 2-(4-Amino-cyclohexyl)-1-(6-methoxy-quinolin-4-yl)-ethanone hydrochloride

Ketone (21a) (190 mg, 0.42 mmol) was dissolved in an aqueous solution of hydrochloric acid (5M, 10 mL). The solution was refluxed under argon for 5 hours and then the volatiles were removed in vacuo. This provided the desired product as a hydrochloride salt (154 mg).

MS (APCI+) m/z 299 (MH+).

(c) {4-[2-(6-Methoxy-quinolin-4-yl)-2-oxo-ethyl]-cyclohexyl}-carbamic acid tert-butyl ester Amine hydrochloride (21b) (2.77 g, 8.28 mmol) was dissolved in dichloromethane (20 mL), triethylamine (3.46 mL, 24.84 mmol) was then added. Di-tert butyl dicarbonate (1.80 g, 8.28 mmol) was added to the solution and the reaction mixture stirred at room temperature for 6 hours. The organic phase was extracted with a saturated solution of sodium hydrogen carbonate (20 mL). The organic phase was dried over magnesium sulfate and the volatiles removed in vacuo. The residue was purified on silica gel using a dichloromethane and methanol solvent gradient. This provided the desired product as a colourless oil.

MS (APCI+) m/z 399 (MH+).

(d) {4-[2-Hydroxy-2-(6-methoxy-quinolin-4-yl)-ethyl]-cyclohexyl}-carbamic acid tert-butyl ester Ketone (21c) (862 mg, 2.17 mmol) was dissolved in iso-propanol (10 mL) and the solution cooled to 0° C. To this, sodium borohydride (125 mg, 3.25 mmol) was added and the resulting slurry stirred at 0° C. for 3 hours. The volatiles were removed under reduced pressure and the residue partitioned between ethyl acetate (2×100 mL) and water (20 mL). The organic phases were combined and dried over magnesium sulfate and then the solvent removed in vacuo. This provided the desired compound which was used without further purification.

MS (APCI+) m/z 401 (MH+).

(e) Title Compound

Alcohol (21d) was dissolved in dichloromethane, cooled to 0° C. and treated with trifluoroacetic acid. The solution was stirred at room temperature for 3 hours and then concentrated under vacuum. The residue was treated with an aqueous solution of sodium hydroxide (1M, 10 mL) and then concentrated in vacuo. The residue was dissolved in chloroform (10 ml) and methanol (5 mL), aldehyde (4c) (170 mg; 0.825 mmol) added, and the mixture was heated at reflux with 3 Å molecular sieves (2 g) for 12 hours. The slurry was then cooled and sodium triacetoxyborohydride (525 mg, 2.48 mmol) adde. This was stirred at room temperature for 48 hours. The slurry was filtered through Celite and concentrated in vacuo. The residue was purified by column chromatography on silica gel employing a dichloromethane and methanol solvent gradient. This provided the desired product as a white solid (226 mg, 57%).

δH (CD$_3$OD, 250 MHz), 8.66 (1H, d), 7.95 (1H, d), 7.66 (1H, d), 7.44–7.33 (3H, m), 7.13 (1H, dd), 7.07 (1H, d), 5.50 (1H, m), 4.18 (2H, s), 3.95 (3H, s), 3.44 (2H, s), 3.14–3.09 (1H, m), 2.36–2.19 (3H, m), 1.91–1.65 (4H, m), 1.55–1.40 (2H, m), 1.25–1.05 (2H, m). MS (APCI+) m/z 478(MH+).

The oxalate salt was prepared by the method of Example 1.

Example 22

Trans-2-{4-[(2,3-Dihydro-benzo[1,4]dioxin-6-ylmethyl)-amino]-cyclohexyl}-1-(6-methoxy-quinolin-4-yl)-ethanol oxalate salt

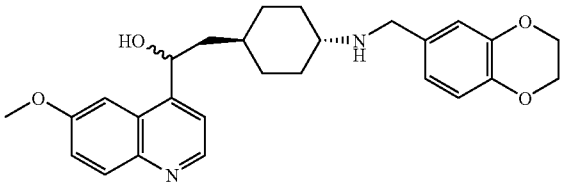

(a) 2-{4-[(2,3-Dihydro-benzo[1,4]dioxin-6-ylmethyl)-amino]-cyclohexyl}-1-(6-methoxy-quinolin-4-yl)-ethanone Amine hydrochloride (21b) (233 mg, 0.697 mmol) was dissolved in N,N'-dimethylformamide (5 mL). To the solution potassium carbonate (289 mg, 2.09 mmol) was added followed by mesylate (5b) (256 mg, 1.045 mmol). The mixture was stirred at room temperature for 10 hours and then the volatiles were removed in vacuo. The residue was purified by column chromatography on silica gel using a methanol and dichloromethane solvent gradient. This provided the desired product as a colourless oil (42 mg, 14%).

MS (APCI+) m/z 447(MH+).

(b) Title Compound

Ketone (22a) was dissolved in iso-propanol (1 mL) and cooled to 0° C. The solution was treated with sodium borohydride (7 mg, 0.168 mmol). Stirring was continued at room temperature for 10 hours and then the volatiles removed under reduced pressure. The residue was purified on silica gel using a dichloromethane and methanol solvent gradient. This provided the free base of the desired compound as a colourless oil. (25 mg, 50%).

δH (CDCl$_3$, 250 MHz), 8.71 (1H, d), 8.01 (1H, d), 7.55 (1H, d), 7.36 (1H, dd), 7.15 (1H, d), 6.76 (3H, m), 5.42 (1H, dd), 4.22 (4H, s), 3.92 (3H, s), 3.69 (2H, s), 2.59–2.50 (2H, m), 2.21–2.08 (1H, m), 2.08–1.95 (2H, m), 1.85–1.60 (4H, m), 1.35–1.20 (2H, m), 1.17–1.00 (2H, m). MS (APCI+) m/z 449 (MH+).

The oxalate salt was prepared according to the method in Example 1.

Example 23

Trans-4-[(6-Nitro-benzo[1,3]dioxol-5-ylmethyl)-amino]-cyclohexanecarboxylic acid (6-methoxy-[1,5]naphthyridin-4-yl)-amide oxalate salt

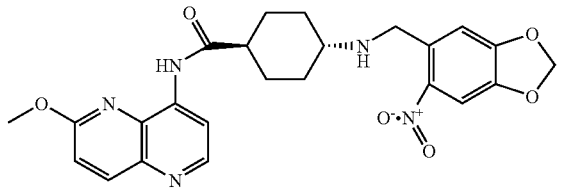

A solution of amine (1e) (0.3 g, 1 mmol) and 6-nitro-benzo[1,3]dioxole-5-carbaldehyde (0.21 g, 1.1 mmol) in chloroform/methanol (2 ml/1 ml) was stirred for 1 h. The resulting precipitate (imine) was dissolved by the addition of more methanol (3 ml) and treated with sodium borohydride (80 mg, 2.2 mmol). After 1 h the mixture was partitioned between chloroform and water. The organic extract was dried and evaporated to give an oil (0.4 g). Chromatography on silica eluting with a methanol-ethyl acetate gradient afforded the free base of the title compound (0.16 g, 33%).

δH (CDCl$_3$, 250 MHz), 9.50 (1H, bs), 8.70 (1H, d), 8.55 (1H, d), 8.20 (1H, d), 7.50 (1H, d), 7.15 (1H, d), 7.10 (1H, s), 6.10 (2H, s), 4.15 (3H, s), 4.00 (2H, s), 2.65–2.60 (1H, m), 2.40–2.35 (1H, m), 2.20–2.10 (4H, m), 1.80–1.60 (2H, m), 1.30–1.20 (2H, m). MS (+ve ion electrospray) m/z 480 (MH+).

This was converted to the oxalate salt according to the procedure of Example 1.

Example 24

Trans-4-[(6-Amino-benzo[1,3]dioxol-5-ylmethyl)-amino]-cyclohexanecarboxylic acid (6-methoxy-[1,5]naphthyridin-4-yl)-amide dioxalate salt

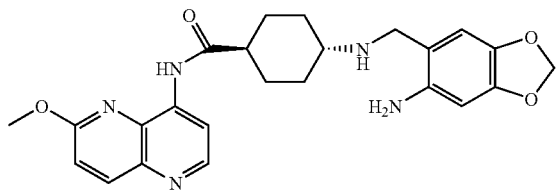

This was prepared from nitro compound (23a) (100 mg, 0.223 mmol) by hydrogenation in the presence of 10% palladium metal on a carbon support (20 mg). After 5 hours the catalyst was removed by filtration through Celite and the solvent removed under reduced pressure. The residue was purified by column chromatography on silica gel using a methanol and dichloromethane solvent gradient. This provided the free base of the desired compound as a colourless oil (56 mg, 60%).

δH (CDCl$_3$, 250 MHz), 9.50 (1H, s), 8.70 (1H, d), 8.51 (1H, d), 8.22 (1H, d), 7.16 (1H, d), 6.59 (1H, s), 6.29 (1H, d), 5.86 (2H, s), 4.12 (3H, m), 3.78 (2H, s), 2.60 (1H, m), 2.43 (1H, m), 2.21–2.15 (4H, m), 1.75–1.61 (2H, m), 1.32–1.26 (2H, m). MS (APCI+) m/z 450 (MH+).

The dioxalate salt was prepared by a method analogous to that of Example 1.

Example 25

Trans-4-[(Benzothiazol-5-ylmethyl)-amino]cyclohexanecarboxylic acid(6-methoxy-[1,5]naphthyridine-4-yl)amide oxalate salt

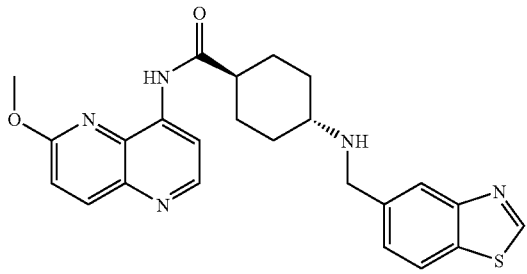

(a) Benzothiazol-5-ylcarboxylic acid

4-Chloro-3-nitrobenzoic acid (22 g, 0.11 mol) was suspended in water, sodium hydroxide (4.33 g, 0.11 mol) and sodium sulfide hydrate (32 g) were added, and the mixture heated at reflux for 24 hours. After acidification with 5M hydrochloric acid the mixture was extracted with ethyl acetate. The extracts were dried over magnesium sulfate and evaporated under reduced pressure. The product from this reaction (1 g, 5.9 mmol) was dissolved in formic acid and heated at reflux in the presence of zinc (0.1 g) for 6 hours. The mixture was allowed to cool and was concentrated under reduced pressure. The residue was diluted with water and neutralised with saturated aqueous sodium hydrogen carbonate. Extraction with tetrahydrofuran and ethyl acetate (1:1) gave a pale yellow solid (0.48 g) that was purified on silica gel using a methanol dichloromethane gradient.

(b) Benzothiazol-5-ylcarbaldehyde.

This was prepared from carboxylic acid 23(b) by the method of 4(b) and (c).

δH (CDCl$_3$ 250 MHz), 10.17 (1H, d), 9.14 (1H, s), 8.60 (1H, d), 8.12 (1H, d), 8.00 (1H, dd), (c) Title Compound Amine (1e) (0.20 g, 0.66 mmol) and benzothiazol-5-ylcarbaldehyde (0.11 g, 0.67 mmol) were heated at reflux in methanol (1 mL) and chloroform (4 mL) in the presence of 3 Å sieves for 8 hours. The mixture was then cooled to room temperature and sodium triacetoxyborohydride (0.4 g) added. After 24 hours further sodium triacetoxyborohydride (0.3 g) was added and a further addition (0.2 g) was made after another 8 hours. After stirring for 14 hours the mixture was diluted with methanol and solid sodium hydrogen carbonate added. After stirring for 0.25 hours the mixture was filtered and evaporated. Purification on silica gel eluting with methanol dichloromethane mixtures gave the free base of the title compound (0.143 g, 48%).

δH (CDCl$_3$,250 MHz), 9.45 (1H, s), 9.02 (1H, s), 8.68 (1H, d), 8.58–8.39 (2H,m), 8.26 (1H, d), 8.17 (1H, d), 7.97 (1H, d), 7.54 (1H, dd), 7.17 (1H, d), 4.20–4.07 (2H, m), 4.13 (3H, s), 2.95–2.80 (1H, m), 2.53–237 (1H, m), 2.33–2.00 (4H, m), 1.72–1.49 (4H, m). MS (APCI+) m/z 448 (MH+).

The oxalate salt was prepared by the method of Example 1.

Example 26

Trans-4-[(4-Oxo-4 H pyrido[1,2-a]pyrimidin-2-ylmethyl)-amino]-cyclohexanecarboxylic acid (6-methoxy-[1,5]naphthyridin-4-yl)-amide oxalate salt

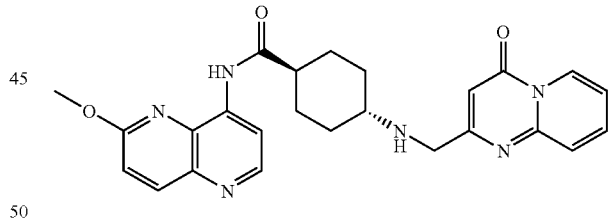

A mixture of amine (1e) (0.5 g, 1.7 mmol) and 2-chloromethyl-pyrido[1,2-a]pyrimidin-4-one (0.32 g, 1.7 mmol) (prepared by the method of W. Boehme and K. Heinrich, Arch Pharm, 1977, 310, 26) and potassium carbonate (0.25 g, 1.8 mmol) in N,N-dimethylformamide (15 ml) was heated at 40° C. for 16 h. The mixture was partitioned between ethyl acetate and water. The organic extract was dried and evaporated. Chromatography on silica gel eluting with a methanol-ethyl acetate gradient afforded the free base of the title compound as an oil (0.17 g, 22%).

δH (CDCl$_3$, 250 MHz), 9.50 (1H, bs), 9.00 (1H, d), 8.70 (1H, d), 8.55 (1H, d), 8.20 (1H, d), 7.70 (1H, m), 7.60 (1H, d), 7.20–7.10 (2H, m), 6.55 (1H, s), 4.10 (3H, s), 3.90 (2H, s), 2.65–2.60 (1H, m), 2.40–2.35 (1H, m), 2.20–2.10 (4H, m), 1.80–1.60 (2H, m), 1.30–1.20 (2H, m), MS (+ve ion electrospray) m/z 459 (MH+).

Example 27

Trans-2-{4-[(2,3-Dihydro-benzo[1,4]dioxin-6-ylmethyl)-amino]-cyclohexyl}-1-(6-methoxy-quinolin-4-yl)-ethanone oxalate salt

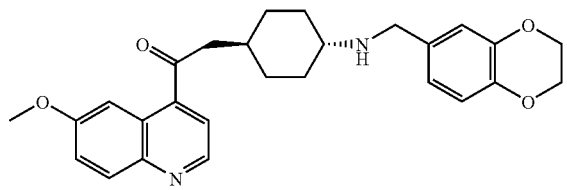

Amine hydrochloride (21b) (233 mg, 0.697 mmol) was dissolved in N,N-dimethylformamide (5 mL). To this was added potassium carbonate (289 mg, 2.09 mmol) and mesylate (5b) (256 mg, 1.045 mmol). The resulting slurry was stirred at room temperature for 48 hours and then the solvent was removed under reduced pressure. The residue was purified by column chromatography on silica gel using a dichloromethane and methanol solvent gradient. This provided the desired compound as a colourless oil (42 mg, 14%).

δH (CDCl$_3$, 250 MHz), 8.85 (1H, d), 8.03 (1H, d), 7.79 (1H, d), 7.55 (1H, d), 7.41 (1 H, dd), 6.87–6.82 (3H, m), 4.23 (4H, s), 3.92 (3H, s), 3.69 (2H, s), 2.91 (2H, d), 2.57–2.48 (1H, m), 2.04–2.01 (2H, m), 1.91–1.86 (2H, m), 1.37–1.25 (2H, m), 1.15–1.0 (2H, m). MS (+ve ion electrospray) m/z 447 (MH+).

This was converted to the oxalate salt according to the procedure of Example 1.

Example 28

Trans 4-[(3-Oxo-3,4-dihydro-2-H-benzo[1,4]thiazin-6-ylmethyl)-amino]-cyclohexanecarboxylic acid (6-methoxy-quinolin-4-yl)-amide

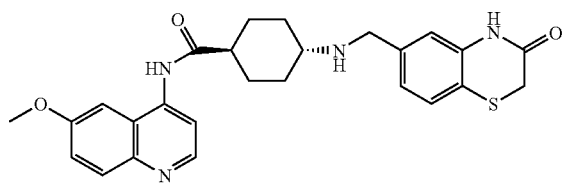

Amine (11c) (389 mg, 1.295 mmol) and aldehyde (4c) (250 mg, 1.295 mmol) were heated at reflux in methanol (1 mL) and chloroform (4 mL) in the presence of 3 Å sieves for 8 hours. The mixture was then cooled to room temperature and sodium triacetoxyborohydride (0.83 g) added. After 24 hours further sodium triacetoxyborohydride (0.55 g). After stirring for 48 hours the mixture was evaporated under reduced pressure. Purification on silica gel eluting with methanol dichloromethane mixtures gave the free base of the title compound as a white solid (311 mg, 56%).

δH (d$_6$-DMSO, 250 MHz), 9.98 (1H, s), 8.62 (1H, d), 7.98 (1H, d), 7.90 (1H, d), 7.60 (1H, d), 7.43 (1H, dd), 7.27 (1H, d), 7.00 (2H, m), 3.95 (3H, s), 3.79 (2H, m), 3.45 (2H, s), 2.69 (1H, m), 2.50 (1H, m), 2.09–1.90 (4H, m), 1.56–1.49 (2H, m), 1.37–1.23 (2H, m). MS (APCI+) m/z 477 (MH+).

Example 29

Trans-4-[(2,3-Dihydro-benzo[1,4]dioxin-6-ylmethyl)-amino]-cyclohexanecarboxylic acid [6-(3-amino-propoxy)-[1,5]naphthyridin-4-yl]-amide dioxalate

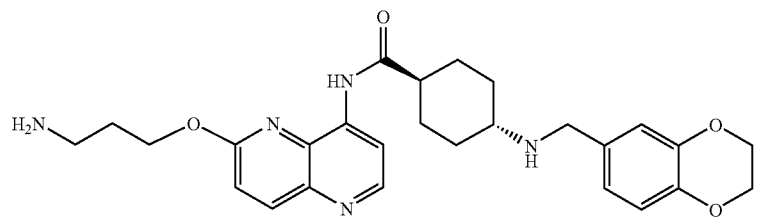

(a) 8-Amino1-H-[1,5]naphthyridin-2-one hydrobromide

A suspension of amine (1c) (4.20 g, 24 mmol) in concentrated hydrobromic acid (35 mL) was heated at 120° C. for 2 h. The mixture was set aside in the fridge for 2 h, then filtered, washing with small amounts of cold water then diethyl ether. Drying in vacuo afforded the product as a white solid (6.1 g, 100%).

MS (+ve ion electrospray) m/z 162 (MH+).

(b) [3-(8-Amino-[1,5]naphthyridin-2-yloxy)-propyl]-carbamic acid benzyl ester

A suspension of hydrobromide salt (29a) (1.2 g, 5 mmol) in N,N-dimethylformamide (10 mL) at 40° C. was treated with potassium carbonate (2.1 g, 15 mmol) then after 0.25 h with a solution of (3-bromo-propyl)-carbamic acid benzyl ester (2 g, 7.4 mmol) in N,N-dimethylformamide (5 mL). The mixture was heated for 4 h at 40° C., then evaporated to dryness. The residue was partitioned between ethyl acetate and dilute aqueous sodium chloride solution. The organic extract was dried and evaporated to give a brown oil (2.2 g) This was chromatographed on silica eluting with a methanol/ethyl acetate gradient affording the product as a clear oil (1.0 g, 57%).

MS (+ve ion electrospray) m/z 353 (MH+).

(c) {4-[6-(3-Benzyloxycarbonylamino-propoxy)-[1,5]naphthyridin-4-ylcarbamoyl]-cyclohexyl}-carbamic acid tert-butyl ester A solution of trans-4-tert-butoxycarbonylamino-cyclohexanecarboxylic acid (0.7 g, 2.8 mmol) and triethylamine (0.43 mL, 0.3 g, 3.1 mmol) in N,N'-dimethylformamide (3 mL) was treated with O-(7-azabenzotriazol-1-yl)-N,N,N',N'-tetramethyluronium hexafluorophosphate (1.1 g, 2.84 mmol). After 0.5 h the amine (29b) (1.0 g, 2.84 mmol) in N,N'-dimethylformamide (7 mL) was added and the mixture was heated at 60° C. for 22 h. The mixture was evaporated and the residue was partitioned between ethyl acetate and dilute aqueous sodium chloride solution. The organic extract was dried and evaporated to give a brown oil (2.1 g) This was chromatographed on silica eluting with a methanol/ethyl acetate gradient affording the product as a clear oil (0.9, 55%).

MS (+ve ion electrospray) m/z 578 (MH+).

(d) [3-(8-{[1-(4-Amino-cyclohexyl)-methanoyl]-amino}-[1,5]naphthyridin-2-yloxy)-propyl]-carbamic acid benzyl ester A solution of (29c) (0.3 g, 0.52 mmol) in trifluoroacetic acid/dichloromethane (5 mL/5 mL) was maintained at room temperature for 0.25 h then evaporated to dryness. The residue was partitioned between ethyl acetate and saturated aqueous sodium bicarbonate solution. The organic extract was dried and evaporated. Chromatography on silica eluting with a methanol/ethyl acetate gradient afforded an oil (0.15 g, 60%).

MS (+ve ion electrospray) m/z 478 (MH+).

(e) (3-{8-[(1-{4-[(2,3-Dihydro-benzo[1,4]dioxin-6-ylmethyl)-amino]-cyclohexyl}-methanoyl)-amino]-[1,5]naphthyridin-2-yloxy}-propyl)-carbamic acid benzyl ester A solution of (29d) (0.15 g, 0.3 mmol) and 2,3-dihydro-benzo[1,4]dioxine-6-carboxaldehyde (82 mg, 0.5 mmol) in methanol/dichloromethane (0.3 mL/2.7 mL) was treated with freshly-activated 3 Å molecular sieves and heated to reflux under argon for 2 h. Sodium triacetoxyborohydride (0.21 g, 1 mol) was added and the mixture was stirred at 40° C. for 1 h. The mixture was partitioned between ethyl acetate and saturated aqueous sodium bicarbonate solution. The organic extract was dried and evaporated to give a brown oil. Chromatography on silica eluting with a methanol/ethyl acetate gradient afforded an oil (105 mg, 54%).

MS (+ve ion electrospray) m/z 626 (MH+).

(f) Title Compound

A solution of (29e) (100 mg, 0.17 mmol) in ethanol (10 mL) was treated with 10% palladium on charcoal (50% dispersion with water, 60 mg) and hydrogenated for 2 h. More 10% palladium on charcoal (100 mg) was added and the mixture hydrogenated for a further 2 h. Filtration and evaporation gave the free base of the product as a white solid (75 mg, 90%)

δH (CD$_3$OD, 250 MHz), 8.65(1H, d), 8.55 (1H, d), 8.20 (1H, d), 8.03 (1H, d), 7.30 (1H, d), 7.00–6.80 (3H, m), 4.75 (2H, t), 4.25 (4H, s), 3.90 (2H, s), 3.20 (2H, t) 2.90–2.70 (2H, m), 2.40–2.10 (7H, m), 1.80–1.40 (3H, m). MS (APCI+) m/z 492 (MH+).

The oxalate salt (90 mg) was prepared by the method of Example 1.

Example 30

Trans-4-[(3-Oxo-3,4-dihydro-2-H-benzo[1,4]thiazin-6-ylmethyl) amino]-cyclohexanecarboxylic acid (8-fluoro-6-methoxy-quinolin-4-yl)-amide oxalate

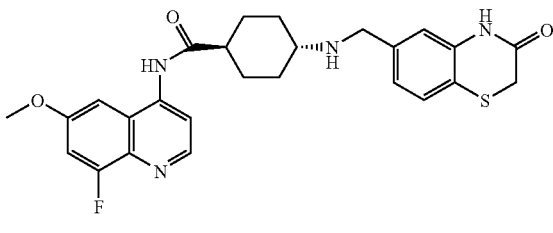

Amine (10e) (225 mg, 0.710 mmol)was reacted aldehyde (4c) (137 mg, 0.710 mmol) according to the procedure in Example 4d. This provided the free base of the desired compound as a white solid (74 mg, 21%).

δH (d$^6$-DMSO, 250 MHz), 8.64 (1H, d), 8.08 (1H, d), 7.47 (1H, m), 7.38 (1H, dd), 7.25 (1H, d), 6.98–6.95 (2H, m), 3.96 (3H, s), 3.69 (2H, m), 3.43 (2H, s), 2.68 (1H, m), 2.49 (1H, m), 1.98–1.90 (4H, m), 1.50–1.46 (2H, m), 1.15–1.00 (2H, m). MS (APCI+) m/z 495 (MH+).

The oxalate salt was prepared by the method of Example 1.

Example 31

Trans-4-[(3-Oxo-3,4-dihydro-2H-pyrido[3,2-b][1,4]oxazin-6-ylmethyl)-amino]-cyclohexanecarboxylic acid (6-methoxy-[1,5]naphthyridin-4-yl)-amide oxalate

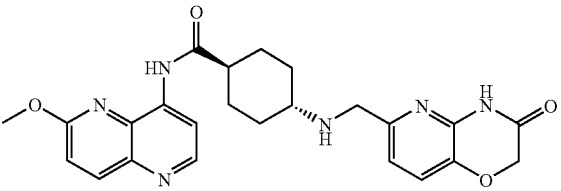

(a) 6-Methyl-4H-pyrido[3,2-b][1,4]oxazin-3-one

A solution of 2-amino-6-methyl-pyridin-3-ol (5.7 g, 46 mmol) (prepared by reduction of 6-methyl-2-nitro-pyridin-3-ol according to the procedure of J. Kaminski et al, [J. Med. Chem, 30 (11), 2031 (1987)1 in dimethylsulphoxide (60 ml) was treated with sodium hydride (44 mmol) under argon. After 0.25 hours methyl chloroacetate (4 mL, 5 g, 46 mmol) was added and the mixture heated at 100° C. for 3.5 hours. The reaction mixture was quenched with saturated aqueous ammonium chloride solution (10 mL), then partitioned between dichloromethane and water. The organic extracts were dried and evaporated and the residue was chromatographed eluting with 0–20% ethyl acetate in dichloromethane affording the product as a white crystalline solid (4.7 g, 62%).

MS (+ve ion electrospray) m/z 165 (MH+).

(b) 6-Methyl-4H-pyrido[3,2-b][1,4]oxazin-3-one N-oxide

A solution of (31a) (4.58 g, 28 mmol) in dichloromethane (100 mL) at 0° C. was treated with a solution of meta-chloroperbenzoic acid (8.75 g, ~55% pure, ~28 mmol) in dichloromethane (100 mL). After 1 hour more meta-chloroperbenzoic acid (1.7 g) was added. After a further 2 hours the mixture was loaded directly onto a silica gel column. Chromatography, eluting with a solvent mixture of aqueous ammonia:methanol:ethyl acetate (3:27:70), afforded the product as a white crystalline solid (3.5 g, 70%).

MS (+ve ion electrospray) m/z 181 (MH+).

(c) Acetic Acid 3-oxo-3,4-dihydro-2H-pyrido[3,2-b][1,4] oxazin-6-ylmethyl ester

A solution of (31 b) (3.0 g) in acetic anhydride (20 mL) was treated with acetyl chloride (0.14 mL) and heated to reflux overnight. The mixture was evaporated to dryness and the residue partitioned between ethyl acetate and half saturated aqueous sodium bicarbonate solution. The ethyl acetate extract was filtered through celite and the filtrate evaporated. The residue was chromatographed eluting with a gradient of 0–10% ethyl acetate in dichloromethane affording an oil (1.0 g). Analysis of this material showed it to be a 2:1 mixture of the product and starting material (31b), equivalent to 19% yield of the desired product (31c).

MS (+ve ion electrospray) m/z 223 (MH+).

(d) 6-Hydroxymethyl-4H-pyrido[3,2-b][1,4]oxazin-3-one

A solution of impure (31c) (1.0 g, equivalent to 3.5 mmol) and sodium hydroxide (3.5 mmol) in water/dioxan (17 mL/30 mL) was stirred at room temperature for 3 days. Silica gel was added and the solvent was removed. Chromatography eluting with 0–100% ethyl acetate in dichloromethane afforded the product as a white foam (0.2 g, 32%).

MS (+ve ion electrospray) m/z 181 (MH+).

(e) 3-Oxo-3,4-dihydro-2H-pyrido[3,2-b][1,4]oxazine-6-carboxaldehyde

A solution of (31d) (0.20 g, 1.1 mmol) in chloroform/dioxan/tetrahydrofuran (10 mL/10 mL/5 mL) was heated at 40° C. with manganese dioxide (1.5 g) for 2 hours. Filtration and evaporation afforded the product as a white solid (0.14 g, 70%).

MS (+ve ion electrospray) m/z 179 (MH+).

(f) Title Compound

A mixture of amine (1e) (210 mg, 0.7 mmol), aldehyde (31e) (0.14 g, 0.78 mmol) and 3A molecular sieves in chloroform/methanol (3 mL/0.5 ml) was heated to reflux for 5 hours, then stabilised at 40° C. Sodium triacetoxyborohydride (0.25 g, 1.2 mmol) was added, and the mixture stirred at 40° C. for 0.5 hours. Water (2 mL) was added and the resulting white solid was isolated by filtration. This solid was partitioned between ethyl acetate and half saturated aqueous sodium bicarbonate solution. The ethyl acetate extract was dried and evaporated giving the free base of the title compound as a white solid (140 mg, 43%).

δH (d6-DMSO, 250 MHz): 8.65(1H, d), 8.35 (1H, d), 8.20 (1H, d), 7.25 (2H, m), 7.00 (1H, m), 4.65 (2H, s), 4.08 (3H, s), 3.65 (2H, s), 2.60 (1H, m), 2.37 (1H, m), 1.90 (4H, m), 1.40 (2H, m), 1.20 (2H, m). MS (+ve ion electrospray) m/z 463 (MH+).

The free base was converted to the oxalate salt (170 mg) by the method of Example 1

Example 32

Trans-4-[([1,2,3]Thiadiazolo[5,4-b]pyridin-6-ylmethyl)-amino]-cyclohexanecarboxylic acid (6-methoxy-[1,5]naphthyridin-4-yl)-amide oxalate

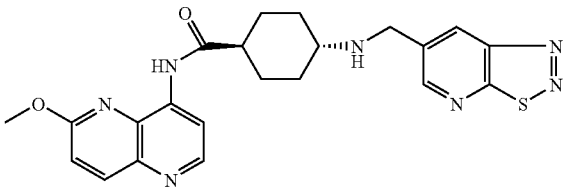

(a) [1,2,3]Thiadiazolo[5,4-b]pyridine-6-carboxylic acid methyl ester

The amine (16a) (1.3 g) was suspended in 0.5 M hydrochloric acid (200 mL) and cooled to −3° C. A solution of sodium nitrite (487 mg) in water (3 mL) was added dropwise over 10 minutes and the mixture was stirred for 2 hours when the solid product was collected and chromatographed on silica gel (chloroform) to afford a solid (0.90 g)

MS (+ve ion electrospray) m/z 196 (MH+)

(b) [1,2,3]Thiadiazolo[5,4-b]pyridine-6-carboxylic acid

The ester (32a) (0.94 g) was hydrolysed with aqueous sodium hydroxide in tetrahydrofuran by the method of Example (4a) to afford a solid (0.84 g).

MS (−ve ion electrospray) m/z 180 (M−H⁻).

(c) [1,2,3]Thiadiazolo[5,4-b]pyridin-6-yl-methanol

The carboxylic acid (32b) (0.82 g) was reacted with isobutylchloroformate and sodium borohydride by the method of Example (4b) to afford a semi-solid (0.12 g), after chromatography on silica gel (chloroform).

(d) [1,2,3]Thiadiazolo[5,4-b]pyridine-6-carboxaldehyde

The alcohol (32c) (0.10 g) was oxidised with manganese dioxide by the method of Example (4c) to afford a solid (51 mg).

MS (+ve ion electrospray in methanol) m/z 198 (MH+ for methanol adduct)

(e) Title Compound

This was prepared from amine (1e) (102 mg) and carboxaldehyde (32d) (51 mg) by the method of Example (4d) (slow reduction with sodium triacetoxyborohydride so mixture of imine and product was retreated with extra sodium acetoxyborohydride for 72 hours) to provide the free base of the desired compound as a colourless solid (44 mg).

δH (CDCl₃ 250 MHz), 9.50 (1H, br.s) 8.95 (1H, d), 8.89 (1H, d), 8.70 (1H, d), 8.52 (1H, d), 8.25 (1H, d), 7.15 (1H, d), 4.16 (2H, s), 4.11 (3H, s), 2.68 (1H, m), 2.45–2.15 (5H, m), 1.70 (2H, m), 1.35 (2H, m). MS (+ve ion electrospray) m/z 450 (MH+).

The oxalate salt was prepared by the method of Example 1

Example 33

Trans-4-(3-Oxo-3,4-dihydro-2H-benzo[1,4]thiazine-6-sulfonylamino)-cyclohexanecarboxylic acid (6-methoxy-[1,5]naphthyridin-4-yl)-amide

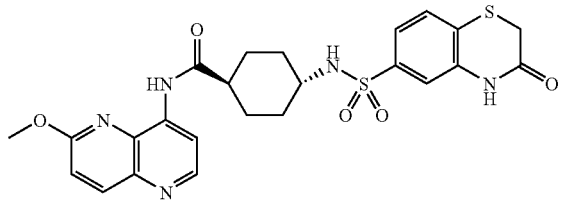

(a) 3-Oxo-3,4-dihydro-2H-benzo[1,4]thiazine-6-sulfonyl chloride

Powdered 4H-benzo[1,4]thiazin-3-one (7.0 g) was added cautiously, portionwise (over 20 minutes), to chlorosulfonic acid (15 mL), cooled in ice. After 1 hour the blue solution was allowed to warm to room temperature and it was heated at 45° C. for 2 hours, cooled and poured into ice. The solid was collected, washed with water, and hexane, and dried in vacuo, to give a white solid (7.0 g).

(b) Title Compound

A solution of amine (1e) (0.20 g, 0.66 mmol) in dichloromethane (20 mL) was treated with triethylamine (0.23 mL, 1.7 mmol) then the sulfonyl chloride (33a) (0.28 g, 1 mmol) was added in one portion. After 1 day the mixture was filtered, washing with dichloromethane. The resulting solid was recrystallised from boiling methanol to afford the title compound as a white solid (7 mg, 2%).

δH (d$_6$-DMSO, 250 MHz): 10.85 (1H, bs), 9.70 (1H, bs), 8.62(1H, d), 8.38 (1H, d), 8.25 (1H, d), 7.75 (1H, d), 7.50 (1H, d), 7.45–7.30 (2H, m), 7.25 (1H, d), 4.10 (3H, s), 3.57 (2H, s), 2.95 (1H, m), 2.60 (1H, m), 1.95 (2H, m), 1.75 (2H, m) 1.50–1.20 (4H, m) MS (+ve ion electrospray) m/z 528 (MH+).

Example 34

Trans-4-[(7-Fluoro-3-oxo-3,4-dihydro-2H-benzo[1,4]thiazin-6-ylmethyl)-amino]-cyclohexanecarboxylic acid (6-methoxy-[1,5]naphthyridin-4-yl)-amide oxalate salt

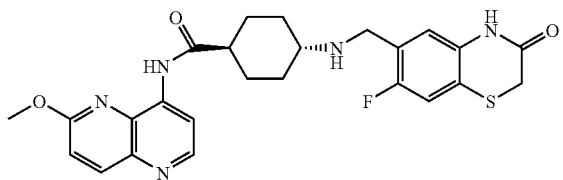

(a) 2,4-Difluoro-5-nitro-benzoic acid ethyl ester 2,4-Difluorobenzoic acid ethyl ester (5.33 g) was cooled to 0° C. and treated with concentrated sulfuric acid (3.5 mL) and then fuming nitric acid (3.5 mL). The mixture was stirred for 2 hours at 0° C. and then partitioned between dichloromethane (2×50 mL) and water (25 mL). The organic phase was back extracted with water (25 mL) and then dried over magnesium sulfate and concentrated in vacuo. This provided the desired compound as a white solid (5.00 g) which was used without further purification.

(b) 2-Fluoro-4-methoxycarbonylmethylsulfanyl-5-nitro-benzoic acid ethyl ester

Ester (34a) (2.82 g, 12.21 mmol) was dissolved in dichloromethane (50 mL) and triethylamine was added (2.04 mL, 14.65 mmol). The mixture was cooled to 0° C. and methyl thioglycolate (0.98 mL, 10.98 mmol) was added dropwise. Stirring was continued at 0° C. for 3 hours after which time the volatiles were removed in vacuo. The residue was purified by column chromatography on silica gel using an ethylacetate and hexanes solvent gradient. This provided the desired compound as a yellow solid (2.05 g).

(c) 7-Fluoro-3-oxo-3,4-dihydro-2H-benzo[1,4]thiazine-6-carboxylic acid ethyl ester This was prepared by an iron mediated reductive cyclisation of nitro compound (34b) using a method similar to Example (13b) This provided the desired compound as a white solid (1.02 g).

(d) 7-Fluoro-3-oxo-3,4-dihydro-2H-benzo[1,4]thiazine-6-carboxylic acid

This was prepared by hydrolysis of ethyl ester (34c) using the method of Example (4a) to give a white solid (1.00 g).

(e) 7-Fluoro-6-hydroxymethyl-4H-benzo[1,4]thiazin-3-one

This was prepared by reduction of the mixed anhydride of acid (34d) according to the method of Example (4b) to give the alcohol (0.93 g). m/z (APCI+) 214 (MH+).

(f) 7-Fluoro-3-oxo-3,4-dihydro-2H-benzo[1,4]thiazine-6-carboxaldehyde

Oxidation of alcohol (34e) with manganese dioxide was performed according to the procedure of Example (4c), to give the aldehyde (1.00 g).

(g) Title Compound

Amine (1e) was reductively alkylated with aldehyde (34f) in the same manner as Example (4d). This provided the free base (30 mg) of the desired compound after purification on silica gel. The oxalate salt was generated in the same fashion as Example 1

MS (APCI+) m/z 496 (MH+) δH (d6-DMSO, 250 MHz) 10.60 (1H, bs), 9.76 (1H, bs), 8.67 (1H, d), 8.39 (1H, d), 8.26 (1H, d), 7.32 (1H, d), 7.22 (1H, bm), 7.11 (1H, d), 4.14 (3H, s), 3.40 (2H, s), 3.30 (2H, s), 2.70 (1H, m), 2.54 (1H, m), 2.05 (4H, m), 1.51 (2H, m), 1.10 (2H, m). m/z (APCI+) 496 (MH+).

Example 35

Trans-4-[(8-Nitro-3-oxo-3,4-dihydro-2H-benzo[1,4]oxazin-6-ylmethyl)-amino]-cyclohexanecarboxylic Acid (6-methoxy)-[1,5]naphthyridin-4-yl)-amide Oxalate

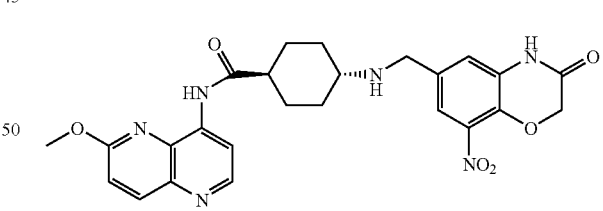

(a) 8-Nitro-3-oxo-3,4-dihydro-2H-benzo[1,4]oxazine-6-carboxaldehyde

The carboxaldehyde (8b) (0.18 g, 1.0 mmol) was stirred and cooled in ice, while fuming nitric acid (0.1 mL) was added. The mixture was stirred at room temperature for 3 hours then diluted with water and extracted with ethyl acetate. the extracts were washed with brine, dried and evaporated. Chromatography on silica gel (0–1% methanol in dichloromethane) gave a solid (0.16 g, 71%).

(b) Title Compound

A solution of the amine (1e) (0.30 g 11.0 mmol) and aldehyde (35a) in methanol (2 mL) and chloroform (8 mL) was stirred at 56° C. over 3A molecular sieves for 7 hours.

Sodium triacetoxyborohydride (1.04 g) was added and the mixture stirred at room temperature for 7 days then at 56° C. for 7 days. The mixture was diluted with methanol and solid sodium bicarbonate added. After being stirred for 15 minutes the mixture was evaporated and chromatographed on silica gel (2–10% methanol in dichloromethane). The mixture of imine and amine (0.103 g) thus obtained was dissolved in methanol (2 mL) and chloroform (5 mL), sodium triacetoxyborohydride (0.13 g) was added and the mixture stirred at room temperature for 24 hours, further sodium triactoxyborohydride (0.13 g) was added and stirring continued for 24 hours. The mixture was worked up as before and chromatographed on silica gel (2–7.5% methanol in DCM) to give the title compound as the free base(0.036 g, 7%).

MS (+ve ion electrospray) m/z 507 (MH+) δH (CDCl$_3$, 250 MHz), 8.68 (1H, d), 8.52 (1H, d), 8.25 (1H, d), 7.77 (1H, s), 7.28 (1H, s), 7.19 (1H, d), 4.62 (2H, s), 4.36 (2H, s), 4.15 (3H, s), 2.63–2.20 (4H, m), 2.18–2.00 (2H, m), 1.78 (4H, m).

The oxalate salt was prepared by the method of Example 1

A mixture of the title compound and 4-[(8-nitro-3-oxo-3,4-dihydro-2H-benzo[1,4]oxazin-6-ylmethyl)-imino]-cyclohexanecarboxylic acid (6-methoxy)-[1,5]naphthyridin-4-yl)-amide (0.059 g) was also obtained during chromatography.

Example 36
Trans-4-[(8-Amino-3-oxo-3,4-dihydro-2H-benzo[1,4]oxazin-6-ylmethyl)-amino]-cyclohexanecarboxylic acid (6-methoxy)-[1,5]naphthyridin-4-yl)-amide Oxalate

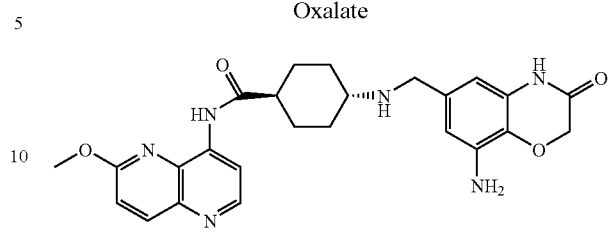

The mixture of compound Example (35) and 4-[(8-nitro-3-oxo-3,4-dihydro-2H-benzo[1,4]oxazin-6-ylmethyl)-imino]-cyclohexanecarboxylic acid (6-methoxy)-[1,5]naphthyridin-4-yl)-amide obtained from Example (35b) (0.059 g) was dissolved in ethanol and hydrogenated over 10% palladium on charcoal for 18 hours. The mixture was filtered through kieselguhr and evaporated. Chromatography on silica gel (5–10% methanol/DCM then 5–10% methanol/dichloromethane containing 0.5–1% NH$_4$OH) gave the title compound as the free base(0.13 g).

MS (+ve ion electrospray) m/z 477 (MH+) δH (CDCl$_3$+MeOD, 250 MHz), 8.68 (1H, d), 8.51 (1H, d), 8.22 (1H, d), 7.17 (1H, d), 6.57 (1H, s), 6.33 (1H, s), 4.52 (2H, s), 4.12 (3H, s), 3.79 (2H, s), 2.61 (1H, m), 2.44 (1H, m), 2.19 (4H, m), 1.72 (2H, m), 1.26 (2H, m).

The oxalate salt was prepared by the method of Example 1
The following Examples were prepared by analogous methods.
A: by method of Example 29
B: by method of Example 4

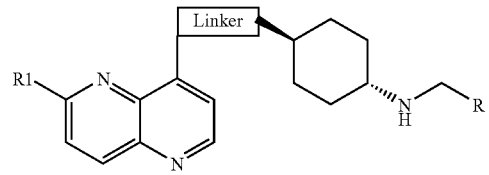

| Example | Method of synthesis | R$_1$ | LINKER | salt<br>G oxalate<br>A Hydrochloride<br>AY Dioxalate | R |
|---|---|---|---|---|---|
| 100 | A | 6-O(CH$_2$)$_3$NH2 | NHCO | G | benzo[1,2,3]thiadiazol-5-yl |
| 101 | B | 6-OMe | NHCO | G | 2-oxo-2,3-dihydro-1H-pyrido[2,3-b][1,4]oxazin-7-yl |
| 102 | B | 6-OMe | NHCO | G | 5-nitro-3-oxo-3,4-dihydro-2H-benzo[1,4]oxazin-6-yl |
| 103 | a | 6-OMe | NHCO | G | 5-amino-3-oxo-3,4-dihydro-2H-benzo[1,4]oxazin-6-yl |
| 104 | B | 6-OMe | NHCO | G | 2,3-dihydro-1H-pyrido[2,3-b][1,4]oxazin-7-yl |
| 105 | A | 6-(OCH$_2$)$_3$NH$_2$ | NHCO | AY | 4H-benzo[1,4]thiazin-3-one-6-yl |
| 106 | b | 6-OMe | NHCO | A | 6-[3-oxo-2,3-dihydro-benzo[1,4]thiazin-4-yl)-acetic acid] |
| 107 | c | 6-OMe | NHCO | G | 6-[3-oxo-2,3-dihydro-benzo[1,4]thiazin-4-yl)-acetic acid tert-butyl ester] |
| 108 | d | 6-OMe | NHCO | G | 1,1,3-Trioxo-1,2,3,4-tetrahydro-1 l$^6$-benzo[1,4]thiazin-6-yl |
| 109 | e | 6-OMe | NHCONH cis stereochem | AY | quinoxalin-2-yl |
| 110 | f | 6-OMe | NHCOO trans stereochem | free base | 3-oxo-3,4-dihydro-2H-pyrido[3,2-b][1,4]thiazin-6-yl |

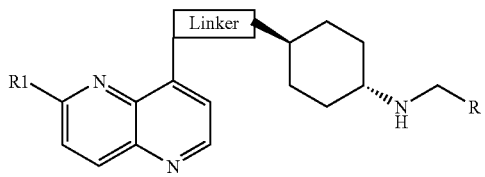

| Example | Method of synthesis | R₁ | LINKER | salt G oxalate A Hydrochloride AY Dioxalate | R |
|---|---|---|---|---|---|
| 111 | g | 6-OMe | NHCOO cis stereochem | free base | 3-oxo-3,4-dihydro-2H-benzo[1,4]thiazin-6-yl | a Prepared from Example 102 by hydrogenation over palladium/carbon following the Method of Example 36
b Prepared from Example 107 by reaction with trifluoroacetic acid in dichloromethane
c Prepared by alkylation of Example (4c) with tert-butyl bromoacetate followed by reaction with amine (1c) and sodium triacetoxyborohydride by Method of Example 4
d Prepared from alcohol (4b) by oxidation with m-chloroperbenzoic acid followed by manganese dioxide and reaction of the carboxaldehyde with amine (1c) and sodium triacetoxyborohydride by Method of Example 4
e Prepared via cis-1-tert-butoxycarbonylamino-4-aminocyclohexane and 6-methoxy[1,5]naphthyridine-4-isocyanate
f Prepared from trans 4-aminocyclohexanol by tert-butyloxycarbonyl protection of the amino group, followed by conversion of the hydroxy group to aminocarbonyloxy by reaction with phosgene followed by ammonia. The resulting trans-(4-carbamoyloxy-cyclohexyl)-carbamic acid tert butyl ester was then coupled with triflate (1b) according to the palladium-catalysed procedure of (300d). Removal of the tert-butoxycarbonyl protecting group and reductive alkylation with aldehyde (301d) using sodium cyanoborohydride according to Example (311e) afforded the final compound.
g Prepared from cis-4-aminocyclohexanol by the same methodology as (f) above, except that aldehyde (4c) was used in place of aldehyde (301d)

Example 150

(R/S)-4-[(3-Oxo-3,4-dihydro-2H-benzo-[1,4]thiazin-6ylmethyl)-amino]-cyclohex-1-ene carboxylic acid (6-methoxy-[1,5]naphthyridin-4-yl)-amide oxalate

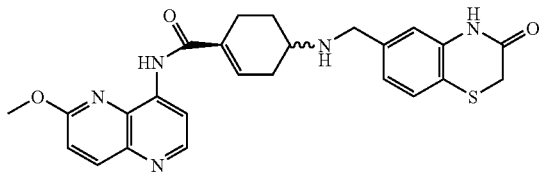

(a) (R/S)-4-tert-Butoxycarbonylamino-cyclohex-1-enecarboxylic acid

A solution of potassium hydroxide (25 g, 446 mmol) in water (30 mL) was added dropwise to a vigorously stirred solution of 4-tert-butoxycarbonylaminocyclohexanone (13.53 g, 63.8 mmol) and benzyltriethylammonium chloride (0.15 g, 0.64 mmol) in bromoform (25 mL) at 0° C. An exothermic reaction occurred, the internal temperature reaching 80–90° C. before falling. Stirring, with external cooling, was continued for 1 hour. Water and dichloromethane were added and the phases were separated. The aqueous phase was washed with dichloromethane, then cooled in ice, acidified to pH 4 (dilute hydrochloric acid) and extracted with dichloromethane. The extracts were dried and evaporated to give the acid (7.78 g, 47%).

(b) (R/S)-4-tert-Butoxycarbonylamino-cyclohex-1-enecarboxylic acid (6-methoxy-[1,5]naphthyridin-4-yl)-amide Method A. To a solution of the acid (150a) (2.58 g, 10 mmol) in dry dichloromethane (20 mL) was added 1,1'-carbonyldiimidazole (2.26 g, 14 mmol). The mixture was stirred for 7 hours at room temperature, then evaporated. The residue was dissolved in dry DMF (20 mL), 6-methoxy-[1, 5]naphthyridin-4-ylamine (Example 1c) [RN 249889-69-8] (2.49 g, 14 mmol) and N,N-dimethylaminopyridine (0.15 g) were added and the mixture was heated at 100° C. for 48 hours. After evaporation of solvent, the residue was partitioned between ethyl acetate and water. The aqueous phase was re-extracted and the combined organics were washed with water, dried and evaporated. Chromatography on silica gel (0–10% methanol/dichloromethane) gave an impure product which was chromatographed again (silica, 1–2% methanoldichloromethane) to give the amide (1.15 g, 29%).

Method B. To a solution of the acid (150a) (5.0 g, 20.8 mmol) in dry DMF (40 mL) were added O-(7-azabenzotriazol-1-yl)-N,N,N',N'-tetramethyluronium hexafluorophosphate (7.98 g, 21 mmol) and triethylamine (5.88 mL, 42 mmol). After 0.5 hours stirring at room temperature 6-methoxy-[1,5]naphthyridin-4-ylamine (Example 1c) (3.64 g, 20.8 mmol) was added and the mixture was stirred at 50° C. for 48 hours. Work-up as for Method A and chromatography on silica gel (1–3% methanol/dichloromethane) gave the amide (5.73 g, 69%).

MS (+ve ion electrospray) m/z 399 (MH+).

(c) (R/S)-4-Amino-cyclohex-1-enecarboxylic acid (6-methoxy-[1,5]-naphthyridin-4-yl)-amide The amide (150b) (0.83 g, 2.1 mmol) was dissolved in dichloromethane (5 mL) and trifluoroacetic acid (5 mL), and the solution was allowed to stand at room temperature for 2 hours, then evaporated. The residue was dissolved in a small volume of aqueous sodium bicarbonate, basified to pH10–11 with 40% sodium hydroxide and extracted thoroughly with 10% methanol/dichloromethane (total 125 mL). The extracts were dried and evaporated to give the amine (0.69 g, 100%).

MS (+ve ion electrospray) m/z 299 (MH+).

(d) Title Compound

A solution of the amine (150c) (0.10 g, 0.33 mmol) and 3-oxo-3,4-dihydro-2H-benzo[1,4]thiazine-6-carboxaldehyde (Example 4c) (0.064 g, 0.33 mmol) in dry chloroform (2 mL) and methanol (0.2 mL) was heated with 3 Å molecular sieves for 15 hours. After cooling, sodium triacetoxyborohydride (0.35 g, 1.65 mmol) was added and the mixture was stirred at room temperature overnight. The mixture was basified with aqueous sodium bicarbonate and the phases were separated. The aqueous phase was extracted with dichloromethane and the combined organics were washed with water, dried and evaporated. Chromatography on silica gel (5–7% methanol/dichloromethane) gave the title compound as free base (0.08 g, 51%).

δH (d₆-DMSO, 400 MHz), 10.49 (1H, s), 9.88 (1H, s), 8.69 (1H, d), 8.43 (1H, d), 8.28 (1H, d), 7.33 (1H, d), 7.24 (1H, d), 7.00–6.97 (2H, m), 6.91 (1H, br s), 4.10 (3H, s), 3.72 (2H, s), 3.42 (2H, s), 2.74 (1H, m), 2.67–2.37 (3H, m), 2.08 (1H, m), 1.98 (1H, m), 1.51 (1H, m). MS (+ve ion electrospray) m/z 476(MH+).

The oxalate salt was prepared by the method of Example 1.

Example 151

(R/S)-4-[(Benzo[1,2,5]thiadiazol-5-ylmethyl)-amino]-cyclohexene carboxylic acid (6-methoxy-[1,5]naphthyridin-4-yl)-amide oxalate

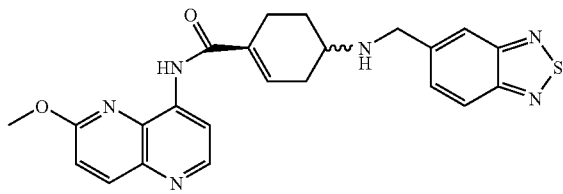

(a) Benzo[1,2,5]thiadiazole-5-carboxaldehyde

This was prepared by oxidation of benzo[1,2,5]thiadiazol-5-yl-methanol (2a) with manganese dioxide in dichloromethane by the method of Example (4c).

(b) Title Compound

A solution of the amine (150c) (0,10 g, 0.3 mmol) and the carboxaldehyde (51a) (0.055 g, 0.33 mmol) in dry chloroform (2 mL) and methanol (0.2 mL) was heated with 3A molecular sieves for 15 hours. After cooling, sodium triacetoxyborohydride (0.35 g, 1.65 mmol) was added and the mixture was stirred at room temperature for 48 hours. The mixture was basified with aqueous sodium bicarbonate and extracted with dichloromethane. The extracts were dried and evaporated. Chromatography on silica gel (2–5% methanol/dichloromethane)gave the title compound as the free base (0.079 g, 53%).

δH (CDCl₃, 250 MHz), 9.37 (1H, s), 8.70 (1H, d), 8.55 (1H, d), 8.21 (1H, d), 7.92–8.03 (2H, m), 7.64 (1H, dd), 7.16 (1H, d), 6.94 (1H, br s), 4.10 (3H, s), 4.08 (2H, s), 3.06–2.91 (1H, m), 2.80–2.39 (2H, m), 2.32–2.07 (2H, m), 1.79–1.45 (3H, m). MS (+ve ion electrospray) m/z 447 (MH+).

The oxalate salt was prepared by the method of Example 1.

Example 152

(R/S)-4-[(Benzo[1,2,3]thiadiazol-5-ylmethyl)-amino]-cyclohex-1-ene carboxylic acid (6-methoxy-[1,5]naphthyridin-4-yl)amide oxalate

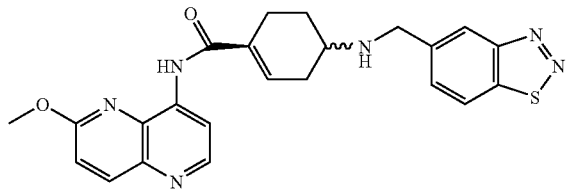

(a) Benzo[1,2,3]thiadiazole-5-carboxaldehyde

This was prepared by oxidation of benzo[1,2,3]thiadiazol-5-yl-methanol (6a) with manganese dioxide in dichloromethane by the method of Example (4c).

(b) Title Compound

This was prepared from the carboxaldehyde (152a) by the method of Example 151 (0.75 g, 47%).

δH (CDCl₃, 250 MHz), 9.85 (1H, s), 8.69 (1H, d), 8.61 (1H, d), 8.54 (1H, d), 8.20 (1H, d), 8.05 (1H, d), 7.73 (1H, dd), 7.15 (1H, d), 6.94 (1H, br-s), 4.14 (2H, s), 4.09 (3H, s), 3.08–2.94 (1H, m), 2.80–2.43 (2H, m), 2.33–2.08 (2H, m), 1.82–1.53 (3H, m). MS (+ve ion electrospray) m/z 447 (MH+).

The oxalate salt was prepared by the method of Example 1.

Example 153

(R/S)-4-[(2-Oxo-2,3-dihydro-1H-pyrido[2,3-b][1,4]thiazin-7-ylmethyl)-amino]-cyclohex-1-ene carboxylic acid (6-methoxy-[1,5]naphthyridin-4-yl)-amide oxalate

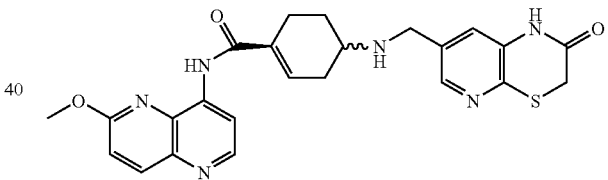

A solution of the amine (150c) (0.10 g, 0.33 mmol) and 2-oxo-2,3-dihydro-1H-pyrido[2,3-b][1,4]thiazine-7-carboxaldehyde (Example 13e) (0.064 g, 0.33 mmol) in dry chloroform (2 mL) and methanol (0.2 mL) was heated with 3A molecular sieves for 15 hours. After cooling, sodium triacetoxyborohydride (0.35 g, 1.65 mmol) was added and the mixture was stirred at room temperature overnight. A further portion of sodium triacetoxyborohydride (0.16 g) was added and stirring continued overnight. The mixture was basified with aqueous sodium bicarbonate and the phases were separated. The aqueous phase was extracted with dichloromethane/methanol and the combined organics were washed with brine, dried and evaporated. Chromatography on silica gel (2–5% methanol/dichloromethane) gave the title compound as the free base (0.055 g, 35%).

δH (CDCl₃/CD₃OD, 250 MHz), 9.93 (1H, s), 8.66 (1H, d), 8.55 (1H, d), 8.21 (1H, d), 8.10 (1H, br s), 7.23–7.19 (2H, m), 6.94 (1H, br s), 4.12 (3H, s), 3.84(2H, s), 3.55 (2H, s), 2.93 (1H, m), 2.80–2.45 (3H, m), 2.16 (2H, m), 1.67 (1H, m). MS (+ve ion electrospray) m/z 477(MH+).

The oxalate salt was prepared by the method of Example 1.

Example 154

(R/S)-4-[(7-Fluoro-3-oxo-3,4-dihydro-2H-benzo[1,4]oxazin-6-ylmethyl)-amino]-cyclohex-1-ene carboxylic acid (6-methoxy-[1,5]naphthyridin-4-yl)-amide oxalate

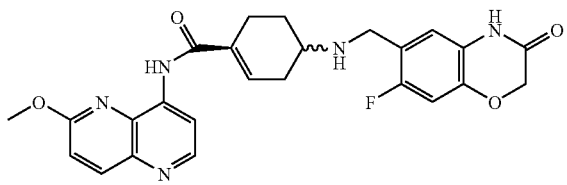

This was prepared from the amine (150c) (0.10 g, 0.33 mmol) and 7-fluoro-3-oxo-3,4-dihydro-2H-benzo[1,4]oxazine-6-carboxaldehyde (Example 9e) (0.065 g, 0.33 mmol) by the method of Example 153. Chromatography on silica gel (2–5% methanol/dichloromethane) gave the title compound as the free base (0.071 g, 39%).

δH (CDCl$_3$, 250 MHz), 9.86 (1H, s), 8.70 (1H, d), 8.55 (1H, d), 8.22 (1H, d), 7.16 (1H, d), 6.93 (1H, br s), 6.84 (1H, d), 6.72 (1H, d), 4.60 (2H, s), 4.10 (3H, s), 3.84(2H, s), 2.90 (1H, m), 2.78–2.43 (3H, m), 2.24–2.00 (2H, m), 1.63 (m). MS (+ve ion electrospray) m/z 478(ME+).

The oxalate salt was prepared by the method of Example 1.

Example 155

(R/S)-4-[(2-Oxo-2,3-dihydro-1H-pyrido[2,3-b][1,4]oxazin-7-ylmethyl)-amino]-cyclohex-1-enecarboxylic Acid (6-methoxy-[1,5]naphthyridin-4-yl)-amide oxalate

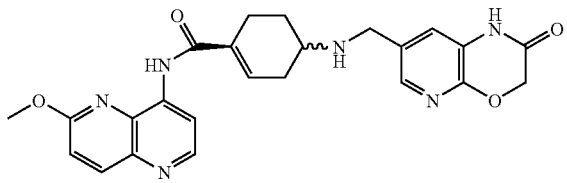

(a) 6-Ethoxycarbonylmethoxy-5-nitro-nicotinic acid methyl ester

A solution of ethyl glyoxalate (2.80 g) in dry dioxan (100 mL), cooled in ice, was treated with sodium hydride (60% dispersion in oil; 1.30 g) and the mixture was heated at 50° C. for 30 minutes and cooled in ice. A solution of 6-chloro-5-nitro-nicotinic acid methyl ester (5.25 g) [prepared as described by A. H. Berrie et al. *J. Chem. Soc.* 2590–2594 (1951)] in dioxan (40 mL) was added and the solution was stirred at 0° C. for 30 minutes and then at room temperature overnight. The reaction mixture was evaporated to dryness, sodium bicarbonate solution was added to pH 7, and the mixture extracted with chloroform, dried (anhydrous sodium sulfate) and evaporated to afford a semi-solid that was chromatographed on silica gel [dichloromethane-hexane (1:1) then dichloromethane] to afford the product (4.70 g).

MS (+ve ion electrospray) m/z 285 (MH+).

(b) 2-Oxo-2,3-dihydro-1H-pyrido[2,3-b][1,4]oxazine-7-carboxylic acid methyl ester The ester (155a) (1.0 g) in acetic acid (80 mL) was treated with iron powder (10 g) and the mixture was stirred and heated at 60° C. for 2.5 hours, cooled and filtered. The filtrate was evaporated, treated with anhydrous sodium carbonate and extracted with warm chloroform-methanol (98:2). It was dried (anhydrous sodium sulfate) and evaporated to give a white solid (5.2 g).

MS (+ve ion electrospray) m/z 209 (MH+).

(c) 2-Oxo-2,3-dihydro-1H-pyrido[2,3-b][1,4]oxazine-7-carboxylic Acid

The ester (155b) (4.5 g) was hydrolysed with aqueous sodium hydroxide in tetrahydrofuran by the method of Example (4a) to afford a solid (3.0 g).

MS (−ve ion electrospray) m/z 193 (M−H$^-$).

(d) 7-Hydroxymethyl-1H-pyrido[2,3-b][1,4]oxazin-2-one

The relatively insoluble carboxylic acid (155c) (1.20 g) was reacted with isobutylchloroformate and sodium borohydride by the method of Example (4b), except the initial solvent was tetrahydrofuran (350 mL), chloroform (50 mL) and dimethylformamide (10 mL). The reaction mixture was evaporated to one quarter volume, extracted with dichloromethane, and the aqueous fraction evaporated to dryness, dissolved in methanol-chloroform (1:3) and chromatographed on silica gel [methanol-dichloromethane (1:9)] to afford a solid (0.43 g).

MS (−ve ion electrospray) m/z 179 (M−H$^-$).

(e) 2-Oxo-2,3-dihydro-1H-pyrido[2,3-b][1,4]oxazine-7-carboxaldehyde

The alcohol (155d) (0.42 g) in tetrahydrofuran (200 mL) and chloroform (100 mL) was oxidised with excess manganese dioxide by the method of Example (4c) to afford the required product (0.30 g), containing 17% of alcohol (55d) by NMR.

MS (−ve ion electrospray) m/z 177 (M−H$^-$).

(f) Title Compound

This was prepared from the amine (150c) (0.132 g) and crude carboxaldehyde (155e) (0.090 g) by the method of Example 153. Chromatography on silica gel (2–10% methanol/dichloromethane) gave the free base of the title compound as a solid (0.090 g).

δH (CD$_3$OD, 250 MHz), 8.55 (1H, d), 8.50 (1H, d), 8.20 (1H, d), 7.86 (1H, d), 7.38 (1H, d), 7.28 (1H, d), 4.84 (2H, s), 4.17 (3H, s), 4.02 (2H, s), 2.93 (1H, m), 2.70 (1H, m) 2.25 (4H, m), 1.75 (2H, m) 1.45 (2H, m). MS (+ve ion electrospray) m/z 463(MH+).

The oxalate salt was prepared by the method of Example 1

Example 156

(R/S)-4-[Carboxymethyl-(3-oxo-3,4-dihydro-2H-benzo[1,4]thiazin-6-ylmethyl)-amino]-cyclohex-1-enecarboxylic Acid (6-methoxy-[1,5]naphthyridin-4-yl)-amide Bis(trifluoroacetate) Salt

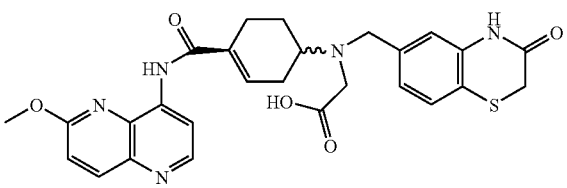

(a) (R/S)-4-(tert-Butoxycarbonylmethylamino)-cyclohex-1-enecarboxylic acid (6-methoxy-[1,5]naphthyridin-4-yl)-amide A solution of the amine (150c) (0.20 g, 0.66 mmol) in dry DMF (5 mL) was treated with tert-butyl bromoacetate (0.107 mL, 0.66 mmol) and potassium carbonate and the mixture was stirred overnight at room temperature. After evaporation of solvent, the residue was chromatographed on silica gel (0–2% methanol/dichloromethane) to give the ester (0.093 g, 34%).

MS (+ve ion electrospray) m/z 413(MH+).

(b) (R/S)-4-[tert-Butoxycarbonylmethyl-(3-oxo-3,4-dihydro-2H-benzo[1,4]thiazin-6-ylmethyl)-amino]-cyclohex-1-enecarboxylic acid (6-methoxy-[1,5]naphthyridin-4-yl)-amide A solution of the ester (156a) (0.09 g, 0.2 mmol) and 3-oxo-3,4-dihydro-2H-benzo[1,4]thiazine-6-carboxaldehyde (Example 4c) (0.064 g, 0.33 mmol) in dry 1,2-dichloroethane (3 mL) was heated under reflux with 4A molecular sieves for 7.5 hours. After cooling to room temperature, sodium triacetoxyborohydride (0.175 g) was added and the mixture was stirred overnight. More sodium triacetoxyborohydride (0.92 g) and aldehyde (0.14 g) were added at intervals during which time the mixture was heated under reflux overnight. Aqueous sodium bicarbonate and dichloromethane were added and the phases separated. The aqueous phase was re-extracted with dichloromethane and the combined organics were washed with water, dried and evaporated. Chromatography on silica gel (2–5% methanol/dichloromethane) gave the alkylated product (0.012 g), plus a 2:1 mixture of product and starting material (0.046 g).

MS (+ve ion electrospray) m/z 590(MH+).

(c) Title Compound.

The pure ester (156b) (0.012 g) was dissolved in dichloromethane (0.5 mL) and trifluoroacetic acid (0.5 mL) and the solution was allowed to stand at room temperature for 2 hours. Evaporation to dryness gave the title compound (0.018 g).

δH (CD$_3$OD, 250 MHz) 8.88 (1H, d), 8.83 (1H, d), 8.38 (1H, d), 7.57 (1H, d), 7.43 (1H, d), 7.24 (1H, dd), 7.17 (1H, d), 7.04 (1H, br s), 4.49 (2H, s), 4.23 (3H, s), 4.06 (2H, s), 3.78 (1H, m), 3.46 (2H, s), 3.00–2.85 (2H, m), 2.85–2.55 (2H, m), 2.44 (1H, m), 1.95 (1H, m). MS (+ve ion electrospray) m/z 534(MH+).

The following Examples were prepared by analogous methods.

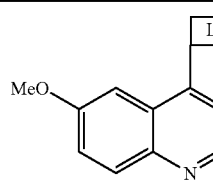

| Example | Method of synthesis | LINKER | salt G oxalate AY Dioxalate | R |
|---|---|---|---|---|
| 200 | a | NHCONH | G | (CH$_2$)$_4$Me |
| 201 | b | NHCONH trans stereochem. | G | (CH$_2$)$_4$Me |
| 202 | a | NHCONH | AY | quinoxalin-2-yl |
| 203 | d | CONR | AY | quinoxalin-2-yl |
| 204 | c | NHCO | | (CH$_2$)$_5$Me |
| 205 | e | CH(OH)CH$_2$NH | G | (CH$_2$)$_4$Me |
| 206 | f | NHCOO | free base | 3-oxo-3,4-dihydro-2H-pyrido[3,2-b][1,4]thiazin-6-yl |

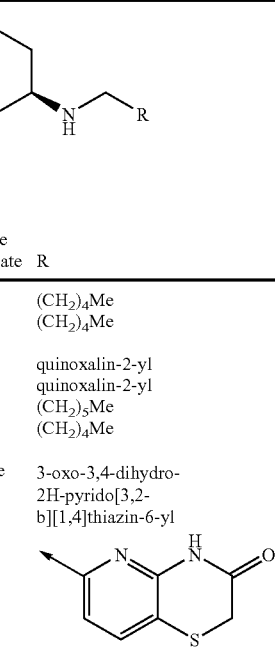

a Prepared via cis-1-tert-butoxycarbonylamino-4-aminocyclohexane and 6-methoxyquinoline-4-isocyanate
b Prepared from trans-1-tert-butoxycarbonylamino-4-aminocyclohexane and 6-methoxyquinoline-4-isocyanate
c Prepared from 4-cis-tert-butoxycarbonylamino-cyclohexanecarboxylic acid and 6-methoxyquinoline-4-ylamine by the Method of Example 1d
d Prepared from from cis-1-tert-butoxycarbonylamino-4-aminocyclohexane and 6-methoxyquinoline-4-carboxylic acid by the method of Example 1d
e Prepared from cis-1-tert-butoxycarbonylamino-4-aminocyclohexane by reaction with [R]-2-(6-methoxyquinolin-4-yl)oxirane
f Prepared by analogous procedures to those of Example 110

Unless otherwise stated, the following compounds were prepared by analogous methods by reaction of an appropriate carboxaldehyde and amine with sodium triacetoxyborohydride (Method of Example 153).

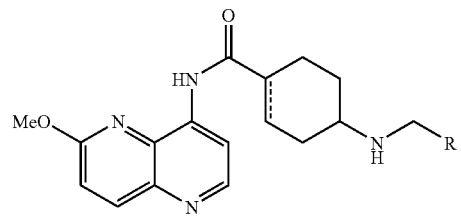

| Example | Method of synthesis (aldehyde) | Stereochemistry | salt<br>B Dihydrochloride<br>A Hydrochloride<br>R Trihydrochloride | R |
|---|---|---|---|---|
| 210 | (Example 301d) | trans-cyclohexane | B | 3-Oxo-3,4-dihydro-2H-pyrido[3,2-b][1,4]thiazin-6-yl |
| 211 | a | cyclohexene single enantiomer (slow) | B | 3-Oxo-3,4-dihydro-2H-benzo[1,4]thiazin-6-yl |
| 212 | a | cyclohexene single enantiomer (fast) | B | 3-Oxo-3,4-dihydro-2H-benzo[1,4]thiazin-6-yl |
| 213 | b | trans-cyclohexane | B | 7-Fluoro-2,3-dihydro-benzo[1,4]dioxin-6-yl |
| 214 | c | trans-cyclohexane | B | 3,4-Dihydro-2H-benzo[1,4]thiazin-6-yl |
| 215 | d | trans-cyclohexane | B | 1-Oxo-1,2-dihydro-isoquinolin-3-yl |

-continued

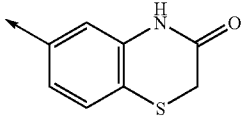

| Example | Method of synthesis (aldehyde) | Stereochemistry | salt B Dihydrochloride A Hydrochloride R Trihydrochloride | R |
|---|---|---|---|---|
| 216 | e | cis-cyclohexane | B | 3-Oxo-3,4-dihydro-2H-benzo[1,4]thiazin-6-yl |

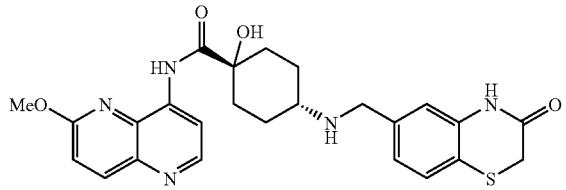

a Prepared from Example 150b by preparative HPLC to give the single enantiomers, which were converted to Examples 211 (from slow-running enantiomer) & Example 212 (from fast-running enantiomer) by method of Example 150c/d
b 7-Fluoro-2,3-dihydro-benzo[1,4]dioxine-6-carboxaldehyde prepared from 6-fluoro-2,3-dihydro-benzo[1,4]dioxine [V. Daukas et al Chemija, 1999, 10 (1), 59] by reaction of dichloromethyl methyl ether and titanium tetrachloride.
c 3,4-Dihydro-2H-benzo[1,4]thiazine-6-carboxaldehyde prepared from 3-oxo-3,4-dihydro-2H-benzo[1,4]thiazine-6-carboxylic acid methyl ester by reaction with lithium aluminium hydride followed by oxidation with manganese dioxide.
d Prepared from 1-oxo-1,2-dihydro-isoquinoline-3-carboxaldehyde [AR. Modi et at Indian J. Chem. 17b 624–6 (1979)]
e Prepared from cis-4-amino-cyclohexanecarboxylic acid (6-methoxy-[1,5]naphthyridin-4-yl)-amide (itself derived from cis-cyclohexane-1,4-dicarboxylic acid mono-tert-butyl ester using the palladium-catalysed chemistry of Example 300d) by analogous methods to the trans-series (Example 1f)

Example 300

1-Hydroxy-t-4-[(3-oxo-3,4-dihydro-2H-benzo[1,4]thiazin-6-ylmethyl)-amino]-r-cyclohexanecarboxylic Acid (6-methoxy-[1,5]naphthyridin-4-yl)-amide Dihydrochloride (a) trans/cis-(4-Cyano-4-hydroxy-cyclohexyl)-carbamic acid tert butyl ester (4-Oxo-cyclohexyl)-carbamic acid tert-butyl ester (50 g, 230 mmol) was added to a vigorously stirred mixture of ethyl acetate (1 liter) and water (750 ml) containing sodium hydrogen carbonate (40 g) and potassium cyanide (23 g, 352 mmol). After 20 hours, the phases were separated and the organic extract washed with water then brine. The ethyl acetate phase was dried (MgSO4) then evaporated to give a pale yellow foam (55.2 g, 100%) which was used without further purification.

MS (+ve ion electrospray) m/z 241 (MH+).

(b) trans/cis-4-Amino-1-hydroxy-cyclohexanecarboxylic acid amide hydrochloride

The cyanohydrins (300a) (27.6 g, 115 mmol) were dissolved in concentrated hydrochloric acid (300 ml) (caution—mildly exothermic on this scale, and evolution of CO2). After 2 hours the mixture was evaporated to dryness, azeotroping with toluene then chloroform (ca 3 times each). The material was used crude.

MS (+ve ion electrospray) m/z 159 (MH+).

(c) (4-Carbamoyl-r-4-hydroxy-c-cyclohexyl)-carbamic acid tert butyl ester (Method A)

The amine (300b) (approximately 115 mmol) was dissolved in 2M aqueous sodium hydroxide (200 ml) then treated with a solution of di-tert-butyl dicarbonate (26.7 g, 123 mmol) in dioxan (125 ml). The mixture was stirred for 2 hours then filtered. The filtrate was partitioned between ethyl acetate (ca 1.5 liters) and brine (ca 1 liter). The organic extract was washed with brine, dried, and evaporated to give a white solid (ca 6.5 g) which was approximately a 1:1 mixture of trans/cis. Chromatography on silica gel, eluting with a 0–10% methanol in dichloromethane gradient, afforded the single carbamate as a white solid (2.5 g) (slower running isomer).

MS (+ve ion electrospray) m/z 259 (MH+).

(d) [r-4-Hydroxy-4-(6-methoxy-[1,5]naphthyridin-4-ylcarbamoyl)-c-cyclohexyl]-carbamic acid tert-butyl ester A mixture of the amide (300c) (0.51 g), cesium carbonate (0.818 g), tris(dibenzylideneacetone)dipalladium(0) (38 mg), and rac-2,2'-bis(diphenylphosphino)-1,1'-binaphthyl (77.4 mg) in dry dioxan (20 ml) under argon, was sonicated for 10 minutes. 1,1,1-trifluoro-methanesulfonic acid 6-methoxy-[1,5]naphthyridin-4-yl ester (1b) (0.64 g) was added, and the mixture was stirred and heated at 85° C. for 18 hours, under argon. The mixture was cooled, filtered, and the filtrate evaporated and chromatographed on silica gel, eluting with chloroform, then (1–2%) methanol-dichloromethane, to afford a solid (0.85 g).

MS (+ve ion electrospray) m/z 417 (MH+).

(e) t-4-Amino-1-hydroxy-r-cyclohexanecarboxylic acid (6-hydroxy-[1,5]naphthyridin-4-yl)-amide The carbamate (300d) (0.85 g) in dichloromethane (30 ml) was treated with trifluoroacetic acid (30 ml) for 2 hours and evaporated. Water and sodium carbonate solution were added and the resulting solid was collected, washed with water and dried in vacuo, to afford a white solid (0.64 g).

MS (+ve ion electrospray) m/z 317 (MH+).

(f) Title Compound

A mixture of carboxaldehyde (4c) (69 mg) and amine (300e) (95 mg) in chloroform (4 ml) and methanol (4 ml) with 3A molecular sieves was heated under reflux for 3 hours, cooled, and treated with sodium triacetoxyborohydride (191 mg). After stirring at room temperature for 4 days, the mixture was diluted with chloroform (20 ml) and washed with aqueous sodium carbonate. The aqueous was re-extracted with chloroform and the combined organic fractions dried ($Na_2SO_4$) and evaporated and chromatographed on silica gel, eluting with 2–10% methanol-dichloromethane to give free base of the title compound (80 mg).

$^1$H NMR δ($CDCl_3/CD_3OD$) 1.5–1.7 (2H, m), 1.8–2.0 (4H, m), 2.0–2.2 (2H, m), 2.72 ((1H, m), 3.45 (2H, s), 3.85 (2H, s), 4.17 (3H, s), 6.92 (1H, d), 7.02 (1H, dd), 7.24 (1H, d), 7.32 (1H, d), 8.20 (1H, d), 8.57 (1H, d), 8.65 (1H, d) MS (+ve ion electrospray) m/z 494 (MH$^+$)

The free base, in chloroform/methanol (1:1) was treated with 4M HCl in dioxan (0.5 ml) and evaporated to dryness. The solid was triturated with ether, filtered and dried in vacuo, to provide title compound (85 mg).

Alternative preparation of Example (300c) (4-Carbamoyl-r-4-hydroxy-c-cyclohexyl)-carbamic acid tert-butyl ester (Method B)

(g) 2-Acetoxycyclohex-3-enecarboxylic Acid Butyl ester

1-Acetoxy-1,3-butadiene (30.1 g, 0.268 mol) was dissolved in toluene (20 mL). To this was added butyl acrylate (37.9 mL, 0.265 mol) and hydroquinone (0.14 g). The colourless solution was heated at 120° C. for 26 h under argon. More 1-acetoxy-1,3-butadiene (10.6 g, 0.095 mol) in toluene (2 mL) was then added, and heating continued for a further 68 h. The solution was cooled then evaporated in vacuo to give a viscous yellow oil (69 g), which was used without further purification.

δH ($CDCl_3$) 0.91–0.95 (3H, m), 1.3–2.2 (1H, m), 2.6–2.72 (1H, m), 4.01–4.16 (2H, m), and 5.48–6.07 (3H, m).

(h) Cyclohexa-1,3-dienecarboxylic Acid Butyl ester

Crude butyl ester (300 g) (55.25 g, max 0.207 mol) was dissolved in dry tetrahydrofuran (320 mL) and cooled in an ice/salt bath. To this was added slowly, over 1 h, potassium t-butoxide in tetrahydrofuran (1 M, 220 mL, 0.22 mol). After 0.5 h water and petroleum ether were added and the mixture filtered quickly through kieselguhr. The phases were separated and the aqueous extracted with more petroleum ether (×2). The combined organic extracts were washed with brine, dried and evaporated to give a mobile orange oil (31.85 g, 86%), which was used immediately without further purification.

δH ($CDCl_3$) 0.93–0.99 (3H, m), 1.3–1.7 (4H, m), 2.2–2.5 (4H, m), 4.1–4.2 (2H, m), 6.0–6.2 (2H, m), and 6.95–7.02 (1H, m).

(i) 2-Oxa-3-aza-bicyclo[2.2.2]oct-5-ene-1,3-dicarboxylic acid 3-benzyl Ester 1-butyl Ester Crude butyl ester(300h) (31.84 g, max 0.176 mol) was dissolved in dichloromethane (300 mL). To this was added N-hydroxy carbamic acid benzyl ester (30.9 g, 0.185 mol). This solution was cooled in an ice/salt bath then a solution of tetrabutylammonium periodate (80.1 g, 0.185 mol) in dichloromethane (100 mL) was added dropwise over 1 h. After stirring for a further 1 h, with cooling, the mixture was reduced to a small volume in vacuo then stirred vigorously while adding diethyl ether (1 L). The mixture was filtered washing well with diethyl ether. The filtrate was then washed with aqueous sodium bisulphite (×2), and brine, dried and evaporated to give a brown oil. This residue was purified by chromatography on silica gel, eluting with 25–28% diethyl ether in petroleum ether, to give a viscous pale orange oil (42.41 g, ~69%) (contaminated with a little benzyl alcohol).

δH($CDCl3$) 0.94 (3H, t), 1.35–1.75 (6H, m)$_7$ 2,15–2.4 (2H, m), 4.2–4.35 (2H, m), 4.84–4.89 (1H, m), 5.12–5.20 (2H, m), 6.59–6.71 (2H, m), and 7.28–7.39 (5H, m).

(j) 2-Oxa-3-aza-bicyclo[2.2.2]oct-5-ene-1,3-dicarboxylic Acid 3-benzyl Ester

To a solution of di-ester (300i) (42.13 g, 0.122 mol) in 1,4-dioxane (250 mL) was added aqueous sodium hydroxide solution (0.5 M, 250 mL, 0.125 mol). The mixture was stirred for 50 min then washed with diethyl ether (×3). The aqueous phase was adjusted to pH2 with 5 M hydrochloric acid, and extracted with ethyl acetate (×3). The combined organic extracts were washed with brine, dried and evaporated to give a cream solid (29.53 g, 84%).

δH ($CDCl_3/CD_3OD$) 1.53–1.79 (2H, m), 2.13–2.39 (2H, m), 4.82–4.89 (1H, m), 5.11–5.23 (2H, m), 6.57–6.69 (2H, m), and 7.3–7.4 (5H, m).

(k) 1-Carbamoyl-2-oxo-3-aza-bicyclo[2.2.2]oct-5-ene-3-carboxylic acid benzyl ester The benzyl ester (300j) (12.0 g, 41.5 mmol) and 1-hydroxy-7-azabenzotriazole (6.26 g, 46 mmol) were dissolved in DMF (100 mL) then 1-ethyl-3-(3-dimethylaminopropyl)carbodiimide hydrochloride (8.79 g, 46 mmol) added. After stirring for 5 min ammonium hydrogen carbonate (8.22 g, 104 mmol) was added. Four further small portions of ammonium hydrogen carbonate were added over the next 7 h. The mixture was then stirred overnight, diluted with water and extracted with ethyl acetate (×4). The combined organic extracts were washed with 5% aqueous citric acid then brine, dried and evaporated to give an off-white solid (9.9 g, 83%).

MS (+ve ion electrospray) m/z 289 (MH+).

(c) (4-Carbamoyl-r-4-hydroxy-c-cyclohexyl)-carbamic acid tert butyl ester

The benzyl ester (300 k) (9.75 g, 33.8 mmol) was dissolved in 1,4-dioxane (150 mL) and water (60 mL) and hydrogenated over 10% palladium on carbon (50% aqueous paste, 3.3 g) at 40° C. and 55 psi for 68 h. More catalyst (2 g) was added after 4 h. The mixture was then filtered through kieselguhr, washing well with 1,4-dioxane and water. To this solution was added 2 N sodium hydroxide (25 mL, 50 mmol) followed by a solution of di-tert-butyl dicarbonate (11.12 g, 51 mmol) in 1,4-dioxane (10 mL). The reaction mixture was stirred for 5 h then reduced in volume in vacuo, before extracting with ethyl acetate (×5). The combined organic extracts were dried and evaporated to give a white solid (5.96 g), which was chromatographed on silica (400 g). Elution with 0–6.5% methanol in dichloromethane gave a white powder (5.52 g, 63%), identical to the material produced earlier.

δH (d₆-DMSO) 1.3–1.76 (17H, m), 3.17 (1H, br s), 4.95 (1H, s), 6.71 (1H, d), 7.0 (1H, s), and 7.14 (1H, s).

Alternative Preparation of 1-carbamoyl-2-oxa-3-aza-bicyclo[2.2.2]oct-5-ene-3-carboxylic acid benzyl ester (300 k)

(1) Acetic acid 6-carbamoyl-cyclohex-2-enyl ester

1-Acetoxy-1,3-butadiene (20.79 g, 0.185 mol) was dissolved in toluene (21 mL). To this was added acrylamide (11.98 g, 0.168 mol) and hydroquinone (0.111 g). The colourless solution was heated at 110° C. for 116 h under argon. More 1-acetoxy-1,3-butadiene (5.67 g, 0.051 mol) was then added, and heating continued for a further 24 h. The solution was cooled then dichloromethane added. This solution was purified by Biotage 75 chromatography twice on silica (2×400 g) to give the title compound as a viscous oil (21.76 g, 71%), which solidified on standing;

δH (CDCl₃) 1.85–2.7 (8H, m), and 5.5–6.08 (5H, m).

(m) Cyclohexa-1,3-dienecarboxylic acid Amide

The ester (300 l) (16.28 g, 89 mmol) was dissolved in dry tetrahydrofuran (200 mL) and cooled in an ice bath. To this was added slowly, over 0.5 h, potassium t-butoxide in tetrahydrofuran (1 M, 100 mL, 100 mmol). After stirring for 0.5 h with cooling and 2.5 h at room temperature, ethyl acetate was added and the solution washed with a little water. The organic phase was dried and evaporated to give a brown oil (>100%). This was used immediately without further purification.

(k) 1-Carbamoyl-2-oxa-3-aza-bicyclo[2.2.2]oct-5-ene-3-carboxylic acid benzyl ester Crude amide (300 m) (max 89 mmol) was dissolved in dichloromethane (150 mL). To this was added N-hydroxy carbamic acid benzyl ester (15.61 g, 93.5 mmol). This solution was cooled in an ice bath then a solution of tetrabutylammonium periodate (40.49 g, 93.5 mmol) in dichloromethane (50 mL) was added dropwise over 0.5 h. After stirring for a further 14 h the mixture was reduced to a small volume in vacuo then diluted with ethyl acetate (500 mL). The mixture was then washed with water, aqueous sodium bisulphite (×3), and brine, dried and evaporated to give a yellow solid. This residue was purified by Biotage 75 chromatography on silica (800 g), eluting with 22–60% ethyl acetate in petroleum ether, to give a white solid (9.47 g, 37%);

δH (CDCl₃) 1.52–1.62 (1H, m), 1.75–1.86 (1H, m), 2.12–2.24 (2H, m), 4.81–4.88 (1H, m), 5.11–5.23 (2H, m), 5.6 (1H, br s), 6.51–6.64 (3H, m), and 7.3–7.4 (5H, m).

Example 301

1-Hydroxy-t-4-[(3-oxo-3,4-dihydro-2H-pyrido[3,2-b][1,4]thiazin-6-ylmethyl)-amino]-r-cyclohexanecarboxylic Acid (6-methoxy-[1,5]naphthyridin-4-yl)-amide Dihydrochloride

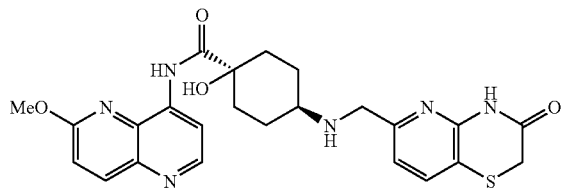

(a) Methyl 3-oxo-3,4-dihydro-2H-pyrido[3,2-b][1,4]thiazine-6-carboxylate

A solution of ethyl 2-mercaptoacetate (1.473 ml) in DMF (48 ml) was ice-cooled and treated with sodium hydride (540 mg of a 60% dispersion in oil). After 1 hour methyl 6-amino-5-bromopyridine-2-carboxylate (3 g) (T. R. Kelly and F. Lang, *J. Org. Chem.* 61, 1996, 4623–4633) was added and the mixture stirred for 16 hours at room temperature. The solution was diluted with EtOAc (1 liter), washed with water (3×300 ml), dried and evaporated to about 10 ml. The white solid was filtered off and washed with a little EtOAc to the ester (0.95 g).

MS (APCI⁻) m/z 223 ([M–H]⁻, 100%)

(b) 3-Oxo-3,4-dihydro-2H-pyrido[3,2-b][1,4]thiazine-6-carboxylic acid

A solution of ester (301a) (788 mg) in dioxan (120 ml)/water (30 ml) was treated dropwise over 2 hours with 0.5M NaOH solution (8 ml) and stirred overnight. After evaporation to approx. 3 ml, water (5 ml) was added and 2N HCl to pH4. The precipitated solid was filtered off, washed with a small volume of water and dried under vacuum to give a solid (636 mg).

MS (APCI⁻) m/z 209 (M–H]⁻, 5%), 165([M-COOH]⁻, 100%)

(c) 6-Hydroxymethyl-3-oxo-3,4-dihydro-2H-pyrido[3,2-b][1,4]thiazine

A solution of the carboxylic acid (301b) (500 mg) in TIF (24 ml) with triethylamine (0.396 ml) was cooled to –10° C. and isobutyl chloroformate (0.339 ml) added. After 20 minutes the suspension was filtered through kieselguhr into an ice-cooled solution of sodium borohydride (272 mg) in water (8 ml), the mixture stirred 30 minutes and the pH reduced to 7 with dilute HCl. The solvent was evaporated and the residue triturated under water. The product was filtered and dried under vacuum to give a white solid (346 mg).

MS (APCI⁻) m/z 195 ([M–H]⁻, 50%), 165(100%)

(d) 3-Oxo-3,4-dihydro-2H-pyrido[3,2-b][1,4]thiazine-6-carboxaldehyde

A solution of the alcohol (301c) (330 mg) in dichloromethane (30 ml)/TBF (30 ml) was treated with manganese dioxide (730 mg) and stirred at room temperature. Further manganese dioxide was added after 1 hour (730 mg) and 16 hours (300 mg). After a total of 20 hours the mixture was filtered through kieselguhr and the filtrate evaporated. The product was triturated with EtOAc/hexane (1:1) and collected to give a solid (180 mg).

MS (APCI⁻) m/z 195 ([M–H]⁻, 95%), 165 (100%)

(e) Title compound

A mixture of the carboxaldehyde (301d) (62 mg) and amine (300e) (100 mg) in chloroform (1.5 ml)/methanol (1.5 ml) with 3A molecular sieves was refluxed 8 hours, cooled and treated with sodium triacetoxyborohydride (237 mg). After stirring overnight, the mixture was diluted with chloroform (20 ml) and washed with aqueous NaHCO₃. The aqueous was re-extracted with chloroform and the combined organic fractions dried over MgSO₄ and evaporated. Chromatography of the residue (CHCl₃/MeOH/NH₄OH 95:5:0.5) gave free base of the title compound (100 mg).

¹HNMR δ(CDCl₃/CD₃OD) 1.5–1.7 (2H, m), 1.8–2.0 (4H, m), 2.0–2.2 (2H, m), 2.6–2.7 (1H, m), 3.50 (2H, s), 3.87 (2H, s), 4.17 (3H, s), 6.98 (1H, d), 7.24 (1H, d), 7.67 (1H, d), 8.18 (1H, d), 8.53 (1H, d), 8.63 (1H, d)

This material as a solution in chloroform/methanol 1:1 was treated with 1M HCl in ether (0.5 ml) and evaporated to dryness. The solid was triturated under ether, filtered and dried under vacuum to provide the title compound (112 mg).

MS (+ve ion electrospray) m/z 495 (MH⁺, 100%)

Example 302

1-Hydroxy-t-4-[(2-oxo-2,3-dihydro-1H-pyrido[3,4-b][1,4]thiazin-7-ylmethyl)-amino]-r-cyclohexanecarboxylic Acid (6-methoxy-[1,5]naphthyridin-4-yl)-amide Dihydrochloride

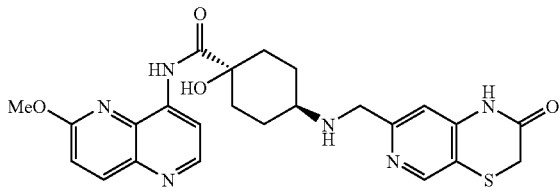

(a) 5-Fluoro-2-picoline N-oxide

The preparation was based on E. J. Blanz, F. A. French, J. R. DoAmaral and D. A. French, *J. Med. Chem.* 13, 1970, 1124–1130. 5-Amino-2-picoline (12.5 g) in ethanol (105 ml) and 50% fluoroboric acid (44.5 ml) was stirred at −5° C. and treated dropwise over 45 minutes. with n-butyl nitrite (31.25 ml). The solution was maintained at this temp. for 3 hours, treated with ether (100 ml, precooled to −20° C.) and the solid filtered off, quickly transferred to a flask and covered with hexane (precooled to −20° C.). After allowing to warm to approx. 20° C. and standing for 3 days the hexane was decanted and 2M NaOH solution added until basic (pH 10). The mixture was filtered and the filtrate extracted with dichloromethane (10×200 ml). The organic solution was dried, evaporated to 200 ml and treated with m-chloroperbenzoic acid (26.5 g). After stirring 16 hours the solution was washed with excess aqueous sodium bicarbonate and the aqueous re-extracted with dichloromethane (10×200 ml). The organic fraction was dried and evaporated and the residue chromatographed (15% EtOH/EtOAc) to give the pyridine N-oxide (5.5 g).

MS (APCI$^+$) m/z 128 (MH$^+$, 100%)

(b) 5-Fluoro-4-nitro-2-picoline N-oxide

The pyridine N-oxide (302a) (2.12 g) was treated with an ice-cooled mixture of fuming nitric acid (7.1 ml) and conc. sulfuric acid (7.1 ml), heated at 35–40° C. for 1 hour and 65–70° C. for 5.5 hours, cooled and ice (45 g) added. 10M NaOH was added to pH 10 and the mixture extracted with EtOAc (3×30 ml). The organic fraction was dried and evaporated to give a yellow solid (2.16 g).

MS (APCI$^+$) m/z 173 (MH$^+$, 30%), 127 (100%)

(c) 5-Ethoxycarbonylmethylthio-4-nitro-2-picoline N-oxide

Ethyl 2-mercaptoacetate (1.51 g) in dioxan (15.6 ml) under argon was treated with sodium hydride (550 mg of a 60% dispersion in oil) and stirred for 4 hours. The pyridine N-oxide (302b) (2.16 g) was added and stirring was continued for 3 days. Water (50 ml) was added and the mixture extracted with chloroform (3×50 ml). The organic fraction was dried and evaporated to give a yellow solid (3.31 g).

MS (APCI$^+$) m/z 273 (MH$^+$, 80%), 125 (100%)

(d) 2-Acetoxymethyl-5-ethoxycarbonylmethylthio-4-nitropyridine

A solution of the ester (302c) (3.31 g) in acetic anhydride (43 ml) was heated to 80° C. for 6 hours, evaporated, xylene (100 ml) added and evaporated. Chromatography of the residue (eluent EtOAc/hexane 1:1) gave the pyridine (1.03 g).

(e) 7-Acetoxymethyl-2-oxo-2,3-dihydro-1H-pyrido[3,4-b][1,4]thiazine

A solution of the pyridine (302d) (1.03 g) in glacial acetic acid (27.5 ml) was treated with iron powder (1.75 g), stirred at 60° C. for 3 hours, filtered through kieselguhr and evaporated to dryness. Saturated aqueous sodium bicarbonate (300 ml) was added and the mixture extracted with EtOAc (3×200 ml). The organic fraction was dried and evaporated. The residue was redissolved in acetic acid (30 ml), heated to 100° C. for 24 hours, evaporated and chromatographed (eluent EtOAc/hexane 1:1) to give a solid (340 mg).

MS (APCI$^-$) m/z 237 ([M–H]$^-$, 90%), 195 (100%)

(f) 7-Hydroxymethyl-2-oxo-2,3-dihydro-1H-pyrido[3,4-b][1,4]thiazine

A solution of the pyridothiazinone (302e) (340 mg) in dioxan (9 ml) was treated dropwise over 2 hours with 0.5M NaOH (3.7 ml), stirred for 18 hours and evaporated. Water (10 ml) was added and the product filtered off, washed with water and dried under vacuum to give a white solid (231 mg).

MS (APCI$^-$) m/z 195 ([M–H]$^-$, 100%)

(g) 2-Oxo-2,3-dihydro-1H-pyrido[3,4-b][1,4]thiazine-7-carboxaldehyde

A mixture of the pyridothiazinone (226 mg) manganese dioxide (600 mg), THF (22.5 ml) and 1,2-dichloroethane (22.5 ml) was heated at 65° C. for 18 hours under argon. Filtration through kieselguhr and evaporation of solvent gave the product as an off-white solid (173 mg).

MS (APCI$^-$) m/z 193 ([M–H]$^-$, 100%)

(h) Title Compound

A mixture of the carboxaldehyde (302 g) (62 mg) and amine (300e) (100 mg) in chloroform (1.5 ml)/methanol (1.5 ml) with 3A molecular sieves was refluxed for 24 hours, cooled and treated with sodium triacetoxyborohydride (237 mg). After stifling overnight, the mixture was diluted with chloroform (20 ml) and washed with aqueous NaHCO$_3$. The aqueous fraction was re-extracted 3 times with 20% ethanol in chloroform and the combined organic fraction dried over MgSO$_4$ and evaporated. Chromatography of the residue (CHCl$_3$/MeOH/NH$_4$OH 95:5:0.5) gave free base of the title compound (88 mg).

$^1$H NMR δ(CDCl$_3$/CD$_3$OD) 1.5–1.7 (2H, m), 1.8–2.2 (6H, m), 2.5–2.7 (1H, m), 3.48 (2H, s), 3.87 (2H, s), 4.17 (3H, s), 6.91 (1H, s), 7.22 (1H, d), 8.17 (1H, d), 8.37 (1H, s), 8.54 (1H, d), 8.62 (1H, d)

This material as a solution in chloroform/methanol 1:1 was treated with 1M HCl in ether (0.5 ml) and evaporated to dryness. The solid was dried under vacuum to provide the title compound (78 mg).

MS (+ve ion electrospray) m/z 495 (MH$^+$, 100%)

Example 303

1-Hydroxy-t-4-[(2-oxo-2,3-dihydro-1H-pyrido[2,3-b][1,4]thiazin-7-ylmethyl)-amino]-r-cyclohexanecarboxylic Acid (6-methoxy-[1,5]naphthyridin-4-yl)-amide Dihydrochloride

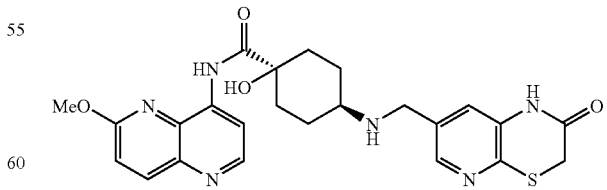

(a) Title Compound

A mixture of the carboxaldehyde (13e) (37 mg) and amine (300e) (55 mg) in chloroform (4 ml)/methanol (4 ml) with 3A molecular sieves was refluxed for 3 hours, cooled and treated with sodium triacetoxyborohydride (300 mg), portionwise. After stirring at room temperature for 7 days, the mixture was diluted with chloroform and washed with aqueous Na₂CO₃ solution, dried over Na₂SO₄ and evaporated. The residue was chromatographed on silica gel, eluting with 2–10% methanol-dichloromethane to give the free base of the title compound (30 mg).

¹H NMR δ(CDCl₃/CD₃OD) 1.5–1.7 (2H, m), 1.8–2.2 (6H, m), 2.65 (1H, m) 3.60 (2H, s), 3.81 (2H, s), 4.17 (3H, s), 6.91 (1H, s), 7.21 (1H, d), 7.25 (1H, d), 8.10 (1H, d), 8.18 (1H, d), 8.55 (1H, d), 8.62 (1H, d)

This material as a solution in chloroform/methanol 1:1 was treated with 4M HCl in dioxan (0.2 ml) and evaporated to dryness. The solid was dried in vacuo to provide the title compound (35 mg).

MS (+ve ion electrospray) m/z 495 (MH⁺, 100%)

Example 304

1-Hydroxy-t-4-[(7-bromo-3-oxo-3,4-dihydro-2H-pyrido[3,2-b][1,4]thiazin-6-ylmethyl)-amino]-r-cyclohexanecarboxylic Acid (6-methoxy-[1,5]naphthyridin-4-yl)-amide Dihydrochloride

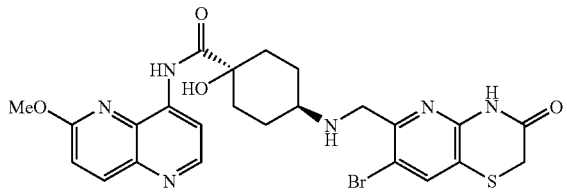

(a) Methyl 6-amino-3,5-dibromopyridine-2-carboxylate

A solution of methyl 6-amino-3-bromopyridine-2-carboxylate (20.62 g) (T. R. Kelly and F. Lang, *J. Org. Chem.* 61, 1996, 4623–4633) in chloroform (570 ml) was treated dropwise over 2 hours with bromine (4.62 ml) in chloroform (115 ml) and stirred 16 hours. The solution was washed with excess aqueous sodium bicarbonate, dried and evaporated. Crystallisation from EtOAc/hexane gave the bromopyridine (13.5 g).

MS (APCI⁺) m/z 309, 311, 313 (MH⁺, 70%), 295, 297, 299 (100%).

(b) Methyl 7-bromo-3-oxo-3,4-dihydro-2H-pyrido[3,2-b][1,4]thiazine-6-carboxylate This was prepared from methyl 6-amino-3,5-dibromopyridine-2-carboxylate (12.75 g) by the method of Example (301a) to give 5.85 g.

MS (APCI⁺) m/z 303, 305 (MH⁺, 30%), 271, 273 (100%)

(c) 7-Bromo-3-oxo-3,4-dihydro-2H-pyrido[3,2-b][1,4]thiazine-6-carboxylic Acid

This compound was prepared (73%) from the ester (304b) by the method of Example (301b)

MS (APCI⁻) m/z 287,289 ([M–H]⁻, 3%), 243, 245 ([M—COOH]⁻, 100%)

(d) 7-Bromo-6-hydroxymethyl-3-oxo-3,4-dihydro-2H-pyrido[3,2-b][1,4]thiazine

This compound was prepared (80%) from carboxylic acid (304c) by the method of Example (301c).

MS (APCI⁺) m/z 275, 277 (MH⁺˙ 20%), 257,259 (100%)

(e) 7-Bromo-3-oxo-3,4-dihydro-2H-pyrido[3,2-b][1,4]thiazine-6-carboxaldehyde

A mixture of the 7-bromo-pyridothiazinone (304d) (518 mg), manganese dioxide (870 mg), THF (45 ml) and 1,2-dichloroethane (45 ml) was heated at 60° C. under argon. Further manganese dioxide was added after 4 hours (870 mg) and 20 hours (600 mg).

After a total of 30 hours filtration through kieselguhr and evaporation of solvent gave a solid (320 mg).

MS (APCI⁻) m/z 271, 273 ([M–H]⁻, 40%), 152 (100%)

(f) Title Compound

A mixture of the carboxaldehyde (304e) (87 mg) and the amine (300e) (100 mg) in chloroform (2 ml)/methanol (2 ml) with 3A molecular sieves was refluxed 18 hours, cooled and treated with sodium triacetoxyborohydride (237 mg). After stirring overnight, the mixture was diluted with chloroform (20 ml) and washed with aqueous NaHCO₃. The aqueous fraction was re-extracted with 20% ethanol in chloroform and the combined organic fractions dried (MgSO₄) and evaporated. Chromatography of the residue (CHCl₃MeOH/NH₄OH 95:5:0.5) gave free base of the title compound (80 mg).

¹H NMR δ(CDCl₃/CD₃OD) 1.5–1.7 (2H, m), 1.8–2.2 (6H, m), 2.6–2.8 (1H, m), 3.51 (2H, s), 3.99 (2H, s), 4.17 (3H, s), 7.22 (1H, d), 7.85 (1H, s), 8.18 (1H, d), 8.54 (1H, d), 8.63 (1H, d)

This material as a solution in chloroform/methanol 1:1 was treated with 1M HCl in ether (0.35 ml) and evaporated to dryness. The solid was triturated under ether, filtered and dried under vacuum to provide the title compound (90 mg).

MS (+ve ion electrospray) m/z 573 and 575 (MH⁺, 100%)

Example 305

1-Hydroxy-t-4-[(3-oxo-3,4-dihydro-2H-pyrido[3,2-b][1,4]oxazin-6-ylmethyl)-amino]-r-cyclohexanecarboxylic Acid (6-methoxy-[1,5]naphthyridin-4-yl)-amide Dihydrochloride

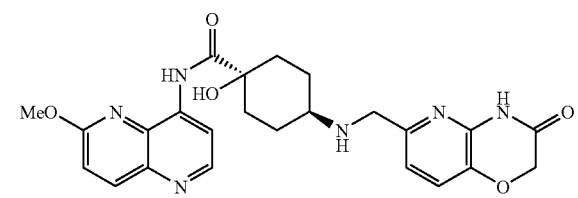

(a) 2-Bromo-5-hydroxy-6-nitropyridine

3-Hydroxy-2-nitropyridine (20 g, 0.143 mole) was dissolved in methanol (400 ml) and a solution of 25% sodium methoxide in methanol (33 ml, 0.13 mole) was added at room temperature. The mixture was stirred for 30 min, then was cooled to 0° C., and bromine (7.2 ml, 0.14 mole) was added slowly. The reaction was then stirred at 0° C. for 30 min, then was quenched with glacial AcOH (2.5 ml). The solvent was removed in vacuo to afford material (30 g, 96%), which was used without further purification.

MS (ES) m/z 219.0 (M+H)⁺.

(b) Ethyl (6-bromo-2-nitro-pyridin-3-yloxy)acetate

The hydroxypyridine (305a) (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et₂O. The precipitate was removed by suction filtration, and the filtrate was concentrated in vacuo to afford material (38 g, 89%), which was used without further purification.

MS (ES) m/z 305.0 M+H)⁺.

(c) 6-Bromo-4H-pyrido[3,2-b][1,4]oxazin-3-one

The nitropyridine (305b) (38 g, 0.125 mole) was dissolved in glacial AcOH (150 ml), and iron powder (20 g, 0.36 mole) was added. The mixture was mechanically stirred and heated at 90° C. for 5 hr, then was cooled to room temperature and diluted with EtOAc (300 ml). The mixture was filtered through a pad of silica gel and the filtrate was

87 concentrated in vacuo and the residue recrystallized from MeOH (15 g, 52%).

MS (ES) m/z 229.0 (M+H)+.

(d) 6-((E)-Styryl)-4H-pyrido[3,2-b][1,4]oxazin-3-one

The bromopyridine (305c) (6.0 g, 26.3 mmole) and trans-2-phenylvinylboronic acid (3.9 g, 26.3 mmole) were dissolved in 1,4-dioxane (150 ml) and the solution was degassed with argon. $(Ph_3P)_4Pd$ (230 mg, 0.2 mmole) was added, followed by a solution of potassium carbonate (6.9 g, 50 mmole) in $H_2O$ (20 ml). The reaction was heated at reflux under argon overnight, then was cooled to room temperature and diluted with EtOAc (200 ml). The solution was washed sequentially with $H_2O$ and brine, dried ($Na_2SO_4$), and concentrated in vacuo. The solid residue was purified by flash chromatography on silica gel (5–10% $EtOAc/CHCl_3$) to afford a solid (2.5 g, 38%).

MS (ES) m/z 253.0 M+H)+.

(e) 3-Oxo-3,4-dihydro-2H-pyrido[3,2-b][1,4]oxazine-6-carboxaldehyde

The pyridine (305d) (1.2 g, 4.8 mmole) was dissolved in $CH_2Cl_2$ (200 ml) and the solution was cooled to −78° C. Ozone was bubbled through the solution with stirring until a pale blue color appeared, then the excess ozone was removed by bubbling oxygen through the solution for 15 min. Dimethylsulfide (1.76 ml, 24 mmole) was added to the solution, and the reaction was stirred at −78° C. for 3 hr, then at room temperature overnight. The solvent was removed in vacuo, and the residue was triturated with $Et_2O$ (50 ml). The collected solid was washed with additional $Et_2O$ and dried to afford a solid (700 mg, 82%).

MS (ES) m/z 179.0 (M+H)+.

(e) Title Compound

A mixture of the carboxaldehyde (305e) (0.5 g; 2.8 mmol) and amine (300e) (0.93 g; 2.94 mmol) in methanol (35 ml)/dimethylformamide (35 ml)/acetic acid (3.5 ml) was heated at 80° C. with 3A molecular sieves for 3 hours, cooled and treated with sodium cyanoborohydride (0.6 g; 9.5 mmol). After stirring overnight at room temperature, the mixture was diluted with methanol-chloroform (1:1), filtered and the filtrate evaporated to dryness. It was treated with aqueous sodium carbonate and extracted (4×) with methanol-chloroform (1:9), dried (sodium sulfate), and evaporated to dryness. Chromatography of the residue (2–10% methanol-dichloromethane) gave free base of the title compound (1.03 g; 74%).

$^1H$ NMR δ($CDCl_3/CD_3OD$) 1.5–1.7 (2H, m), 1.8–2.0 (4H, m), 2.0–2.12 (2H, m), 2.6–2.7 (1H, m), 3.38 (2H, s), 3.83 (2H, s), 4.17 (3H, s), 6.96 (1H, d), 7.25 (2H, m), 8.18 (1H, d), 8.53 (1H, d), 8.62 (1H, d).

This material as a solution in chloroform/methanol 1:1 was treated with excess 4M HCl in dioxan and evaporated to dryness. The solid was triturated with ether, filtered and dried in vacuo to give the title compound, as a white solid.

MS (+ve ion electrospray) m/z 479 (MH+)

88

Example 306

1-Hydroxy-t-4-[(7-chloro-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide Dihydrochloride

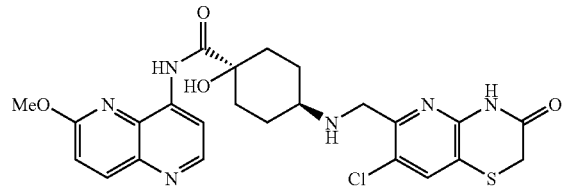

(a) Methyl 6-amino-5-bromo-3-chloropyridine-2-carboxylate

To a solution methyl 6-amino-5-bromopyridine-2-carboxylate (20.04 g) in acetic acid (900 ml) was added N-chlorosuccinimide (13.96 g) and the resultant solution was heated to 120° C. for 1 hour. The solution was then evaporated and treated with excess aqueous sodium bicarbonate and extracted with dichloromethane. The organic fraction was dried and evaporated to give the product (21.98 g).

MS (+ve ion electrospray) m/z 265 and 267 (MN+, 100%)

(b) Methyl 7-chloro-3-oxo-3,4-dihydro-2H-pyrido[3,2-b][1,4]thiazine-6-carboxylate This was prepared (51%) from the ester (306a) (23.8 g) by the method of Example (301a) to give a solid (11.8 g).

MS (+ve ion electrospray) m/z 257 (MH+, 100%)

(c) 7-Chloro-3-oxo-3,4-dihydro-2H-pyrido[3,2-b][1,4]thiazine-6-carboxylic acid

This compound was prepared (96%) from the ester (306b) (11.84 g) by the method of Example (301b) to give a solid (9.6 g).

MS (APCI-) m/z 243 ([M−H]−, 2%), 199 ([M-COOH]−, 100%)

(d) 7-Chloro-6-hydroxymethyl-3-oxo-3,4-dihydro-2H-pyrido[3,2-b][1,4]thiazine

This compound was prepared (70%) from the carboxylic acid (306c) by the method of Example (301c).

MS (+ve ion electrospray) m/z 231 (MH+, 100%)

(e) 7-Chloro-3-oxo-3,4-dihydro-2H-pyrido[3,2-b][1,4]thiazine-6-carboxaldehyde

This compound was prepared (49%) from the alcohol (306d) by the method of Example (304e) to give a solid (2.01 g).

MS (+ve ion electrospray) m/z 229 (MH+, 100%)

(f) Title Compound

A mixture of the carboxaldehyde (306e) (134 mg) and the amine (300e) (187 mg) in chloroform (3 ml)/methanol (3 ml) with 3A molecular sieves was refluxed 18 hours, cooled and treated with sodium triacetoxyborohydride (376 mg). After stirring overnight, the mixture was diluted with dichloromethane (50 ml) and washed with aqueous $NaHCO_3$. The aqueous fraction was re-extracted with 10% methanol in dichloromethane and the combined organic fractions dried ($MgSO_4$) and evaporated. Chromatography of the residue ($CH_2Cl_2$:MeOH 90:10) gave free base of the title compound (84 mg).

$^1H$ NMR δ(DMSO) 1.4–1.5 (2H, m), 1.7–1.9 (6H, m), 2.49–2.54 (1H, m), 3.59 (2H, s), 3.89 (2H, s), 4.10 (3H, s), 6.09 (1H, s), 7.33 (1H, d), 7.95 (1H, s), 8.28 (1H, d), 8.44 (1H, d), 8.69 (1H, d), 11.09 (2H, br s)

This material as a solution in dichloromethane:methanol 1:1 was treated with 4M HCl in dioxane (0.10 ml) and evaporated to dryness. The solid was triturated under ether, filtered and dried under vacuum to provide the title compound (75 mg).

MS (+ve ion electrospray) m/z 529 (MH+, 100%).

Example 307

1-Hydroxy-t-4-[(7-oxo-5,6,7,8-tetrahydro-[1,8]naphthyridine-2-ylmethyl)-amino]-r-cyclohexanecarboxylic acid (6-methoxy-[1,5]naphthyridine-4-yl)-amide Dihydrochloride

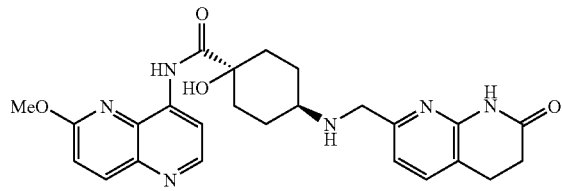

(a) 6-Amino-5-((E)-ethoxycarbonyl-vinyl)-pyridine-2-carboxylic acid methyl ester To a degassed solution of methyl 6-amino-5-bromopyridine-2-carboxylate (1.06 g), ethyl acrylate (2.49 ml), tri-o-tolylphosphine (280 mg), triethylamine (3.18 ml) in dimethylformamide (50 ml) was added tris (dibenzylideneacetone)palladium (0) (211 mg) and the resultant solution was heated at 50° C. for 72 h. After stirring overnight, the mixture was evaporated and the residue treated with dichloromethane (50 ml) and washed with $H_2O$. The aqueous fraction was re-extracted with 10% methanol in dichloromethane and the combined organic fractions dried ($MgSO_4$) and evaporated. Chromatography of the residue (60–80 petroleum ether-ethyl acetate 4:1) gave the product (360 mg, 31%).

MS (+ve ion electrospray) m/z 251 (MH+, 100%)

(b) 6-Amino-5-(2-ethoxycarbonyl-ethyl)-pyridine-2-carboxylic acid methyl ester

A solution of the ester (307a) (350 mg) in MeOH (50 ml) was hydrogenated over palladium on carbon (10%) (35 mg) for 24 h. The suspension was filtered and evaported to give the product (345 mg, 97%).

MS (+ve ion electrospray) m/z 253 (MH+, 100%)

(c) 7-Oxo-5,6,7,8-tetrahydro-[1,8]naphthyridine-2-carboxylic acid methyl ester

A solution of amine (307b) (345 mg) in acetic acid (20 ml) was heated at 100° C. for 1 h. The acetic acid was then evaporated to give a solid (276 mg, 98%).

MS (+ve ion electrospray) m/z 206 (MH+, 100%)

(d) 7-Oxo-5,6,7,8-tetrahydro-[1,8]naphthyridine-2-carboxylic acid

This compound was prepared (96%) from the ester (307c) (272 mg) by the method of Example (301b) to give a solid (263 mg).

MS (APCI−) m/z 191 ([M−H]−, 1%), 147 ([M−COOH]−, 100%)

(e) 7-Hydroxymethyl-3,4-dihydro-1-H-[1,8]naphthyridin-2-one

This compound was prepared (80%) from the carboxylic acid (307d) by the method of Example (301c).

MS (+ve ion electrospray) m/z 179 (MH+, 100%)

(f) 7-Oxo-5,6,7,8-tetrahydro-[1,8]napthyridine-2-carboxaldehyde

This compound was prepared (28%) from alcohol (307e) by the method of Example (304e) to give a solid (72 mg).

MS (+ve ion electrospray) m/z 229 (MH+, 100%)

(g) Title Compound

A mixture of the carboxaldehyde (307f) (72 mg) and amine (300e) (130 mg) in methanol (5 ml)/dimethylformamide (5 ml)/acetic acid (0.5 ml) was heated at 80° C. with 3A molecular sieves for 3 hours, cooled and treated with sodium cyanoborohydride (0.6 g; 9.5 mmol). After stirring overnight at room temperature, the mixture was diluted with methanol-chloroform (1:1), filtered and the filtrate evaporated to dryness. It was treated with aqueous sodium carbonate and extracted (4×) with methanol-chloroform (1:9), dried (sodium sulfate), and evaporated to dryness. Chromatography of the residue (0–10% methanol-dichloromethane) gave free base of the title compound (102 mg; 52%).

1H NMR δ(DMSO) 1.4–1.5 (2H, m), 1.7–1.9 (6H, m), 2.47–2.51 (1H, m), 2.83–2.87 (2H, t), 3.17–3.31 (4H, m), 3.75 (2H, s), 4.10 (3H, s), 6.08 (1H, s), 7.04 (1H, d), 7.33 (1H, d), 7.54 (2H, m), 8.27 (1H, d), 8.44 (1H, d), 8.68 (1H, d), 10.32, 11.08.

This material as a solution in chloroform/methanol 1:1 was treated with excess 4M HCl in dioxan and evaporated to dryness. The solid was triturated with ether, filtered and dried in vacuo to give the title compound, as a white solid.

MS (+ve ion electrospray) m/z 477 (MH+)

Example 308

1-Hydroxy-t-4-[(7-fluoro-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide dihydrochloride

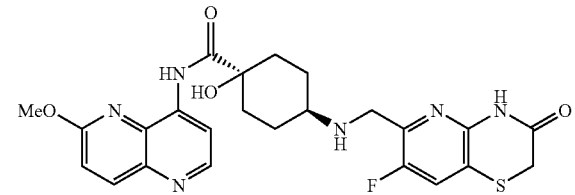

(a) Methyl 6-amino-5-bromo-3-fluoropyridine-2-carboxylate

A mixture of methyl 6-amino-5-bromopyridine-2-carboxylate (19.8 g) (T. R. Kelly and F. Lang, *J. Org. Chem.* 61, 1996, 4623–4633) and 1-chloromethyl-4-fluoro-1,4-diazoniabicyclo[2.2.2]octane bis(tetrafluoroborate) (34.3 g) in acetonitrile (340 ml) under argon was heated to 40° C. for 1 hour, 60° C. for 1 hour and then 80° C. overnight. After partitioning between EtOAc and water (500 ml each) the aqueous fraction was re-extracted with EtOAc (300 ml) and the combined organic solution dried with $MgSO_4$ and evaporated. Chromatography (20% then 30% EtOAc in hexane) separated various byproducts from the required ester (2.09 g).

MS (+ve ion electrospray) m/z 249 and 251 (MH+, 100%)

(b) Methyl 6-amino-5-ethoxycarbonylmethylthio-3-fluoropyridine-2-carboxylate

A solution of ethyl mercaptoacetate (1.15 ml) in DMF (40 ml) was ice-cooled under argon, treated with sodium hydride (420 mg of a 60% dispersion in oil) and stirred until all was in solution (about 1 hour). The ester (308a) (2.48 g) was added, the mixture allowed to warm to room temp. and stirred overnight. EtOAc (150 ml) was added, the solution washed with water (3×150 ml), dried and evaporated. Chromatography of the residue (30 then 40% EtOAc in hexane) gave the product as an oil (1.7 g).

MS (+ve ion electrospray) m/z 289 (MH+, 100%)

(c) Methyl 7-fluoro-3-oxo-3,4-dihydro-2H-pyrido[3,2-b][1,4]thiazine-6-carboxylate A solution of the fluoropyridine (308b) (1.7 g) in acetic acid (100 ml) was heated at 110° C. overnight, evaporated and dried under vacuum to give the product as a white solid (1.55 g, containing 0.33 equivalent of acetic acid).

MS (+ve ion electrospray) in/z 243 (MH+, 85%), 211 (100%)

(d) 7-Fluoro-3-oxo-3,4-dihydro-2H-pyrido[3,2-b][1,4]thiazine-6-carboxylic acid

This compound was prepared from the ester (308c) by the method of Example (301b) (86%).

(e) 7-Fluoro-6-hydroxymethyl-3-oxo-3,4-dihydro-2H-pyrido[3,2-b][1,4]thiazine

This compound was prepared from carboxylic acid (308d) by the method of Example (301c) (73%).

MS (−ve ion electrospray) m/z 213 ([M−H]−, 100%)

(f) 7-Fluoro-3-oxo-3,4-dihydro-2H-pyrido[3,2-b][1,4]thiazine-6-carboxaldehyde

A mixture of the 7-fluoro-pyridothiazinone (308e) (971 mg), manganese dioxide (3.72 g), THF (70 ml) and 1,2-dichloroethane (70 ml) was heated at 60° C. under argon for 20 hours. Filtration through kieselguhr and evaporation of solvent gave a solid which was triturated under EtOAc/hexane 1:3 and collected (608 mg).

MS (+ve ion electrospray) m/z 213 (MH+, 100%)

(g) Title Compound

A mixture of the carboxaldehyde (308f) (94 mg) and the amine (300e) (120 mg) in chloroform (2.5 ml)/methanol (2.5 ml) with 3A molecular sieves was refluxed 18 hours, cooled and treated with sodium triacetoxyborohydride (285 mg). After stirring for 6 hours, the mixture was filtered, diluted with chloroform (20 ml) and washed with aqueous NaHCO₃. The aqueous fraction was re-extracted with 10% ethanol in chloroform and the combined organic fractions dried (MgSO₄) and evaporated. Chromatography of the residue (CHCl₃/MeOH/NH₄OH 95:5:0.5) gave the free base of the title compound (117 mg).

$^1$H NMR δ(CDCl₃/CD₃OD) 1.5–1.7 (2H, m), 1.8–2.0 (4H, m), 2.0–2.2 (2H, m), 2.6–2.7 (1H, m), 3.50 (2H, s), 3.93 (2H, s), 4.16 (3H, s), 7.21 (1H, d), 7.47 (1H, d), 8.16 (1H, d), 8.55 (1H, d), 8.63 (1H, d)

This material as a solution in chloroform/ethanol 1:1 was treated with 1M HCl in ether (0.5 ml) and evaporated to dryness. The solid was triturated under ether, filtered and dried under vacuum to provide the title compound (135 mg).

MS (+ve ion electrospray) m/z 513 (MH+, 100%)

Example 309

1-Hydroxy-t-4-[(2-oxo-2,3-dihydro-1H-pyrido[3,4-b][1,4]oxazin-7-ylmethyl)-amino]-r-cyclohexanecarboxylic acid (6-methyl-[1,5]naphthyridin-4-yl)-amide

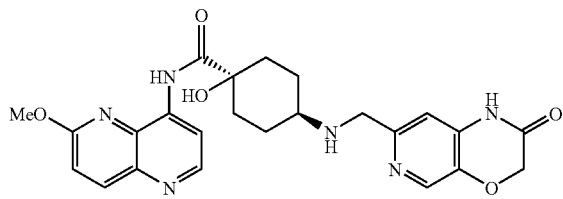

(a) 5-Hydroxy-2-methylpyridine N-oxide

5-Hydroxy-2-methylpyridine (25 g) was suspended in chloroform (500 ml) and treated with m-chloroperbenzoic acid (57 g of material described as 57–86% pure). After stirring for 1 hour the solution was dried with MgSO₄ and poured onto a silica column. Elution with EtOAc to remove byproducts and then with 20–50% EtOH in EtOAc gave the product (27.7 g).

MS (APCI+) m/z 126 (MH+, 60%), 109 (100%)

(b) 5-Methoxycarbonylmethoxy-2-methylpyridine N-oxide

A solution of the pyridine N-oxide (309a) (21.12 g) in DMF (450 ml) was treated with potassium carbonate (26.2 g) and, after 30 mins., with methyl bromoacetate (16 ml), and stirred overnight. Solvent was evaporated, saturated brine (500 ml) added and the mixture extracted with chloroform (6×200 ml). The combined organic solution was dried and evaporated and the residue chromatographed (20% EtOH in EtOAc) to give product (18.5 g).

MS (APCI+) m/z 198 (MH+, 100%)

(c) 5-Carboxymethoxy-2-methyl-4-nitropyridine N-oxide

The pyridine N-oxide (309b) (18.5 g) was dissolved in a cold mixture of fuming nitric acid (90 ml) and conc. sulfuric acid (90 ml) and heated to 40° C. for 1 hour, then 65° C. overnight. The mixture was cooled, poured onto ice and EtOAc (250 ml) added. When the ice had melted, the mixture was shaken and solid filtered off. The EtOAc was dried and evaporated, the residue triturated under ether and solid filtered. The solids filtered off were combined, giving the product (8.4 g).

MS (+ve ion electrospray) m/z 229 (MH+, 70%), 154 (100%)

(d) 5-Methoxycarbonylmethoxy-2-methyl-4-nitropyridine N-oxide

The carboxylic acid (309c) (8.4 g) in DMF (100 ml) was treated with potassium carbonate (7.6 g) and iodomethane (2.8 ml) and stirred for 3 days. After evaporation of solvent, water (200 ml) was added, the mixture stirred 10 mins. and solid filtered off and dried under vacuum to give the product (5.32 g).

MS (+ve ion electrospray) m/z 243 (MH+, 100%)

(e) 5-Methoxycarbonylmethoxy-4-nitro-2-trifluoroacetoxymethylpyridine

The pyridine N-oxide (309d) (3.8 g) in trifluoroacetic anhydride (120 ml) was refluxed under argon for 24 hours, the solvent evaporated and the residue partitioned between chloroform and aqueous NaHCO₃ (50 ml each). The aqueous fraction was re-extracted with chloroform (3×50 ml) and the combined organic solution dried and evaporated to give the product (1.8 g).

MS (+ve ion electrospray) m/z 339 (MH+, 100%)

(f) Mixture of 5-methoxycarbonylmethoxy-4-nitro-2-trifluoroacetoxymethylpyridine and 2-hydroxymethyl-5-methoxycarbonylmethoxy-4-nitropyridine When material (309e) was chromatographed on silica gel, partial loss of trifluoroacetyl group occurred to give the product mixture.

(g) 7-Acetoxymethyl-2-oxo-2,3-dihydro-1H-pyrido[3,4-b][1,4]oxazine

The mixture of nitropyridines (309f) (7.37 mmole) in acetic acid (55 ml) was treated with iron powder (4.2 g) and stirred at 60° C. for 1 hour, cooled and filtered through kieselguhr. The filtrate was heated to 110° C. overnight, evaporated to dryness and partitioned between chloroform and aqueous NaHCO₃ (100 ml each). After filtration to remove iron salts and separation of the layers, the aqueous fraction was re-extracted with chloroform (10×50 ml) and the combined organic solution dried and evaporated to give product (1.17 g).

MS (−ve ion electrospray) m/z 221 ([M−H]−, 100%)

(h) 7-Hydroxymethyl-2-oxo-2,3-dihydro-1H-pyrido[3,4-b][1,4]oxazine

A solution of acetate (309g) (1.17 g) in dioxan (75 ml)/water (15 ml) was treated dropwise with 2M NaOH solution (3 ml) and left overnight. The pH was reduced to 6 with dilute HCl and the solvent evaporated. Water (5 ml) was added, the pH readjusted to 6 and the solid filtered off and dried under vacuum to give product (877 mg).

MS (−ve ion electrospray) m/z 179 ([M−H]⁻, 100%)

(i) 2-Oxo-2,3-dihydro-1H-pyrido[3,4-b][1,4]oxazine-7-carboxaldehyde

A mixture of the hydroxymethyloxazinone (309h) (584 mg), manganese dioxide (2.3 g), THF (50 ml) and 1,2-dichloroethane (50 ml) was heated at 60° C. under argon for 20 hours. Filtration through kieselguhr and evaporation of solvent gave a solid which was triturated under EtOAc/hexane 1:3, filtered off and dried (383 mg).

MS (−ve ion electrospray) m/z 177 ([M−H]⁻, 100%)

(j) Title Compound

A mixture of the carboxaldehyde (309i) (68 mg) and the amine (300e) (120 mg) in chloroform (2.5 ml)/methanol (2.5 ml) with 3A molecular sieves was refluxed 18 hours, cooled and treated with sodium triacetoxyborohydride (285 mg). After stirring for 3 hours at room temp. and 1 hour at 60° C., the mixture was filtered, diluted with chloroform (20 ml) and washed with aqueous NaHCO₃. The aqueous fraction was re-extracted with 10% ethanol in chloroform (6×10 ml) and the combined organic fractions dried (MgSO₄) and evaporated. Chromatography of the residue on silica gel (CHCl₃/MeOH/NH₄OH 95:5:0.5) gave the free base of the title compound (92 mg).

¹H NMR δ(CDCl₃/CD₃OD) 1.5–1.7 (2H, m), 1.8–2.0 (4H, m), 2.0–2.2 (2H, m), 2.6–2.7 (1H, m), 3.85 (2H, s), 4.17 (3H, s), 4.68 (2H, s), 6.89 (1H, s), 7.20 (1H, d), 8.13 (1H, s), 8.18 (1H, d), 8.54 (1H, d), 8.61 (1H, d)

This material as a solution in chloroform/ethanol 1:1 was treated with 1M HCl in ether (0.4 ml) and evaporated to dryness. The solid was triturated under ether, filtered and dried under vacuum to provide the title compound (98 mg).

MS (+ve ion electrospray) m/z 479 (MH⁺, 100%)

Example 310

1-Hydroxy-t-4-[(7-methyl-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide dihydrochloride

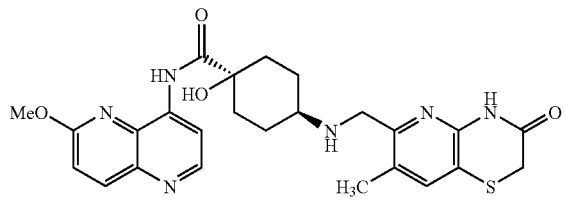

(a) Methyl 7-methyl-3-oxo-3,4-dihydro-2H-pyrido[3,2-b][1,4]thiazine-6-carboxylate Methyl 7-bromo-3-oxo-3,4-dihydro-2H-pyrido[3,2-b][1,4]thiazine-6-carboxylate (Example 304b) (1.50 g, 4.95 mmol), tetramethyltin (1.71 mL, 12 mmol) and bis(triphenylphosphine)palladium(II) chloride (0.84 g, 1.2 mmol) in dimethylformamide (30 mL) were heated at 120° C. for 24 h. The mixture was filtered through Kieselguhr, washed through with ethyl acetate and evaporated. Chromatography on silica gel (10–50% ethyl acetate/petroleum ether) gave the title compound (1.0 g, 85%).

MS (+ve ion electrospray) m/z 239 (MH⁺)

(b) 7-Methyl-3-oxo-3,4-dihydro-2H-pyrido[3,2-b][1,4]thiazine-6-carboxylic acid

Aqueous sodium hydroxide (2M, 2.5 mL, 5 mmol) was added slowly to a stirred suspension of ester (310a) (0.99 g, 4.16 mmol) in tetrahydrofuran (25 mL). The mixture, which gradually formed a clear solution, was stirred at room temperature for 24 h, then extracted with ethyl acetate. The aqueous phase, containing a heavy precipitate, was acidified to pH2 and extracted several times with ethyl acetate/methanol. The extracts were dried and evaporated to give the product (0.87 g, 93%).

MS (+ve ion electrospray) m/z 225 (MH⁺)

(c) 6-Hydroxymethyl-7-methyl-3-oxo-3,4-dihydro-2H-pyrido[3,2-b][1,4]thiazine

This compound was prepared from acid (310b) (0.87 g, 3.9 mmol) by the method of Example (301c). After neutralisation, the mixture was extracted several times with ethyl acetate. The extracts were dried and evaporated and the residue was chromatographed on silica (1:1 ethyl acetate/hexane, then ethyl acetate) to give a solid (0.48 g, 59%).

MS (+ve ion electrospray) m/z 211 (MH⁺)

(d) 7-Methyl-3-oxo-3,4-dihydro-2H-pyrido[3,2-b][1,4]thiazine-6-carboxaldehyde

A solution of alcohol (310c) (0.47 g, 2.2 mmol) in dichloromethane (50 mL) was stirred with manganese dioxide (2.8 g) at room temperature for 16 h. The mixture was filtered through Kieselguhr, washed through with dichloromethane/methanol and evaporated to give the title compound (0.34 g), containing some of the corresponding methyl hemiacetal.

MS (+ve ion electrospray) m/z 209 (MH⁺)

(e) Title compound

The aldehyde (310d) (0.13 g, 0.63 mmol) and amine (Example 300e) (0.20 g, 0.63 mmol) in anhydrous chloroform/dimethylformamide/methanol (10:5:1, 16 mL) was heated over 3A molecular sieves at 100° C. for 16 h. After cooling, sodium (triacetoxy)borohydride (0.60 g) was added and the mixture was stirred at room temperature for 3 days. The mixture was basified with sodium bicarbonate and diluted with dichloromethane and water. The aqueous phase was extracted several times with 10% methanol/dichloromethane and the combined organics were washed with water, dried and evaporated. Chromatography on silica gel (5–8% methanol/dichloromethane) gave the free base of the title compound (0.143 g, 45%).

¹H NMR δ(CDCl₃) 1.9–2.2 (8H, m), 2.13 (3H, s), 2.96 (1H, m), 3.38 (2H, s), 3.99 (3H, s), 4.02 (2H, s), 7.06(1H, d), 7.31(1H, s), 8.15(1H, d), 8.46 (1H, d), 8.62 (1H, d), 11.04 (1H, s)

MS (+ve ion electrospray) m/z 509 (MH⁺)

The free base in chloroform was treated with 2 equivalents of 0.4 M hydrochloric acid in dioxan. Evaporation of solvent and trituration with ether gave the dihydrochloride salt.

Example 311

1-Hydroxy-t-4-[(7-ethyl-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide dihydrochloride

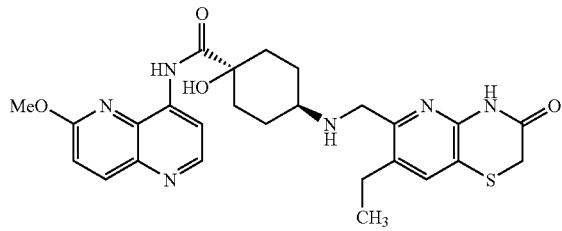

(a) Methyl 7-ethyl-3-oxo-3,4-dihydro-2H-pyrido[3,2-b][1,4]thiazine-6-carboxylate Methyl 7-bromo-3-oxo-3,4-dihydro-2H-pyrido[3,2-b][1,4]thiazine-6-carboxylate (Example 304b) (2.00 g, 6.6 mmol), tetraethyltin (3.17 mL, 16 mmol) and bis(triphenylphosphine)palladium(II) chloride (1.12 g, 1.6 mmol) in dimethylformamide (40 mL) were heated at 120° C. for 24 h. The mixture was filtered through Kieselguhr, washed through with ethyl acetate and evaporated. Chromatography on silica gel (20–50% ethyl acetate/petroleum ether) gave a mixture of the 7-ethyl and 7-vinyl compounds (0.29 g). This mixture was hydrogenated in methanol/ethyl acetate (2:1, 60 mL) over 10% palladium on carbon (60 mg) (1 atmosphere, room temperature) for 24 h. Filtration and evaporation of solvent gave the product (0.28 g).

MS (+ve ion electrospray) m/z 253 (MH$^+$)

(b) 7-Ethyl-3-oxo-3,4-dihydro-2H-pyrido[3,2-b][1,4]thiazine-6-carboxylic acid

Aqueous sodium hydroxide (2M, 0.67 mL, 1.33 mmol) was added slowly to a stirred suspension of ester (311a) (0.28 g, 1.11 mmol) in tetrahydrofuran (10 mL). The mixture was stirred at room temperature for 16 h, then additional sodium hydroxide (2M, 0.4 mL, 0.8 mmol) was added. After stirring for another 8 h, the mixture was evaporated. The residue was dissolved in water. acidified to pH3 and the precipitate was filtered off, washed with water and dried to give a solid (0.25 g, 95%).

MS (+ve ion electrospray) m/z 239 (MH$^+$)

(c) 7-Ethyl-6-hydroxymethyl-3-oxo-3,4-dihydro-2H-pyrido[3,2-b][1,4]thiazine

This compound was prepared from acid (311b) (0.25 g, 1.05 mmol) by the method of Example (310c). Chromatography on silica gel (ethyl acetate) gave the alcohol (0.11 g, 47%).

MS (+ve ion electrospray) m/z 225 (MH$^+$)

(d) 7-Ethyl-3-oxo-3,4-dihydro-2H-pyrido[3,2-b][1,4]thiazine-6-carboxaldehyde

A solution of alcohol (311c) (0.11 g, 0.49 mmol) in dichloromethane (10 mL) was stirred with manganese dioxide (0.7 g) at room temperature for 16 h. The mixture was filtered through Kieselguhr, washed through with dichloromethane/methanol and evaporated to give the title compound (0.078 g), containing some of the corresponding methyl hemiacetal.

MS (+ve ion electrospray) m/z 223 (MH$^+$)

(e) Title Compound

The aldehyde (311d) (0.078 g, 0.35 mmol) and amine (Example 300e) (0.11 g, 0.35 mmol) in dimethylformamide/methanol/acetic acid (10:10:1, 11.5 mL) was heated over 3A molecular sieves at 80° C. for 4 h. After cooling, sodium cyanoborohydride (0.066 g, 1.05 mmol) was added and the mixture was stirred at room temperature for 16 h. The mixture was evaporated and the residue was basified with sodium bicarbonate, diluted with water and extracted several times with 10% methanol/dichloromethane. The combined organics were dried and evaporated. Chromatography on silica (2–10% methanol/dichloromethane) gave the free base of the title compound (0.082 g, 45%).

$^1$H NMR δ(CDCl$_3$/CD$_3$OD) 1.25 (3H, t), 1.68(2H, q), 1.88(2H, d), 1.97(2H, d), 2.08(2H, m), 2.65(2H, q), 2.70 (1H, m), 3.49 (2H, s), 3.90(2H, s), 4.17 (3H, s), 7.24(1H, d), 7.68(1H, s), 8.18(1H, d), 8.54 (1H, d), 8.62 (1H, d)

MS (+ve ion electrospray) m/z 523 (MH$^+$)

The free base in chloroform/methanol was treated with 2 equivalents of 0.4M hydrochloric acid in dioxan. Evaporation of solvent and trituration with ether gave the dihydrochloride salt.

Example 312

1-Hydroxy-t-4-[(6-oxo-6,7-dihydro-5H-pyridazino[3,4-b][1,4]thiazin-3-ylmethyl)-amino]-r-cyclohexanecarboxylic acid (6-methoxy-[1,5]naphthyridin-4-yl)-amide dihydrochloride

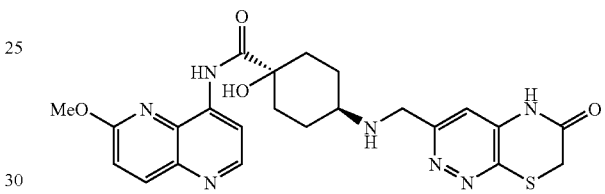

(a) 4-Amino-3,6-dichloropyridazine

A suspension of 3,4,6-trichloropyridazine (prepared by the method of B. Kasnar et al, *Nucleosides and Nucleotides*, 1994, 13, 459) (10.0 g) in conc. aqueous ammonia (1 L) was heated at 75° C. for 16 h. The mixture was concentrated to a small volume and extracted several times with ethyl acetate. The extracts were washed with brine, dried and evaporated. The crude product was recrystallised from ethyl acetate to give the product (5.03 g).

(b) 3-Chloro-6-oxo-6,7-dihydro-5H-pyridazino[3,4-b][1,4]thiazine

To a well-stirred suspension of sodium hydride (60% in mineral oil, 0.35 g, 8.5 mmol) in anhydrous dimethylformamide (10 mL) at 0° C. was added methyl mercaptoacetate (0.70 mL, 7.9 mmol). After stirring at this temperature for 20 min, a solution of amine (312a) (1.29 g, 7.87 mmol) in dimethylformamide (10 mL) was added. The mixture was stirred at room temperature for 16 h, then most of the solvent was removed in vacuo. The residue was diluted with water, the precipitate was filtered off, washed with water and dried. Chromatography on silica gel (0–2% methanol/dichloromethane) gave the product (0.21 g, 13%).

MS (+ve ion electrospray) m/z 202/204 (MH$^+$)

(c) 6-Oxo-3-vinyl-6,7-dihydro-5H-pyridazino[3,4-b][1,4]thiazine

To a mixture of the pyridazinothiazinone (312b) (0.15 g, 0.75 mmol), bis(triphenylphosphine)palladium(II) chloride (84 mg, 0.12 mmol) and lithium chloride (63 mg, 1.2 mmol) in dimethylformamide (3 mL) was added tributyl(vinyl)tin (0.36 mL, 1.2 mmol). The mixture was heated at 110–120° C. for 16 h, then evaporated. The residue was partitioned between water and ethyl acetate, the aqueous phase was extracted further with ethyl acetate and the combined organics were dried and evaporated. Chromatography on silica gel (0–3% methanol/dichloromethane) gave the product (45 mg, 31%).

MS (+ve ion electrospray) m/z 194 (MH$^+$)

(d) 6-Oxo-6,7-dihydro-5H-pyridazino[3,4-b][1,4]thiazine-3-carboxaldehyde

To a suspension of vinyl compound (312c) (0.6 g, 3.35 mmol) in 1,4-dioxan (60 mL) was added osmium tetroxide (4% in water, 2 mL, 0.335 mmol), sodium periodate (1.43 g, 6.7 mmol) and water (20 mL). The mixture was stirred at room temperature for 7 h, then diluted with water and dichloromethane and phases separated. The aqueous phase was extracted twice with 10% methanol/dichloromethane and the combined organics were dried and evaporated. Chromatography on silica gel (0–2% methanol/dichloromethane) gave the aldehyde (0.206 g), containing some of the corresponding methyl hemiacetal.

(e) Title Compound

The aldehyde (312d) (84 mg, 0.4 mmol) and amine (300e) (0.13 g, 0.4 mmol) in 1:1 methanol/chloroform (10 mL) were stirred over 3A molecular sieves at 65° C. for 16 h. The cooled mixture was diluted with 1:1 methanol/chloroform (20 mL) and sodium (triacetoxy)borohydride (excess) was added. The mixture was stirred over 5 days with periodic further additions of sodium (triacetoxy)borohydride. The mixture was then diluted with chloroform, filtered and evaporated to a small volume. The residue was basified with aqueous sodium carbonate and extracted four times with 10% methanol/chloroform. The extracts were dried and evaporated, and the residue was chromatographed on silica gel (2–10% methanol/dichloromethane) to give the free base of the title compound (31 mg, 16%).

$^1$H NMR δ(CDCl$_3$/CD$_3$OD) 1.61(2H, m), 1.80–2.15(6H, m), 2.65 (1H, m), 3.70 (2H, s), 4.06(2H, s), 4.17(3H, s), 7.04(1H, s), 7.22(1H, d), 8.18(1H, d), 8.54 (1H, d), 8.62 (1H, d)

MS (+ve ion electrospray) 7 m/z 496 (MH$^+$)

The free base in chloroform/methanol was treated with 2 equivalents of 4M hydrochloric acid in dioxan. Evaporation of solvent and trituration with ether gave the dihydrochloride salt.

Example 313

1-Hydroxy-t-4-[(3-oxo-3,4-dihydro-2H-pyrido[3,2-b][1,4]thiazin-6-ylmethyl)-amino]-r-cyclohexanecarboxylic acid [6-(2-methoxy-ethoxy)-[1,5]naphthyridin-4-yl]-amide dihydrochloride

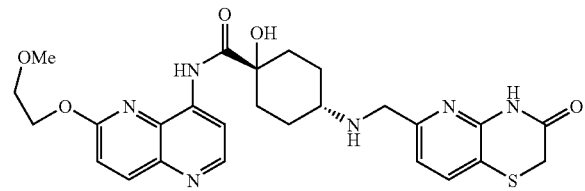

(a) 6-(2-Methoxy-ethoxy)-[1,5]naphthyridin-4-ylamine

This was prepared in 42% yield (1.9 g) from Example (29a) according to the procedure for (29b) with 2-bromoethylmethyl ether as the alkylating agent.

MS (+ve ion electrospray) m/z 220 (MH+).

(b) 8-Bromo-2-(2-methoxy-ethoxy)-[1,5]naphthyridine

A solution of (313a) (1.9 g, 8.7 mmol), copper(II) sulphate (4.2 g, 26.1 mmol) and sodium bromide (3.6 g, 34.8 mmol) in 9M sulphuric acid/methanol (35 ml/18 ml) was treated at 0° C. with a solution of sodium nitrite (0.9 g, 13.1 mol) in water (18 ml). The mixture was allowed to come to room temperature over 0.5 hour, then heated at 40° C. for 0.5 hour. The mixture was partitioned between dilute aqueous sodium hydroxide solution and ethyl acetate. The organic extract was dried, filtered and evaporated. The residue was chromatographed on silica eluting with 0–50% ethyl acetate in dichloromethane affording an oil (1.1 g, 45%).

MS (+ve ion electrospray) m/z 284 (MH+).

(c) {r-4-Hydroxy-4-[6-(2-methoxy-ethoxy)-[1,5] naphthyridin-4-ylcarbamoyl]-c-cyclohexyl}-carbamic acid tert-butyl ester This was prepared in approximately quantitative yield (1.8 g) from (313b) according to the procedure of Example (300d).

MS (+ve ion electrospray) m/z 461 (MH+).

(d) t-4-Amino-1-hydroxy-r-cyclohexanecarboxylic acid [6-(2-methoxy-ethoxy)-[1,5]naphthyridin-4-yl]-amide This was prepared from (313c) in 40% yield (280 mg) by treatment with trifluoroacetic acid followed by a basic workup according to the procedure of Example (300e).

MS (+ve ion electrospray) m/z 361 (MH+).

(e) Title Compound

This was prepared from amine (313d) and aldehyde (301d) by reductive alkylation with sodium cyanoborohydride according to the procedure of Example (357), affording the free base of the title compound as a white solid (62 mg, 29%)

δH (CDCl$_3$, 250 MHz): 8.62 (1H, d), 8.45 (1H, d), 8.15 (1H, d), 7.55 (1H, d), 7.15 (1H, d), 6.90 (1H, d), 4.65 (2H, m), 4.00 (2H, s), 3.85 (2H, s), 3.80 (2H, m), 3.45 (2H, s), 3.30 (3H, s), 2.65 (1H, m), 2.20–1.50 (8H, m)

MS (+ve ion electrospray) m/z 539 (MH+).

This was converted to the title compound (70 mg) by the same procedure as for Example 300.

Example 314

1-Hydroxy-t-4-[(3-oxo-3,4-dihydro-2H-pyrido[3,2-b][1,4]thiazin-6-ylmethyl)-amino]-r-cyclohexanecarboxylic acid (2,3-dihydro-[1,4]dioxino[2,3-f]quinolin-10-yl)-amide dihydrochloride

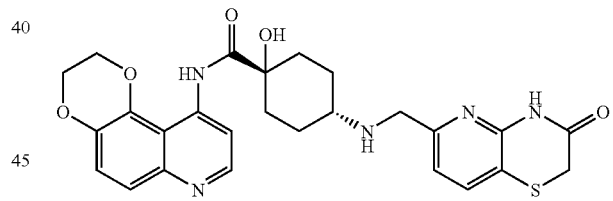

(a) 7-Bromo-2,3-dihydro-benzo[1,4]dioxin-6-ylamine

A solution of 2,3-dihydro-benzo[1,4]dioxin-6-ylamine (32 g, 212 mmol) in dichloromethane (1 liter) was treated with a solution of bromine (10.8 ml, 212 mmol) in dichloromethane (100 ml) at 0° C. After the addition the mixture was stirred at room temperature for 1 hour then washed with saturated aqueous sodium bicarbonate solution containing a small amount of sodium sulphite. The organic organic extract was dried and evaporated affording an oil that was chromatographed on silica gel eluting with dichloromethane to afford an oil (14.8 g, 30%).

MS (+ve electrospray) m/z 231 (MH+).

(b) 5-[(7-Bromo-2,3-dihydro-benzo[1,4]dioxin-6-ylamino)-methylene]-2,2-dimethyl-[1,3]dioxane-4,6-dione A mixture of aniline (314a) (14.8 g, 64.3 mmol), triethyl orthoformate (12.7 ml, 77.2 mmol) and 2,2-dimethyl-[1,3] dioxane-4,6-dione (Meldrum's acid) (11.1 g, 77.2 mmol) in ethanol (70 ml) was heated to reflux. After 1 hour the mixture was allowed to cool to room temperature then filtered, washing with ethanol then ether, to afford a white solid (22.9 g, 93%).

MS (+ve ion electrospray) m/z 385 (MH+).

(c) 6-Bromo-2,3-dihydro-7H-[1,4]dioxino[2,3-f]quinolin-10-one

Enamine (314b) (22.9 g) was added portionwise to refluxing Dowtherm A (45 ml) over 3 minutes. After a further 3 minutes at reflux the mixture was cooled to room temperature. Ethyl acetate/hexane (10 ml/20 ml) was added and a black solid isolated by filtration. This residue was dissolved in hot methanol (400 ml) and filtered through Keiselguhr. Water (800 ml) was added and the mixture stored at 5° C. overnight. Filtration and drying afforded a pale yellow solid (10.3 g, 61%).

MS (APCI⁻) m/z 281 [M–H]⁻

(d) 2,3-Dihydro-7H-[1,4]dioxino[2,3-f]quinolin-10-one

A suspension of (314c) (3.4 g, 12 mmol) in water/dioxan (150 ml/80 ml) was treated with 1M aqueous sodium hydroxide solution then hydrogenated over 10% palladium on charcoal (1.5 g) for 20 hours. The mixture was filtered then acidified with 5M aqueous hydrochloric acid. On concentrating to ca 100 ml, a solid began to crystallise out. The mixture was stored at 5° C. overnight. Filtration and drying afforded a pale yellow solid (2.8 g, 100%).

MS (APCI⁻) m/z 202 [M–H]⁻

(e) 10-Bromo-2,3-dihydro-[1,4]dioxino[2,3-f]quinoline

A mixture of (314d) (2.5 g) and phosporus oxybromide (7.8 g) was heated at 120° C. for 0.75 hour. After cooling to room temperature the mixture was treated with water, basified with potassium carbonate and extracted with ethyl acetate. The organic extract was dried and evaporated to afford an oil (475 mg, 14%).

MS (+ve ion electrospray) m/z 268 (MH+).

(f) [4-(2,3-Dihydro-[1,4]dioxino[2,3-f]quinolin-10-ylcarbamoyl)-r-4-hydroxy-c-cyclohexyl]-carbamic acid tert-butyl ester This was prepared in 25% yield (0.2 g) from (314e) according to the procedure of Example (300d).

MS (+ve ion electrospray) m/z 444 (MH+).

(g) t-4-Amino-1-hydroxy-c-cyclohexanecarboxylic acid (2,3-dihydro-[1,4]dioxino[2,3-f]quinolin-10-yl)-amide This was prepared from carbamate (314f) in 52% yield (80 mg) by treatment with trifluoroacetic acid followed by a basic workup, according to the procedure of Example (300e).

MS (+ve ion electrospray) m/z 344 (MH+).

(h) Title Compound

This was prepared from amine (314 g) and aldehyde (301d) by reductive alkylation with sodium cyanoborohydride according to the procedure of Example (357) to afford the free base of the title compound as a white solid (21 mg, 17%).

δH (CD₃OD, 250 MHz): 8.60 (1H, d), 8.50 (1H, d), 7.65 (1H, d), 7.50 (1H, d), 7.35 (1H, d), 7.05 (1H, d), 4.55 (2H, m), 4.42 (2H, m), 4.15 (2H, s), 3.50 (2H, s), 2.62 (1H, m), 2.20–1.50 (8H, m)

MS (+ve ion electrospray) m/z 522 (MH+).

This was converted to thetitle compound (18 mg) by the same procedure as for Example (300).

Unless otherwise stated, the following Examples were prepared from amine (300e) and the appropriate carboxaldehyde by analogous methods to that of Example (300f)

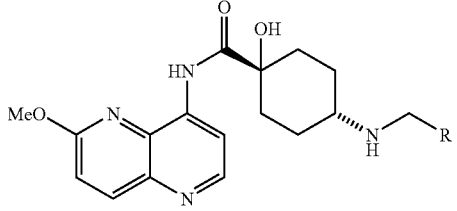

| Example | Method of synthesis (aldehyde) | salt B Dihydrochloride A Hydrochloride R Trihydrochloride | R |
|---|---|---|---|
| 320 | a | B | 4-Fluoro-1H-benzo-imidazol-2-yl |
| | | |  |
| 321 | | B | 2,3-Dihydro-benzo[1,4]dioxin-6-yl |
| | | | 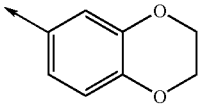 |

-continued
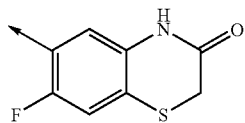
| | Method of synthesis | salt<br>B Dihydrochloride<br>A Hydrochloride<br>R | |
|---|---|---|---|
| Example | (aldehyde) | Trihydrochloride | R |
| 322 | (Example 9e) | B | 7-Fluoro-3-oxo-3,4-dihydro-2H-benzo[1,4]thiazin-6-yl |
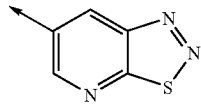
| 323 | (Example 32d) | B | [1,2,3]thiadiazolo[5,4-b]pyridin-6-yl |
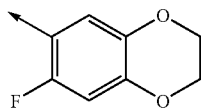
| 324 | b | B | 7-Fluoro-2,3-dihydro-benzo[1,4]dioxin-6-yl |
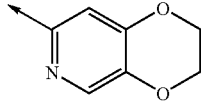
| 325 | (Example 19d) | B | 2,3-Dihydro-[1,4]dioxino[2,3-c]pyridin-7-yl |
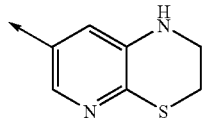
| 326 | c | B | 2,3-Dihydro-1H-pyrido[2,3-b][1,4]thiazin-7-yl |
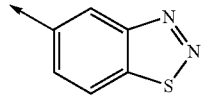
| 327 | (mesylate 6b) | B | Benzo[1,2,3]thiadiazol-5-yl |

-continued

| Example | Method of synthesis (aldehyde) | salt<br>B Dihydrochloride<br>A Hydrochloride<br>R Trihydrochloride | R |
|---|---|---|---|
| 328 | d | B | 3,4-Dihydro-2H-benzo[1,4]thiazin-6-yl |
| 329 | (Example 20e) | B | 2,3-Dihydro-[1,4]dioxino[2,3-b]pyridin-7-yl |
| 330 | e | B | 3,4-Dihydro-2H-pyrido[3,2-b][1,4]thiazin-6-yl |
| 331 | f | R | 3,4-Dihydro-2H-pyrido[3,2-b][1,4]oxazin-6-y |
| 332 | g | A | 5,6,7,8-Tetrahydro-[1,8]naphthyridin-2-yl |
| 333 | h | B | 3-Thia-1,2,5-triaza-inden-6-yl |

-continued

| Example | Method of synthesis (aldehyde) | salt<br>B Dihydrochloride<br>A Hydrochloride<br>R Trihydrochloride | R |
|---|---|---|---|
| 334 | cis-isomer | B | 3-Oxo-3,4-dihydro-2H-benzo[1,4]thiazin-6-yl |
| 335 | (Example 25b) | B | Benzothiazol-5-yl |
| 336 | j | B | 2-Methyl-thiazolo[5,4-b]pyridin-6-yl |
| 337 | (Example 16d) | B | Thiazolo[5,4-b]pyridin-6-yl |
| 338 | k | B | 2-Methyl-benzothiazol-5-yl |
| 339 | l | B | 4-Oxo-4H-pyrido[1,2-a]pyrimidin-2-yl |

-continued

| Example | Method of synthesis (aldehyde) | salt<br>B Dihydrochloride<br>A Hydrochloride<br>R Trihydrochloride | R |
|---|---|---|---|
| 340 | m | B | 5-Amino-2,3-dihydro-[1,4]dioxino[2,3-c]pyridin-7-yl |
| 341 | n | B | Thiazolo[4,5-b]pyridin-5-yl |
| 342 | o | B | 8-Chloro-2,3-dihydro-[1,4]dioxino[2,3-c]pyridin-7-yl |
| 343 | p | | 6,7-Dihydro-[1,4]dioxino[2,3-d]pyrimidin-2-yl | a Prepared from 4-fluoro-1H-benzoimidazole-2-carboxaldehyde, itself prepared from 3-fluoro-benzene-1,2-diamine by reaction with glycolic acid followed by oxidation with manganese dioxide
b 7-Fluoro-2,3-dihydro-benzo[1,4]dioxine-6-carboxaldehyde prepared from 6-fluoro-2,3-dihydro-benzo[1,4]dioxine [V. Daukas et al Chemija, 1999, 10 (1), 59] by reaction of dichloromethyl methyl ether and titanium tetrachloride - see Example 213.
c Prepared by reacting ester (13b) with lithium aluminium hydride followed by oxidation with manganese dioxide to give the carboxaldehyde
d Prepared by reacting 3-oxo-3,4-dihydro-2H-benzo[1,4]thiazine-6-carboxylic acid methyl ester with lithium aluminium hydride followed by oxidation with manganese dioxide to give the carboxaldehyde
e Prepared by reacting ester (301a) with lithium aluminium hydride followed by oxidation with manganese dioxide to give the carboxaldehyde
f Prepared by reacting (305e) with lithium aluminium hydride followed by oxidation with manganese dioxide to give the carboxaldehyde
g 5,6,7,8-Tetrahydro-[1,8]naphthyridine-2-carboxaldehyde prepared according to the procedure of WO 98/08840
h Prepared from [1,2,3]thiadiazolo[5,4-b]pyridine-6-carboxaldehyde, itself prepared from (302b) by reaction with sodium benzylmercaptan in dioxan, heating in acetic anhydride to form the acetoxymethyl-pyridine, reducing the nitro group with iron in acetic acid at 60° C., reaction with sodium nitrite in cold dilute hydrochloric acid to form the thiadiazole ring, and oxidising the resulting alcohol with manganese dioxide.

-continued

| | | salt |
|---|---|---|
| | | B |
| | | Dihydrochloride |
| | Method of | A Hydrochloride |
| | synthesis | R |
| Example | (aldehyde) | Trihydrochloride R | i Prepared from (4-carbamoyl-r-4-hydroxy-t-cyclohexyl)-carbamic acid tert-butyl ester (see Example 300c-faster running isomer) by the method of Example (300d–f)
j The carboxaldehyde was prepared by heating amine (16a) with acetic anhydride/acetic acid/sodium acetate to afford the 2-methylthiazole, followed by reduction of the ester with lithium aluminium hydride at −30° C., followed by oxidation with manganese dioxide
k The carboxaldehyde was prepared from the zinc salt of 4-mercapto-3-nitro-benzoic acid ethyl ester by heating in acetic anhydride followed by reduction of the ester with lithium aluminium hydride at −30° C., followed by oxidation with manganese dioxide.
l Prepared by reaction of amine (300e) with 2-chloromethyl-pyrimido[1,2-a]pyrimidin-4-one in DMF containing anhydrous potassium carbonate (by the method of Example 26).
m Prepared from Example (19c) by nitration, manganese (II) oxidation to give 8-nitro-2,3-dihydro-benzo[1,4]dioxine-6-carbaldehyde, reductive ailcylation with amine (300e) according to the method of Example (300f), and finally hydrogenation of the nitro group to amino giving the free base of the title compound.
n Prepared from Example (304a) by reaction with the sodium salt of 3-mercapto-propionic acid ethyl ester to unexpectedly give 6-amino-3-bromo-5-mercapto-pyridine-2-carboxylic acid methyl ester, followed by cyclisation with formic acid at 100° C. to give the thiazolopyridine, which was debrominated by hydrogenation (Pd/C in ethanol). Treatment of the ester with LiAlH4 in THF gave the thiazolo[45-b]pyridine-5-carboxaldehyde, which was converted to Example (341).
o Prepared from 5-benzyloxy-2-hydroxymethyl-1H-pyridin-4-one (T. Teitei, Aust. 3. Chem., 1983, 36, (11), 2307) by chlorination with N-cblorosuccinimide in acetic acid to give 5-benzyloxy-3-chloro-2-hydroxymethyl-1H-pyridin-4-one, followed by hydrogenation to remove the benzyl group and reaction with 1,2-dibromoethane and potassium carbonate to give (8-cbloro-2,3-dihydro-[1,4]dioxino[2,3-c]pyridin-7-yl)-methanol, followed by oxidation with manganese (II)oxide to give 8-chloro-2,3-dihydro-[1,4]dioxino[2,3-c]pyridine-7-carboxaldehyde, followed by reductive alkylation with amine (300e) according to the method of Example (300k) giving the free base of the title compound.
p Prepared from 5-benzyloxy-2-hydroxymethyl-3H-pyrimidin-4-one (A. Harris, Aust. J. Chem., 1976, 29, 1335) by hydrogenolysis of the beuzyl protecting group and cydlisation with dibromoethane to give (6,7-dihydro-[1,4]dioxmo[2,3-d]pyrimidin-2-yl)-methanol followed by oxidation with manganese(II)oxide to give 6,7-dihydro-[1,4]dioxino[2,3-d]pyrimidine-2-carbaldehyde and reductive alkylation with amine 300e according to the method of Example (300f)

Example 350

(1S,3S,4S)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride and (1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride

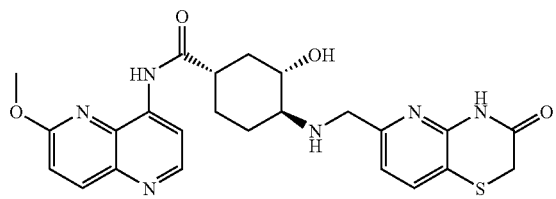

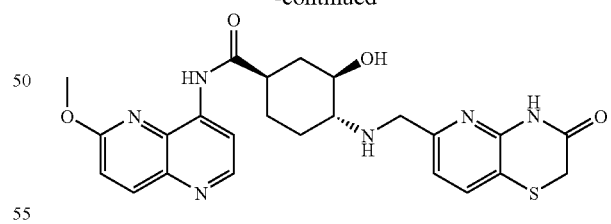

(a) (1R,3S,4S)— and (1S,3R,4R)-4-tert-Butoxycarbonylamino-3-hydroxy-cyclohexanecarboxylic acid methyl ester This was prepared essentially as described by K. Krajewski et al Tetrahedron: Asymmetry 10 (1999) 4591–4598, and contained about 20% of the 3-tert-butoxycarbonylamino-4-hydroxy-regioisomer.

A portion was purified by silica gel chromatography (hexane-ethyl acetate 2:1) and recrystallised from ether-pentane to afford crystals that gave an X-ray structure confirming the configuration above.

(b) (1S,3S,4S)— and (1R,3R,4R)-4-tert-Butoxycarbonylamino-3-hydroxy-cyclohexanecarboxylic acid methyl ester The crude ester (350a) (21.19 g) in dry methanol (200 ml) was treated with 25% sodium methoxide in methanol (33.5 ml) and heated at 70° C. for 3 days. It was cooled in ice, neutralised with 2N hydrochloric acid, and evaporated to dryness. Water was added and the resulting solid collected, washed with water and dried to give the product (8.0 g). Extraction of the aqueous fraction with dichloromethane, followed by silica gel chromatography (2% methanol-dichloromethane) gave a further 4.3 g of less pure material.

(c) (1S,3S,4S)— and (1R,3R,4R)-4-tert-Butoxycarbonylamino-3-hydroxy-cyclohexanecarboxylic acid The ester (350b) (2.4 g) in dioxan (100 ml) and water (5 ml) was treated with 2N sodium hydroxide (6.6 ml) and stirred overnight at room temperature. The mixture was acidified with 2N hydrochloric acid, evaporated to one quarter volume, extracted (5×) with ethyl acetate, washed with a little water, dried (sodium sulfate), and evaporated to give the product as a foam (2.4 g).

MS (−ve ion electrospray) m/z 258 (M−H⁻)

(d) ((1S,4S,5S)— and -(R,4R,5R)-7-Oxo-6-oxa-bicyclo[3.2.1]oct-4-yl)-carbamic acid tert-butyl ester The carboxylic acid (350c) (26 g) in dry dichloromethane (50 ml) was treated with triethylamine (1.01 g) and 1-[3-(dimethylamino)propyl]-3-ethylcarbodiimide hydrochloride (2.11 g) and stirred at room temperature overnight. The product was evaporated to dryness, water and sodium bicarbonate were added and the solution was extracted with dichloromethane and dried (sodium sulfate). It was chromatographed on silica gel (0.5–2% methanol-dichloromethane) to afford a white solid (0.90 g).

vmax 1,780 cm⁻¹

(e) (1S,2S,4S) and -(1R,2R,4R)-4-Carbamoyl-2-hydroxy-cyclohexyl)-carbamic acid tert-butyl ester The lactone (350d) (3.14 g) in tetrahydrofuran (150 ml) was treated with 32% ammonia in water (100 ml) and the mixture was well stirred overnight and evaporated to dryness to afford a solid (3.25 g).

MS (−ve ion electrospray) m/z 257 (M−H⁻)

(f) [(1S,2S,4S)— and (1R,2R,4R)-2-Hydroxy-4-(6-methoxy-[1,5]naphthyridin-4-ylcarbamoyl)-cyclohexyl]-carbamic acid A mixture of the amide (350e) (0.215 g), cesium carbonate (0.344 g), tris(dibenzylideneacetone)dipalladium(0) (16.3 mg), and rac-2,2'-bis(diphenylphosphino)-1,1'-binaphthyl (32.6 mg) in dry dioxan (9 ml) under argon, was sonicated for 10 minutes, 1,1-trifluoro-methanesulfonic acid 6-methoxy-[1,5]naphthyridin-4-yl ester (1b) (0.27 g) was added, and the mixture was stirred and heated at 80–85° C. for 24 hours, under argon. The mixture was cooled, filtered, and the filtrate evaporated and chromatographed on silica gel, eluting with chloroform, then (1-2%) methanol-dichloromethane, to afford a solid (0.21 g).

MS (+ve ion electrospray) m/z 417 (MH+).

(g) (1S,3S,4S)— and (1R,3R,4R)-4-Amino-3-hydroxy-cyclohexanecarboxylic acid (6-methoxy-[1,5]naphthyridin-4-yl)-amide The carbamate (350f) (0.21 g) in dichloromethane (10 ml) was treated with trifluoroacetic acid (10 ml) for 2 hours and evaporated. Sodium carbonate solution was added and the solution was extracted (5×) with 10% methanol-chloroform, dried (sodium sulfate) and evaporated to give a white solid (0.148 g).

MS (+ve ion electrospray) m/z 317 (MH⁺).

(h) Title Compound

A mixture of carboxaldehyde (301d) (45 mg) and amine (350g) (70 mg) in chloroform (5 ml) and methanol (5 ml) with 3A molecular sieves was heated under reflux for 4 hours, cooled, treated with sodium triacetoxyborohydride (300 mg). and heated at 40° C. overnight. The mixture was cooled, diluted with chloroform and methanol, filtered and evaporated. The residue was treated with aqueous sodium carbonate and extracted (3×) with 10% methanol-chloroform and the combined organic fractions dried (MaSO₄), evaporated and chromatographed on silica gel, eluting with 2–10% methanol-dichloromethane to give free base of the title compound (80 mg).

¹H NMR δ(250 MHz, CDCl₃/CD₃OD) 1.2–1.8 (3H, m), 2.15 (2H, m), 2.35 (1H, m), 2.5 (1H, m), 2.72 (1H, m), 3.49 (2H, s), 3.55 (1H, m), 3.80 (1H, d), 3.95 (1H, d), 4.17 (3H, s), 6.96 (1H, d), 7.23 (1H, d), 7.62 (1H, d), 8.20 (1H, d), 8.50 (1H, d), 8.65 (1H, d)

MS (+ve ion electrospray) m/z 495 (MH⁺)

The free base in chloroform/methanol (1:1) was treated with 4M HCl in dioxan (0.5 ml) and evaporated to dryness. The solid was triturated with ether, filtered and dried in vacuo, to provide title compound (87 mg).

The racemic free base was subjected to preparative HPLC [Chiralpak AD 250 mm×20 mm i.d.; 10 micron particle size; eluent:n-hexane-ethanol (both with 0.1% DEA), 70:30 v/v; flow-rate:15.0 ml min⁻¹] to afford a faster eluting single enantiomer [retention time 13.4 mins] and a slower eluting single enantiomer [retention time 16.9 mins], both with 100% ee.

Example 351

(1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5] naphthyridin-4-yl)-amide dihydrochloride

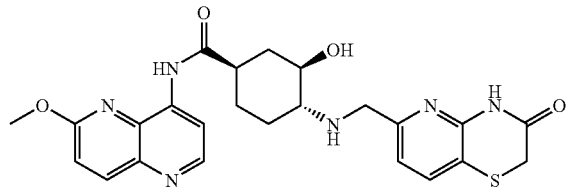

(a) (1R,4S,5R)-4-bromo-6-oxabicyclo[3.2.1]octan-7-one (R)-Cyclohex-3-enecarboxylic acid (2.30 g, 18.2 mmol) ([α]_D=+83.8° (c=1, CHCl₃)=88.2% e.e., resolved by the method of Schwartz et al, J. Am. Chem. Soc., 100, 5199, (1978)) was reacted with trimethylsilyl bromide and DMSO (by the method of Iwata et al, Heterocycles., 31, 987 (1990)) to give a white solid, (2.13 g, 10.4 mmol, 57%);

¹H NMR δ(400 MHz, CDCl₃) 1.68 (1H, dddd), 1.86 (1H, d), 1.98–2.02 (1H, m), 2.20 (1H, dddd), 2.42 (1H, ddd), 2.50–2.56 (1H, m), 2.73 (1H, br s), 4.15 (1H, dd), 4.91 (1H, d).

(b) (1R,3R,4S)-4-bromo-3-hydroxycyclohexanecarboxylic amide (1R,4S,5R)-4-bromo-6-oxabicyclo[3.2.1]octan-7-one (351a) (2.13 g, 10.4 mmol) was taken up in THF (20 mL) and treated with 0.880 ammonia (5.3 mL) at 20° C. for 24 h with stirring. The solvent was then removed in vacuo to give a white solid in quantitative yield; [α]_D=+40.6° (c=1, MeOH).

¹H NMR δ(400 MHz; CD₃OD) 1.63 (1H, dd, 1.73–1.80 (1H, m), 1.85–2.03 (3H, m), 2.16–2.21 (1H, m), 2.36 (1H, tt), 3.54 (1H, dt), 4.55 (1H, bs).

(c) (1R,3R,4R)-4-azido-3-hydroxy-cyclohexanecarboxylic acid amide (1R,3R,4S)-4-Bromo-3-hydroxycyclohexanecarboxylic amide (351b) (2.31 g, 10.4 mmol) was treated with sodium azide (1.35 g, 20.8 mmol) in DMF (100 mL) at 60° C. for 15.5 h. The solvent was removed in vacuo and the residue purified by flash column chromatography (Silica gel, DCM:MeOH 0–10%) to give a white solid (1.09 g, 5.93 mmol, 57%); $[\alpha]_D$=15.5° (c=1, MeOH).

$^1$H NMR δ(400 MHz; CD$_3$OD) 1.30 (1H, dq), 1.42–1.56 (2H, m), 1.83 (1H, dt), 1.99–2.08 (2H, m), 2.30 (1H, tt), 3.16(1H, ddd), 3.41 (1H, ddd).

(d) (1R,3R,4R)-4-amino-3-hydroxy-cyclohexanecarboxylic acid amide, acetate salt

To (1R,3R,4R)-4-azido-3-hydroxy-cyclohexanecarboxylic acid amide (351c) (765 mg, 4.15 mmol) in MeOH/AcOH (9:1, 30 mL) was added Pd/C (10%, 300 mg), and the mixture hydrogenated under atmospheric pressure for 22 h. On completion of reaction the mixture was filtered through Celite®, the filter pad washed with MeOH, and the combined organic solutions concentrated in vacuo to give a white solid in quantitative yield.

$^1$H NMR δ(400 MHz; CD$_3$OD) 1.42–1.59 (3H, m), 1.87–1.92 (1H, m), 1.92 (3H, s), 2.07–2.14 (2H, m), 2.37 (1H, tt), 2.84 (1H, dt), 3.50 (1H, dt).

(e) ((1R,2R,4R)-4-Carbamoyl-2-hydroxy-cyclohexyl)-carbamic acid tert-butyl ester The amide, acetate salt (351d) (905 mg, 4.15 mmol) was treated with N,N-diisopropylethylamine (868 uL, 4.98 mmol) and di-tert-butyl-dicarbonate (1.08 g, 4.98 mmol) in dioxane (30 mL), and MeOH (50 mL) for 16 h. The solvent was then removed in vacuo and the residue purified by flash column chromatography (Silica gel, DCM:MeOH 0–10%) to give a white solid (804 mg, 3.11 mmol, 75%); $[\alpha]_D$=−17.0° (c=1, MeOH).

$^1$H NMR δ(400 MHz; CD$_3$OD) 1.18–1.32 (1H, m), 1.44 (9H, s), 1.43–1.55 (2H, m), 1.81 (1H, bd), 1.98 (1H, bd), 2.09 (1H, bd), 2.29 (1H, tt), 3.22 (1H, dt), 3.33 (1H, dt).

(f) [(1R,2R,4R)-2-Hydroxy-4-(6-methoxy-[1,5]naphthyridin-4-ylcarbamoyl)-cyclohexyl]-carbamic acid tert-butyl ester The amide (351e) (671 mg, 2.60 mmol) was reacted with the triflate ester (1b) (801 mg, 2.60 mmol) by the procedure of Example (350f), but carried out at 60° C., to give a white solid (889 mg, 2.13 mmol, 82%);

$^1$H NMR δ(400 MHz; CD$_3$OD) 1.34–1.50 (1H, m), 1.46 (9H, s), 1.62–1.71 (2H, m), 2.04–2.12 (2H, m), 2.32–2.38 (1H, m), 2.70–2.78 (1H, m), 3.27–3.34 (1H, m), 3.45–3.51 (1H, m), 4.15 (3H, s), 7.24 (1H, d), 8.17 (1H, d), 8.47 (1H, d), 8.60 (1H, d);

MS (+ve ion electrospray) m/z 417 (MH$^+$, 100%).

(g) (1R,3R,4R)-Amino-3-hydroxy-cyclohexanecarboxylic acid (6-methoxy-[1,5]naphthyridin-4-yl)-cyclohexyl]-amide The carbamate (351f) (860 mg, 2.06 mmol) in DCM (30 mL) was treated with trifluoroacetic acid (10 mL). After 35 min the solvent was removed in vacuo and the residue purified by flash column chromatography (silica gel, DCM:MeOH/NH$_3$ (2M) 0–15%) to give a white solid (624 mg, 1.97 mmol, 95%); $[\alpha]_D$=−0.8° (c=1, MeOH).

$^1$H NMR δ(400 MHz; CD$_3$OD) 1.30–1.41 (1H, m), 1.57–1.70 (2H, m), 1.99–2.10 (2H, m), 2.25–2.31 (1H, m), 2.53–2.59 (1H, m), 2.76–2.84 (1H, m), 3.30–3.36 (1H, m), 4.17 (3H, s), 7.26 (1H, d), 8.19 (1H, d), 8.49 (1H, d), 8.61 (1H, d);

MS (+ve ion electrospray) m/z 317 (MH$^+$, 100%).

(h) Title Compound

The amine (351 g) (0.664 mmol) under argon in MeOH (21 mL) and DMF (21 mL) was treated with carboxaldehyde (301d) (0.664 µmol), and 3A molecular sieves (1 g), followed by AcOH (2.1 mL). Sodium cyanoborohydride (83 mg, 1.33 mmol) was added after 20 min. Once the reaction had gone to completion the mixture was adsorbed onto an SCX cartridge, washed with MeOH, eluted with MeOH/NH$_3$ (2M), and the solvent removed in vacuo from the appropriate fractions. The residue was purified by flash column chromatography (Silica gel, DCM:MeOH/NH$_3$ (2M) 0–12%) to give the free base of the title compound (72% yield);

$^1$H NMR δ(400 MHz; CDCl$_3$/CD$_3$OD) 1.23–1.33 (1H, m), 1.58–1.74 (2H, m), 2.10–2.22 (2H, m), 2.32–2.38 (1H, m), 2.43–2.50 (1H, m), 2.62 (1H, tt), 3.46–3.53 (1H, m), 3.48 (2H, s), 3.78, 3.95 (2H, ABq), 4.14 (3H, s), 6.93 (1H, d), 7.20 (1H, d), 7.60 (1H, d), 8.20 (1H, d), 8.50 (1H, d), 8.64 (1H, d);

MS (+ve ion electrospray) m/z 495 (MH$^+$, 100%).

Analytical HPLC [Chiralpak AD 250 mm×4.6 mm i.d.; 10 micron particle size; eluent: n-hexane-ethanol (both with 0.1% DEA), 25:75 v/v; flow-rate:1.2 ml min$^{-1}$] indicated that this material had an ee of 69.8% with the faster eluting single enantiomer [retention time 34.2 mins] being the minor component relative to the slower eluting single enantiomer [retention time 50.9 mins].

This material as a solution in DCM/MeOH 1:1 was treated with 4M HCl in dioxane (0.5 mL), evaporated to dryness, then dried under vacuum to provide the title compound.

Example 352

(1S,3S,4S)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride

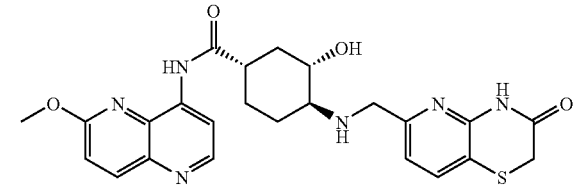

(a) (1S,4R,5S)-4-Bromo-6-oxabicyclo[3.2.1]octan-7-one (S)-Cyclohex-3-enecarboxylic acid (1.98 g, 15.7 mmol) ($[\alpha]_D$=−92.7° (c=1, CHCl$_3$)=97.5% e.e., resolved by the method of Schwartz et al, J. Am. Chem. Soc., 100, 5199, (1978)) was reacted with trimethylsilyl bromide (4.10 mL, 31.3 mmol), DMSO (2.23 mL, 31.3 mmol), and N,N-diisopropylethylamine (4.45 mL, 31.3 mmol) (by a modification of the method of Iwata et al, Heterocycles., 31, 987 (1990)) to give a white solid, (2.91 g, 14.2 mmol, 90%);

$^1$H NMR δ (400 MHz; CDCl$_3$) 1.68 (1H, dddd), 1.86 (1H, d), 1.97–2.06 (1H, m), 2.20 (1H, dddd), 2.42 (1H, ddd), 2.50–2.57 (1H, m), 2.73 (1H, br s), 4.16 (1H, dd), 4.92 (1H, d).

(b) (1S,3S,4R)-4-Bromo-3-hydroxycyclohexanecarboxylic amide (1S,4R,5S)-4-Bromo-6-oxabicyclo[3.2.1]octan-7-one (352a) (2.88 g, 14.0 mmol) was taken up in THF (27 mL) and treated with 0.880 ammonia (7.1 mL) at 20° C. for 24 h with stirring. The solvent was then removed in vacuo to give a white solid in quantitative yield; $[\alpha]_D$=−55.4° (c=1, MeOH).

$^1$H NMR δ (400 MHz; CD$_3$OD) 1.64 (1H, dd), 1.74–1.82 (1H, m), 1.85–2.05 (3H, m), 2.13–2.22 (1H, m), 2.37 (1H, tt), 3.53 (1H, dt), 4.55 (1H, bs).

(c) (1S,3S,4S)-4-Azido-3-hydroxy-cyclohexanecarboxylic acid amide (1S,3S,4R)-4-Bromo-3-hydroxycyclohexanecarboxylic amide (352b) (3.11 g, 14.0 mmol) was treated with sodium azide (1.82 g, 28.0 mmol) in DMF (140 mL) at 60° C. for 16 h. The solvent was removed in vacuo and the residue purified by flash column chromatography (silica gel, DCM:MeOH/NH$_3$ (2N) 0–5%) to give the a white solid (1.30 g, 7.0 mmol, 50%); $[\alpha]_D$=+17.7° (c=1, MeOH).

$^1$H NMR δ(400 Mz; CD$_3$OD) 1:30 (1H, dq), 1.44–1.57 (2H, m), 1.82 (1H, dt), 2.00–2.10 (2H, m), 2.30 (1H, tt), 3.16(1H, ddd), 3.41 (1H, ddd).

(d) (1S,3S,4S)-4-amino-3-hydroxy-cyclohexanecarboxylic acid amide

To (1S,3S,4S)-4-azido-3-hydroxy-cyclohexanecarboxylic acid amide (352c) (760 mg, 4.13 mmol) in MeOH (30 mL) was added Pd/C (10%, 500 mg), and the mixture hydrogenated under atmospheric pressure for 18 h. On completion of reaction the mixture was filtered through Celite®, the filter pad washed with MeOH, and the combined organic solutions concentrated in vacuo to give a white solid in quantitative yield;

$^1$H NMR δ (400 MHz; CD$_3$OD) 1.22 (1H, dq). 1.4–1.54 (2H, m), 1.76–1.83 (1H, m), 1.89–1.96 (1H, m), 1.99–2.07 (1H, m), 2.32 (1H, tt), 2.47 (1H, dt), 3.19 (1H, dt).

(e) ((1S,2S,4S)-4-Carbamoyl-2-hydroxy-cyclohexyl)-carbamic acid tert-butyl ester The amide (352d) (653 mg, 4.13 mmol) was treated with di-tert-butyl-dicarbonate (1.08 g, 4.95 mmol) in dioxane (30 mL), and MeOH (50 mL) for 16 h. The solvent was then removed in vacuo and the residue purified by flash column chromatography (silica gel, DCM:MeOH 5–10%) to give a white solid (890 mg, 3.45 mmol, 84%); $[\alpha]_D$=+17.0° (c=1, MeOH).

$^1$H NMR δ (400 MHz; CD$_3$OD) 1.21–1.31 (1H, m), 1.44 (9H, s), 1.43–1.56 (2H, m), 1.81 (1H, bd), 1.98 (1H, bd), 2.09 (1H, bd), 2.29 (1H, tt), 3.21 (1H, dt), 3.34 (1H, dt (f) [(1S,2S,4S)-2-Hydroxy-4-(6-methoxy-[1,5]naphthyridin-4-ylcarbamoyl)-cyclohexyl]-carbamic acid tert-butyl ester The carbamate (352e) (400 mg, 1.55 mmol) was reacted with the triflate ester (1b) (477 mg, 1.55 mmol) by the procedure of Example (350f) to give a white solid (400 mg, 0.960 mmol, 62%);

$^1$H NMR δ (400 MHz; CD$_3$OD) 1.34–1.50 (1H, m), 1.46 (9H, s), 1.60–1.71 (2H, m), 2.04–2.12 (2H, m), 2.32–2.38 (1H, m), 2.75 (1H, bt), 3.27–3.34 (1H, m), 3.42–3.51 (1H, m), 4.16 (3H, s), 7.26 (1H, d), 8.18 (1H, d), 8.49 (1H, d), 8.61 (1H, d); MS (+ve ion electrospray) m/z 417 (MH$^+$, 100%).

(g) (1S,3S,4S)-4-Amino-3-hydroxy-cyclohexanecarboxylic acid (6-methoxy-[1,5]naphthyridin-4-yl)-amide The amide (352f) (691 mg, 1.66 mmol) in DCM (30 mL) was treated with trifluoroacetic acid (20 mL). After 45 min the solvent was removed in vacuo and the residue purified by flash column chromatography (silica gel, DCM:MeOH/NH$_3$ (2M) 5%) to give a white solid (376 mg, 1.19 mmol, 72%); $[\alpha]_D$=+0.50 (c=1, MeOH).

$^1$H NMR δ (400 MHz; CD$_3$OD) 1.33–1.46 (1H, m), 1.59–1.71 (2H, m), 2.00–2.12 (2H, m), 2.27–2.32 (1H, m), 2.57–2.65 (1H, m), 2.76–2.84 (1H, m), 3.32–3.40 (1H, m), 4.17 (3H, s), 7.27 (1H, d), 8.19 (1H, d), 8.50 (1H, d), 8.61 (1H, d); MS (+ve ion electrospray) m/z 317 (MH$^+$, 100%).

(h) Title Compound

This was prepared following the method of Example (351h) on a 0.657 mmol scale from amide (352 g), and aldehyde (301d), to give the free base of the title compound in 53% yield;

$^1$H NMR δ (400 MHz; CDCl$_3$) 1.29–1.41 (1H, m), 1.6–1.8 (2H, m), 2.15 (1H, bd), 2.24 (1H, bd), 2.41 (1H, bd), 2.49–2.63 (2H, m), 3.40, 3.44 (2H, ABq), 3.58 (1H, m), 3.85 (1H, d), 4.05 (1H, d), 4.10 (3H, s), 4.5 (1H, b) 6.91 (1H, d), 7.13 (1H, d), 7.54 (1H, d), 8.20 (1H, d), 8.48 (1H, d), 8.67 (1H, d), 9.49 (1H, s); MS (+ve ion electrospray) m/z 495 (MH$^+$, 100%).

Analytical HPLC [Chiralpak AD 250 mm×4.6 mm i.d.; 10 micron particle size; eluent; n-hexane-ethanol (both with 0.1% DEA), 25:75 v/v; flow-rate:1.2 ml min$^{-1}$] indicated that this material had an ee of 89.6% with the faster eluting single enantiomer [retention time 33.5 mins] being the major component relative to the slower eluting single enantiomer [retention time 50.9 mins].

This material as a solution in DCM/MeOH 1:1 was treated with 4M HCl in dioxane (0.5 mL), evaporated to dryness, then dried under vacuum to provide the title compound.

Example 353

(1S,3S,4S)-4-[(7-Chloro-3-oxo-3,4-dihydro-2H-pyrido[3,2-b][1,4]thiazin-6-ylmethyl)-amino]-3-hydroxy-cyclohexanecarboxylic acid (6-methoxy-[1,5]naphthyridin-4-yl)-amide and (1R,3R,4R)-4-[(7-chloro-3-oxo-3,4-dihydro-2H-pyrido[3,2-b][1,4]thiazin-6-ylmethyl)-amino]-3-hydroxy-cyclohexanecarboxylic acid (6-methoxy-[1,5]naphthyridin-4-yl)-amide dihydrochloride

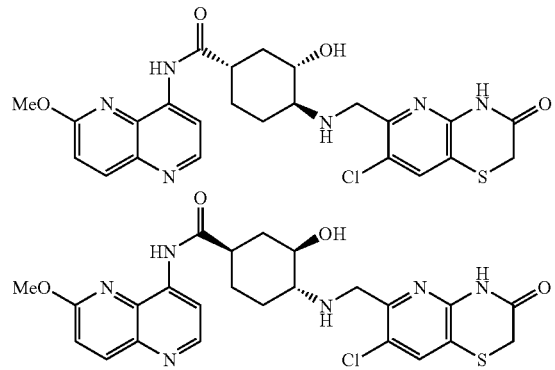

(a) Title Compound

A mixture of the carboxaldehyde (306e)(54 mg) and racemic amine (350 g) (74 mg) in chloroform (3 ml)/methanol (3 ml) with 3A molecular sieves was refluxed 18 hours, cooled and treated with sodium triacetoxyborohydride (149 mg). After stirring overnight, the mixture was diluted with dichloromethane (50 ml) and washed with aqueous NaHCO$_3$. The aqueous fraction was re-extracted with 10% methanol in dichloromethane and the combined organic fractions dried (MgSO$_4$) and evaporated. Chromatography of the residue (CH$_2$Cl$_2$:MeOH 90:10) gave the free base of the title compound (23 mg).

$^1$H NMR δ(DMSO) 1.11–1.56 (3H, m), 1.91–2.32 (4H, m), 2.7–2.9 (1H, m), 3.55 (2H, s), 3.7–4.1 (3H, m), 4.12 (3H, s), 4.75 (1H,s), 7.3 (1H, d), 7.9 (1H, s), 8.2 (1H, d), 8.4 (1H, d), 8.7 (1H, d), 9.7 (1H, s), 11.10 (1H, s).

This material as a solution in dichloromethane:methanol 1:1 was treated with 4M HCl in dioxane (0.10 ml) and evaporated to dryness. The solid was triturated under ether, filtered and dried under vacuum to provide the title compound (25 mg).

MS (+ve ion electrospray) m/z 529 (MH+, 100%).

Example 354

(1S,3S,4S)-3-Hydroxy-4-[(7-fluoro-3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride and (1R,3R,4R)-3-Hydroxy-4-[(7-fluoro-3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride

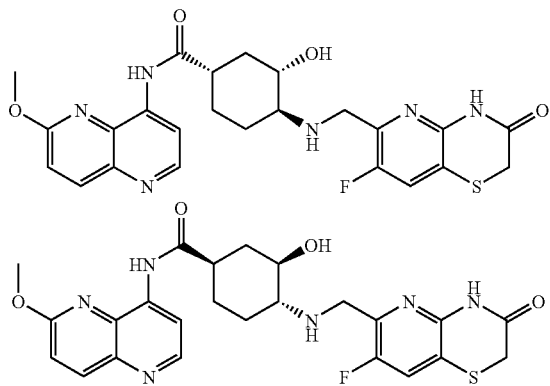

A mixture of the carboxaldehyde (308f) (41 mg) and the amine (350 g) (60 mg) in chloroform (1.5 ml)/methanol (1.5 ml) with 3A molecular sieves was refluxed 18 hours, cooled and treated with sodium triacetoxyborohydride (143 mg). After stirring for 5 hours at room temp., the mixture was filtered, diluted with chloroform (20 ml) and washed with aqueous NaHCO$_3$. The aqueous fraction was re-extracted with 10% ethanol in chloroform (2×10 ml) and the combined organic fractions dried (MgSO$_4$) and evaporated. Chromatography of the residue on silica gel (CHCl$_3$/MeOH/NH$_4$OH 95:5:0.5) gave the free base of the title compound (80 mg).

$^1$H NMR δ(CDCl$_3$) 1.3–1.5 (1H, m), 1.6–1.8 (2H, m), 2.13 (1H, broad d), 2.26 (1H, broad d), 2.41 (1H, broad d), 2.45–2.6 (2H, m), 3.44 (2H, s), 3.55–3.65 (1H, m), 3.93 (1H, d), 4.05–4.15 (4H, m including 3H, s at δ 4.09), 7.14 (1H, d), 7.32 (1H, d), 8.21 (1H, d), 8.48 (1H, d), 8.68 (1H, d), 9.48 (1H, s)

This material as a solution in chloroform/ethanol 1:1 was treated with 1M HCl in ether (0.4 ml) and evaporated to dryness to provide the title compound (89 mg).

MS (+ve ion electrospray) m/z 513 (MH$^+$, 100%)

Example 355

(1S,3S,4S)-3-Hydroxy-4-[(2-oxo-2,3-dihydro-1H-pyrido[3,4-b][1,4]oxazin-7-ylmethyl)-amino]-cyclohexanecarboxylic acid (6-methoxy-[1,5]naphthyridin-4-yl)-amide dihydrochloride and (1R,3R,4R)-3-Hydroxy-4-[(2-oxo-2,3-dihydro-1H-pyrido[3,4-b][1,4]oxazin-7-ylmethyl)-amino]-cyclohexanecarboxylic acid (6-methoxy-[1,5]naphthyridin-4-yl)-amide dihydrochloride

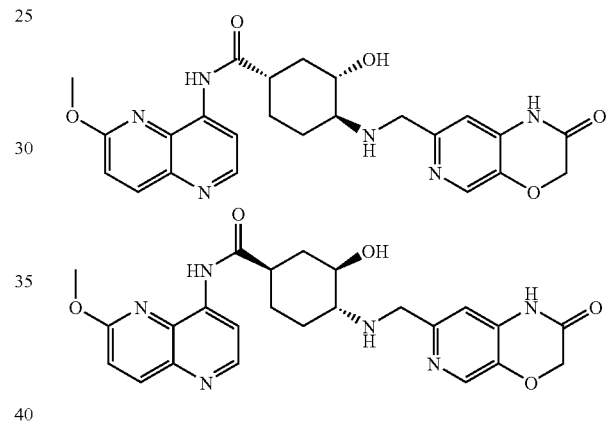

A mixture of the carboxaldehyde (309i) (34 mg) and the amine (350 g) (60 mg) in chloroform (1.5 ml)/methanol (1.5 ml) with 3A molecular sieves was refluxed 18 hours, cooled and treated with sodium triacetoxyborohydride (143 mg). After stirring for 5 hours at room temp. and 2 hours at 45° C., the mixture was filtered, diluted with chloroform (20 ml) and washed with aqueous NaHCO$_3$. The aqueous fraction was re-extracted with 10% ethanol in chloroform (3×10 ml) and the combined organic fractions dried (MgSO$_4$) and evaporated. Chromatography of the residue on silica gel (CHCl$_3$/MeOH/NH$_4$OH 95:5:0.5) gave the free base of the title compound (45 mg).

$^1$H NMR δ(CDCl$_3$/CD$_3$OD) 1.2–1.4 (1H, m), 1.5–1.8 (2H, m), 2.1–2.3 (2H, m), 2.3–2.6 (2H, m), 2.6–2.8 (1H, m), 3.4–3.6 (1H, m), 3.80 (1H, d), 3.94 (1H, d), 4.16 (3H, s), 4.67 (2H, s), 6.91 (1H, s), 7.22 (1H, d), 8.13 (1H, s), 8.20 (1H, d), 8.50 (1H, d), 8.62 (1H, d) This material as a solution in chloroform/ethanol 1:1 was treated with 1M HCl in ether (0.2 ml) and evaporated to dryness to provide the title compound (50 mg).

MS (+ve ion electrospray) m/z 479 (MH$^+$, 100%)

Example 356

(1S,3S,4S)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5]naphthyridin-4-yl)-amide dihydrochloride and (1R,3R,4R)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5]naphthyridin-4-yl)-amide dihydrochloride

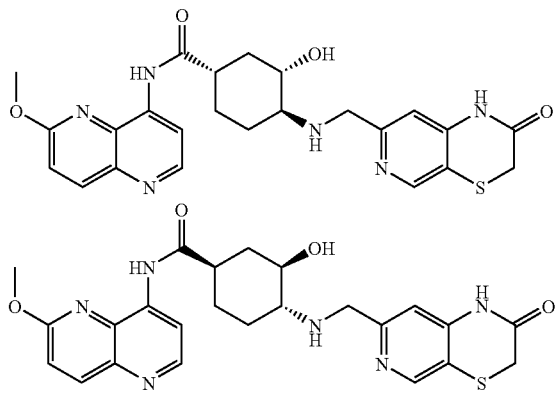

A mixture of the carboxaldehyde (302 g) (20 mg) and the amine (350 g) (33 mg) in DMF (1.5 ml)/methanol (1.5 ml)/acetic acid (0.15 ml) was refluxed 3 hours, cooled and treated with sodium cyanoborohydride (13 mg). After stirring for 18 hours at room temp., the mixture was diluted with 10% methanol in chloroform (20 ml), filtered and evaporated to dryness. The residue was treated with aqueous NaHCO$_3$ (10 ml), extracted with 10% methanol in chloroform (4×10 ml) and the combined organic fractions dried (MgSO$_4$) and evaporated. Chromatography of the residue on silica gel (CHCl$_3$/MeOH/NH$_4$OH 93:7:0.7) gave the free base of the title compound (25 mg).

This material as a solution in chloroform was treated with 1M HCl in ether (0.12 ml) and evaporated to dryness to provide the title compound (24 mg).

Example 357

(1S,3S,4S)-3-Hydroxy-4-[(6-oxo-6,7-dihydro-5H-8-thia-1,2,5-triaza-naphthalen-3-ylmethyl)-amino]-cyclohexanecarboxylic acid (6-methoxy-[1,5]naphthyridin-4-yl)-amide dihydrochloride and (1R,3R,4R)-3-hydroxy-4-[6-oxo-6,7-dihydro-5H-8-thia-1,2,5-triaza-naphthalen-3-ylmethyl)-amino]-cyclohexanecarboxylic acid (6-methoxy-[1,5]naphthyridin-4-yl)-amide dihydrochloride

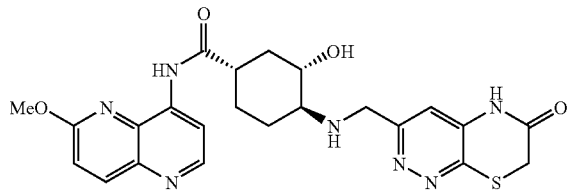

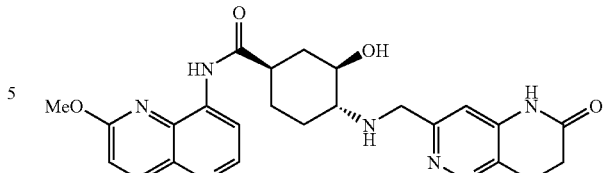

A mixture of the carboxaldehyde (312d) (55 mg) and the amine (350 g) (40 mg) in DMF (1.5 ml)/methanol (1.5 ml)/acetic acid (0.15 ml) was refluxed 8 hours with 3A molecular sieves, cooled and treated with sodium cyanoborohydride (24 mg). After stirring for 18 hours at room temp., the mixture was diluted with 10% methanol in chloroform, filtered and evaporated to dryness. The residue was treated with aqueous Na$_2$CO$_3$, extracted with 10% methanol in chloroform (4×) and the combined organic fractions dried (Na$_2$SO$_4$) and evaporated. Chromatography of the residue on silica gel (CHCl$_3$ then 2–10% methanol-dichloromethane) gave the free base of the title compound (32 mg).

$^1$H NMR δ(CDCl$_3$/CD$_3$OD) 1.2–1.4 (1H, m), 1.5–1.8 (2H, m), 2.1–2.6 (4H, m), 2.6–2.8 (1H, m), 3.5 (1H, m), 3.7 (2H, s), 4.1 (2H, q), 4.16 (3H, s), 7.05 (1H, s), 7.22 (1H, d), 8.20 (1H, d), 8.50 (1H, d), 8.62 (1H, d). MS (+ve ion electrospray) m/z 496 (MH$^+$)

This material as a solution in chloroform/methanol was treated with 4M HCl in dioxan, evaporated to dryness and triturated with ether, to provide the title compound (38 mg).

Example 358

(1S,3S,4S)-3-Hydroxy-4-[(3-oxo-3,4-dihydro-2H-pyrido[3,2-b][1,4]thiazin-6-ylmethyl)-amino]-cyclohexanecarboxylic acid (6,8-difluoro-quinolin-4-yl)amide dihydrochloride and (1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (6,8-difluoroquinolin-4-yl)-amide dihydrochloride

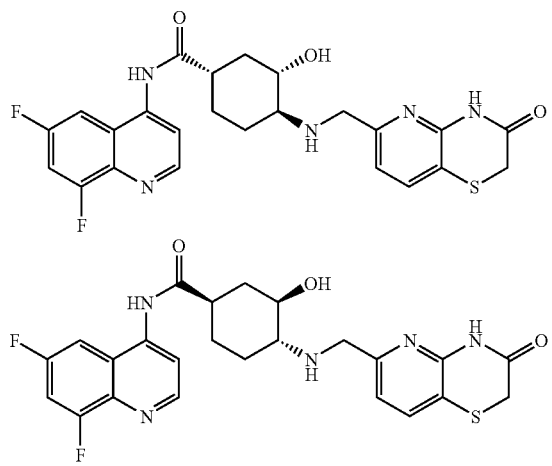

(a) 4-Bromo-6,8-difluoro-quinoline

This was prepared from 4-hydroxy-6,8-difluoro-quinoline by heating with phosphorus tribromide in dimethylformamide.

(b) (1R,3S,4S)- and (1S,3R,4R)-4-(6,8-Difluoro-quinolin-4-ylcarbamoyl)-2-hydroxy-cyclohexyl]-carbamic acid tert butyl ester A mixture of the amide (350e) (0.34 g), cesium carbonate (0.52 g), tris(dibenzylideneacetone)dipalladium(0) (24.5 mg), and rac-2,2'-bis(diphenylphosphino)-1,1'-binaphthyl (49 mg) in dry dioxan (15 ml) under argon, was sonicated for 10 minutes, the bromo-quinoline (358a) (0.32 g) was added, and the mixture was stirred and heated at 95° C. for 12 hours, under argon. The mixture was cooled, filtered, and the filtrate evaporated and chromatographed on silica gel, eluting with chloroform, then (2–5%) methanol-dichloromethane, to afford a solid (0.34 g).

MS (+ve ion electrospray) m/z 422 (MH+).

(c) (1S,3S,4S)- and (1R,3R,4R-4-Amino-3-hydroxy-cyclohexanecarboxylic acid (6,8-difluoro-quinolin-4-yl)-amide The carbamate (358b) (0.34 g) in dichloromethane (20 ml) was treated with trifluoroacetic acid (20 ml) for 2 hours and evaporated. Sodium carbonate solution was added and the solution was extracted (5×) with 10% methanol-chloroform, dried (sodium sulfate) and evaporated to give a white solid (0.245 g).

MS (+ve ion electrospray) m/z 322 (MH+).

(d) Title Compound

A mixture of carboxaldehyde (301d) (43 mg) and amine (358c) (72 mg) in anhydrous dimethylformamide (2 ml), methanol (2 ml) and acetic acid (0.2 ml) was heated over 3A molecular sieves at 80° C. for 2 h. After cooling, sodium cyanoborohydride (42 mg) was added and the mixture was stirred at room temperature overnight. The mixture was filtered, and evaporated and the residue basified with sodium carbonate and extracted several times with 10% methanol/chloroform and the combined organic fractions were dried and evaporated. Chromatography on silica gel (2–10% methanol/dichloromethane) gave the free base of the title compound (50 mg).

$^1$H NMR δ(CDCl$_3$/CD$_3$OD) 1.2–1.8 (3H, m), 2.03 (1H, m), 2.25 (2H, m), 2.5 (1H, m), 2.78 (1H, m), 3.49 (3H, m), 3.78 (1H, d), 3.95 (1H, d), 6.96 (1H, d), 7.35 (1H, m), 7.65 (1H, d), 7.8 (1H, m), 8.28 (1H, d), 8.75 (1H, d) MS (+ve ion electrospray) m/z 500 (MH$^+$)

The free base in chloroform/methanol (1:1) was treated with 4M HCl in dioxan (0.2 ml) and evaporated to dryness. The solid was triturated with ether, filtered and dried in vacuo, to provide title compound (59 mg).

Example 359

(1R,3R,4R)-3-Hydroxy-4-[(3-oxo-3,4-dihydro-2H-pyrido[3,2-b][1,4]oxazin-6-ylmethyl)-amino]-cyclohexanecarboxylic acid (6-methoxy-[1,5] naphthyridin-4-yl)-amide dihydrochloride

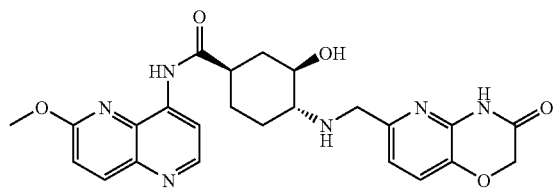

The amine (351 g) (0.47 nmol) under argon in MeOH (15 mL) and DMF (15 mL) was treated with the carboxaldehyde (305e) (0.47 mmol), and 3A molecular sieves (1 g), followed by AcOH (1.5 mL). (Polystyryhmethyl)trimethylammonium cyanoborohydride (0.940 mmol) was added after 20 min. Once the reaction had gone to completion the resin was removed by filtration, and the solvent removed in vacuo. The residue was purified by flash column chromatography (silica gel, DCM:MeOH/NH$_3$ (2M) 0–12%) to give the free base of the title compound in 79% yield.

$^1$H NMR δ (CD$_3$OD/CDCl$_3$) 1.24–1.35 (1H, m), 1.58–1.74 (2H, m), 2.10–2.16 (1H, m), 2.17–2.23 (1H, m), 2.32–3.38 (1H, m), 2.43–2.50 (1H, m), 2.62 (1H, tt), 3.48–3.52 (1H, m), 3.75, 3.94 (2H, ABq), 4.14 (3H, s), 4.64 (2H, s), 6.88 (1H, d), 7.20 (1H, d), 7.21 (1H, d), 8.21 (1H, d), 8.50 (1H, d), 8.65 (1H, d); MS (+ve ion electrospray) m/z 479 (MH$^+$, 100%).

This material as a solution in DCM/MeOH 1:1 was treated with 4M HCl in dioxane (0.5 mL), evaporated to dryness, then dried under vacuum to provide the title compound.

Example 360

(1R,3R,4R)-3-Hydroxy-4-[(7-methyl-3,4-dihydro-2H-pyrido[3,2-b][1,4]thiazin-6-ylmethyl)-amino]-cyclohexanecarboxylic acid (6-methoxy-[1,5] naphthyridin-4-yl)-amide dihydrochloride

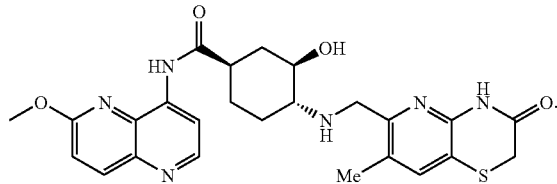

This was prepared by the method of Example (359) on a 0.449 mmol scale from amine (351 g) and aldehyde (310d), to give the free base of the title compound in 74% yield; $^1$H NMR δ (CD$_3$OD/CDCl$_3$) 1.28–1.40 (1H, m), 1.61–1.77 (2H, m), 2.12–2.18 (1H, m), 2.21–2.27 (1H, m), 2.25 (3H, s), 2.37–2.43 (1H, m), 2.48–2.55 (1H, m), 2.62 (1H, tt), 3.45 (2H, s), 3.52–3.58 (1H, m), 3.77, 3.97 (2H, ABq), 4.14 (3H, s), 7.18 (1H, d), 7.40 (1H, s), 8.22 (1H, d), 8.50 (1H, d), 8.66 (1H, d); MS (+ve ion electrospray) m/z 509 (MH$^+$, 100%).

This material as a solution in DCM/MeOH 1:1 was treated with 4M HCl in dioxane (0.5 mL), evaporated to dryness, then dried under vacuum to provide the title compound.

Example 361

(1R,3R,4R)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5] naphthyridin-4-yl)-amide dihydrochloride

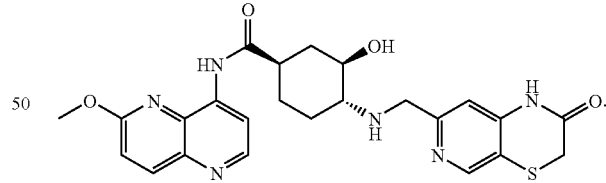

This was prepared by the method of Example (359) on a 0.470 mmol scale from amine (351 g) and aldehyde (302 g), to give the free base of the title compound in 79% yield $^1$H NMR δ(400 MHz, CD$_3$OD/CDCl$_3$) 1.25–1.36 (1H, m), 1.59–1.72 (2H, m), 2.11–2.17 (1H, m), 2.18–2.24 (1H, m), 2.34–2.40 (1H, m), 2.43–2.50 (1H, m), 2.63 (1H, tt), 3.46 (2H, m), 3.46–3.52 (1H, m), 3.83, 3.97 (2H, ABq), 4.15 (3H, s), 6.91 (1H, s), 7.22 (1H, d), 8.20 (1H, d), 8.36 (1H, s), 8.50 (1H, d), 8.63 (1H, d); MS (+ve ion electrospray) m/z 495 (MH$^+$, 100%).

This material as a solution in DCM/MeOH 1:1 was treated with 4M HCl in dioxane (0.5 mL), evaporated to dryness, then dried under vacuum to provide the title compound.

Example 362

(1S,3S,4S)-3-Hydroxy-4-[(7-methyl-3,4-dihydro-2H-pyrido[3,2-b][1,4]thiazin-6-ylmethyl)-amino]-cyclohexanecarboxylic acid (6-methoxy-[1,5]naphthyridin-4-yl)-amide dihydrochloride

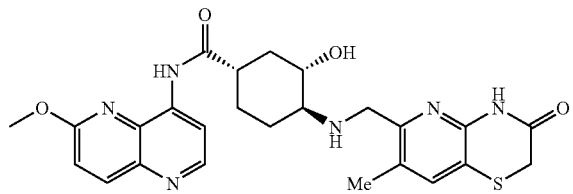

This was prepared by the method of Example (359) on a 0.432 mmol scale from amine (352 g), and aldehyde (310d), to give the free base of the title compound in 85% yield; $^1$H NMR δ (400 MHz; CD$_3$OD/CDCl$_3$) 1.28–1.37 (1H, m), 1.59–1.76 (2H, m), 2.13 (1H, bd), 2.20–2.24 (1H, m), 2.25 (3H, s), 2.38 (1H, bd), 2.51 (1H, dt), 2.65 (1H, tt), 3.45 (2H, s), 3.52–3.58 (1H, m), 3.75, 3.95 (2H, ABq), 4.15 (3H, s), 7.21 (1H, d), 7.42 (1H, s), 8.20 (1H, d), 8.50 (1H, d), 8.64 (1H, d); MS (+ve ion electrospray) m/z 509 (MH$^+$, 100%).
This material as a solution in DCM/MeOH 1:1 was treated with 4M HCl in dioxane (0.5 mL), evaporated to dryness, then dried under vacuum to provide the title compound.

Example 363

(1S,3S,4S)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5]naphthyridin-4-yl)-amide dihydrochloride

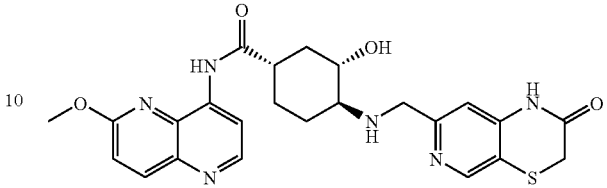

This was prepared by the method of Example (359) on a 0.463 mmol scale from amine (352 g) and aldehyde (302 g), to give the free base of the title compound in 52% yield; $^1$H NMR δ (400 MHz; CD$_3$OD/CDCl$_3$) 1.25–1.36 (1H, m), 1.59–1.74 (2H, m), 2.15 (1H, bd), 2.18–2.24 (1H, m), 2.38 (1H, bd), 2.47 (1H, dt), 2.65 (1H, tt), 3.45 (2H, m), 3.46–3.53 (1H, m), 3.83, 3.97 (2H, ABq), 4.15 (3H, s), 6.92 (1H, s), 7.22 (1H, d), 8.19 (1H, d), 8.36 (1H, s), 8.50 (1H, d), 8.63 (1H, d); MS (+ve ion electrospray) m/z 495 (MH$^+$, 100%).
This material as a solution in DCM/MeOH 1:1 was treated with 4M HCl in dioxane (0.5 mL), evaporated to dryness, then dried under vacuum to provide the title compound.
The following compounds were made by the method of Example (350h).

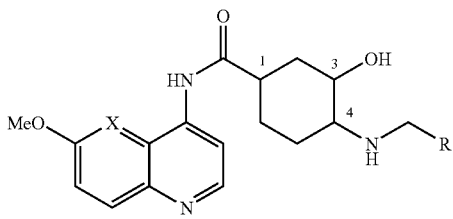

| Example | Method of synthesis (aldehyde) | Stereochemistry | salt B Dihydrochloride | X | R |
|---|---|---|---|---|---|
| 380 | (4c) | 1S,3S,4S/1R,3R,4R | B | N | 3-Oxo-3,4-dihydro-2-benzo[1,4]thiazin-6-yl 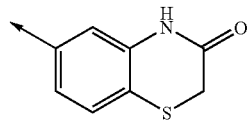 |
| 381 | (13e) | 1S,3S,4S/1R,3R,4R | B | N | 2-Oxo-2,3-dihydro-1H-pyrido[2,3-b][1,4]thiazin-7-yl 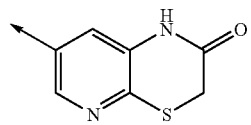 |

-continued

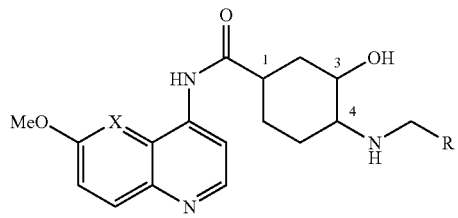

| Example | Method of synthesis (aldehyde) | Stereochemistry | salt B Dihydrochloride | X | R |
|---|---|---|---|---|---|
| 382 | (20e) | 1S,3S,4S/1R,3R,4R | B | N | 2,3-Dihydro-[1,4]dioxino[2,3-b]pyridin-7-yl 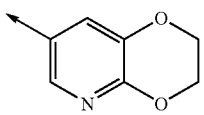 |
| 383 | a | 1S,3S,4S/1R,3R,4R | B | CH | 3-Oxo-3,4-dihydro-2H-pyrido[3,2-b][1,4]thiazin-6-yl 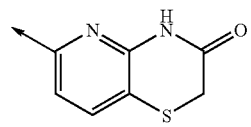 | a prepared from 4-bromo-6-methoxyquinoline (itself prepared from 6-methoxy-quinolin-4-ol by the method of Example 391a) by the method of Example 350(f–h)

Example 390

1-Hydroxy-t-4-[(3-oxo-3,4-dihydro-2H-pyrido[3,2-b][1,4]thiazin-6-ylmethyl)-amino-r-cyclohexanecarboxylic acid (8-fluoro-6-methoxy-quinolin-4-yl)-amide dihydrochloride

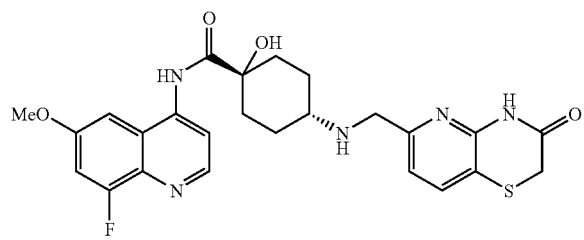

(a) [4-(8-Fluoro-6-methoxy-quinolin-4-ylcarbamoyl)-r-4-hydroxy-c-cyclohexyl]-carbamic acid tert-butyl ester A mixture of amide (300c) (1.46 g, 5.66 mmol) and cesium carbonate (2.66 g, 8.18 mmol) in 1,4-dioxan was deoxygenated by bubbling in a stream of argon for 5 mins. Tris(dibenzylideneacetone)dipalladium(0) (0.125 g, 0.13 mmol) and rac-2,2'-bis(diphenylphosphino)-1,1'-binaphthyl (0.25 g, 0.40 mmol) were added and deoxygenation continued for 2 mins. The mixture was the sonicated for 15 mins. Triflate ester (10b) (2.2 g, 6.77 mmol) was added and the mixture heated at 105° C. overnight. The reaction mixture was filtered and the filtered solids extracted with hot chloroform/methanol. The combined organics were evaporated and the crude product purified on silica gel eluting with 5% methanol/dichloromethane to give a solid (1.29 g, 53%). MS (+ve ion electrospray) m/z 434 (MH+).

(b) t-4-Amino-1-hydroxy-r-cyclohexanecarboxylic acid (8-fluoro-6-methoxy-quinolin-4-yl)-amide The carbamate (390a) (1.28 g, 2.96 mmol) in dichloromethane (20 ml) and trifluoroacetic acid (10 ml) was stirred for 2 hours at room temperature and then evaporated. The residue was basified with sodium carbonate and ice-water, the precipitate washed with water and dried, to give a solid (0.97 g, 98%).

(c) Title Compound

The amine (390b) (0.17 g, 0.51 mmol) and carboxaldehyde (301d) (0.099 g, 0.51 mmol) in methanol (5 ml) and chloroform (5 ml) were stirred at 65° C. with 3A sieves for 18 hours. The mixture was allowed to cool and sodium triacetoxyborohydride (0.50 g, 2.36 mmol) was added. After the mixture had been stirred for 3 days it was filtered and evaporated. The residue was neutralised with sodium carbonate solution and extracted with 10% methanol in chloroform. The extracts were dried and evaporated and the crude product purified on silica gel eluting with 0–10% methanol in dichloromethane to give the free base of the title compound (0.224 g, 91%).

$^1$H NMR δ(CDCl$_3$/CD$_3$OD) 1.6–1.8 (2H, m), 1.8–2.2 (7H, m), 2.72 (1H, m), 3.4 (2H, d), 3.5 (2H, s), 3.95 (2H, s), 3.97 (3H, s), 6.92 (2H, m), 7.15 (1H, d), 7.65 (1H, d), 8.35 (1H, d), 8.7 (1H, d).

Addition of 4M hydrochloric acid in dioxan and trituration of the precipitate with ether effected conversion to the title compound.

MS (+ve ion electrospray) m/z 483 (MH+)

Example 391

1-Hydroxy-t-4-[(3-oxo-3,4-dihydro-2H-pyrido[3,2-b][1,4]thiazin-6-ylmethyl)-amino-r-cyclohexanecarboxylic acid (6-methoxy-quinolin-4-yl)-amide dihydrochloride

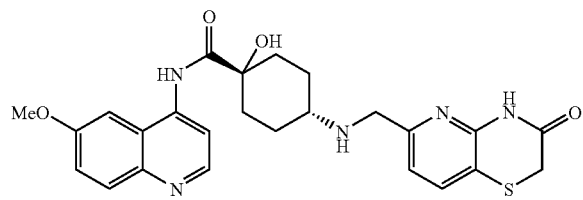

(a) 4-Bromo-6-methoxy-quinoline

This was prepared by heating 6-methoxy-quinolin-4-ol (1 g) and phosphorus oxybromide (5 g) in chloroform (40 ml) under reflux for 18 hours. The mixture was cooled, basified with sodium bicarbonate, extracted with 5% methanol-chloroform, and dried (sodium sulfate). The product was chromatographed on silica gel (2–5% methanol-dichloromethane) to afford a solid (0.68 g).

MS (+ve ion electrospray) m/z 238/240 (MH+)
Alternatively, this material was prepared in approximately 90% yield by treatment with one equivalent of phosphorous tribromide in N,N-dimethylformamide.

(b) [4-(6-Methoxy-quinolin-4-ylcarbamoyl)-r-4-hydroxy-c-cyclohexyl]-carbamic acid tert-butyl ester A mixture of amide (300c) (0.84 g) and cesium carbonate (1.20) in 1,4-dioxan (40 ml) was deoxygenated by bubbling in a stream of argon for 5 mins. Tris(dibenzylideneacetone) dipalladium(0) (60 mg) and rac-2,2'-bis(diphenylphosphino)-1,1'-binaphthyl (120 mg) were added and deoxygenation continued for 2 mins. The mixture was the sonicated for 10 mins. The bromide (391a) (0.8 g) was added and the mixture heated at 103° C. overnight. The reaction mixture was filtered and the filtered solids extracted with hot chloroform/methanol. The combined organics were evaporated and the crude product purified on silica gel eluting with chloroform then 2% methanol/dichloromethane to give a solid (1.27 g).

MS (+ve ion electrospray) m/z 416 (MH+).

(c) t-4-Amino-1-hydroxy-r-cyclohexanecarboxylic acid (6-methoxy-quinolin-4-yl)-amide The carbamate (391b) (1.43 g) in dichloromethane (50 ml) and trifluoroacetic acid (50 ml) was stirred for 2 hours at room temperature and then evaporated. The residue was basified with sodium carbonate and ice-water, the precipitate washed with water and dried, to give a solid (0.8 g).

MS (+ve ion electrospray) m/z 316 (MH+).

(d) Title Compound

The amine (391c) (0.162 g) and carboxaldehyde (301d) (0.1 g) in methanol (8 ml) and chloroform (8 ml) were stirred at 65° C. with 3A sieves for 18 hours. The mixture was allowed to cool and sodium triacetoxyborohydride (0.50 g) was added. After the mixture had been stirred for 2 days it was filtered and evaporated. The residue was neutralised with sodium carbonate solution and extracted with 5% methanol in chloroform. The extracts were dried and evaporated and the crude product purified on silica gel eluting with chloroform then 2–10% methanol in dichloromethane to give the free base of the title compound (0.2 g).

$^1$H NMR δ(CDCl$_3$/CD$_3$OD) 1.6–1.8 (2H, m), 1.8–2.2 (6H, m), 2.62 (1H, m), 3.4 (2H, d), 3.5 (2H, s), 3.87 (2H, s), 4.0 (3H, s), 6.98 (2H, m), 7.2 (1H, d), 7.42 (1H, dd), 7.65 (1H, d), 7.95 (1H, d), 8.25 (1H, d), 8.62 (1H, d).

Addition of 4M hydrochloric acid in dioxan and trituration of the precipitate with ether effected conversion to the title compound.

MS (+ve ion electrospray) m/z 494 (MH+)

Example 392

1-Hydroxy-t-4-[(3-oxo-3,4-dihydro-2H-pyrido[3,2-b][1,4]thiazin-6-ylmethyl)-amino-r-cyclohexanecarboxylic acid (6,8-difluoro-quinolin-4-yl)-amide dihydrochloride

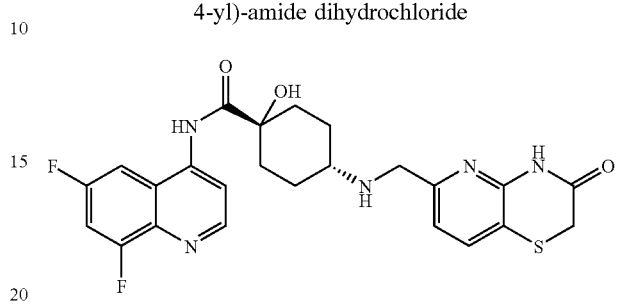

(a) 1,1,1-Trifluoro-methanesulfonic acid 6,8-difluoro-quinolin-4-yl ester

Sodium hydride 60% dispersion in oil (0.062 g, 1.55 mmol) was washed with hexane and suspended in DMF. After cooling to 0° C. 6,8-difluoro-quinolin-4-ol (0.20 g, 1.1 mmol) was added and the mixture stirred at 0° C. for 15 mins. N-Phenyltrifluoromethane sulfonimide (0.47 g, 1.3 mmol) was added and the mixture allowed to warm to room temperature and stirred overnight. The solvent was evaporated and the residue partitioned between ethyl acetate and water. The aqueous phase was extracted with ethyl acetate and the combined organics dried evaporated and chromatographed on silica gel eluting with dichloromethane to give the triflate (0.318 g, 92%)

MS (+ve ion electrospray) m/z 314 (MH+).

(b) [4-(6,8-Difluoro-quinolin-4-ylcarbamoyl)-r-4-hydroxy-c-cyclohexyl]-carbamic acid tert-butyl ester The carboxamide (300c) (0.25 g, 0.97 mmol) and the triflate ester (392a) (0.318 g, 1.0 mmol) were reacted by the method of Example(391b) except that the mixture was heated at 100–105° C. to give the carbamate (0.165 g, 40%).

MS (+ve ion electrospray) m/z 422 (MH+).

(c) t-4-Amino-1-hydroxy-r-cyclohexanecarboxylic acid (6,8-difluoro-quinolin-4-yl)-amide The carbamate was deprotected with trifluoroacetic acid by the method of Example (391c).

(d) Title Compound

The amine (392c) (0.067 g, 0.21 mmol) was reacted with carboxaldehyde (301d) (0.049 g, 0.25 mmol) in methanol (3 ml) and chloroform (3 ml) in the presence of 3A sieves at 65° C. overnight. The mixture was allowed to cool and further chloroform added (5 ml) to give a clear solution. Sodium triacetoxyborohydride (0.4 g) was added and the mixture stirred at room temperature for 48 hours. After decanting from the sieves the mixture was evaporated, treated with sodium carbonate solution and extracted with 10% methanol in dichloromethane. The extracts were dried, evaporated and chromatographed on silica gel eluting with 2–10% methanol in dichloromethane to give the free base of the title compound (0.076 g, 73%).

MS (+ve ion electrospray) m/z 500 (MH+).

$^1$H NMR δ(CDCl$_3$/CD$_3$OD) 1.55–1.7 (2H, m), 1.85–2.2 (6H, m), 2.68 (1H, m), 3.5 (2H, s), 3.87 (2H, s), 6.92 (1H, d), 7.25–7.4 (2H, m), 7.65 (1H, d), 8.43 (1H, d), 8.81 (1H, d).

Addition of 4M hydrochloric acid in dioxan and trituration of the precipitate with ether effected conversion to the title compound.

The following compounds were prepared by analogous methods.
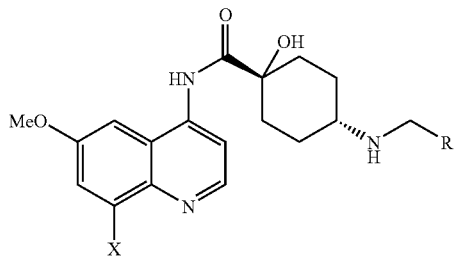
| Example | Method of synthesis (aldehyde) | salt B Dihydrochloride | X | R |
|---|---|---|---|---|
| 400 | a (19d) | B | F | 2,3-Dihydro-[1,4]dioxino[2,3-c]pyridin-7-yl |
| 421 | a (13e) | B | F | 2-oxo-2,3-dihydro-1H-pyrido[2,3-b][1,4]thiazin-7-yl |
| 422 | b (304g) | B | H | 7-Bromo-3-oxo-3,4-dihydro-2H-pyrido[3,2-b][1,4]thiazin-6-yl |
| 423 | b (19d) | B | H | 2,3-Dihydro-[1,4]dioxino[2,3-c]pyridin-7-yl |
| 424 | b (305e) | B | H | 3-oxo-3,4-dihydro-2H-pyrido[3,2-b][1,4]oxazin-6-yl |
| 425 | c (301d) | B | OMe | 3-oxo-3,4-dihydro-2H-pyrido[3,2-b][1,4]thiazin-6-yl |

-continued

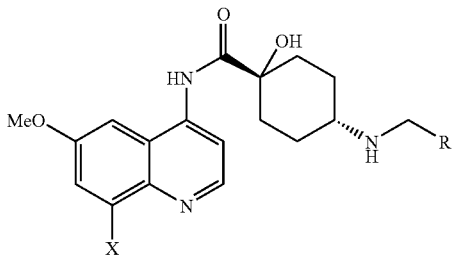

| Example | Method of synthesis (aldehyde) | salt B Dihydrochloride | X | R |
|---|---|---|---|---|
| 426 | a (306e) | B | F | 7-Chloro-3-oxo-3,4-dihydro-2H-pyrido[3,2-b][1,4]thiazin-6-yl |

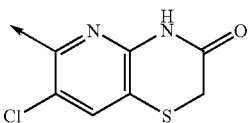

a prepared by the method of Example (390)
b prepared by the method of Example (391)
c prepared from 4-bromo-6,8-dimethoxy-quinoline by the method of Example (391)

Example 430

6-({4-hydroxy-4-[2-(6-methoxy-[1,5]naphthyridin-4-yl)-ethyl]-cyclohexylamino}-methyl)-4H-pyrido [3,2-b][1,4]oxazin-3-one

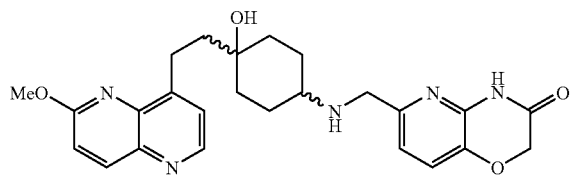

(a) (4-Hydroxy-4-trimethylsilanyl-cyclohexyl)-carbamic acid tert-butyl ester

A solution of trimethylsilyl acetylene at −78° C.(4.14 g, 0.042 mol) in THF (60 mL) was treated with n-butyl lithium (29 mL, 0.042 mol; 1.6 M solution in THF). The resulting mixture was stirred at −78° C. for 15 min. A solution of N-4-Boc-aminocyclohexanone (3 g, 0.014 mol; Astatech, Inc) in THF (120 mL) was added dropwise over a period of 30 min. The resulting mixture was stirred at −78° C. for 1 h and then allowed to slowly warm up to room temperature over 1 h. The reaction was quenched with a saturated solution of ammonium chloride and diluted with EtOAc and washed with saturated aqueous $NaHCO_3$ solution, $H_2O$, and saturated aqueous NaCl solution. The organic layer was dried over $MgSO_4$ and concentrated to yield an off-white foam (4.38 g, 100%).

MS (+ve ion electrospray) m/z 312 (M+H)$^+$.

(b) (4-Ethynyl-4-hydroxy-cyclohexyl)-carbamic acid tert-butyl ester

A solution of the carbamate (430a) (4.38 g, 0.014 mol) in MeOH (50 mL) was treated with $K_2CO_3$ (5.83 g, 0.42 mol) and stirred at room temperature for 3 h. The solvent was removed in vacuo and the residue was partitioned between EtOAc and aqueous NaCl, and the organic layer was dried ($MgSO_4$) and concentrated to yield an oil (2.7 g, 89%).

MS (+ve ion electrospray) m/z 240 (M+H)$^+$.

(c) [4-Hydroxy-4-(6-methoxy-[1,5]naphthyridin-4-ylethynyl)-cyclohexyl]-carbamic acid tert-butyl ester A solution of carbamate (430b) (2.7 g, 0.011 mol) and the triflate ester (1b) (3.13 g, 0.01 mol) in a 1:1 mixture of triethylamine and DMF (10 mL total volume) was treated with $(Ph_3P)_2PdCl_2$ (0.3 g; 4% mol) and CuI (0.24 g, 8% mol). The resulting mixture was heated at 70° C. for 24 h. The solvent was removed under reduced pressure and the residue was partitioned between $CH_2Cl_2$ and aqueous NaCl, and the organic layer was dried ($MgSO_4$), and concentrated in vacuo. The resulting oil was purified by flash column chromatography on silica gel (gradient: 20–50% EtOAc/hexane) to afford an oil (2.24 g, 50%).

MS (+ve ion electrospray) m/z 398 (M+H)$^+$.

d) {4-Hydroxy-4-[2-(6-methoxy-[1,5]naphthyridin-4-yl)-ethyl]-cyclohexyl}-carbamic acid tert-butyl ester A solution of carbamate (430c) (0.8 g, 2 mmol) in MeOH (10 mL) was treated with 10% palladium on carbon (catalytic) and hydrogenated in a Parr bottle for 6 h at 40 psi. The solution was filtered through a plug of celite®, and the filter pad was washed with MeOH. The filtrate was concentrated to yield a yellow oil (0.7 g, 80%). The product was used without further purification.

MS (+ve ion electrospray) m/z 402 (M+H)$^+$. NMR analysis indicated that the compound was a 5:1 mixture of isomers. The isomeric mixture was not further characterized and was carried on through the remaining steps.

(e) 4-Amino-1-[2-(6-methoxy-[1,5]naphthyridin-4-yl)-ethyl]-cyclohexanol

A solution of carbamate (430d) (0.4 g, 1 mmol) in $CH_2Cl_2$ (10 mL) was treated with trifluoroacetic acid (0.15 mL, 2 mmol). The solution was allowed to stir for 1 h at room temperature and then concentrated under reduced pressure. MeOH was added and the solution was again concentrated to remove any excess TFA. The remaining solid was dissolved in MeOH (5 mL) and treated with MP-Carbonate resin (1.00 g, 2.87 mmol; Argonaut Technologies, Inc.). The solution was then filtered and concentrated to yield a brown oil (0.3 g, 70%). The product was used without further purification.

MS (+ve ion electrospray) m/z 302 (M+H)+.

(f) Title Compound

The amine (430e) (0.169 g, 0.561 mmol) was added to a solution of the carboxaldehyde (305e) (0.100 g, 0.561 mmol) dissolved in DMF (3 mL), MeOH (2 mL) and acetic acid (0.2 mL). 3Å molecular sieves were then added to the reaction mixture and the solution was allowed to stir at 80° C. for 40 h. The solution was cooled to 0° C. and sodium borohydride (0.042 g, 1.12 mmol) was added. The reaction was stirred at ambient temperature for 4 h. The reaction mixture was partitioned between ethyl acetate and water. The organic layer was washed with water (2×) and brine, dried ($Na_2SO_4$) and concentrated to yield a yellow oil. The product was purified using flash column chromatography on silica gel (90:10:1 $CHCl_3/MeOH/NH_4OH$) to yield a yellow solid (0.025 g, 11%).

MS (+ve ion electrospray) m/z 464 (M+H)+. $^1$H NMR (400 MHz, $CDCl_3$) δ 8.72 (d, J=4.5 Hz, 1H), 8.18 (d, J=9.0 Hz, 1H), 7.40 (d, J=4.5 Hz, 1H), 7.20 (d, J=9.0 Hz, 1H), 7.10 (d, J=9.0 Hz, 1H), 6.8 (d, J=9.0 Hz, 1H), 4.60(s, 2H), 4.04 (s, 3H), 3.75 (s, 2H), 3.25 (m, 2H), 2.55 (m, 1H), 1.91 (br m, 6H); 1.69 (m, 2H); 1.45 (m, 2H).

Biological Activity

The MIC (μg/ml) of test compounds against various organisms was determined: S. aureus Oxford, S. aureus WCUH29, S. pneumoniae 1629, S. pneumoniae N1387, S. pueumoniae ERY 2, E. faecalis I, E. faecalis 7, H. influenzae Q1, H. influenzae NEMC1, M. catarrhalis 1502.

Examples 2–6, 8, 9, 12, 13, 19–21, 23, 28, 30, 31, 32, 34, 35, 101, 150, 153, 154, 210–214, 300–305, 320–333, 380, 381, 390, 391, 400, 422, 423 had MIC values ≦4 μg/ml versus all these organisms.

Examples 10, 11, 14–17, 22, 24, 26, 29, 102, 104, 155, 156, 215, 334–336, 382 had MIC values ≦16 μg/ml versus all these organisms.

Examples 7, 18, 25, 27, 36, 100, 103, 105, 337 and 338 had MIC values ≦64 μg/ml versus all these organisms.

The MIC (mg/ml) of further test compounds against an alternative selection of organisms was determined:
S. aureus WCUH29, S. pneumoniae 1629, H. influenzae ATCC 51907, M. catarrhalis Ravisio.

Examples 306–310,312,314,350–363, 392, 421, 424–426, 430 had MIC values ≦4 μg/ml versus all these organisms.

Examples 311, 313, 340, 342, 343, 383 had MIC values ≦16 μg/ml versus all these organisms.

Examples 110, 111, 206, 341 had MIC values ≦16 μg/ml versus some1 of these organisms.

Other examples except 106 and 203 had MIC values ≦64 μg/ml versus at least one of these organisms.

What is claimed is:

1. A compound of formula (I) or a pharmaceutically acceptable salt, solvate or N-oxide thereof:

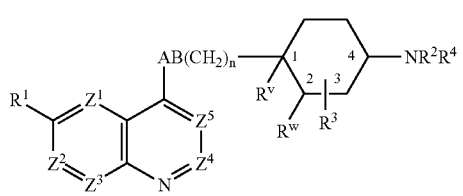

(I)

wherein:
one of $Z^1$, $Z^2$, and $Z^3$ is N, one of the remainder of $Z_1$, $Z_2$, $Z_3$, $Z_4$ and $Z_5$ is $CR^{1a}$ and the remainder are CH;

$R^v$ and $R^w$ are hydrogen; $R^v$ and $R^3$; or $R^v$ and $R^w$ together are a bond;

$R^1$ and $R^{1a}$ are independently selected from hydrogen; hydroxy; $(C_{1-6})$ alkoxy optionally substituted by $(C_{1-6})$alkoxy, amino, piperidyl, guanidino or amidino any of which is optionally N-substituted by one or two $(C_{1-6})$alkyl, $(C_{1-6})$alkoxycarbonyl, formyl, $(C_{1-6})$ alkylcarbonyl, or $(C_{1-6})$alkylsulphonyl groups, CONH2, hydroxy, $(C_{1-6})$alkylthio, heterocyclylthio, heterocyclyloxy, arylthio, aryloxy, $(C_{1-6})$ alkyloxycarbonylthio, formylthio, $(C_{1-6})$ alkylcarbonylthio, $(C_{1-6})$alkyloxycarbonyloxy, formyloxy, $(C_{1-6})$alkylcarbonyloxy or $(C_{1-6})$ alkylsulphonyloxy; $(C_{1-6})$alkoxy-substituted $(C_{1-6})$ alkyl; halogen; $(C_{1-6})$alkyl; $(C_{1-6})$alkylthio; trifluoromethyl; nitro; azido; $(C_{1-6})$alkoxycarbonyl; formyl; $(C_{1-6})$alkylcarbonyl; $(C_{1-6})$alkyloxycarbonyloxy, formyloxy, $(C_{1-6})$alkylcarbonyloxy, $(C_{1-6})$ alkyloxycarbonylthio, formylthio; $(C_{1-6})$ alkylcarbonylthio; $(C_{1-6})$alkylsulphonyl; $(C_{1-6})$ alkylsulphoxide; arylsulphonyl; arylsulphoxide or an amino, piperidyl, guanidino or amidino group optionally N-substituted by one or two $(C_{1-6})$alkyl, $(C_{1-6})$ alkoxycarbonyl, formyl, $(C_{1-6})$alkylcarbonyl or $(C_{1-6})$ alkylsulphonyl groups, or when $Z^1$ is $CR^{1a}$, $R^1$ and $R^{1a}$ may together represent $(C_{1-2})$alkylenedioxy;

or when $Z^5$ is $CR^{1a}$, $R^{1a}$ may instead be cyano, hydroxymethyl or carboxy;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$ alkylcarbonyl; $(C_{2-4})$alkenyloxycarbonyl; $(C_{2-4})$ alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$ alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$ alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$ alkyl, $(C_{2-4})$alkenyl, $(C_{1-4})$alkoxycarbonyl, $(C_{1-4})$ alkylcarbonyl, $(C_{2-4})$alkenyloxycarbonyl, $(C_{2-4})$ alkenylcarbonyl; oxo; $(C_{1-4})$alkylsulphonyl; $(C_{2-4})$ alkenylsulphonyl; or $(C_{1-4})$aminosulphonyl wherein the amino group is optionally substituted by $(C_{1-4})$alkyl or $(C_{2-4})$alkenyl;

when $R^v$ and $R^w$ are a bond, $R^3$ is in the 2-, 3- or 4-position and when $R^v$ and $R^w$ are not a bond, $R^3$ is in the 1-, 2-, 3- or 4-position and $R^3$ is:

hydrogen; carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$ alkylsulphonyl, trifluoromethylsulphonyl, $(C_{2-6})$ alkenylsulphonyl, $(C_{1-6})$alkoxycarbonyl, $(C_{1-6})$ alkylcarbonyl, $(C_{2-6})$alkenyloxycarbonyl or $(C_{2-6})$ alkenylcarbonyl and optionally further substituted by $(C_{1-6})$alkyl, hydroxy$(C_{1-6})$alkyl, aminocarbonyl$(C_{1-6})$ alkyl or $(C_{2-6})$alkenyl; cyano; tetrazolyl; 2-oxo-oxazolidinyl optionally substituted by $R^{10}$; 3-hydroxy- 3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; or amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

provided that when $R^3$ is in the 4-position it is not optionally substituted hydroxyl or amino;

in addition when $R^3$ is disubstituted with a hydroxy or amino containing substituent and a carboxy containing substituent these may optionally together form a cyclic ester or amide linkage, respectively;

$R^{10}$ is selected from $(C_{1-4})$alkyl and $(C_{2-4})$alkenyl either of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

$R^4$ is a group $-CH_2-R^5{}_1$ in which $R^5{}_1$ is selected from: $(C_{4-8})$alkyl; hydroxy$(C_{4-8})$alkyl; $(C_{1-4})$alkoxy$(C_{4-8})$alkyl; $(C_{1-4})$alkanoyloxy$(C_{4-8})$alkyl; $(C_{3-8})$cycloalkyl$(C_{4-8})$alkyl; hydroxy-, $(C_{1-6})$alkoxy- or $(C_{1-6})$alkanoyloxy-$(C_{3-8})$cycloalkyl$(C_{4-8})$alkyl; cyano$(C_{4-8})$alkyl; $(C_{4-8})$alkenyl; $(C_{4-8})$alkynyl; tetrahydrofuryl; mono- or di-$(C_{1-6})$alkylamino$(C_{4-8})$alkyl; acylamino$(C_{4-8})$alkyl; $(C_{1-6})$alkyl- or acylaminocarbonyl$(C_{4-8})$alkyl; mono- or di-$(C_{1-6})$alkylamino(hydroxy) $(C_{4-8})$alkyl; or $R^4$ is a group $-U-R^5{}_2$ where $R^5{}_2$ is an optionally substituted bicyclic carbocyclic or heterocyclic ring system (A):

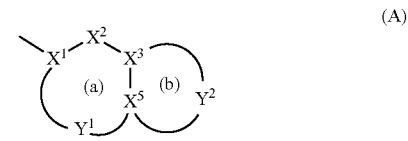

(A)

containing up to four heteroatoms in each ring in which at least one of rings (a) and (b) is aromatic;

$X^1$ is C or N when part of an aromatic ring or $CR^{14}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; halo$(C_{1-4})$alkoxy, halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl; aryl$(C_{1-4})$alkyl; aryl$(C_{1-4})$alkoxy;

each $R^{13}$ is independently H; trifluoromethyl; $(C_{1-4})$alkyl optionally substituted by hydroxy, carboxy, $(C_{1-6})$alkoxycarbonyl, $(C_{1-6})$alkoxy, $(C_{1-6})$alkylthio, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

each x is independently 0, 1 or 2;

U is CO, $SO_2$ or $CH_2$; or $R^4$ is a group $-X^{1a}-X^{2a}-X^{3a}-X^{4a}$ in which:

$X^{1a}$ is $CH_2$, CO or $SO_2$;

$X^{2a}$ is $CR^{14a}R^{15a}$;

$X^{3a}$ is $NR^{13a}$, O, S, $SO_2$ or $CR^{14a}R^{15a}$; wherein:

each of $R^{14a}$ and $R^{15a}$ is independently selected from the groups listed above for $R^{14}$ and $R^{15}$, provided that $R^{14a}$ and $R^{15a}$ on the same carbon atom are not both selected from optionally substituted hydroxy and optionally substituted amino; or $R^{14a}$ and $R^{15a}$ together represent oxo;

$R^{13a}$ is hydrogen; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl; or two $R^{14a}$ groups or an $R^{13a}$ and an $R^{14a}$ group on adjacent atoms together represent a bond and the remaining $R^{13a}$, $R^{14a}$ and $R^{15a}$ groups are as above defined; or two $R^{14a}$ groups and two $R^{15a}$ groups on adjacent atoms together represent bonds such that $X^{2a}$ and $X^{3a}$ is triple bonded;

$X^{4a}$ is phenyl or C or N linked monocyclic aromatic 5- or 6-membered heterocycle containing up to four heteroatoms selected from O, S and N and: optionally C-substituted by up to three groups selected from $(C_{1-4})$alkylthio; halo; carboxy$(C_{1-4})$alkyl; halo $(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$alkoxy, nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; aryl, aryl$(C_{1-4})$alkyl or aryl$(C_{1-4})$alkoxy; and optionally N substituted by trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl$(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

n is 0 or 1 and AB is $NR^{11}CO$, $CONR^{11}$, $CO—CR^8R^9$, $CR^6R^7$-CO, $O—CR^8R^9$, $CR^6R^7$-O, $NR^{11}—CR^8R^9$, $CR^6R^7—NR^{11}$, $NR^{11}SO_2$, $CR^6R^7—SO_2$ or $CR^6R^7—CR^8R^9$, provided that when $R^v$ and $R^w$ are a bond and n=0, B is not $NR^{11}$, O or $SO_2$, or n is 0 and AB is NH—CO—NH or NH—CO—O and $R^v/R^w$ are not a bond;

or n is 0 and AB is $CR^6R^7SO_2NR^2$, $CR^6R^7CONR^2$ or $CR^6R^7CH_2NR^2$ and $R^v/R^w$ are not a bond;

provided that $R^6$ and $R^7$, and $R^8$ and $R^9$ are not both optionally substituted hydroxy or amino;

and wherein:

each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

and each $R^{11}$ is independently H; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl.

2. A compound according to claim 1 wherein $Z^1$ is N, $Z^3$ is CH or CF and $Z^2$, $Z^4$ and $Z^5$ are each CH.

3. A compound according to claim 1 wherein $R^1$ is methoxy or fluoro and $R^{1a}$ is H or when $Z^3$ is $CR^{1a}$ it may be C—F.

4. A compound according to claim 1 wherein $R^2$ is hydrogen.

5. A compound according to claim 1 wherein $R^3$ is hydrogen or hydroxy substituted in the 1-or 3-position.

6. A compound according to claim 1 wherein n is 0 and either A is CHOH or $CH_2$ and B is $CH_2$ or A is NH and B is CO, and $AB(CH_2)_n$ and $NR^2R^4$ are trans.

7. A compound according to claim 1 wherein $R^4$ is —U—$R^5_2$, the group —U— is —$CH_2$—, and $R^5_2$ is an aromatic heterocyclic ring (A) having 8–11 ring atoms including 2–4 heteroatoms of which at least one is N or $NR^{13}$ in which $Y^2$ contains 2–3 heteroatoms, one of which is S and 1–2 are N, with one N bonded to $X^3$, or the heterocyclic ring (A) has ring (a) aromatic selected from optionally substituted benzo and pyrido and ring (b) non-aromatic and $Y^2$ has 3–5 atoms including heteroatom bonded to $X^5$ selected from $NR^{13}$, O or S, where R13 is other than hydrogen, and NHCO bonded via N to $X^3$, or O bonded to $X^3$.

8. A compound according to claim 1 wherein $R^5_2$ is selected from: benzo[1,2,5]thiadiazol-5-yl 3-oxo-3,4-dihydro-2H-benzo[1,4]thiazin-6-yl (4H-benzo[1,4]thiazin-3-one-6-yl)

2,3-dihydro-benzo[1,4]dioxin-6-yl benzo[1,2,3]thiadiazol-5-yl 3-oxo-3,4-dihydro-2H-benzo[1,4]oxazin-6-yl 7-fluoro-3-oxo-3,4-dihydro-2H-benzo[1,4] oxazin-6-yl 2-oxo-2,3-dihydro-1H-pyrido[2,3-b]thiazin-7-yl 2,3-Dihydro-[1,4]dioxino[2,3-c]pyridin-7-yl 3-oxo-3,4-dihydro-2H-pyrido[2,3-b]oxazin-6-yl

[1,2,3]thiadiazolo[5,4-b]pyridin-6-yl.

9. A compound according to claim 1, selected from:

Trans-4-[(8-Hydroxy-quinolin-2-ylmethyl)-amino]-cyclohexanecarboxylic acid (6-methoxy-[1,5]naphthyridin-4-yl)-amide;

Trans-4-[(Benzo[1,2,5]thiadiazol-5-ylmethyl)-amino]-cyclohexanecarboxylic acid (6-methoxy-[1,5]naphthyridin-4-yl)-amide;

Trans-4-[(1H-Pyrrolo[2,3-b]pyridin-2-ylmethyl)-amino]-cyclohexanecarboxylic acid (6-methoxy-[1,5]naphthyridin-4-yl)-amide;

Trans-4-[(3-Oxo-3,4-dihydro-2H-benzo[1,4]thiazin-6-ylmethyl)-amino]-cyclohexane carboxylic acid (6-methoxy-[1,5]naphthyridin-4-yl)-amide;

Trans-4-[(2,3-Dihydro-benzo[1,4]dioxin-6-ylmethyl)-amino]-cyclohexanecarboxylic acid (6-methoxy-[1,5]naphthyridin-4-yl)-amide;
Trans-4-[(Benzo[1,2,3]thiadiazol-5-yl-ylmethyl)-amino]-cyclohexanecarboxylic acid (6-methoxy-[1,5]naphthyridin-4-yl)-amide;
Trans-4-[(3-Methyl-2-oxo-2,3-dihydro-benzooxazol-6-ylmethyl)-amino-cyclohexanecarboxylic acid (6-methoxy-[1,5]naphthyridin-4-yl)-amide;
Trans-4-[(3-Oxo-3,4-dihydro-2H-benzo[1,4]oxazin-6-ylmethyl)-amino]-cyclohexanecarboxylic acid (6-methoxy-[1,5]naphthyridin-4-yl)-amide;
Trans-4-[(7-Fluoro-3-oxo-3,4-dihydro-2H-benzo[1,4]oxazin-6-ylmethyl)-amino]-cyclohexanecarboxylic acid (6-methoxy-[1,5]naphthyridin-4-yl)-amide;
Trans-4-[(2-Oxo-2,3-dihydro-1H-pyrido[2,3-b][1,4]thiazin-7-ylmethyl)-amino]-cyclohexanecarboxylic acid (6-methoxy-[1,5]naphthyridin-4-yl)-amide;
Trans-4-[(3,4-Dihydro-2H-benzo[1,4]oxazin-6-ylmethyl)-amino]-cyclohexanecarboxylic acid (6-methoxy-[1,5]naphthyridin-4-yl)-amide;
Trans-4-[(Thiazolo[5,4-b]-pyridin-6-ylmethyl)-amino]-cyclohexanecarboxylic acid (6-methoxy-[1,5]naphthyridin-4-yl)-amide;
Trans-4-[(8-Hydroxy-1-oxo-1,2-dihydro-isoquinolin-3-ylmethyl)-amino]-cyclohexanecarboxylic acid (6-methoxy-[1,5]naphthyridin-4-yl)-amide;
Trans-4-[(2,3-Dihydro-[1,4]dioxino[2,3-b]pyridin-6-ylmethyl)-amino]-cyclohexanecarboxylic acid (6-methoxy-[1,5]naphthyridin-4-yl)-amide;
Trans-4-[(2,3-Dihydro-[1,4]dioxino[2,3-c]pyridin-7-ylmethyl)-amino]-cyclohexanecarboxylic acid (6-methoxy-[1,5]naphthyridin-4-yl)-amide;
Trans-4-[(2,3-Dihydro-[1,4]dioxino[2,3-b]pyridin-7-ylmethyl)-amino]-cyclohexanecarboxylic acid (6-methoxy-[1,5]naphthyridin-4-yl)-amide;
Trans-4-[(6-Nitro-benzo[1,3]dioxol-5-ylmethyl)-amino]-cyclohexanecarboxylic acid (6-methoxy-[1,5]naphthyridin-4-yl)-amide;
Trans-4-[(6-Amino-benzo[1,3]dioxol-5-ylmenthyl)-amino]-cyclohexanecarboxylic acid (6-methoxy-[1,5]naphthyridin-4-yl)-amide;
Trans-4-[(Benzothiazol-5-ylmethyl)-amino]cyclohexanecarboxylic acid(6-methoxy-[1,5]naphthyridine-4-yl)amide;
Trans-4-[(4-Oxo-4 H pyrido[1,2-a]pyrimidin-2-ylmethyl)-amino]-cyclohexanecarboxylic acid (6-methoxy-[1,5]naphthyridin-4-yl)-amide;
Trans-4-[(2,3-Dihydro-benzo[1,4]dioxin-6-ylmethyl)-amino]-cyclohexanecarboxylic acid [6-(3-amino-propoxy)-[1,5]naphthyridin-4-yl]-amide;
Trans-4-[(3-Oxo-3,4-dihydro-2H-pyrido[3,2-b][1,4]oxazin-6-ylmethyl)-amino]-cyclohexanecarboxylic acid (6-methoxy-[1,5]naphthyridin-4-yl)-amide;
Trans-4-[([1,2,3]Thiadiazolo[5,4-b]pyridin-6-ylmethyl)-amino]-cyclohexanecarboxylic acid (6-methoxy-[1,5]naphthyridin-4-yl)-amide;
Trans-4-(3-Oxo-3,4-dihydro-2H-benzo[1,4]thiazine-6-sulfonylamino)-cyclohexanecarboxylic acid (6-methoxy-[1,5]naphthyridin-4-yl)-amide;
Trans-4-[(7-Fluoro-3-oxo-3,4-dihydro-2H-benzo[1,4]thiazin-6-ylmethyl)-amino]-cyclohexanecarboxylic acid (6-methoxy-[1,5]naphthyridin-4-yl)-amide;
Trans-4-[(8-Nitro-3-oxo-3,4-dihydro-2H-benzo[1,4]oxazin-6-ylmethyl)-amino]-cyclohexanecarboxylic acid (6-methoxy)-[1,5]naphthyridin-4-yl)-amide;
Trans-4-[(8-Amino-3-oxo-3,4-dihydro-2H-benzo[1,4]oxazin-6-ylmethyl)-amino]-cyclohexanecarboxylic acid (6-methoxy)-[1,5]naphthyridin-4-yl)-amide;
(R/S)-4-[(3-Oxo-3,4-dihydro-2H-benzo[1,4]thiazin-6-ylmethyl)-amino]-cyclohex-1-ene carboxylic acid (6-methoxy-[1,5]naphthyridin-4-yl)-amide;
(R/S)-4-[(Benzo[1,2,5]thiadiazol-5-ylmethyl)-amino]-cyclohexene carboxylic acid (6-methoxy-[1,5]naphthyridin-4-yl)-amide;
(R/S)-4-[(Benzo[1,2,3]thiadiazol-5-ylmethyl)-amino]-cyclohex-1-ene carboxylic acid (6-methoxy-[1,5]naphthyridin-4-yl)amide;
(R/S)-4-[(2-Oxo-2,3-dihydro-1H-pyrido[2,3-b][1,4]thiazin-7-ylmethyl)-amino]-cyclohex-1-ene carboxylic acid (6-methoxy-[1,5]naphthyridin-4-yl)-amide;
(R/S)-4-[(7-Fluoro-3-oxo-3,4-dihydro-2H-benzo[1,4]oxazin-6-ylmethyl)-amino]-cyclohex-1-ene carboxylic acid (6-methoxy-[1,5]naphthyridin-4-yl)-amide;
(R/S)-4-[(2-Oxo-2,3-dihydro-1H-pyrido[2,3-b][1,4]oxazin-7-ylmethyl)-amino]-cyclohex-1-enecarboxylic acid (6-methoxy-[1,5]naphthyridin-4-yl)-amide;
(R/S)-4-[Carboxymethyl-(3-oxo-3,4-dihydro-2H-benzo[1,4]thiazin-6-ylmethyl)-amino]-cyclohex-1-enecarboxylic acid (6-methoxy-[1,5]naphthyridin-4-yl)-amide;
1-Hydroxy-t-4-[(3-oxo-3,4-dihydro-2H-benzo[1,4]thiazin-6-ylmethyl)-amino]-r-cyclohexanecarboxylic acid (6-methoxy-[1,5]naphthyridin-4-yl)-amide;
1-Hydroxy-t-4-[(3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide;
1-Hydroxy-t-4-[(2-oxo-2,3-dihydro-1H-pyrido[3,4-b][1,4]thiazin-7-ylmethyl)-amino]-r-cyclohexanecarboxylic acid (6-methoxy-[1,5]naphthyridin-4-yl)-amide;
1-Hydroxy-t-4-[(2-oxo-2,3-dihydro-1H-pyrido[2,3-b][1,4]thiazin-7-ylmethyl)-amino]-r-cyclohexanecarboxylic acid (6-methoxy-[1,5]naphthyridin-4-yl)-amide;
1-Hydroxy-t-4-[(7-bromo-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide;
1-Hydroxy-t-4-[(3-oxo-3,4-dihydro-2H-pyrido[3,2-b][1,4]oxazin-6-ylmethyl)-amino]-r-cyclohexanecarboxylic acid (6-methoxy-[1,5]naphthyridin-4-yl)-amide;
1-Hydroxy-t-4-[(7-chloro-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide;
1-Hydroxy-t-4-[(7-oxo-5,6,7,8-tetrahydro-[1,8]naphthyridine-2-ylmethyl)-amino]-r-cyclohexanecarboxylic acid (6-methoxy-[1,5]naphthyridine-4-yl)-amide;
1-Hydroxy-t-4-[(7-fluoro-3-oxo-3,4-dihydro-2H-pyrido[3,2-b][1,4]thiazin-6-ylmethyl)-amino]-r-cyclohexanecarboxylic acid (6-methoxy-[1,5]naphthyridin-4-yl)-amide;
1-Hydroxy-t-4-[(2-oxo-2,3-dihydro-1H-pyrido[3,4-b][1,4]oxazin-7-ylmethyl)-amino]-r-cyclohexanecarboxylic acid (6-methyl-[1,5]naphthyridin-4-yl)-amide;
1-Hydroxy-t-4-[(7-methyl-3-oxo-3,4-dihydro-2H-pyrido[3,2-b][1,4]thiazin-6-ylmethyl)-amino]-r- cyclohexanecarboxylic acid (6-methoxy-[1,5] naphthyridin-4-yl)-amide;

1-Hydroxy-t-4-[(7-ethyl-3-oxo-3,4-dihydro-2H-pyrido[3,2-b][1,4]thiazin-6-ylmethyl)-amino]-r-cyclohexanecarboxylic acid (6-methoxy-[1,5] naphthyridin-4-yl)-amide;

1-Hydroxy-t-4-[(6-oxo-6,7-dihydro-5H-pyridazino[3,4-b][1,4]thiazin-3-ylmethyl)-amino]-r-cyclohexanecarboxylic acid (6-methoxy-[1,5] naphthyridin-4-yl)-amide;

1-Hydroxy-t-4-[(3-oxo-3,4-dihydro-2H-pyrido[3,2-b][1,4]thiazin-6-ylmethyl)-amino]-r-cyclohexanecarboxylic acid [6-(2-methoxy-ethoxy)-[1,5]naphthyridin-4-yl]-amide;

(1S,3S,4S)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide and (1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5]naphthyridin-4-yl)-amide;

(1R,3R,4R)-3-Hydroxy-4-[(3-oxo-3,4-dihydro-2H-pyrido[3,2-b][1,4]thiazin-6-ylmethyl)-amino]-cyclohexanecarboxylic acid (6-methoxy-[1,5] naphthyridin-4-yl)-amide;

(1S,3S,4S)-3-Hydroxy-4-[(3-oxo-3,4-dihydro-2H-pyrido[3,2-b][1.4]thiazin-6-ylmethyl)-amino]-cyclohexanecarboxylic acid (6-methoxy-[1,5] naphthyridin-4-yl)-amide;

(1S,3S,4S)-4-[(7-Chloro-3-oxo-3,4-dihydro-2H-pyrido[3,2-b][1,4]thiazin-6-ylmethyl)-amino]-3-hydroxy-cyclohexanecarboxylic acid (6-methoxy-[1,5] naphthyridin-4-yl)-amide and (1R,3R,4R)-4-[(7-chloro-3-oxo-3,4-dihydro-2H-pyrido[3,2-b][1,4]thiazin-6-ylmethyl)-amino]-3-hydroxy-cyclohexanecarboxylic acid (6-methoxy-[1,5] naphthyridin-4-yl)-amide;

(1S,3S,4S)-3-Hydroxy-4-[(7-fluoro-3-oxo-3,4-dihydro-2H-pyrido[3,2-b][1,4]thiazin-6-ylmethyl)-amino]-cyclohexanecarboxylic acid (6-methoxy-[1,5] naphthyridin-4-yl)-amide and (1R,3R,4R)-3-Hydroxy-4-[(7-fluoro-3-oxo-3,4-dihydro-2H-pyrido[3,2-b][1,4] thiazin-6-ylmethyl)-amino]-cyclohexanecarboxylic acid (6-methoxy-[1,5]naphthyridin-4-yl)-amide;

(1S,3S,4S)-3-Hydroxy-4-[(2-oxo-2,3-dihydro-1H-pyrido[3,4-b][1,4]oxazin-7-ylmethyl)-amino]-cyclohexanecarboxylic acid (6-methoxy-[1,5] naphthyridin-4-yl)-amide and (1R,3R,4R)-3-Hydroxy-4-[(2-oxo-2,3-dihydro-1H-pyrido[3,4-b][1,4]oxazin-7-ylmethyl)-amino]-cyclohexanecarboxylic acid (6-methoxy-[1,5]naphthyridin-4-yl)-amide;

(1S,3S,4S)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5] naphthyridin-4-yl)-amide and (1R,3R,4R)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5]naphthyridin-4-yl)-amide;

(1S,3S,4S)-3-Hydroxy-4-[(6-oxo-6,7-dihydro-5H-8-thia-1,2,5-triaza-naphthalen-3-ylmethyl)-amino]-cyclohexanecarboxylic acid (6-methoxy-[1,5] naphthyridin-4-yl)-amide and (1R,3R,4R)-3-hydroxy-4-[6-oxo-6,7-dihydro-5H-8-thia-1,2,5-triaza-naphthalen-3-ylmethyl)-amino]-cyclohexanecarboxylic acid (6-methoxy-[1,5] naphthyridin-4-yl)-amide;

(1R,3R,4R)-3-Hydroxy-4-[(3-oxo-3,4-dihydro-2H-pyrido[3,2-b][1,4]oxazin-6-ylmethyl)-amino]-cyclohexanecarboxylic acid (6-methoxy-[1,5] naphthyridin-4-yl)-amide;

(1R,3R,4R)-3-Hydroxy-4-[(7-methyl-3,4-dihydro-2H-pyrido[3,2-b][1,4]thiazin-6-ylmethyl)-amino]-cyclohexanecarboxylic acid (6-methoxy-[1,5] naphthyridin-4-yl)-amide;

(1R,3R,4R)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5] naphthyridin-4-yl)-amide;

(1S,3S,4S)-3-Hydroxy-4-[(7-methyl-3,4-dihydro-2H-pyrido[3,2-b][1,4]thiazin-6-ylmethyl)-amino]-cyclohexanecarboxylic acid (6-methoxy-[1,5] naphthyridin-4-yl)-amide;

(1S,3S,4S)-3-Hydroxy-4-[(2-oxo-2,3-dihydro-1H-pyrido[3,4-b][1,4]thiazin-7-ylmethyl)-amino]-cyclohexanecarboxylic acid (6-methoxy-[1,5] naphthyridin-4-yl)-amide;

1-Hydroxy-t-4-[(2,3-dihydro-[1,4]dioxino[2,3-c]pyridin-7-ylmethyl)-amino]-r-cyclohexanecarboxylic acid (6-methoxy-[1,5]napthyridin-4-yl)-amide;

6-({4-hydroxy-4-[2-(6-methoxy-[1,5]naphthyridin-4-yl)-ethyl]-cyclohexylamino}-methyl)-4H-pyrido[3,2-b][1,4]oxazin-3-one; or a pharmaceutically acceptable salt, solvate or N-oxide thereof.

10. A method of treatment of bacterial infections in mammals, which method comprises the administration to a mammal in need of such treatment an effective amount of a compound according to claim 1.

11. A pharmaceutical composition comprising a compound according to claim 1, and a pharmaceutically acceptable carrier.

12. A compound of formula (VI):

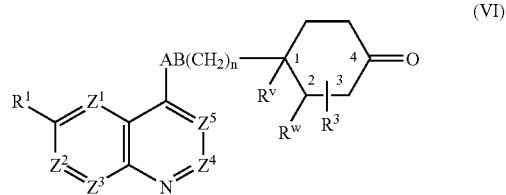

wherein
one of $Z^1$, $Z^2$, or $Z^3$ is N, and one of the remainder of $Z_1$, $Z_2$, $Z_3$, $Z_4$, and $Z_5$ is $CR^{1a}$ and the remainder are CH;

$R^v$ and $R^w$ are hydrogen; $R^v$ and $R^3$; or $R^v$ and $R^w$ together are a bond;

$R^1$ and $R^{1a}$ are independently selected from hydrogen; hydroxy; $(C_{1-6})$ alkoxy optionally substituted by $(C_{1-6})$alkoxy, amino, piperidyl, guanidino or amidino any of which is optionally N-substituted by one or two $(C_{1-6})$alkyl, $(C_{1-6})$alkoxycarbonyl, formyl, $(C_{1-6})$ alkoxycarbonyl, or $(C_{1-6})$alkylsulphonyl groups, CONH2, hydroxy, $(C_{1-6})$alkylthio, heterocyclylthio, heterocyclyloxy, arylthio, aryloxy, $(C_{1-6})$ alkyloxycarbonylthio, formylthio, $(C_{1-6})$ alkylcarbonylthio; $(C_{1-6})$alkyloxycarbonyloxy; formyloxy, $(C_{1-6})$alkylcarbonyloxy or $(C_{1-6})$ alkylsulphonyloxy; $(C_{1-6})$alkoxy-substituted $(C_{1-6})$ alkyl; halogen; $(C_{1-6})$alkyl; $(C_{1-6})$alkylthio; triflurom-ethyl; nitro; azido; $(C_{1-6})$alkoxycarbonyl; formyl; $(C_{1-6})$alkylcarbonyl; $(C_{1-6})$alkyloxycarbonyloxy; formyloxy; $(C_{1-6})$alkylcarbonyloxy; $(C_{1-6})$ alkyloxycarbonylthio; formylthio; $(C_{1-6})$alkylcarbonylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, $(C_{1-6})$alkoxycarbonyl, formyl, $(C_{1-6})$alkylcarbonyl or $(C_{1-6})$alkylsulphonyl groups, or when $Z^1$ is $CR^{1a}$, $R^1$ and $R^{1a}$ may together represent $(C_{1-2})$alkylenedioxy; or when $Z^5$ is $CR^{1a}$, $R^{1a}$ may be cyano, hydroxymethyl or carboxy;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

when $R^v$ and $R^w$ are a bond, $R^3$ is in the 2- or 3-position and when $R^v$ and $R^w$ are not a bond, $R^3$ is in the 1-, 2-, or 3-position and $R^3$ is:

hydrogen; carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; or amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

in addition when $R^3$ is disubstituted with a hydroxy or amino containing substituent and a carboxy containing substituent these may optionally together form a cyclic ester or amide linkage, respectively;

n is 0 or 1 and AB is $NR^{11}CO$, $CONR^{11}$, $CO—CR^8R^9$, $CR^6R^7$-CO, $O—CR^8R^9$, $CR^6R^7$-O, $NR^{11}—CR^8R^9$, $CR^6R^7$-$NR^{11}$, $NR^{11}SO_2$, $CR^6R^7—SO_2$ or $CR^6R^7$-$CR^8R^9$, provided that when $R^v$ and $R^w$ are a bond and n=0, B is not $NR^{11}$, O or $SO_2$, or n is 0 and AB is NH—CO—NH or NH—CO—O and $R^v/R^w$ are not a bond;

or n is 0 and AB is $CR^6R^7SO_2NR^2$, $CR^6R^7CONR^2$ or $CR^6R^7CH_2NR^2$ and $R^v/R^w$ are not a bond;

provided that $R^6$ and $R^7$, and $R^8$ and $R^9$ are not both optionally substituted hydroxy or amino:

and wherein:

each of $R^6$, $R^7$, $R^8$ and $R^9$ is independently selected from: H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

$R^{10}$ is selected from $(C_{1-4})$alkyl and $(C_{2-4})$alkenyl either of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl or $(C_{2-6})$ alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

and each $R^{11}$ is independently H; trifluoromethyl; $(C_{1-6})$ alkyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$ alkylcarbonyl, $(C_{2-6})$alkenyloxycarbonyl, $(C_{2-6})$ alkenyloxycarbonyl, $(C_{1-6})$alkyl or $(C_{2-6})$alkenyl and optionally further substituted by $(C_{1-6})$alkyl or $(C_{2-6})$ alkenyl.

13. A compound of formula (VII):

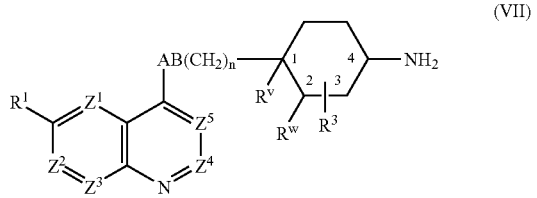

(VII)

wherein one of $Z^1$, $Z^2$, or $Z^3$ is N, one of the remainder of $Z^1$, $Z^2$, $Z^3$, $Z^4$, and $Z^5$ is $CR^{1a}$ and the remainder are CH;

$R^v$ and $R^w$ are hydrogen; $R^v$ is $R^3$; or $R^v$ and $R^w$ together are a bond;

$R^1$ and $R^{1a}$ are independently selected from hydrogen; hydroxy; $(C_{1-6})$ alkoxy optionally substituted by $(C_{1-6})$alkoxy, amino, piperidyl, guanidino or amidino any of which is optionally N-substituted by one or two $(C_{1-6})$alkyl, $(C_{1-6})$alkoxycarbonyl, formyl, $(C_{1-6})$ alkylcarbonyl, or $(C_{1-6})$alkylsulphonyl groups, CONH2, hydroxy, $(C_{1-6})$alkylthio, heterocyclylthio, heterocyclyloxy, arylthio, aryloxy, $(C_{1-6})$ alkyloxycarbonylthio; formylthio; $(C_{1-6})$ alkylcarbonylthio; $(C_{1-6})$alkyloxycarbonyloxy; formyloxy, $(C_{1-6})$alkylcarbonyloxy or $(C_{1-6})$ alkylsulphonyloxy; $(C_{1-6})$alkoxy-substituted $(C_{1-6})$ alkyl; halogen; $(C_{1-6})$alkyl; $(C_{1-6})$alkylthio; trifluromethyl; nitro; azido; $(C_{1-6})$alkoxycarbonyl; formyl; $(C_{1-6})$alkylcarbonyl; $(C_{1-6})$alkyloxycarbonyloxy; formyloxy; $(C_{1-6})$alkylcarbonyloxy; $(C_{1-6})$ alkyloxycarbonylthio; formylthio; $(C_{1-6})$ alkylcarbonylthio; $(C_{1-6})$alkylsulphonyl; $(C_{1-6})$ alkylsulphoxide; arylsulphonyl; arylsulphoxide or an amino, piperidyl, guanidino or amidino group optionally N-substituted by one or two $(C_{1-6})$alkyl, $(C_{1-6})$ alkoxycarbonyl, formyl, $(C_{1-6})$alkylcarbonyl or $(C_{1-6})$ alkylsulphonyl groups, or when $Z^1$ is $CR^{1a}$, $R^{1a}$ may together represent $(C_{1-2})$alkylenedioxy;

or when $Z^5$ is $CR^{1a}$, $R^{1a}$ may instead by cyano, hydroxymethyl or carboxy;

$R^2$ is hydrogen, or $(C_{1-4})$alkyl or $(C_{2-4})$alkenyl optionally substituted with 1 to 3 groups selected from:

amino optionally substituted by one or two $(C_{1-4})$alkyl groups; carboxy; $(C_{1-4})$alkoxycarbonyl; $(C_{1-4})$ alkylcarbonyl; $(C_{2-4})$alkenyloxycarbonyl; $(C_{2-4})$ alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$ alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$ alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-$^{1,2,4}$-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl; $(C_{1-4})$alkylcarbonyl; $(C_{2-4})$alkenyloxycarbonyl, $(C_{2-4})$ alkenylcarbonyl; oxo; $(C_{1-4})$alkylsulphonyl; $(C_{2-4})$ alkenylsulphonyl; or $(C_{1-4})$aminosulphonyl wherein the amino group is optionally substituted by $(C_{1-4})$alkyl or $(C_{2-4})$alkenyl;

when $R^{10}$ and $R^w$ are a bond, $R^3$ is in the 2- or 3-position and when $R^v$ and $R^w$ are not a bond, $R^3$ is in the 1-, 2-, 3-, and 4-position and $R^3$ is;

hydrogen; carboxy; $(C_{1-6})$alkoxycarbonyl; aminocarbonyl wherein the amino group is optionally substituted by hydroxy, $(C_{1-6})$alkyl, hydroxy$(C_{1-4})$alkyl, aminocarbonyl$(C_{1-6})$alkyl, $(C_{2-6})$alkenyl, $(C_{1-6})$ alkylsulphonyl, trifluoromethylsulphonyl, $(C_{2-6})$ alkenylsulphonyl, $(C_{1-6})$alkoxycarbonyl, $(C_{1-6})$ alkylcarbonyl, $(C_{2-6})$alkenyloxycarbonyl or $(C_{2-6})$ alkenylcarbonyl and optionally further substituted by $(C_{1-6})$alkyl, hydroxy$(C_{1-6})$alkyl, aminocarbonyl$(C_{1-6})$ alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the groups listed above for $R^3$ and/or 0 to 2 groups $R^{12}$ independently selected from:

halogen; $(C_{1-6})$alkylthio; trifluoromethyl; $(C_{1-6})$ alkoxycarbonyl; $(C_{1-6})$alkylcarbonyl; $(C_{2-6})$ alkenyloxycarbonyl; $(C_{2-6})$alkenylcarbonyl; hydroxy optionally substituted by $(C_{1-6})$alkyl, $(C_{2-6})$ alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$ alkylcarbonyl or $(C_{2-6})$alkenylcarbonyl; amino optionally mono- or disubstituted by $(C_{1-6})$ alkoxycarbonyl, $(C_{1-6})$alkylcarbonyl, $(C_{2-6})$ alkenyloxycarbonyl, $(C_{2-6})$alkenylcarbonyl, $(C_{1-6})$ alkyl, $(C_{2-6})$alkenyl, $(C_{1-6})$alkylsulphonyl, $(C_{2-6})$ alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy $(C_{1-6})$alkyl, aminocarbonyl$(C_{1-6})$alkyl, $(C_{2-6})$alkenyl, $(C_{1-6})$alkoxycarbonyl, $(C_{1-6})$ alkylcarbonyl, $(C_{2-6})$alkenyloxycarbonyl or $(C_{2-6})$ alkenylcarbonyl and optionally further substituted by $(C_{1-6})$alkyl, hydroxy$(C_{1-6})$alkyl, aminocarbonyl $(C_{1-6})$alkyl or $(C_{2-6})$alkenyl; oxo; $(C_{1-6})$ alkylsulphonyl; $(C_{2-6})$alkenylsulphonyl; or $(C_{1-6})$ aminosulphonyl wherein the amino group is optionally substituted by $(C_{1-6})$alkyl or $(C_{2-6})$alkenyl; or hydroxy optionally substituted by $(C_{1-6})$alkyl, $(C_{2-6})$ alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$ alkylcarbonyl or $(C_{2-6})$alkenylcarbonyl; or amino optionally mono- or disubstituted by $(C_{1-6})$alkoxycarbonyl, $(C_{2-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl;

in addition when $R^3$ is disubstituted with a hydroxy or amino containing substituent and a carboxy containing substituent these may optionally together form a cyclic ester or amide linkage, respectively;

provided that when $R^3$ is in the 4-position it is not optionally substituted hydroxyl or amino;

n is 0 or 1 and AB is $NR^{11}CO$, $CONR^{11}$, $CO-CR^8R^9$, $CR^6R^7-CO$, $O-CR^8R^9$, $CR^6R^7-O$, $NR^{11}-CR^8R^9$, $CR^6R^{7-}NR^{11}$, $NR^{11}SO_2$, $CR^6F^7-SO_2$ or $CR^6R^{7-}CR^8R^9$, provided that when $R^v$ and $R^w$ are a bond and n=0, B is not $NR^{11}$, O or $SO_2$, or n is 0 and AB is NH—CO—NH or NH—CO—O and $R^v/R^w$ are not a bond;

or n is 0 and AB is $CR^6R^7SO_2NR^2$, $CR^6R^7CONR^2$ or $CR^6R^7CH_2NR^2$ and $R^v/R^w$ are not a bond;

provided that $R^6$ and $R^7$, and $R^8$ and $R^9$ are not both optionally substituted hydroxy or amino;

and wherein;

each of $R^6$, $R^7$, $R^8$ and $R^9$ is independently selected from; H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{1-6})$alkenylsulphonyl; or $(C_{1-6})$aminosulphonyl wherein the amino group is optionally substituted by $(C_{1-6})$alkyl or $(C_{2-6})$alkenyl;

or $R^6$ and $R^8$ together represent a bond and $R^7$ and $R^9$ are as above defined;

$R^{10}$ is selected from $(C_{1-4})$alkyl and $(C_{2-4})$alkenyl either of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{1-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl;

and each $R^{11}$ is independently H; trifluoromethyl; $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl; $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl.

14. The method of claim 10 wherein the mammal is human.

* * * * *